US012661366B2

(12) United States Patent
Lawrence et al.

(10) Patent No.: US 12,661,366 B2
(45) Date of Patent: Jun. 23, 2026

(54) OLIGOSACCHARIDE COMPOSITIONS AND METHODS OF USE THEREOF FOR TREATING VIRAL INFECTIONS

(71) Applicant: DSM Nutritional Products, LLC, Parsippany, NJ (US)

(72) Inventors: Jonathan Lawrence, Lexington, MA (US); Jeffrey Meisner, Lexington, MA (US); Christopher Matthew Liu, Somerville, MA (US); Madeline Rosini, Lexington, MA (US); Max Hecht, Lexington, MA (US); Mark Wingertzahn, Lexington, MA (US); Geoffrey A. von Maltzahn, Boston, MA (US)

(73) Assignee: DSM Nutritional Products, LLC, Plainsboro, NJ (US)

( * ) Notice: Subject to any disclaimer, the term of this patent is extended or adjusted under 35 U.S.C. 154(b) by 777 days.

(21) Appl. No.: 17/920,720

(22) PCT Filed: Apr. 29, 2021

(86) PCT No.: PCT/US2021/030013

§ 371 (c)(1),
(2) Date: Oct. 21, 2022

(87) PCT Pub. No.: WO2021/222660

PCT Pub. Date: Nov. 4, 2021

(65) Prior Publication Data

US 2023/0165881 A1 Jun. 1, 2023

Related U.S. Application Data

(60) Provisional application No. 63/165,091, filed on Mar. 23, 2021, provisional application No. 63/137,093, filed on Jan. 13, 2021, provisional application No. 63/112,625, filed on Nov. 11, 2020, provisional application No. 63/022,377, filed on May 8, 2020, provisional application No. 63/018,489, filed on Apr. 30, 2020.

(51) Int. Cl.
*A61K 31/702* (2006.01)
*A61P 31/14* (2006.01)
*A61P 31/16* (2006.01)

(52) U.S. Cl.
CPC ............ *A61K 31/702* (2013.01); *A61P 31/14* (2018.01); *A61P 31/16* (2018.01)

(58) Field of Classification Search
None
See application file for complete search history.

(56) References Cited

U.S. PATENT DOCUMENTS

| | | | |
|---|---|---|---|
| 8,466,242 | B2 | 6/2013 | Geremia et al. |
| 8,476,388 | B2 | 7/2013 | Geremia et al. |
| 9,079,171 | B2 | 7/2015 | Geremia et al. |
| 9,205,418 | B2 | 12/2015 | Geremia et al. |
| 9,238,845 | B2 | 1/2016 | Baynes et al. |
| 9,492,473 | B2 | 11/2016 | von Maltzahn et al. |
| 9,757,403 | B2 | 9/2017 | von Maltzahn et al. |
| 9,901,595 | B2 | 2/2018 | von Maltzahn et al. |
| 10,131,721 | B2 | 11/2018 | Geremia et al. |
| 10,314,853 | B2 | 6/2019 | von Maltzahn et al. |
| 10,702,542 | B2 | 7/2020 | von Maltzahn et al. |
| 10,752,705 | B2 | 8/2020 | Geremia et al. |
| 10,787,527 | B2 | 9/2020 | Geremia et al. |
| 10,849,337 | B2 | 12/2020 | Geremia et al. |
| 10,881,676 | B2 | 1/2021 | von Maltzahn et al. |
| 10,894,057 | B2 | 1/2021 | von Maltzahn et al. |
| 11,169,101 | B2 | 11/2021 | Liu et al. |
| 11,229,660 | B2 | 1/2022 | von Maltzahn et al. |
| 11,584,805 | B2 | 2/2023 | Geremia et al. |
| 11,653,676 | B2 | 5/2023 | Geremia et al. |
| 11,697,692 | B2 | 7/2023 | Geremia et al. |
| 11,883,422 | B2 | 1/2024 | von Maltzahn et al. |
| 2012/0141541 | A1 | 6/2012 | Stahl et al. |
| 2012/0220740 | A1 | 8/2012 | Geremia et al. |
| 2012/0252957 | A1 | 10/2012 | Geremia et al. |
| 2013/0042859 | A1 | 2/2013 | Geremia et al. |
| 2013/0233308 | A1 | 9/2013 | Geremia et al. |
| 2014/0060522 | A1 | 3/2014 | Baynes et al. |
| 2015/0202607 | A1 | 7/2015 | Geremia et al. |
| 2015/0238948 | A1 | 8/2015 | Geremia |
| 2016/0007642 | A1 | 1/2016 | Geremia et al. |
| 2016/0032038 | A1 | 2/2016 | Baynes et al. |
| 2016/0122447 | A1 | 5/2016 | Geremia et al. |
| 2016/0213702 | A1 | 7/2016 | von Maltzahn et al. |
| 2016/0366909 | A1 | 12/2016 | Geremia et al. |

(Continued)

FOREIGN PATENT DOCUMENTS

| | | | |
|---|---|---|---|
| WO | WO-2006/022542 | A1 | 3/2006 |
| WO | WO-2012/118767 | A1 | 9/2012 |

(Continued)

OTHER PUBLICATIONS

Extended European Search Report for European Patent Application No. 21797776.8, dated Apr. 30, 2024 (8 pages).

(Continued)

*Primary Examiner* — Dale R Miller
(74) *Attorney, Agent, or Firm* — Clark & Elbing LLP

(57) ABSTRACT

Aspects of the disclosure relate to oligosaccharide compositions and methods of making the same. Also provided are methods of using oligosaccharide compositions as microbiome metabolic therapies for treating respiratory viral illnesses, such as COVID-19.

12 Claims, 32 Drawing Sheets

(56) References Cited

U.S. PATENT DOCUMENTS

| | | | |
|---|---|---|---|
| 2017/0151268 | A1 | 6/2017 | von Maltzahn et al. |
| 2017/0151269 | A1 | 6/2017 | von Maltzahn et al. |
| 2017/0246201 | A1 | 8/2017 | von Maltzahn et al. |
| 2018/0000145 | A1 | 1/2018 | Geremia et al. |
| 2018/0000146 | A1 | 1/2018 | Geremia |
| 2018/0147221 | A1 | 5/2018 | von Maltzahn et al. |
| 2018/0147222 | A1 | 5/2018 | von Maltzahn et al. |
| 2018/0235987 | A1 | 8/2018 | von Maltzahn et al. |
| 2018/0296582 | A1 | 10/2018 | von Maltzahn et al. |
| 2019/0062468 | A1 | 2/2019 | Geremia et al. |
| 2019/0091249 | A1 | 3/2019 | von Maltzahn et al. |
| 2019/0290675 | A1 | 9/2019 | Gibson et al. |
| 2019/0307159 | A1 | 10/2019 | Geremia et al. |
| 2020/0000831 | A1 | 1/2020 | Geremia et al. |
| 2020/0009168 | A1 | 1/2020 | von Maltzahn et al. |
| 2020/0093845 | A1 | 3/2020 | von Maltzahn et al. |
| 2020/0093851 | A1 | 3/2020 | von Maltzahn et al. |
| 2020/0352980 | A1 | 11/2020 | Mahowald et al. |
| 2020/0354481 | A1 | 11/2020 | Geremia et al. |
| 2020/0390798 | A1 | 12/2020 | Gibson et al. |
| 2021/0002387 | A1 | 1/2021 | Geremia et al. |
| 2021/0076705 | A1 | 3/2021 | Geremia et al. |
| 2021/0113596 | A1 | 4/2021 | von Maltzahn et al. |
| 2021/0121486 | A1 | 4/2021 | Geremia et al. |
| 2021/0137956 | A1 | 5/2021 | von Maltzahn et al. |
| 2021/0137964 | A1 | 5/2021 | von Maltzahn et al. |
| 2021/0161942 | A1 | 6/2021 | von Maltzahn et al. |
| 2021/0164926 | A1 | 6/2021 | Liu et al. |
| 2021/0198302 | A1 | 7/2021 | Liu et al. |
| 2021/0352945 | A1 | 11/2021 | Geremia |
| 2021/0401861 | A1 | 12/2021 | von Maltzahn et al. |
| 2022/0233560 | A1 | 7/2022 | Yatsunenko et al. |
| 2022/0233577 | A1 | 7/2022 | Gibson et al. |
| 2022/0395521 | A1 | 12/2022 | von Maltzahn et al. |
| 2022/0400728 | A1 | 12/2022 | Geremia et al. |
| 2022/0409644 | A1 | 12/2022 | Geremia et al. |
| 2023/0113218 | A1 | 4/2023 | Mahowald et al. |
| 2023/0123695 | A1 | 4/2023 | von Maltzahn et al. |
| 2023/0165881 | A1 | 6/2023 | Lawrence et al. |
| 2023/0255240 | A1 | 8/2023 | Geremia et al. |
| 2023/0255989 | A1 | 8/2023 | von Maltzahn et al. |
| 2023/0277573 | A1 | 9/2023 | Millet et al. |
| 2024/0108642 | A1 | 4/2024 | von Maltzahn et al. |

FOREIGN PATENT DOCUMENTS

| | | | |
|---|---|---|---|
| WO | WO-2014/031956 | A1 | 2/2014 |
| WO | WO-2014/032004 | A1 | 2/2014 |
| WO | WO-2014/159558 | A1 | 10/2014 |
| WO | WO-2015/071391 | A1 | 5/2015 |
| WO | WO-2016/007778 | A1 | 1/2016 |
| WO | WO-2016/014473 | A1 | 1/2016 |
| WO | WO-2016/122884 | A1 | 8/2016 |
| WO | WO-2016/122885 | A1 | 8/2016 |
| WO | WO-2016/122887 | A1 | 8/2016 |
| WO | WO-2016/122889 | A1 | 8/2016 |
| WO | WO-2016/122940 | A1 | 8/2016 |
| WO | WO-2016/139328 | A1 | 9/2016 |
| WO | WO-2016/172657 | A2 | 10/2016 |
| WO | WO-2016/172658 | A2 | 10/2016 |
| WO | WO-2017/035412 | A1 | 3/2017 |
| WO | WO-2017/083520 | A1 | 5/2017 |
| WO | WO-2018/013871 | A1 | 1/2018 |
| WO | WO-2018/106845 | A1 | 6/2018 |
| WO | WO-2019/014645 | A1 | 1/2019 |
| WO | WO-2019/046646 | A1 | 3/2019 |
| WO | WO-2019/090180 | A1 | 5/2019 |
| WO | WO-2019/090181 | A1 | 5/2019 |
| WO | WO-2019/090182 | A2 | 5/2019 |
| WO | WO-2020/041531 | A2 | 2/2020 |
| WO | WO-2020/097568 | A2 | 5/2020 |
| WO | WO-2020/227689 | A1 | 11/2020 |
| WO | WO-2021/222660 | A1 | 11/2021 |
| WO | WO-2021/231750 | A1 | 11/2021 |
| WO | WO-2021/231751 | A1 | 11/2021 |
| WO | WO-2022/016105 | A1 | 1/2022 |
| WO | WO-2022/067131 | A1 | 3/2022 |
| WO | WO-2023/059530 | A1 | 4/2023 |
| WO | WO-2024/023198 | A1 | 2/2024 |

OTHER PUBLICATIONS

International Search Report and Written Opinion for for PCT/US2021/030013, dated Aug. 31, 2021 (14 pages).

Overall Study Population

| Statistics | SSC + Oligo. (N=169) | SSC alone (N=181) | Overall (N=350) | % change (SSC + Oligo. vs SSC alone) |
|---|---|---|---|---|
| N (%) | 7 (4.1%) | 15 (8.3%) | 22 (6.29%) | -50.6% |

Comorbidity Patient Subgroup

| Statistics | SSC + Oligo. (N=69) | SSC alone (N=66) | Overall (N=135) | % change (SSC + Oligo. vs SSC alone) |
|---|---|---|---|---|
| N (%) | 4 (5.8%) | 10 (15.2%) | 14 (10.4%) | -61.8% |

FIG. 19

OLIGOSACCHARIDE COMPOSITIONS AND METHODS OF USE THEREOF FOR TREATING VIRAL INFECTIONS

RELATED APPLICATIONS

This application is a national stage filing under 35 U.S.C. § 371 of International Application No. PCT/US2021/030013, filed Apr. 29, 2021, which claims the benefit under 35 U.S.C. § 119(e) of U.S. Provisional Application No. 63/018,489, entitled "OLIGOSACCHARIDE COMPOSITIONS AND METHODS OF USE THEREOF FOR TREATING VIRAL INFECTIONS", filed Apr. 30, 2020; U.S. Provisional Application No. 63/022,377, entitled "OLIGOSACCHARIDE COMPOSITIONS AND METHODS OF USE THEREOF FOR TREATING VIRAL INFECTIONS", filed May 8, 2020; U.S. Provisional Application No. 63/112,625, entitled "OLIGOSACCHARIDE COMPOSITIONS AND METHODS OF USE THEREOF FOR TREATING VIRAL INFECTIONS", filed Nov. 11, 2020; U.S. Provisional Application No. 63/137,093, entitled "OLIGOSACCHARIDE COMPOSITIONS AND METHODS OF USE THEREOF FOR TREATING VIRAL INFECTIONS", filed Jan. 13, 2021; and U.S. Provisional Application No. 63/165,091, entitled "OLIGOSACCHARIDE COMPOSITIONS AND METHODS OF USE THEREOF FOR TREATING VIRAL INFECTIONS", filed Mar. 23, 2021; the entire contents of which are incorporated herein by reference.

FIELD OF THE INVENTION

The present disclosure relates to oligosaccharide compositions aid uses thereof for treating viral infections (e.g., coronavirus infections).

BACKGROUND OF INVENTION

Viral epidemics such as the COVID-19 pandemic threaten individuals, societies and healthcare systems around the world and new treatments which can either decrease infection risk or disease severity are desperately sought.

SUMMARY OF INVENTION

Aspects of this disclosure relate to the recognition that a patient's gut microbiome can be modulated to combat viral infections and related illnesses. In particular, in some embodiments, microbiome metabolic therapies (MMTs) are provided that utilize oligosaccharide compositions to modulate a patient's gut microbiome to treat infections caused by a virus (e.g., infections caused by respiratory viruses), e.g., an RNA virus.

In some embodiments, a patient's gut microbiome is modulated to produce short-chain fatty acids (e.g., acetate, butyrate, and/or propionate) that act to reduce severity of viral illnesses including viral respiratory illnesses caused by, for example, coronavirus, enterovirus, adenovirus, parainfluenza virus, respiratory syncytial virus (RSV), influenza virus, metapneumovirus, rhinovirus, bocavirus and others. Accordingly, in some embodiments, oligosaccharide compositions are utilized to stimulate production of such short-chain fatty acids by the gut microbiome that are more consistent and reproducible across patient samples than commercial fibers (see, e.g., FIGS. 1A-1B and FIG. 2).

In some embodiments, oligosaccharide compositions and related methods provided herein are useful for treating viral respiratory illnesses (such as the exemplary viral respiratory illness, COVID-19, and others, such as, e.g., RSV and influenza). In some embodiments, oligosaccharide compositions and related methods are useful for treating subjects with mild-to-moderate viral respiratory illnesses. In certain embodiments, such treat ents minimize the need for hospitalization or extended hospitalized care. In certain embodiments, such treatments minimize or prevent progression of the illness (e.g., progression from mild or moderate symptoms to severe symptoms, e.g., such that subject requires further intervention, e.g., a ventilator or respirator). In some embodiments, such treatments involve the administration of the oligosaccharide composition in combination with a standard of care treatment such as anti-viral agents, antibiotics, anti-inflammatory compounds, angiotensin-converting enzyme (ACE) inhibitors or angiotensin receptor blockers (ARBs). In some embodiments, standard of care treatments are self-administered. In some embodiments, standard of care treatments are home care treatments (i.e., administered at home, e.g., self-administered at home). In some embodiments, self-administered and/or home care treatments include, but are not limited to, bed rest, hydration, over-the-counter medication, and/or anti-viral medication. In some embodiments, such treatments involve the administration of the oligosaccharide composition following a standard of care treatment. In some embodiments, such treatments reduce the risk of acquiring viral infections, and thus, are useful for preventive care in frontline healthcare workers and others who may be exposed to viruses causing such infections.

Short-chain fatty acids, in some embodiments, modulate the immune and inflammatory responses of a subject, for example in response to a viral infection. The methods described herein are, in some embodiments, based on the realization that the oligosaccharide compositions of the disclosure can provide consistent, reliable and beneficial health effects by modulating short-chain fatty acid metabolism in the gastrointestinal tract.

In further aspects, the disclosure relates to a recognition that modulating a patient's gut to produce short-chain fatty acids is useful for reducing the risk of secondary pathogenic infections after a viral infection. Accordingly, in some embodiments, MMTs are provided that utilize oligosaccharide compositions for preventing or attenuating secondary infections in subjects having or recovering from a primary viral infection. In such embodiments, commensal microbe populations are modulated by the oligosaccharide compositions to enhance protection from pathogen infection and pathogen colonization.

In some embodiments, a method of treating a subject for a viral respiratory illness is provided. For example, the method, in some embodiments, comprises administering to the gastrointestinal tract of a subject an effective amount of an oligosaccharide composition, wherein the oligosaccharide composition has an average degree of polymerization of 5-20 and comprises a plurality of oligosaccharides selected from Formula (I), Formula (II), and Formula (III):

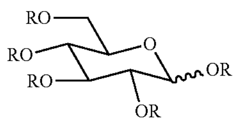

(I)

-continued (II)

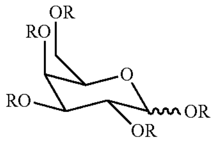

(III)

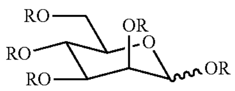

wherein each R independently is selected from hydrogen, and Formulae (Ia), (Ib), (Ic), (Id), (IIa), (IIb), (IIc), (IId), (IIIa), (IIIb), (IIc), (IIId):

(Ia)

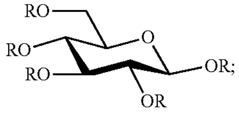

(IIa)

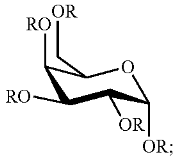

(IIIa)

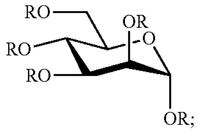

(Ib)

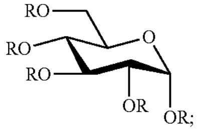

(IIb)

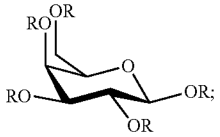

(IIIb)

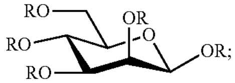

(Ic)

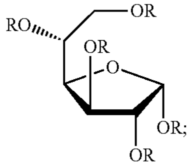

(IIc)

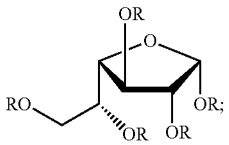

-continued (IIIc)

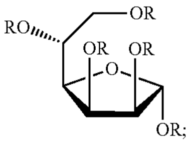

(Id)

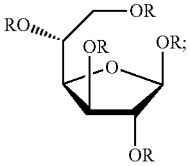

and (IId)

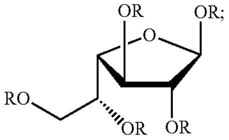

(IIId)

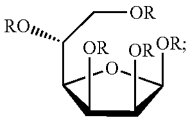

wherein each R independently is as defined above; thereby treating the subject.

In some embodiments, the disclosure is directed to a method of attenuating an immune response in a subject having one or more symptoms of a viral respiratory illness, the method comprising administering to the gastrointestinal tract of the subject an effective amount of an oligosaccharide composition, wherein the oligosaccharide composition has an average degree of polymerization of 5-20 and comprises a plurality of oligosaccharides selected from Formula (I), Formula (II), and Formula (III):

(I)

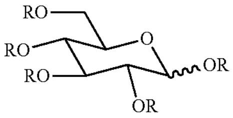

(II)

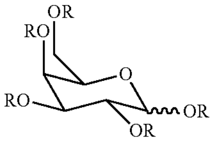

(III)

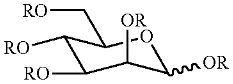

wherein each R independently is selected from hydrogen, and Formulae (Ia), (Ib), (Ic), (Id), (IIa), (IIb), (IIc), (IId), (IIIa), (IIIb), (IIIc), (IIId):

(Ia)

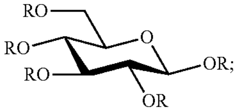

-continued (IIa)

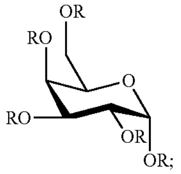

(IIIa)

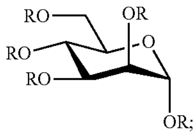

(Ib)

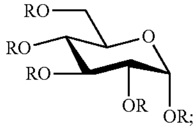

(IIb)

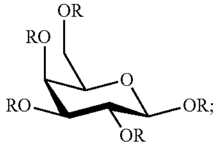

(IIIb)

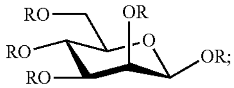

(Ic)

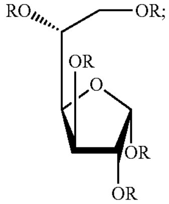

(IIc)

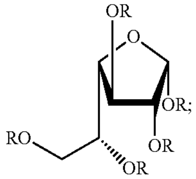

(IIIc)

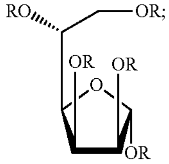

(Id)

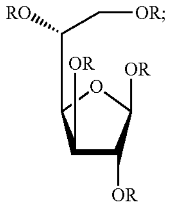

and

-continued (IId)

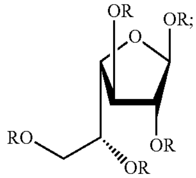

(IIId)

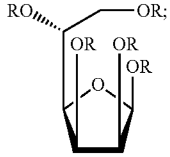

wherein each R independently is as defined above; thereby attenuating an immune response in the subject.

Further methods of the disclosure comprise identifying a human subject having one or more symptoms associated with a viral respiratory infection; and treating the subject with an oligosaccharide composition as described herein.

In some embodiments, a subject has one or more symptoms selected from the group consisting of: fever, shivering, chills, malaise, fatigue, cough, shortness of breath, sore throat, loss of appetite, loss of taste, loss of smell, body aches, muscle pain, headache, diarrhea and nausea. In some embodiments, a subject has a low-grade fever characterized by a body temperature of >101.5° F., a persistent cough, and discomfort with no evidence of pneumonia.

In some embodiments, the viral respiratory illness is caused by an RNA virus. In some embodiments, the viral respiratory illness is caused by a coronavirus, enterovirus, adenovirus, parainfluenza virus, respiratory syncytial virus, influenza virus, metapneumovirus, rhinovirus, measles virus, or bocavirus (e.g., a coronavirus, respiratory syncytial virus, or influenza virus). In some embodiments, a viral respiratory illness (e.g., COVID-19) is caused by a severe acute respiratory syndrome-related coronavirus (e.g., SARS-CoV-2).

In some embodiments, a subject has been determined to have a viral respiratory illness based on a molecular diagnostic assay, e.g., a PCR test (e.g., performing a PCR test on a sample from a subject) or an immunoassay (e.g., an immunoassay that detects a viral antigen or antibody against a viral antigen).

In some embodiments, the subject has not been determined to have (e.g., diagnosed as having) the viral respiratory illness. In some embodiments, the subject has been determined to have (e.g., diagnosed as having) the viral respiratory illness.

In some embodiments, an oligosaccharide composition is administered to a subject 1, 2, 3, 4, 5, 6, 7, 8, 9, 10, 11, 12, 13, or 14 days (e.g., 1-14, 2-14, 3-14, 1-13, 2-13, 3-13, 1-12, 2-12, 3-12, or 5-10 days) after exposure to the virus causing the viral respiratory infection. In some embodiments, an oligosaccharide composition is administered to a subject 1, 2, 3, 4, 5, 6, 7, 8, 9, 10, 11, 12, 13, or 14 days (e.g., 1-14, 2-14, 3-14, 1-13, 2-13, 3-13, 1-12, 2-12, 3-12, or 5-10 days) after onset of the viral respiratory infection.

In some embodiments, a subject is at risk for contracting the viral respiratory illness (e.g., as a result of having been exposed to the virus causing the viral respiratory illness). In some embodiments, a subject is a healthcare worker. In some embodiments, a subject is living with a person infected with the virus causing the viral respiratory illness.

In some embodiments, the subject has at least one comorbidity condition (e.g., selected from chronic lung disease (e.g., asthma, emphysema, or chronic obstructive pulmonary disease (COPD)), diabetes mellitus, cardiovascular disease, hypertension, renal disease (e.g., chronic renal disease), liver disease (e.g., chronic liver disease), an immunocompromised condition, cancer, a neurologic disorder, or stroke). In some embodiments, the subject has at least one high-risk comorbidity condition (e.g., selected from chronic lung disease (e.g., asthma, emphysema, or Copd), diabetes mellitus, cardiovascular disease, hypertension, chronic renal disease, or cancer). In some embodiments, the subject has an age-related risk factor (e.g., is at least 45 years old). In some embodiments, the subject is overweight or obese. In some embodiments, the subject has a body mass index (BMI) of at least 25, at least 30, or at least 35. In some embodiments, the subject is a high risk subject. In some embodiments, the the subject has two or all of: i) an age-related risk factor (e.g., is at least 45 years old); ii) at least one comorbidity (e.g., a high-risk comorbidity); or iii) is overweight or obese.

In some embodiments, a subject being treated with an oligosaccharide composition of the disclosure is at risk of a secondary infection (e.g., a secondary bacterial, fungal or viral infection). In some embodiments, a secondary infection is an infection of the gastrointestinal tract, lungs, bloodstream, central nervous system, lymphatic system, and/or soft tissues. A secondary infection may be caused, for example, by a vancomycin resistant *Enterococcus* (VRE), carbapenem resistant Enterobacteriaceae (CRE), or other antibiotic resistant bacteria. In some embodiments, a secondary infection may be caused by non-resist t bacteria, including *Mycobacterium tuberculosis, Streptococcus pneumoniae, Haemophilus influenzae, Moraxella catarrhalis, mycoplasma, Staphylococcus aureus*, or *Pseudomonas*. In some embodiments, a secondary infection may be caused by pathogens that preferentially reside in the gastrointestinal tract that are not resistant to antibiotics (e.g., *Enterococcus*, Enterobacteriaceae such as, e.g., *E. coli, Klebsiella pneumonae*; and *Enterobacter*).

In some embodiments, a subject experiences fewer treatment emergent adverse events (TEAEs) (e.g., 1, 2, 3, 4, or 5 fewer TEAEs) following administration to the oligosaccharide composition relative to a control subject. In some embodiments, a subject experiences a reduction of the severity of any one individual symptom score (e.g., self reported score of symptom from mild-to-moderate-to-severe) relative to a control subject (e.g., untreated subject) or a baseline measurement, wherein the any one individual symptom is elected from the group consisting of: fever, shivering, chills, malaise, cough (e.g., dry cough), loss of appetite, body aches, diarrhea, nausea, shortness of breath, chest tightness, and headache. In some embodiments, a subject experiences a reduction of the severity of 2, 3, 4 or 5 symptom scores. In some embodiments, a subject experiences a reduction in bed rest time measured as a patient-assessed daily cumulative total resting in a supine position (measured in hours).

Further aspects of the disclosure provide a method of increasing the amount of short-chain fatty acids in the gastrointestinal tract of a subject. In some embodiments, a method of increasing the amount of short-chain fatty acids in the gastrointestinal tract of a subject comprises administering to the gastrointestinal tract an effective amount of an oligosaccharide composition, wherein the oligosaccharide composition has an average degree of polymerization of 5-20 and comprises a plurality of oligosaccharides selected from Formula (I), Formula (II), and Formula (III):

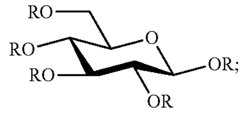
(Ia)

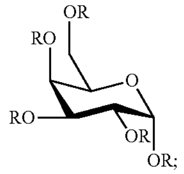
(IIa)

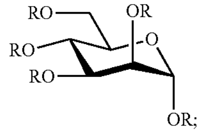
(IIIa)

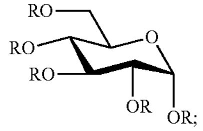
(Ib)

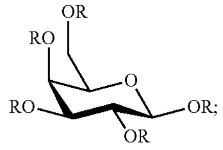
(IIb)

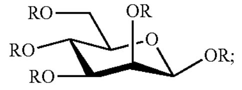
(IIIb)

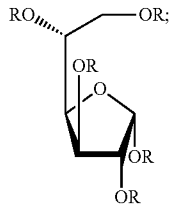
(Ic)

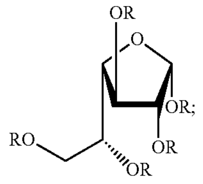
(IIc)

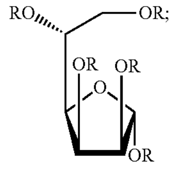
(IIIc)

-continued (Id)

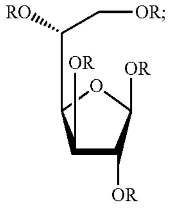

and (IId)

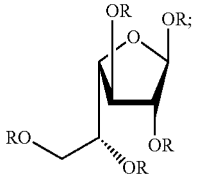

(IIId)

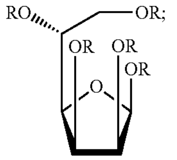

wherein each R independently is as defined above.

In some embodiments, short-chain fatty acids comprise propionate, butyrate and/or acetate. In some embodiments, administration of an oligosaccharide composition of the disclosure results in an increase in the amounts of short-chain fatty acid by at least 2-fold (e.g., at least 3-fold, at least 4-fold, at least 5-fold) in an ex vivo fecal sample collected from the subject relative to a baseline measurement or control. In some embodiments, the amount of propionate is increased by at least 1.2 fold (e.g., at least 1.2, 1.3, 1.4, 1.5, 1.75, 2, 2.25, 2.5, 2.75, 3, 3.25, 3.5, 3.75, 4, 4.25, 4.5, 4.75, or 5 fold) in an ex vivo fecal sample collected from the subject relative to a baseline measurement or control subject (e.g., a sample from a control subject). In some embodiments, the relative amounts of acetate, propionate, and butyrate produced (e.g., in the gastrointestinal tract and/or an ex vivo fecal sample treated with the olig saccharide composition) are: about 40-70% acetate, about 30-50% propionate, and about 5-20% butyrate; about 45-65% acetate, about 30-45% propionate, and about 5-10% butyrate; about 50-60% acetate, about 30-40% propionate, and about 5-10% butyrate; or about 54-60% acetate, about 34-40% propionate, and about 6-10% butyrate. In some embodiments, the relative increase of the amounts of short-chain fatty acids in the ex vivo fecal sample collected from the subject is substantially the same as the relative increase of the amounts of short-chain fatty acids in ex vivo fecal samples collected from other subjects receiving administration of the oligosaccharide composition (e.g., relative increase for the subject is within ±20% of the relative increase for other subjects). In some embodiments, the relative increase of the amount of propionate in the ex vivo fecal sample collected from the subject is substantially the same as the relative increase of the amount of propionate in ex vivo fecal samples collected from other subjects receiving administration of the oligosaccharide composition (e.g., relative increase for the subject is within ±50%, ±40%, ±30%, or ±20% of the relative increase for other subjects). In some embodiments, the increase of the amounts of short-chain fatty acids in an ex vivo fecal sample collected from the subject is also present in ex vivo fecal samples collected from other subjects receiving administration of the oligosaccharide composition (e.g., in at least 1, 2, 3, 4, 5, 6, 7, 8, 9, 10, 5, or 20 samples from other subjects).

In some embodiments, an oligosaccharide composition for use in methods of the disclosure is produced from a mixture comprising 30-60% dextrose monomers, 30-60% galactose monomers, and 5-15% mannose monomers. In some embodiments, an oligosaccharide composition is produced from a mixture comprising about 45% dextrose monomers, about 45% galactose monomers, and about 10% mannose monomers. In some embodiments, the mixture further comprises an acid catalyst and is heated at a temperature in a range of 100° C. to 160° C.

In some embodiments, an oligosaccharide composition for use in methods of the disclosure has an average degree of polymerization of 8-15.

In some embodiments, an oligosaccharide composition is administered to the intestines (e.g., the large intestine). In some embodiments, an oligosaccharide composition is self-administered to the subject. In some embodiments, an oligosaccharide composition is formulated as a pharmaceutical composition for oral delivery. In some embodiments, an oligosaccharide composition is orally administered to the subject. In some embodiments, an oligosaccharide composition is administered to the subject once per day or twice per day.

In some embodiments, an oligosaccharide composition is characterized by a multiplicity-edited gradient-enhanced $^{1}H$—$^{13}C$ heteronuclear single quantum correlation (HSQC) NMR spectrum comprising signals 5, 6, 7, and 15 of the following table, wherein the spectrum is generated using a sample of the oligosaccharide composition having less than 2% monomer:

| | Center Position (ppm) | | Area under the curve (AUC) |
|---|---|---|---|
| Signal | $^{1}H$ | $^{13}C$ | (% of total areas of all signals) |
| 1 | 3.68 | 63.42 | 20.38-25.74 |
| 2 | 3.75 | 66.06 | 3.69-6.38 |
| 3 | 3.97 | 66.15 | 2.21-3.40 |
| 4 | 3.96 | 69.28 | 1.46-3.71 |
| 5 | 3.96 | 70.62 | 9.28-10.71 |
| 6 | 3.92 | 71.26 | 1.52-2.03 |
| 7 | 3.55 | 71.34 | 3.40-6.13 |
| 8 | 3.97 | 71.56 | 3.40-4.41 |
| 9 | 3.72 | 72.35 | 5.66-10.14 |
| 10 | 3.33 | 73.74 | 10.21-12.09 |
| 11 | 4.06 | 77.34 | 3.68-4.50 |
| 12 | 4.11 | 81.59 | 3.10-3.82 |
| 13 | 4.96 | 98.7 | 10.65-12.31 |
| 14 | 4.5 | 103.29 | 5.03-6.41 |
| 15 | 4.44 | 103.86 | 1.84-2.44 |

In some embodiments, an oligosaccharide composition is characterized the oligosaccharide composition is characterized by a multiplicity-edited gradient-enhanced $^{1}H$—$^{13}C$ heteronuclear single quantum correlation (HSQC) NMR spectrum comprising signals 5, 6, 7, 10, 14, and 15 of the following table, wherein the spectrum is generated using a sample of the oligosaccharide composition having less than 2% monomer:

| | Center Position (ppm) | | Area under the curve (AUC) |
|---|---|---|---|
| Signal | $^{1}H$ | $^{13}C$ | (% of total areas of all signals) |
| 1 | 3.68 | 63.42 | 20.38-25.74 |
| 2 | 3.75 | 66.06 | 3.69-6.38 |
| 3 | 3.97 | 66.15 | 2.21-3.40 |
| 4 | 3.96 | 69.28 | 1.46-3.71 |
| 5 | 3.96 | 70.62 | 9.28-10.71 |
| 6 | 3.92 | 71.26 | 1.52-2.03 |
| 7 | 3.55 | 71.34 | 3.40-6.13 |
| 8 | 3.97 | 71.56 | 3.40-4.41 |
| 9 | 3.72 | 72.35 | 5.66-10.14 |
| 10 | 3.33 | 73.74 | 10.21-12.09 |
| 11 | 4.06 | 77.34 | 3.68-4.50 |
| 12 | 4.11 | 81.59 | 3.10-3.82 |
| 13 | 4.96 | 98.7 | 10.65-12.31 |
| 14 | 4.5 | 103.29 | 5.03-6.41 |
| 15 | 4.44 | 103.86 | 1.84-2.44 |

In some embodiments, an oligosaccharide composition is characterized by a multiplicity-edited gradient-enhanced $^{1}H$—$^{13}C$ heteronuclear single quantum correlation (HSQC) NMR spectrum comprising signals 5, 6, 7, and 10-15 of the following table, wherein the spectrum is generated using a sample of the oligosaccharide composition ha s than 2% monomer:

| | Center Position (ppm) | | Area under the curve (AUC) |
|---|---|---|---|
| Signal | $^{1}H$ | $^{13}C$ | (% of total areas of all signals) |
| 1 | 3.68 | 63.42 | 20.38-25.74 |
| 2 | 3.75 | 66.06 | 3.69-6.38 |
| 3 | 3.97 | 66.15 | 2.21-3.40 |
| 4 | 3.96 | 69.28 | 1.46-3.71 |
| 5 | 3.96 | 70.62 | 9.28-10.71 |
| 6 | 3.92 | 71.26 | 1.52-2.03 |
| 7 | 3.55 | 71.34 | 3.40-6.13 |
| 8 | 3.97 | 71.56 | 3.40-4.41 |
| 9 | 3.72 | 72.35 | 5.66-10.14 |
| 10 | 3.33 | 73.74 | 10.21-12.09 |
| 11 | 4.06 | 77.34 | 3.68-4.50 |
| 12 | 4.11 | 81.59 | 3.10-3.82 |
| 13 | 4.96 | 98.7 | 10.65-12.31 |
| 14 | 4.5 | 103.29 | 5.03-6.41 |
| 15 | 4.44 | 103.86 | 1.84-2.44 |

In some aspects, the disclosure provides an oligosaccharide composition comprising a plurality of oligosaccharides that are minimally digestible in humans, the composition being characterized by a multiplicity-edited gradient-enhanced $^{1}H$—$^{13}C$ heteronuclear single quantum correlation (HSQC) NMR spectrum comprising signals 5, 6, 7, and 15 of the following table, wherein the spectrum is generated using a sample of the oligosaccharide composition having less than 2% monomer:

| | Center Position (ppm) | | Area under the curve (AUC) |
|---|---|---|---|
| Signal | $^{1}H$ | $^{13}C$ | (% of total areas of all signals) |
| 1 | 3.68 | 63.42 | 21.57-25.73 |
| 2 | 3.75 | 66.06 | 3.87-5.54 |
| 3 | 3.97 | 66.15 | 2.63-3.43 |
| 4 | 3.96 | 69.28 | 1.28-3.86 |
| 5 | 3.96 | 70.62 | 9.08-11.04 |
| 6 | 3.92 | 71.26 | 1.49-2.70 |
| 7 | 3.55 | 71.34 | 4.48-5.90 |

-continued

| | Center Position (ppm) | | Area under the curve (AUC) |
|---|---|---|---|
| Signal | $^{1}H$ | $^{13}C$ | (% of total areas of all signals) |
| 8 | 3.97 | 71.56 | 3.07-3.99 |
| 9 | 3.72 | 72.35 | 6.87-8.66 |
| 10 | 3.33 | 73.74 | 10.79-11.70 |
| 11 | 4.06 | 77.34 | 3.28-3.99 |
| 12 | 4.11 | 81.59 | 2.82-3.39 |
| 13 | 4.96 | 98.7 | 10.60-12.69 |
| 14 | 4.5 | 103.29 | 4.90-6.25 |
| 15 | 4.44 | 103.86 | 1.81-2.42 |

In some embodiments, the oligosaccharide composition is characterized by a multiplicity-edited gradient-enhanced $^{1}H$—$^{13}C$ heteronuclear single quantum correlation (HSQC) NMR spectrum comprising signals 5, 6, 7, 10, 14, and 15 of the following table, wherein the spectrum is generated using a sample of the oligosaccharide composition having ess than 2% monomer:

| | Center Position (ppm) | | Area under the curve (AUC) |
|---|---|---|---|
| Signal | $^{1}H$ | $^{13}C$ | (% of total areas of all signals) |
| 1 | 3.68 | 63.42 | 21.57-25.73 |
| 2 | 3.75 | 66.06 | 3.87-5.54 |
| 3 | 3.97 | 66.15 | 2.63-3.43 |
| 4 | 3.96 | 69.28 | 1.28-3.86 |
| 5 | 3.96 | 70.62 | 9.08-11.04 |
| 6 | 3.92 | 71.26 | 1.49-2.70 |
| 7 | 3.55 | 71.34 | 4.48-5.90 |
| 8 | 3.97 | 71.56 | 3.07-3.99 |
| 9 | 3.72 | 72.35 | 6.87-8.66 |
| 10 | 3.33 | 73.74 | 10.79-11.70 |
| 11 | 4.06 | 77.34 | 3.28-3.99 |
| 12 | 4.11 | 81.59 | 2.82-3.39 |
| 13 | 4.96 | 98.7 | 10.60-12.69 |
| 14 | 4.5 | 103.29 | 4.90-6.25 |
| 15 | 4.44 | 103.86 | 1.81-2.42 |

In some embodiments, the oligosaccharide composition is characterized by a multiplicity-edited gradient-enhanced $^{1}H$—$^{13}C$ heteronuclear single quantum correlation (HSQC) NMR spectrum comprising signals 5, 6, 7, and 10-15 of the following table, wherein the spectrum is generated using a sample of the oligosaccharide composition having les than 2% monomer:

| | Center Position (ppm) | | Area under the curve (AUC) |
|---|---|---|---|
| Signal | $^{1}H$ | $^{13}C$ | (% of total areas of all signals) |
| 1 | 3.68 | 63.42 | 21.57-25.73 |
| 2 | 3.75 | 66.06 | 3.87-5.54 |
| 3 | 3.97 | 66.15 | 2.63-3.43 |
| 4 | 3.96 | 69.28 | 1.28-3.86 |
| 5 | 3.96 | 70.62 | 9.08-11.04 |
| 6 | 3.92 | 71.26 | 1.49-2.70 |
| 7 | 3.55 | 71.34 | 4.48-5.90 |
| 8 | 3.97 | 71.56 | 3.07-3.99 |
| 9 | 3.72 | 72.35 | 6.87-8.66 |
| 10 | 3.33 | 73.74 | 10.79-11.70 |
| 11 | 4.06 | 77.34 | 3.28-3.99 |

-continued

| Signal | Center Position (ppm) $^1H$ | $^{13}C$ | Area under the curve (AUC) (% of total areas of all signals) |
|---|---|---|---|
| 12 | 4.11 | 81.59 | 2.82-3.39 |
| 13 | 4.96 | 98.7 | 10.60-12.69 |
| 14 | 4.5 | 103.29 | 4.90-6.25 |
| 15 | 4.44 | 103.86 | 1.81-2.42 |

In some embodiments, the oligosaccharide composition is characterized by a multiplicity-edited gradient-enhanced $^1H$—$^{13}C$ heteronuclear single quantum correlation (HSQC) NMR spectrum comprising signals 1-15 of the following table, wherein the spectrum is generated using a sample of the oligosaccharide composition having less than 2% monomer:

| Signal | Center Position (ppm) $^1H$ | $^{13}C$ | Area under the curve (AUC) (% of total areas of all signals) |
|---|---|---|---|
| 1 | 3.68 | 63.42 | 21.57-25.73 |
| 2 | 3.75 | 66.06 | 3.87-5.54 |
| 3 | 3.97 | 66.15 | 2.63-3.43 |
| 4 | 3.96 | 69.28 | 1.28-3.86 |
| 5 | 3.96 | 70.62 | 9.08-11.04 |
| 6 | 3.92 | 71.26 | 1.49-2.70 |
| 7 | 3.55 | 71.34 | 4.48-5.90 |
| 8 | 3.97 | 71.56 | 3.07-3.99 |
| 9 | 3.72 | 72.35 | 6.87-8.66 |
| 10 | 3.33 | 73.74 | 10.79-11.70 |
| 11 | 4.06 | 77.34 | 3.28-3.99 |
| 12 | 4.11 | 81.59 | 2.82-3.39 |
| 13 | 4.96 | 98.7 | 10.60-12.69 |
| 14 | 4.5 | 103.29 | 4.90-6.25 |
| 15 | 4.44 | 103.86 | 1.81-2.42 |

In some embodiments, an oligosaccharide composition is characterized by a multiplicity-edited gradient-enhanced $^1H$—$^{13}C$ heteronuclear single quantum correlation (HSQC) NMR spectrum comprising signals 1-15 of the following table, wherein the spectrum is generated using a sample of the oligosaccharide composition having less than 2% monomer:

| Signal | Center Position (ppm) $^1H$ | $^{13}C$ | Area under the curve (AUC) (% of total areas of all signals) |
|---|---|---|---|
| 1 | 3.68 | 63.42 | 20.38-25.74 |
| 2 | 3.75 | 66.06 | 3.69-6.38 |
| 3 | 3.97 | 66.15 | 2.21-3.40 |
| 4 | 3.96 | 69.28 | 1.46-3.71 |
| 5 | 3.96 | 70.62 | 9.28-10.71 |
| 6 | 3.92 | 71.26 | 1.52-2.03 |
| 7 | 3.55 | 71.34 | 3.40-6.13 |
| 8 | 3.97 | 71.56 | 3.40-4.41 |
| 9 | 3.72 | 72.35 | 5.66-10.14 |
| 10 | 3.33 | 73.74 | 10.21-12.09 |
| 11 | 4.06 | 77.34 | 3.68-4.50 |
| 12 | 4.11 | 81.59 | 3.10-3.82 |
| 13 | 4.96 | 98.7 | 10.65-12.31 |
| 14 | 4.5 | 103.29 | 5.03-6.41 |
| 15 | 4.44 | 103.86 | 1.84-2.44 |

In some embodiments, an oligosaccharide composition is characterized by a multiplicity-edited gradient-enhanced $^1H$—$^{13}C$ heteronuclear single quantum correlation (HSQC)

NMR spectrum wherein signals 1-15 are each further characterized by an $^1H$ integral region and a $^{13}C$ integral region, defined as follows:

| Signal | $^1H$ Position (ppm) Center Position | $^1H$ Integral Region from | To | $^{13}C$ Position (ppm) Center Position | $^{13}C$ Integral Region from | to |
|---|---|---|---|---|---|---|
| 1 | 3.68 | 3.61 | 3.75 | 63.42 | 62.64 | 64.20 |
| 2 | 3.75 | 3.72 | 3.78 | 66.06 | 65.50 | 66.62 |
| 3 | 3.97 | 3.94 | 4.00 | 66.15 | 65.81 | 66.49 |
| 4 | 3.96 | 3.94 | 3.98 | 69.28 | 69.04 | 69.52 |
| 5 | 3.96 | 3.9 | 4.03 | 70.62 | 70.20 | 71.05 |
| 6 | 3.92 | 3.9 | 3.94 | 71.26 | 71.02 | 71.50 |
| 7 | 3.55 | 3.51 | 3.59 | 71.34 | 71.06 | 71.62 |
| 8 | 3.97 | 3.94 | 4.00 | 71.56 | 71.29 | 71.84 |
| 9 | 3.72 | 3.67 | 3.77 | 72.35 | 71.95 | 72.74 |
| 10 | 3.33 | 3.27 | 3.4 | 73.74 | 73.26 | 74.22 |
| 11 | 4.06 | 4.04 | 4.09 | 77.34 | 76.89 | 77.78 |
| 12 | 4.11 | 4.08 | 4.14 | 81.59 | 81.16 | 82.01 |
| 13 | 4.96 | 4.92 | 5.01 | 98.7 | 98.02 | 99.39 |
| 14 | 4.5 | 4.47 | 4.54 | 103.29 | 102.87 | 103.70 |
| 15 | 4.44 | 4.41 | 4.46 | 103.86 | 103.56 | 104.15 |

In some embodiments, an NMR spectrum is obtained by subjecting a sample of the composition to a multiplicity-edited gradient-enhanced $^1H$—$^{13}C$ heteronuclear single quantum coherence (HSQC) experiment using an echo-antiecho scheme for coherence selection using the following pulse sequence diagram, acquisition parameters and processing parameters: Pulse sequence diagram as shown in FIG. 27 having Acquisition Parameters
- $^1H$ Carrier Frequency=4 ppm
- $^3C$ Carrier Frequency=65 ppm
- Number of points in acquisition dimension=596
- Spectral range in acquisition dimension=6.23 ppm to 1.83 ppm
- Number of points in indirect dimension=300 complex points
- Spectral range in indirect dimension=120 ppm to 10 ppm
- Recycle delay=1 second
- One-bond $^1H$—$^{13}C$ coupling constant=$J_{CH}$=146 Hz
- Number of scans=8
- Temperature=298-299 K
- Solvent=$D_2O$ Processing Parameters
- Window function in direct dimension=Gaussian broadening, 7.66 Hz
- Window function in indirect dimension=Gaussian broadening 26.48 Hz
- Processing=512 complex points in direct dimension, 1024 complex points in indirect dimension In some embodiments, an NMR spectrum is obtained by subjecting a sample of the oligosaccharide composition to HSQC NMR, wherein the sample is dissolved in D2O.

In some embodiments, an oligosaccharide composition has been subjected to a de-monomerization procedure.

In some embodiments, an oligosaccharide composition comprises a plurality of oligosaccharides, each oligosaccharide comprising a plurality of monomer radicals;

the plurality of oligosaccharides comprising two or more types of monomer radicals selected from radicals (1)-(40):

(1) t-manopyranose monoradicals, representing 3.0-4.1 mol % of monomer radicals in the plurality of oligosaccharides;

(2) t-glucopyranose monoradicals, representing 11.4-16.3 mol % of monomer radicals in the plurality of oligosaccharides;

(3) t-galactofuranose monoradicals, representing 1.3-7.8 mol % of monomer radicals in the plurality of oligosaccharides;

(4) t-glucofuranose monoradicals, representing 0-1.4 mol % of monomer radicals in the plurality of oligosaccharides;

(5) t-galactopyranose monoradicals, representing 8.3-12.5 mol % of monomer radicals in the plurality of oligosaccharides;

(6) 3-glucopyranose monoradicals, representing 3.0-4.9 mol % of monomer radicals in the plurality of oligosaccharides;

(7) 2-manopyranose and/or 3-manopyranose monoradicals, representing 1.2-1.9 mol % of monomer radicals in the plurality of oligosaccharides;

(8) 2-glucopyranose monoradicals, representing 2.4-3.2 mol % of monomer radicals in the plurality of oligosaccharides;

(9) 2-galactofuranose and/or 2-glucofuranose monoradicals, representing 0.9-2.3 mol % of monomer radicals in the plurality of oligosaccharides;

(10) 3-galactopyranose monoradicals, representing 2.9-3.9 mol % of monomer radicals in the plurality of oligosaccharides;

(11) 4-manopyranose and/or 5-manofuranose and/or 3-galactofuranose monoradicals, representing 1.7-2.9 mol % of monomer radicals in the plurality of oligosaccharides;

(12) 6-manopyranose monoradicals, representing 2.0-2.9 molo of monomer radicals in the plurality of oligosaccharides;

(13) 2-galactopyranose monoradicals, representing 1.8-2.7 mol % of monomer radicals in the plurality of oligosaccharides;

(14) 6-glucopyranose monoradicals, representing 7.6-10.8 mol % of monomer radicals in the plurality of oligosaccharides;

(15) 4-galactopyranose and/or 5-galactofuranose monoradicals, representing 2.6-3.8 mol % of monomer radicals in the plurality of oligosaccharides;

(16) 4-glucopyranose and/or 5-glucofuranose and/or 6-manofuranose monoradicals, representing 3.0-4.5 mol % of monomer radicals in the plurality of oligosaccharides;

(17) 6-glucofuranose monoradicals, representing 0-1.6 mol % monomer radicals in the plurality of oligosaccharides;

(18) 6-galactofuranose monoradicals, representing 1.4-5.0 mol % of monomer radicals in the plurality of oligosaccharides;

(19) 6-galactopyranose monoradicals, representing 5.8-9.1 mol % of monomer radicals in the plurality of oligosaccharides;

(20) 3,4-galactopyranose and/or 3,5-galactofuranose and/or 2,3-galactopyranose diradicals, representing 0.9-1.4 mol % of monomer radicals in the plurality of oligosaccharides;

(21) 3,4-glucopyranose and/or 3,5-glucofuranose diradicals, representing 0-1.1 mol % of monomer radicals in the plurality of oligosaccharides;

(22) 2,4-glucopyranose and/or 2,5-glucofuranose and/or 2,4-galactopyranose and/or 2,5-galactofuranose diradicals, representing 0.9-1.4 mol % of monomer radicals in the plurality of oligosaccharides;

(23) 4,6-manopyranose and/or 5,6-manofuranose diradicals, representing 0.5-0.7 mol % of monomer radicals in the plurality of oligosaccharides;

(24) 3,6-manofuranose diradicals, representing 0-0.1 mol % of monomer radicals in the plurality of oligosaccharides;

(25) 3,6-glucopyranose diradicals, representing 1.4-2.8 mol % of monomer radicals in the plurality of oligosaccharides;

(26) 3,6-manopyranose and/or 2,6-manofuranose diradicals, representing 0.4-0.7 mol % of monomer radicals in the plurality of oligosaccharides;

(27) 2,6-manopyranose diradicals, representing 0.3-0.5 mol % of monomer radicals in the plurality of oligosaccharides;

(28) 3,6-glucofuranose diradicals, representing 0.1-0.4 mol % of monomer radicals in the plurality of oligosaccharides;

(29) 2,6-glucopyranose and/or 4,6-glucopyranose and/or 5,6-glucofuranose diradicals, representing 1.1-3.6 mol % of monomer radicals in the plurality of oligosaccharides;

(30) 3,6-galactofuranose diradicals, representing 0.9-1.4 molo of monomer radicals in the plurality of oligosaccharides;

(31) 4,6-galactopyranose and/or 5,6-galactofuranose diradical, representing 2.1-2.9 mol % of monomer radicals in the plurality of oligosaccharides;

(32) 3,6-galactopyranose and/or 2,6-galactofuranose diradical, representing 1.6-3.0 mol % of monomer radicals in the plurality of oligosaccharides;

(33) 2,6-galactopyranose diradicals, representing 0.7-1.6 mol % of monomer radicals in the plurality of oligosaccharides;

(34) 3,4,6-manopyranose and/or 3,5,6-manofuranose and/or 2 3,6-manofuranose triradicals, representing 0-0.3 mol % of monomer radicals in the plurality of oligosaccharides;

(35) 3,4,6-galactopyranose and/or 3,5,6-galactofuranose and/or 2,3,6-galactofuranose triradicals, representing 0.5-1.1 mol % of monomer radicals in the plural ty of oligosaccharides;

(36) 3,4,6-glucopyranose and/or 3,5,6-glucofuranose triradicals, representing 0.2-0.5 mol % of monomer radicals in the plurality of oligosaccharides;

(37) 2,3,6-manopyranose and/or 2,4,6-manopyranose and/or 2,5,6-manofuranose triradicals, representing 0-0.5 mol % of monomer radicals in the plurality of oligosaccharides;

(38) 2,4,6-glucopyranose and/or 2,5,6-glucofuranose triradicals, representing 0-1.4 mol % of monomer radicals in the plurality of oligosaccharides;

(39) 2,3,6-galactopyranose and/or 2,4,6-galactopyranose and/or 2,5,6-galactofuranose triradicals, representing 0.4-0.9 mol % of monomer radicals in the plurality of oligosaccharides; and

(40) 2,3,6-glucopyranose triradicals, representing 0.1-0.5 mol % of monomer radicals in the plurality of oligosaccharides.

In some aspects, the disclosure provides an oligosaccharide composition comprising a plurality of oligosaccharides that are minimally digestible in humans, each oligosaccharide comprising a plurality of monomer radicals;

the plurality of oligosaccharides comprising two or more types of monomer radicals selected from radicals (1)-(43):

(1) t-mannopyranose monoradicals, representing 3.0-4.1 mol % of monomer radicals in the plurality of oligosaccharides;

(2) t-glucopyranose monoradicals, representing 13.6-17.6 mol % of monomer radicals in the plurality of oligosaccharides;

(3) t-galactofuranose monoradicals, representing 3.0-4.2 mol % of monomer radicals in the plurality of oligosaccharides;

(4) t-glucofuranose monoradicals, representing 0.1-0.7 mol % of monomer radicals in the plurality of oligosaccharides;

(5) t-galactopyranose monoradicals, representing 9.7-11.7 mol % of monomer radicals in the plurality of oligosaccharides;

(6) 3-glucopyranose monoradicals, representing 3.8-4.6 mol % of monomer radicals in the plurality of oligosaccharides;

(7) 2-mannopyranose and/or 3-mannopyranose monoradicals, representing 0.8-2.0 mol % of monomer radicals in the plurality of oligosaccharides;

(8) 2-glucopyranose monoradicals, representing 2.7-3.0 mol % of monomer radicals in the plurality of oligosaccharides;

(9) 2-galactofuranose and/or 2-glucofuranose monoradicals and/or 3-glucofuranose, representing 0.8-1.8 mol % of monomer radicals in the plurality of oligosaccharides;

(10) 3-galactopyranose monoradicals, representing 2.8-3.8 mol % of monomer radicals in the plurality of oligosaccharides;

(11) 3-galactofuranose monoradicals, representing 1.6-2.2 mol % of monomer radicals in the plurality of oligosaccharides;

(12) 6-mannopyranose monoradicals, representing 2.1-2.5 mol % of monomer radicals in the plurality of oligosaccharides;

(13) 2-galactopyranose monoradicals, representing 1.7-2.4 mol % of monomer radicals in the plurality of oligosaccharides;

(14) 6-glucopyranose monoradicals, representing 9.5-11.1 mol % of monomer radicals in the plurality of oligosaccharides;

(15) 4-galactopyranose and/or 5-galactofuranose monoradicals, representing 2.5-3.1 mol % of monomer radicals in the plurality of oligosaccharides;

(16) 4-glucopyranose and/or 5-glucofuranose and/or 6-mannofuranose monoradicals, representing 3.0-3.9 mol % of monomer radicals in the plurality of oligosaccharides;

(17) 2,3-galactofuranose diradicals, representing 0.1-0.4 mol % of monomer radicals in the plurality of oligosaccharides;

(18) 6-glucofuranose monoradicals, representing 0.1-0.8 mol % of monomer radicals in the plurality of oligosaccharides;

(19) 6-galactofuranose monoradicals, representing 2.3-2.7 mol % of monomer radicals in the plurality of oligosaccharides;

(20) 6-galactopyranose monoradicals, representing 7.1-8.8 mol % of monomer radicals in the plurality of oligosaccharides;

(21) 3,4-galactopyranose and/or 3,5-galactofuranose and/or 2,3-galactopyranose diradicals, representing 0.9-1.1 mol % of monomer radicals in the plurality of oligosaccharides;

(22) 3,4-glucopyranose and/or 3,5-glucofuranose diradicals, r presenting 0.5-0.8 mol % of monomer radicals in the plurality of oligosaccharides;

(23) 2,3-glucopyranose diradicals, representing 0.1-2.1 mol % of monomer radicals in the plurality of oligosaccharides;

(24) 2,4-mannopyranose and/or 2,5-mannofuranose diradicals representing 0.1-0.9 mol % of monomer radicals in the plurality of oligosaccharides;

(25) 2,4-glucopyranose and/or 2,5-glucofuranose and/or 2,4-galactopyranose and/or 2,5-galactofuranose diradicals, representing 0.5-1.9 mol % of monomer radicals in the plurality of oligosaccharides;

(26) 4,6-mannopyranose and/or 5,6-mannofuranose diradicals, representing 0.4-0.7 mol % of monomer radicals in the plurality of oligosaccharides;

(27) 3,6-glucopyranose diradicals, representing 2.0-2.9 mol % of monomer radicals in the plurality of oligosaccharides;

(28) 3,6-mannopyranose diradicals, representing 0.4-0.7 mol % of monomer radicals in the plurality of oligosaccharides;

(29) 2,6-mannopyranose diradicals, representing 0.4-0.5 mol % of monomer radicals in the plurality of oligosaccharides;

(30) 3,6-glucofuranose diradicals, representing 0.1-0.3 mol % of monomer radicals in the plurality of oligosaccharides;

(31) 2,6-glucopyranose and/or 4,6-glucopyranose and/or 5,6-glucofuranose diradicals, representing 1.7-2.6 mol % of monomer radicals in the plurality of oligosaccharides;

(32) 3,6-galactofuranose diradicals, representing 0.9-1.2 mol % of monomer radicals in the plurality of oligosaccharides;

(33) 4,6-galactopyranose and/or 5,6-galactofuranose diradicals, representing 2.1-2.9 mol % of monomer radicals in the plurality of oligosaccharides;

(34) 3,6-galactopyranose diradicals, representing 2.0-2.7 mol % of monomer radicals in the plurality of oligosaccharides;

(35) 2,6-galactopyranose diradicals, representing 1.0-1.5 mol % of monomer radicals in the plurality of oligosaccharides;

(36) 3,4,6-mannopyranose and/or 3,5,6-mannofuranose and/or 2,3,6-mannofuranose triradicals, representing 0.1 mol % of monomer radicals in the plurality of oligosaccharides;

(37) 3,4,6-galactopyranose and/or 3,5,6-galactofuranose and/or 2,3,6-galactofuranose triradicals, representing 0.5-1.0 mol % of monomer radicals in the plurality of oligosaccharides;

(38) 3,4,6-glucopyranose and/or 3,5,6-glucofuranose triradicals, representing 0.1-0.6 mol % of monomer radicals in the plurality of oligosaccharides;

(39) 2,3,6-mannopyranose triradicals, representing 0.1-0.3 mol % of monomer radicals in the plurality of oligosaccharides;

(40) 2,4,6-glucopyranose and/or 2,5,6-glucofuranose triradicals, representing 0.1-0.8 mol % of monomer radicals in the plurality of oligosaccharides;

(41) 2,3,6-galactopyranose and/or 2,4,6-galactopyranose and/or 2,5,6-galactofuranose triradicals, representing 0.1-1.3 mol % of monomer radicals in the plurality of oligosaccharides;

(42) 2,4,6-galactopyranose and/or 2,5,6-galactofuranose triradicals, representing 0.1-0.9 mol % of monomer radicals in the plurality of oligosaccharides;

(43) 2,3,6-glucopyranose triradicals, representing 0.1-0.7 mol % of monomer radicals in the plurality of oligosaccharides;

the oligosaccharide composition comprising at least one glucofuranose or glucopyranose radical, at least one mannofuranose or mannopyranose radical, and at least one galactofuranose or galactopyranose radical.

In some embodiments, an oligosaccharide composition comprises at least one glucofuranose or glucopyranose radical, at least one manofuranose or manopyranose radical, and at least one galactofuranose or galactopyranose radical.

In some embodiments, the molar percentages of the monomer radicals are determined using a permethylation assay.

In some embodiments, an oligosaccharide composition is produced by a process comprising:

(a) forming a reaction mixture comprising dextrose monomer, galactose monomer, and mannose monomer wherein the molar ratio of dextrose to galactose is about 1:1 and the molar ratio of dextrose to mannose is about 4.5:1 with an acid catalyst comprising positively charged hydrogen ions; and (b) promoting acid catalyzed oligosaccharide formation in the reaction mixture by transferring sufficient heat to the reaction mixture to maintain the reaction mixture at its boiling point.

In some embodiments, step (b) comprises promoting acid catalyzed oligosaccharide formation in the reaction mixture by transferring sufficient heat to the reaction mixture to maintain the reaction mixture at its boiling point until the weight percent of total monomer content in the oligosaccharide composition is in a range of 2% to 20%, wherein the total monomer content comprises dextrose monomer, galactose monomer, and/or mannose monomer. In some embodiments, step (b) comprises loading the preparation with an acid catalyst comprising positively charged hydrogen ions, in an amount such that the molar ratio of positively charged hydrogen ions to total dextrose monomer, galactose monomer, and mannose monomer content is in an appropriate range.

In some embodiments, steps (a) and (b) occur simultaneously.

In some embodiments, step (a) comprises heating the reaction mixture under agitation conditions to a temperature in a range of 100° C. to 160° C. In some embodiments, step (a) comprises heating the reaction mixture under agitation conditions to a temperature in a range of 135° C. to 145° C. In some embodiments, step (a) comprises heating the reaction mixture under agitation conditions at a temperature in a range of 100° C. to 160° C. In some embodiments, step (a) comprises heating the reaction mixture under agitation conditions at a temperature in a range of 135° C. to 145° C. In some embodiments, step (a) comprises gradually increasing the temperature (e.g., from room temperature) to about 140° C., under suitable conditions to achieve homogeneity and uniform heat transfer.

In some embodiments, step (b) comprises maintaining the reaction mixture at atmospheric pressure or under vacuum, at a temperature in a range of 135° C. to 145° C., under conditions that promote acid catalyzed oligosaccharide composition formation, until the weight percent of dextrose monomer, galactose monomer, and mannose monomer in the oligosaccharide composition is in a range of 4-14. In some embodiments, step (b) comprises gradually increasing the temperature (e.g., from room temperature) to about 140° C., under suitable conditions to achieve homogeneity and uniform heat transfer.

In some embodiments, said heating comprises melting the preparation and/or heating the preparation under suitable conditions to achieve homogeneity and uniform heat transfer. In some embodiments, the acid catalyst is a soluble catalyst. In some embodiments, the soluble catalyst is an organic acid, optionally a weak organic acid. In some embodiment, the acid catalyst is citric acid, acetic acid, or propionic acid. In some embodiments, the acid catalyst is a strong acid cation exchange resin having one or more physical and chemical properties according to Table 1 and/or wherein the catalyst comprises >3.0 mmol/g sulfonic acid moieties and <1.0 mmol/gram cationic moieties.

In some embodiments, an oligosaccharide composition comprises a mean degree of polymerization is in a range of 5-20, 6-18, 7-15.5, 8-15, 9-15, 10-15, or 11-15. In some embodiments, an oligosaccharide composition comprises mean degree of polymerization is in a range of 11-15.

In some embodiments, the composition has a MWw (g/mol) in a range of 1905-2290. In some embodiments, the composition has a MWw (g/mol) in a range of 1740-2407. In some embodiments, the composition has a MWw (g/mol) in a range of 1863-2268. In some embodiments, the composition has a MWw (g/mol) in a range of 1700-2295. In some embodiments, the composition has a MWn (g/mol) in a range of 1033-1 84. In some embodiments, the composition has a MWn (g/mol) in a range of 975-1155. In some embodiments, the composition has a MWn (g/mol) in a range of 984-1106. In some embodiments, the composition has a MWn (g/mol) in a range of 938-1120.

In some embodiments, a solution comprising the oligosaccharide composition has a pH in a range of 2.50-7.00, optionally 2.50-3.50.

In some embodiments, the composition comprises oligomers haling two or more repeat units (DP2+) in a range of 86-96 weight percent. In some embodiments the composition comprises oligomers having two or more repeat units (DP2+) in a range of 81-100 weight percent. In some embodiments, the composition comprises oligomers having at least three linked monomer units (DP3+) in a range of 85-90 weight percent.

In some embodiments, the composition further comprises: 0.18-0.51% w/w levoglucosan, 0.01-0.05% w/w lactic acid, and/or 0.04-0.07% w/w formic acid.

In some embodiments, the composition further comprises: 0.40-0.53% w/w levoglucosan, 0.01-0.02% w/w lactic acid, 0.01-0.04% w/w formic acid, and/or 0.01-0.04% w/w citric acid.

In some embodiments, the oligosaccharide composition reduces the abundance of pathogenic bacteria. In some embodiments, the oligosaccharide compos tion promotes the abundance of commensal bacteria. In some embodiments, the oligosaccharide composition promotes the abundance of one or both of *Parabacteroides* and *Bacteroides*.

In some embodiments, treating a subject with an oligosaccharide composition provided herein reduces the time to resolution of at least one (e.g., at least 1, 2, 3, 4, 5, 6, 7, 8, 9, 10, 11, 12, 13, or all) symptom of a viral respiratory illness by 1-3, 1-5, 1-10, 3-5, 3-10, 3-15, 5-10, or 5-15 days (e.g., relative to an otherwise similar subject not having received the oligosaccharide composition (and optionally having received a standard of care therapy)). In some embodiments, the symptoms of a viral respiratory illness comprise one or more of cough, chills and/or repeated shaking with chills, muscle pain, fever, headache, anosmia/ageusia, shortness of breath, sore throat, gastrointestinal disturbance symptoms, diarrhea, fatigue, nasal congestion, and chest tightness.

In some embodiments, a method described herein (e.g., comprising administering an oligosaccharide composition provided herein to a subject in need thereof) further comprises administering a standard of care anti-viral treatment to the subject (e.g., self-administered or home care treatment (e.g., bed rest, hydration, over-the-counter medication, antiviral medication)). In some embodiments, a method described herein (e.g., comprising administering an oligosaccharide composition provided herein to a subject in need thereof) further comprises administering one or more monoclonal antibodies against an antigen of the viral respiratory illness (e.g., an antibody cocktail) to the subject. In some embodiments, the standard of care anti-viral treatment and/or one or more monoclonal antibodies are administered in combination with the oligosaccharide composition.

In one aspect, the disclosure is directed to a method of treating a subject having one or more symptoms of a viral respiratory illness, the method comprising administering to the gastrointestinal tract of the subject an effective amount of an oligosaccharide composition. In one aspect, the disclosure is directed to a method of attenuating an immune response in a subject having one or more symptoms of a viral respiratory illness, the method comprising administering to the gastrointestinal tract of the subject an effective amount of an oligosaccharide composition. In one aspect, the disclosure is directed to a method of increasing the amount of short-chain fatty acids in the gastrointestinal tract of a subject, the method comprising administering to the gastrointestinal tract an effective amount of an oligosaccharide composition. In some embodiments, the oligosaccharide composition is produced from a mixture comprising glucose, galactose, and mannose. In some embodiments, the mixture comprises 45±15% glucose, 45±15% galactose, and 5-20% mannose; 45±10% glucose, 45±10% galactose, and 5-20% mannose; 45±10% glucose, 45±10% galactose, and 10±5%; or 45±5% glucose, 45±5% galactose, and 10±5%. In some embodiments, the mixture comprises 45% glucose, 45% galactose, and 10% mannose.

BRIEF DESCRIPTION OF THE DRAWING

FIG. 1A shows the amounts (in mM) of acetate, propionate, and butyrate produced in fecal samples incubated with either the selected oligosaccharide composition or water. FIG. 1B shows the fold change in total concentration of short-chain fatty acids (SCFA) in fecal samples incubated with the selected oligosaccharide composition relative to the same fecal samples incubated with water.

FIG. 7A is a graph showing reduction of pathogens in fecal samples spiked with carbapenem-resistant Enterobacteriaceae. FIG. 7B is a graph showing reduction of pathogens in fecal samples spiked with vancomycin-resistant Enterococcaceae.

FIG. 10A provides graphs specific for ATCC 66035 strain. FIG. 10B provides graphs specific for ATCC 42720 strain.

FIG. 17A as measured using 13 overall COVID-19 related symptoms (1. Cough, 2. chills/repeated shaking with chills, 3. muscle pain, 4. fever, 5. headache, 6. anosmia/ageusia, 7. shortness of breath, 8. sore throat, 9. gastrointestinal disturbance/symptoms, 10. diarrhea, 11. fatigue, 12. nasal congestion, and 13. chest tightness); FIG. 17B as measured using 8 cardinal symptoms (1. cough, 2. chills/repeated shaking with chills, 3. muscle pain, 4. fever, 5. headache, 6. anosmia/ageusia, 7. shortness of breath, and 8. sore throat). Data shown is for for patients with comorbidities (red line) and without comorbidities (blue line).

FIG. 19 shows tables of healthcare utilization of study participants (overall population at top, patients with at least one comorbidity at bottom) treated with SSC and oligosaccharide composition or SSC alone.

FIG. 26 depicts only the anomeric region and as obtained by setting a lower threshold to aid peak annotation of less prominant peaks.

DETAILED DESCRIPTION OF INVENTION

Figure 1A:
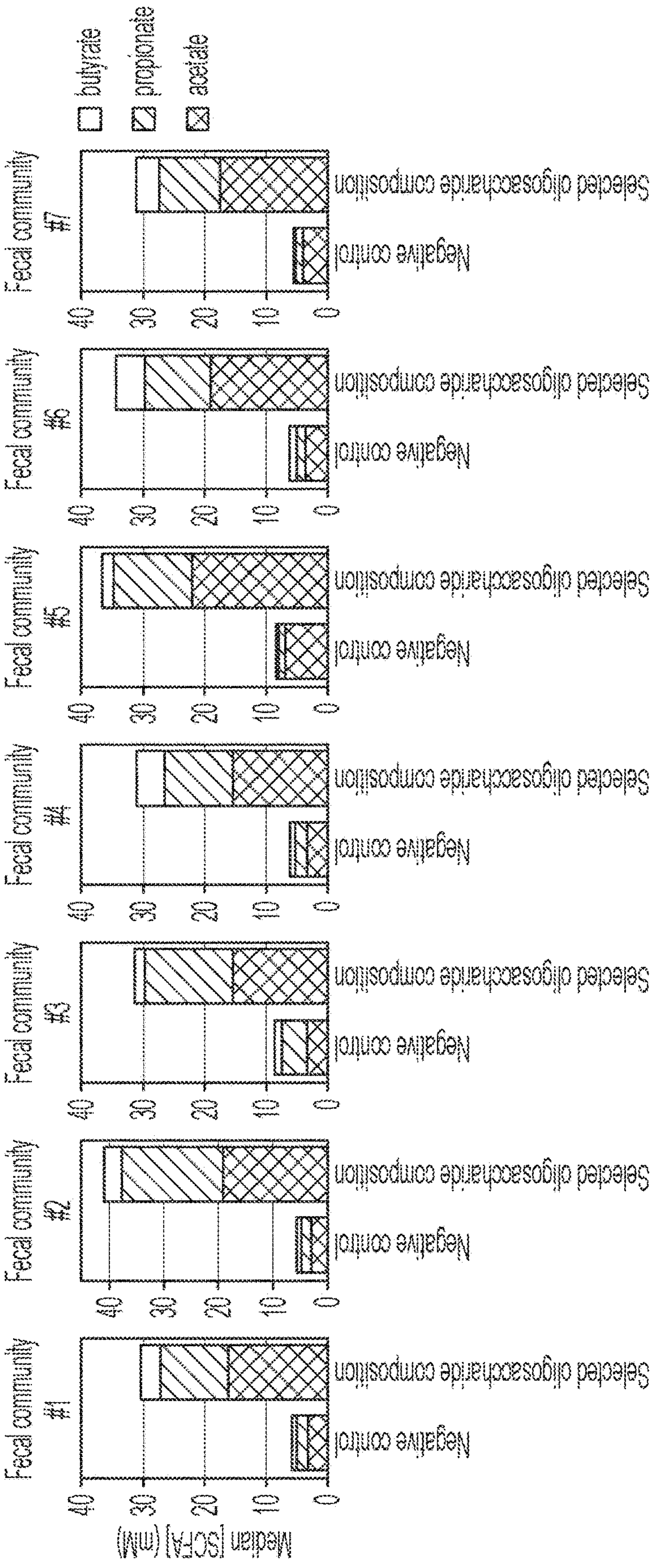
FIGS. 1A-1B provide graphs showing the ability of the selected oligosaccharide composition to produce an increase in concentration of short-chain fatty acids (acetate, propionate, butyrate) in fecal samples from seven healthy human subjects relative to a negative control (water).

Aspects of the disclosure relate to oligosaccharide compositions that are effective for increasing the concentration and amounts of short-chain fatty acids (SC As) (e.g., acetate, propionate, and/or butyrate) in the gut of a subject; reducing pathogen levels, abundance and/or colonization in a subject; and treating and preventing viral infections (e.g., coronavirus infections) in a subject. The intestinal microbiome is a complex ecosystem that integrates environmental inputs, such as diet, with genetic and immune signals to affect a subject's metabolism, immunity and response to infection. Aspects of the disclosure relate to a recognition that beyond the local gut immune regulation by the resident microbiota, long-reaching immuno-modulatory impact in other organs, including the pulmonary immune system, is brought about by the gut microbiota.

Modulation of the gut microbiome of a subject (e.g., a human subject), as described herein, provides an opportunity to have a beneficial impact on the progression and/or severity of respiratory infectious disease and to reduce the risk of pathogenic infections after a viral infection (e.g., secondary infections).

In some embodiments, oligosaccharide compositions described herein (e.g., orally administered, non-absorbed synthetic oligosaccharide compositions) that modulate the composition and metabolic output of the gut microbiome are useful in combating pulmonary infections, including coronavirus infections (e.g., COVID-19 infections). Without wishing to be bound by theory, coronavirus infections (e.g., COVID-19 infections) may serve as a model viral respiratory illness, such that oligosaccharide compositions effective at combating one or more symptoms of a coronavirus infection are effective generally for treating viral respiratory illnesses. In some embodiments, selected oligosaccharide compositions f the disclosure provide modulation over the taxonomic composition of the gut microbiome and its metabolic output, including the absolute quantities and relative abundance of SCFAs and other metabolites. Specifically, in some embodiments, selected oligosaccharide compositions promote beneficial SCFA profiles in the gut and growth of bacterial taxa that support the ability of a subject to mount an appropriate immune and inflammatory response while, in some embodiments, also preventing an over-aggressive response such as, for example, a cytokine storm.

A cytokine storm (also known as hypercytokinemia), in some embodiments, involves an immune reaction in which the body releases too many cytokines into the blood too quickly (e.g., at the same time). The release of a large amount of cytokines at one time can be harmful. In some embodiments, a cytokine storm is characterized by high fever, inflammation (e.g., redness and swelling), severe fatigue and/or nausea. In some embodiments, a cytokine storm is severe or life threatening and/or can lead to multiple organ failure.

In some embodiments, selected oligosaccharide compositions are not significantly digested by the limited number of human carbohydrate-modifying enzymes in the small intestine and pass into the large intestine where they can be enzymatically digested by a repertoire of carbohydrate-active enzymes produced by a community of resident commensal bacteria (e.g., *Parabacteroides* and *Bacteroides*). In some embodiments, major products of digestion of selected oligosaccharide composition by the gut bacteria are SCFAs (e.g., butyrate, propionate, and acetate). In some embodiments, these SCFAs serve an important role in the maintenance of healthy gut epithelial function. In some embodiments, butyrate, for example, is used as the primary source of energy for gut epithelial cells and promotes maintenance of epithelial integrity. In some embodiments, maintenance of epithelial integrity is important to prevent inappropriate activation of innate and adaptive immune cells. In some embodiments, butyrate activates G-protein coupled receptors (GPCRs) displayed on the surface of epithelial and immune cells, as well as inhibits histone deacetylases in the nucleus of these cell types. In certain embodiments, propionate promotes gut immune homeostasis by activating these same PCRs. In some embodiments, in addition to producing SCFAs, digestion of the selected oligosaccharide composition results in the preferential growth of commensal bacteria relative to unwanted pathogenic bacteria.

In some embodiments, gut derived metabolites (e.g., SCFAs) an the direct interaction and migration of immune cells from gut to lung by the common mucosal immune system can have a beneficial impact on pulmonary infections (such as caused by coronavirus infections). For example, SCFAs produced by gut bacteria (e.g., resulting from treatment with selected oligosaccharide compositions provided herein) migrate through the circulation (blood stream) to stimulate immune response in the lung, and, in some cases, different factors from the lung effect immune response in the gastrointestinal tract. Additionally, in some embodiments, immune cells induced by certain antigens move through lymphatic duct between both of these organs leading to modulation of the immune response according to the methods provided herein.

Some methods provided herein result in induction of SCFAs in the gut microbiome. In some embodiments, such SCFAs modulate host inflammation, control adaptive immunity, and/or promote immune tolerance locally in the gut and/or systemically throughout body of the subject. In particular, such SCFAs and SCFA-producing taxa contribute to reduced risk of acquiring viral infections, including coronavirus infections, e.g., in at-risk populations such as HSCT patients. In some embodiments, such SCFAs and SCFA-producing microbial tax induce virus-specific CD4+ and CD8+ T cells, type 1 interferon, and antibody responses involved in the reduction of viral infection severity. In another example, protection against a viral infection (e.g., RSV infection) is conferred by acetate through induction of IFN-β in the lung through GPR43 and IFNAR-mediated pathways. In addition, in some embodiments, SCFAs produced according to methods provided herein influence macrophage functionality to mitigate neutrophil-mediated tissue damage. In some embodiments, this effect is advantageous because viral infections may be accompanied by an aggressive pro-inflammatory response that can elicit a syndrome known as cytokine storm.

In addition to gut microbiome derived metabolites (e.g., SCFAs) influencing peripheral inflammatory responses, direct activation of host immune cells and pathways by microbiota in the gut impacts the progression of pulmonary infections. In some embodiments, a dysbiosis in the gut microbiome community (e.g., exhibited as a loss in overall commensal diversity or pathobiont overgrowth) contribute to unfavorable outcomes in respiratory infections. Accordingly, in some embodiments, methods and oligosaccharide compositions provided herein are useful for shifting gut microbiome community activity in a manner that supports or promotes immune responses against such infections.

Some methods and compositions provided herein modulate an immune response to pulmonary infections (such as caused by coronavirus infections) by altering the microbiota of the gut. Without wishing to be bound by theory, the disclosure is directed, in part, to the idea that host metabolites processed by the gut microbiota as well as gut microbiota-secreted metabolites can influence features of a host immune response to a pulmonary infection (such as an infection caused by coronavirus). By altering the microbiota with a method or oligosaccharide composition described herein, a host immune response may be enhance(or attenuated. In some embodiments, one or more symptoms of a viral respiratory illness are caused, entirely or in part, by undesirably high levels of host immune activity. As such, an oligosaccharide composition effective at treating one or more symptom of an exemplary viral respiratory illness (e.g., COVID19) by reducing undesirably high levels of host immune activity may be effective at treating multiple (e.g., all) different viral respiratory illnesses. In some embodiments, a method or oligosaccharide composition described herein can be used to attenuate a subject's immune response against a viral respiratory illness, thereby reducing the severity of one or more symptoms and/or reducing the time to resolution of one or more (e.g., all) symptoms. In some embodiments, a method or oligosaccharide composition described herein, may be used to treat the symptoms of a viral respiratory illness (e.g., COVID-19) or prevent worsening of a viral respiratory illness (e.g., progression from mild or moderate COVID-19 to severe COVID-19) by attenuating a subject's immune response to the respiratory virus. The di closure is directed, in part, to the idea that attenuation of a host immune response via an alteration in the gut microbiota represents an immune modulation with a low risk of adverse side effects to a subject (e.g., due to the oligosaccharide compositions described herein lacking additional drugs or biologics (e.g., antibody biologics)) and/or an immune modulation that may be effective independent of the identity or type of viral illness afflicting the subject. As such, the oligosaccharide compositions described herein may represent an advantageous path to treating viral illnesses where one or more symptoms relate to undesirable levels of host immune response or specifically targeted treatments are not available.

Further aspects of the disclosure, including a description of defined terms, are provided below.

I. Definitions

Agitation conditions: As used herein, the term "agitation conditions" refers to conditions that promote or maintain a substantially uniform or homogeneous state of a mixture (e.g., a reaction mixture comprising dextrose monomer, galactose monomer, and mannose monomer) with respect to dispersal of solids (e.g., solid catalysts), uniformity of heat transfer, or other similar parameters. Agitation conditions generally include stirring, shaking, and/or mixing of a reaction mixture. In some embodiments, agitation conditions may include the addition of gases or other liquids into a solution. In some embodiments, agitation conditions are used to maintain substantially uniform or homogenous distribution of a catalyst, e.g., an acid catalyst. In some embodiments, a monosaccharide preparation is heated in the presence of an acid catalyst under suitable conditions to achieve homogeneity and uniform heat transfer in order to synthesize an oligosaccharide composition.

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dextrose monomer: As used herein, the term "dextrose monomer" refers to a D-isomer of a glucose monomer, known as $_D$-glucose. In some embodiments, a dextrose monomer is dextrose monohydrate or 70DS corn syrup.

Effective amount: As used herein, the term "effective amount" refers to an administered amount or concentration of an oligosaccharide composition that is necessary and sufficient to elicit a biological response, e.g., in a subject or patient. In some embodiments, an effective amount of an oligosaccharide composition is capable of modulating, e.g., increasing or decreasing, the processing of a metabolite (e.g., an SCFA). In some embodiments, an effective amount of an oligosaccharide composition is capable of modulating, e.g., increasing or decreasing, the concentration or number of at least one microbial species (e.g., SCFA-producing species). In some embodiments, an effective amount of an oligosaccharide composition is capable of modulating, e.g., increasing or decreasing, the activity or lev is of an enzyme in a subject. In some embodiments, an effective amount of an oligosaccharide composition is capable of modulating, e.g., decreasing, the symptoms of a disease (e.g. a respiratory disease) associated with elevated pathogen (e.g., viral or bacterial) colonization a subject (e.g., the severity or number of symptoms). In some embodiments, an effective amount of an oligosaccharide composition is capable of reducing the acquisition of, colonization of, or reducing the reservoir of a pathogen (e.g., a drug or antibiotic resistant pathogen, or an MDR pathogen or a virus (e.g., viral load) in a subject. In some embodiments an effective amount of an oligosaccharide composition is capable of treating a subject having a viral infection (e.g., a viral respiratory illness). In some embodiments, an effective amount of an oligosaccharide composition is capable of treating a subject having intestinal colonization with a pathogen, e.g., CRE or VRE.

Galactose monomer: As used herein, the term "galactose monomer" generally refers to a D-isomer of a galactose monomer, known as D-galactose.

Mannose monomer: As used herein, the term "mannose monomer" generally refers to a D-isomer of a mannose monomer, known as $_D$-mannose.

Monosaccharide Preparation: As used herein, the term "monosaccharide preparation" refers to a preparation that comprises two or more monosaccharides (e.g., dextrose monomer, galactose monomer, and mannose monomer). In some embodiments, a monosaccharide preparation comprises dextrose monomers, galactose monomers, and mannose monomers.

Oligosaccharide: As used herein, the term "oligosaccharide" (which may be used interchangeably with the term "glycan" in some contexts) refers to a saccharide molecule comprising at least two monosaccharides (e.g., dextrose monomers, galactose monomers, mannose monomers) linked together via a glycosidic bond (having a degree of polymerization (DP) of at least 2 (e.g., DP2+)). In some embodiments, an oligosaccharide comprises at least two, at least three, at least four, at least five, at least six, at least seven, at least eight, at least nine, or at least ten monosaccharides subunits linked by glycosidic bonds. In some embodiments, an oligosaccharide is in the range of 3-20, 4-16, 5-15, 8-12, 5-25, 10-25, 20-50, 40-80, or 75-100 monosaccharides linked by glycosidic bonds. In some embodiments, an oligosaccharide comprises at least one 1,2; 1,3; 1,4; and/or 1,6 glycosidic bond. Oligosaccharides may be linear or branched. Oligosaccharides may ha e one or more glycosidic bonds that are in alpha-configurations and/or one or more glycosidic bonds that are in beta-configurations.

Pharmaceutical Composition: As used herein, a "pharmaceutical composition" refers to a composition having pharmacological activity or other direct effect in the mitigation, treatment, or prevention of disease, and/or a finished dosage form or formulation thereof and is for human use. A pharmaceutical composition or pharmaceutical preparation is typically produced under good manufacturing practices (GMP) conditions. Pharmaceutical compositions or preparations may be sterile or non-sterile. If non-sterile, such pharmaceutical compositions or preparations typically meet the microbiological specifications and criteria for non-sterile pharmaceutical products as described in the U.S. Pharmacopeia (USP) or European Pharmacopoeia (EP). Any oligosaccharide composition described herein may be formulated as a pharmaceutical composition.

Subject: As used herein, the term "subject" refers to a n man subject or patient. Subjects may include a newborn (a preterm newborn, a full-term newborn), an infant up to one year of age, young children (e.g., 1 yr to 12 yrs), teenagers, (e.g., 13-19 yrs), adults (e.g., 20-64 yrs), and elderly adults (65 yrs and older). In some embodiments, the subject is between 1 month and 36 months old. In some embodiments, the subject is at least 12 years old or at least 16 years old. In some embodiments, the subject is at least 40 years old or at least 45 years old. In some embodiments, the subject is at least 16 years old. In some embodiments, the subject is at least 60 years old or at least 65 years old. In some embodiments, the subject exhibits at least one comorbidity. In some embodiments, a subject is a healthy subject. In some embodiments, a healthy subject is a person who is at high risk for contracting a viral infection or coronavirus infection (e.g., an essential worker, a hospital employee, an employee at a nursing or elder care facility, an immunocompromised subject). In some embodiments, a subject has or is suspected of having a viral infection or coronavirus infection (e.g., COVID-19). In s me embodiments, a subject is recently recovered from a viral infection or coronavirus infection. In some embodiments, the subject has a detectable viral load (e.g., viral RNA measured by RT-PCR). In some embodiments, the viral load of a subject is below the limit of detection. In some embodiments, a subject has or is suspected of having one or more of the following co-morbidities: cardiovascular disease, diabetes, chronic respiratory disease, hypertension, cancer, heart disease, hypertension, prior stroke, and chronic kidney disease. In some embodiments, a subject is asymptomatic or exhibits a pre-symptomatic viral infection. n some embodiments, an oligosaccharide composition is administered to a subject 1-14, 3-12, or 5-10 days after exposure to the virus causing the viral respiratory infection. In some embodiments, an oligosaccharide composition is administered to a subject 1-14, 3-12, or 5-10 days after onset of the viral respiratory infection. In some embodiments, a subject has developed dyspnea but not yet acute respiratory distress syndrome (ARDS). In some embodiments, a subject has developed acute respiratory distress syndrome (ARDS) but has not yet been admitted to the intensive care unit (ICU). In some embodiments, a subject has a mild clinical presentation (e.g., absence of viral pneumonia and hypoxia). In some embodiments, a subject is able to manage their illness at home (e.g., in an outpatient setting, without hospitalization). A subject may be able to manage their illness at home depending on the clinical presentation, requirement for supportive care, potential risk factors for severe disease, and the ability of the subject to self-isolate at home. In some embodiments, a subject is hospitalized. In some embodiments, a subject having a viral infection or coronavirus infection is a candidate for being treated with a ventilator. In some embodiments, a subject has recently been taken off of a ventilator. In some embodiments, a subject has one or more of the following symptoms: a cough, fever, nasal congestion, gastrointestinal symptoms, fatigue, anosmia, ageusia, vomiting, diarrhea, shortness of breath, chest tightness, and headache. A symptom may be rated, in some embodiments, on a scale of 0-3, wherein 0 means that the symptom is absent, 1 means that the symptom is mild (present but easily tolerated), 2 means that the symptom is moderately severe (bothersome but tolerable), and 3 means that the symptom is very severe (hard to tolerate; interferes considerably with daily activity). For example, a mild symptom may be mild pneumonia if the subject has a respiratory viral infection. In some embodiments, a severe symptom is dyspnea, hypoxia, or >50% lung involvement on imaging if the subject has a respiratory viral infection. In some embodiments, a subject is not in critical condition (e.g., (respiratory failure, shock, or multiorgan system dysfunction). In some embodiments, a subject is a patient having higher abundance of pathogen relative to a healthy subject, e.g., a subject colonized with a pathogen (e.g., CRE and/or VRE pathogens) in their gastrointestinal tract (e.g., their colon or intestines). In some embodiments, a subject is a patient receiving broad spectrum antibiotics. In some embodiments, the subject is particularly susceptible to pathogen infection, e.g., the subject is critically-ill and/or immunocompromised. In some embodiments, the subject is a patient having a lower abundance of commensal bacteria relative to a healthy subject in their gastrointestinal tract (e.g., their colon or intestines).

Treatment and Treating: As used herein, the terms “treating” and “treatment” refer to the administration of a composition to a subject to manage or improve one or more symptoms associated with a disease or illness. In some embodiments, treatment affects a reduction in severity and/or frequency of a symptom or treatment emergent adverse event (TEAE) in a subject (e.g., a symptomatic subject afflicted with a viral infection, e.g., a coronavirus infection or recently recovered from a viral infection, e.g., recently recovered from a coronavirus infection). In some embodiments, a treatment reduces the severity or eliminates a symptom or TEAE and/or its underlying cause. In some embodiments, a treatment facilitates improvement or remediation of damage, and/or preventing an adverse condition or viral infection, e.g., coronavirus infection, in an asymptomatic subject who is suspected of developing or at risk of developing a viral infection, e.g., a coronavirus infection. In some embodiments, a symptom or TEAE resulting from a viral infection, e.g., a coronavirus infection, may include a cough, fever, nasal congestion, gastrointestinal symptoms, fatigue, anosmia, ageusia, diarrhea, shortness of breath, chest tightness, and/or headache. In some embodiments, treatment of a viral infection in a subject results in elimination of the infection. In some embodiments, treatment of a viral infection in a subject results in the subject experiencing fewer treatment emergent adverse events (TEAEs) following administration of the oligosaccharide composition relative to a control subject (e.g., untreated subject) or a baseline. In some embodiments, a subject who has been administered an oligosaccharide composition experiences only mild adverse effects relating to the oligosaccharide composition, e.g., mild gastrointestinal adverse effects. In some embodiments, mild gastrointestinal adverse effects include one or more of diarrhea, abdominal distension, nausea, abdominal pain, or flatulence. In some embodiments treatment of a viral infection in a subject results in the subject experiencing less severe symptoms. In some embodiments, treatment of a viral infection in a subject prevents the hospitalization of a subject. In some embodiments, treatment of a viral infection in a subject reduces the likelihood that the subject will need to be hospitalized. In some embodiments, treatment of a viral infection in a subject minimizes or prevents progression of the infection (e.g., progression from mild or moderate symptoms to severe symptoms, e.g., such that subject requires further intervention, e.g., a ventilator or respirator). In some embodiments, treatment of a subject prevents or reduces the severity of a secondary infection (e.g., secondary infection of the lungs or the gut). In some embodiments, treatment of a viral infection in a subject reduces the viral load in the subject. In some embodiments, treatment of a viral infection in a subject reduces inflammation or the likelihood of a cytokine storm in the subject.

II. Oligosaccharide Compositions

Provided herein are oligosaccharide compositions, their methods of use for promoting the production of SCFAs in a human subject, and their methods of use in treating or preventing viral infections (e.g., coronavirus infections) in a human subject.

In one aspect, oligosaccharide compositions are provided herein that comprise a plurality of oligosaccharides selected from Formula (I), Formula (II), and Formula (III):

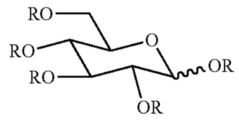

(I)

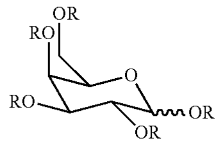

(II)

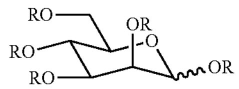

(III)

wherein each R independently is selected from hydrogen, and Formulae (Ia), (Ib), (Ic), (Id), (IIa), (IIb), (IIc), (IId), (IIIa), (IIIb), (IIIc), (IIId):

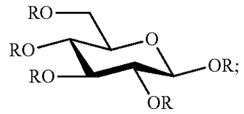

(Ia)

-continued (IIa)

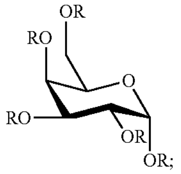

(IIIa)

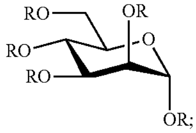

(Ib)

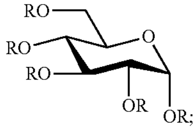

(IIb)

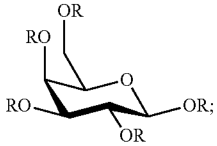

(IIIb)

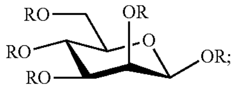

(Ic)

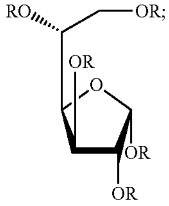

(IIc)

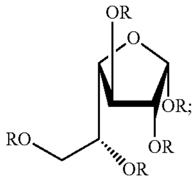

(IIIc)

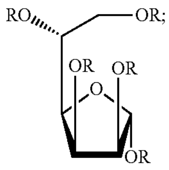

(Id)

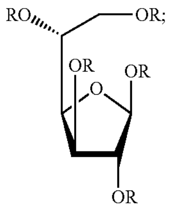

and

-continued (IId)

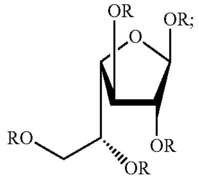

(IIId)

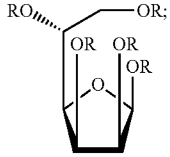

wherein each R independently is as defined above.

In some embodiments, oligosaccharide compositions are produced by a process that initially involves heating a preparation comprising dextrose monomers, galactose monomers, and mannose monomers to a temperature in a range of 100° C. to 160°,100° C. to 120° C., 110° C. to 130° C., 120° C. to 140° C., 130° C. to 150° C., or about 140° C. The ratio of dextrose monomers to galactose monomers may be 1:1. The ratio of dextrose monomers to mannose monomers may be 4.5:1. The ratio of galactose monomers to mannose monomers may be 4.5:1. Heating may be performed under agitation conditions. Heating may comprises gradually increasing the temperature (e.g., from room temperature) to about 130° C., about 135° C. about 140° C. about 145° C., or about 150° C. under suitable conditions to achieve homogeneity and uniform heat transfer. An acid catalyst comprising positively charged hydrogen ions is added to the preparation (e.g., following heating). In some embodiments, the acid catalyst is a soluble catalyst. In some embodiments, the acid catalyst is citric acid, acetic acid, or propionic acid. In some embodiments, the acid catalyst is a solid catalyst. In some embodiments, the catalyst is a strong acid cation exchange resin having one or more physical and chemical properties according to Table 1.

TABLE 1

Non-Limiting Example of Strong Acid Cation Exchange Resin Properties

| Physical Form | | Amber translucent spherical beads |
|---|---|---|
| Matrix | | Styrene-DVB, gel |
| Function group | | Sulfonic acid |
| Ionic form as shipped | | $H^+$ form |
| Total volume capacity, min. | eq/L | 1.8 |
| | $kgr/ft^3$ as $CaCO_3$ | 39.3 |
| Moisture retention capacity | % | 50-56 |
| Particle size | | |
| Uniformity coefficient, max. | | 1.1 |
| Harmonic mean diameter | μm | 600 ± 50 |
| Whole uncracked beads | % | 95-100 |
| Total swelling ($Na^+ \rightarrow H^+$) | % | 8 |
| Particle density | g/mL | 1.2 |
| Shipping density | g/L | 800 |
| | $lbs/ft^3$ | 50 |

In some embodiments, the catalyst comprises >3.0 mmol/g sulfonic acid moieties and <1.0 mmol/gram cationic moieties. In certain embodiments, the catalyst has a nominal moisture content of 45-50 weight percent. In certain embodiments, the catalyst is added at the same time as the dextrose monomers, galactose monomers, and mannose monomers. In some embodiments, after loading of the catalyst with the preparation, the resultant reaction mixture is held at atmospheric pressure and at a temperature in a range of 100° C. to 160° C., 100° C. to 120° C., 110° C. to 130° C., 120° C. to 140° C., 130° C. to 150° C., or about 140° C. under conditions that promote acid catalyzed oligosaccharide formation. In some embodiments, once the weight percent of total monomer content in the oligosaccharide composition (total monomer content comprises the amount of dextrose monomer, galactose monomer, and/or mannose monomer) is in a range of 4-14% (optionally 4-8%, 7-10%, 9-14%, or 12-14%), the r action mixture is quenched. Quenching typically involves using water (e.g., deionized water) to dilute the reaction mixture, and gradually decrease the temperature of the reaction mixture to 55° C. to 95° C. In some embodiments, the water used for quenching is about 95° C. The water may be added to the reaction mixture under conditions sufficient to avoid solidifying the mixture. In certain embodiments, water may be removed from the reaction mixture by evaporation. In some embodiments, the reaction mixture may contain 93-94 weight percent dissolved solids. Finally, to obtain a purified oligosaccharide composition, the composition is generally separated from the acid catalyst, typically by diluting the quenched reaction mixture with water to a concentration of about 45-55 weight percent and a temperature of below about 85° C. and then passing the mixture through a filter or a series of chromatographic resins. In certain embodiments, the filter used is a 0.45 μm filter. Alternatively, a series of chromatographic resins may be used and generally involves a cationic exchange resin, an anionic exchange resin, and/or a decolorizing polymer resin. In some embodiments, any or all of the types of resins may be used one or more times in any order. In some embodiments, the oligosaccharide composition comprises water at a level below that which is necessary for microbial growth upon storage at room temperature. In certain embodiments, the mean degree of polymerization of all oligosaccharide is in a range of 7-15.5, optionally 11-15. In some embodiments, the oligosaccharide composition comprises water in a range of 45-55 weight percent. In some embodiments, the oligosaccharide composition comprises oligosaccharides that have a MWw (weight-average molecular weight) (g/mol) in a range of 1905-2290. In some embodiments, the oligosaccharide composition comprises oligosaccharides that have a MWn (number-average molecular weight) (g/mol) in a range of 1030-1095. In some embodiments, the oligosaccharide composition has a pH in a range of 2.50-3.50. In some embodiments, the oligosaccharide composition comprises oligomers having two or more repeat units (DP2+) in a range of 86-96 weight percent.

Further, in some embodiments, oligosaccharide compositions may be de-monomerized. In some embodiments, de-monomerization involves the removal of residual saccharide monomers. In some embodiments, de-monomerization is performed using chromatographic resin. Accordingly, in some embodiments, different compositions can be prepared depending upon the percent of monomer present. In some embodiments, oligosaccharide compositions are de-monomerized to a monomer content of about 1%, about 3%, about 5%, about 10%, or about 15%. In some embodiments, oligosaccharide compositions are de-monomerized to a monomer content of about 1-3%, about 3-6%, about 5-8%, about 7-10%, or about 10-15%. In one embodiment, the oligosaccharide compositions is de-monomerized to a monomer content of less than 1%. In one embodiment, the oligosaccharide composition is de-monomerized to a monomer content between about 7% and 10%. In one embodiment, the oligosaccharide compositions is de-monomerized to a monomer content between about 1% and 3%. In one embodiment, de-monomerization is achieved by osmotic separation. In a second embodiment de-monomerization is achieved by tangential flow filtration (TFF). In a third embodiment de-monomerization is achieved by ethanol precipitation.

In some embodiments, oligosaccharide compositions with different monomer contents may also have different measurements for total dietary fiber, moisture, total dietary fiber (dry basis), or percent Dextrose Equivalent (DE). In some embodiments, total dietary fiber is measured according to the methods of AOAC 2011.25. In some embodiments, moisture is measured by using a vacuum oven at 60° C. In some embodiments, total dietary fiber is (dry basis) is calculated. In some embodiments, the percent DE is measured according to the Food Chemicals Codex (FCC).

In some embodiments, the oligosaccharide compositions have a total dietary fiber content of 87.4 percent (on dry basis). In some embodiments, the oligosaccharide compositions have a total dietary fiber content of 81.9-93.0, 82-85, 85-88, 88-90, or 90-93 percent (on dry basis). In some embodiments, the oligosaccharide compositions have a total dietary fiber content of about 82, about 85, about 87, about 90, or about 93 percent (on dry basis). In some embodiments, the oligosaccharide compositions have a total dietary fiber content of 78-97 percent (on dry basis). In some embodiments, the oligosaccharide compositions have a total dietary fiber content of 82-93 percent (on dry basis). In some embodiments, the oligosaccharide compositions have a total dietary fiber content of 14.5-100 percent (on dry basis). In some embodiments, the oligosaccharide compositions have a total dietary fiber content of 34-94 percent (on dry basis).

In some embodiments, the oligosaccharide compositions have a total reducing sugar content (Dextrose Equivalence (DE) (dry solids)) of 6.5-35 percent. In some embodiments, the oligosaccharide compositions have a total reducing sugar content (Dextrose Equivalence (DE) (dry solids)) of 12-29 percent. In some embodiments, the oligosaccharide compositions have a total reducing sugar content (Dextrose Equivalence (DE) (dry solids)) of 5-40, 5-30, 5-25, 10-30, 10-25, 10-20, 15-30, 15-25, or 15-20 percent.

In some embodiments, production of oligosaccharides compositions according to methods provided herein can be performed in a batch process or a continuous process. For example, in one embodiment, oligosaccharide compositions are produced in a batch process, where the contents of the reactor are subjected to agitation conditions (e.g., continuously mixed or blended), and all or a substantial amount of the products of the reaction are removed (e.g., isolated and/or recovered).

In certain embodiments, the methods of using the catalyst are carried out in an aqueous environment. One suitable aqueous solvent is water, which may be obtained from various sources. Generally, water sources with lower concentrations of ionic species (e.g., salts of sodium, phosphorous, ammonium, or magnesium) may be used, in some embodiments, as such ionic species may reduce effectiveness of the catalyst. In some embodiments where the aqueous solvent is water, the water has less than 10% of ionic species (e g., salts of sodium, phosphorous, ammonium, magnesium). In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least 10 megaohm-centimeters.

In some embodiments, as reactions of methods provided herein progress, water (such as evolved water) is produced with each glycosidic coupling of the one or more saccharide monomer. In certain embodiments, the methods described herein may further include monitoring the amount of water present in the reaction mixture and/or the ratio of water to monomer or catalyst over a period of time. Thus, in some embodiments, the water content of the reaction mixture may be altered over the course of the reaction, for example, removing evolved water produced. Appropriate methods may be used to remove water (e.g., evolved water) in the reaction mixture, including, for example, by evaporation, such as via distillation. In some embodiments, the method comprises including water in the reaction mixture. In certain embodiments, the method comprises removing water from the reaction mixture through evaporation.

In some embodiments, the ratio of dextrose monomer to galactose monomer is about 1:2, 1:1.5, 1:1.4, 1:1.3, 1:1.2, 1:1.1, 1:1, 1.1:1, 1.2:1, 1.3:1, 1.4:1, 1.5:1, or 2:1. In some embodiments, the ratio of dextrose monomer to galactose monomer is about 1:1.

In some embodiments, the ratio of dextrose monomer to mannose monomer is about 1:1, 1.5:1, 2:1, 2.5:1, 3:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, 5:1, or 5.5:1. In some embodiments, the ratio of dextrose monomer to mannose monomer is about 4.5:1.

In some embodiments, the ratio of galactose monomer to mannose monomer is about 1:1, 1.5:1, 2:1, 2.5:1, 3:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, 5:1, or 5.5:1. In some embodiments, the ratio of galactose monomer to mannose monomer is about 4.5:1.

In some embodiments, the monosaccharide preparation comprises about 30-60% dextrose monomer, about 30-60% galactose monomer, and 1-25% mannose monomer. In some embodiments, the monosaccharide preparation comprises about 30-60% dextrose monomer, about 30-60% galactose monomer, and about 5-15% mannose monomer In some embodiments, the monosaccharide preparation comprises about 40-50% dextrose monomer, about 40-50% galactose monomer, and about 5-15% mannose monomer. In some embodiments, the monosaccharide preparation comprises about 45% dextrose monomer, about 45% galactose monomer, and about 10% mannose monomer.

In certain embodiments, the preparation is loaded with an acid catalyst comprising positively charged hydrogen ions. In some embodiments, an acid catalyst is a solid catalyst (e.g., Dowex Marathon C). In some embodiments, an acid catalyst is a soluble catalyst (e.g., citric acid).

In some embodiments, the molar ratio of positively char ed hydrogen ions to total dextrose monomer, galactose monomer, and mannose monomer content is in an appropriate range. In some embodiments, the molar ratio of positively charged hydrogen ions to total dextrose monomer, galactose monomer, and mannose monomer content is in a range of 0.01 to 0.1, 0.02 to 0.08, 0.03 to 0.06, or 0.05 to 0.06. In some embodiments, the molar ratio of positively charged hydrogen ions to total dextrose monomer, galactose monomer, and mannose monomer content is in a range of 0.003 to 0.01, 0.005 to 0.02, 0.01 to 0.02, 0.01 to 0.03, 0.02 to 0.03, 0.02 to 0.04, 0.03 to 0.05, 0.03 to 0.08, 0.04 to 0.07, 0.05 to 0.1, 0 05 to 0.2, 0.1 to 0.2, 0.1 to 0.3, or 0.2 to 0.3. In some embodiments, the molar ratio of positively charged hydrogen ions to total dextrose monomer, galactose monomer, and mannose monomer content is in a range of 0.050 to 0.052. In some embodiments, the molar ratio of positively charged hydrogen ions to total dextrose monomer, galactose monomer, and mannose monomer content is in a range of 0.020 to 0.035. In some embodiments, the molar ratio of positively charged hydrogen ions to total dextrose monomer, galactose monomer, and mannose monomer content is 0.028.

In some embodiments, the molar ratio of soluble acid catalyst (e.g., citric acid catalyst) to total dextrose monomer, galactose monomer, and mannose monomer content is in an appropriate range. In some embodiments, the molar ratio of soluble acid catalyst (e.g., citric acid catalyst) to total dextrose monomer, galactose monomer, and mannose monomer content is in a range of 0.01 to 0.1, 0.02 to 0.08, 0.03 to 0.06, or 0.05 to 0.06. In some embodiments, the molar ratio of soluble acid catalyst (e.g., citric acid catalyst) to total dextrose monomer, galactose monomer, and mannose monomer content is in a range of 0.003 to 0.01, 0.005 to 0.02, 0.01 to 0.02, 0.01 to 0.03, 0.02 to 0.03, 0.02 to 0.04, 0.03 to 0.05, 0.03 to 0.08, 0.04 to 0.07, 0.05 to 0.1, 0.05 to 0.2, 0.1 to 0.2, 0.1 to 0.3, or 0.2 to 0.3. In some embodiments, the molar ratio of soluble acid catalyst (e.g., citric acid catalyst) to total dextrose monomer, galactose monomer, and mannose monomer content is in a range of 0.050 to 0.052. In some embodiments, the molar ratio of soluble acid catalyst (e.g., citric acid catalyst) to total dextrose monomer, galactose monomer, and mannose monomer content is in a range of 0.020 to 0.035. In some embodiments, the molar ratio of soluble acid catalyst (e.g., citric acid catalyst) to total dextrose monomer, galactose monomer, and mannose monomer content is 0.028.

In some embodiments, water is added to the reaction mixture to quench the reaction by bringing the temperature of the reaction mixture to 100° C. or below. In some embodiments, the water used for quenching is deionized water. In some embodiments, the water used for quenching is USP water. In some embodiments, the water has a temperature of about 60° C. to about 100° C. In certain embodiments, the water used for quenching is about 95° C. In some embodiments, the water is added to the reaction mixture under conditions sufficient to avoid solidifying the mixture.

The viscosity of the reaction mixture may be measured and/or altered over the course of the reaction. In general, viscosity refers to a measurement of a fluid's internal resistance to flow (e.g., "thickness") and is expressed in centipoise (cP) or pascal-seconds. In some embodiments, the viscosity of the reaction mixture is between about 100 cP and about 95,000 cP, about 5,000 cP and about 75,000 cP, about 5,000 and about 50,000 cP, or about 10,000 and about 50,000 cP. In certain embodiments, the viscosity of the reaction mixture is between about 50 cP and about 200 cP.

In some embodiments, oligosaccharide compositions provided herein may be subjected to one or more additional processing steps. Additional processing steps may include, for example, purification steps. Purification steps may include, for example, separation, demonomerization, dilution, concentration, filtration, desalting or ion-exchange, chromatographic separation, or decolorization, or any combination thereof.

In certain embodiments, the methods described herein further include a dilution step. In some embodiments, deionized water is used for dilution. In certain embodiments, USP water is used for dilution. In certain embodiments, after dilution, the oligosaccharide composition comprises water in a range of about 5-75, 25-65, 35-65, 45-55, or 47-53 weight percent. In certain embodiments, after dilution, the oligosaccharide composition comprises water in a range of about 45-55 weight percent.

In some embodiments, the methods described herein further include a decolorization step. The one or more oligosaccharide compositions produced may undergo a decolorization step using appropriate methods, including, for example, treatment with an absorbent, activated carbon, chromatography (e.g., using ion exchange resin), and/or filtration (e.g., microfiltration).

In some embodiments, the one or more oligosaccharide compositions produced are contacted with a material to remove salts, minerals, and/or other ionic species. For example, in certain embodiments, the one or more oligosaccharide compositions produced are flowed through an anionic exchange column. In other embodiments, oligosaccharide compositions produced are flowed through an anionic/cationic exchange column pair.

In some embodiments, the methods described herein may further include a concentration step. For example, in some embodiments, the oligosaccharide compositions may be subjected to evaporation (e.g., vacuum evaporation) to produce a concentrated oligosaccharide composition. In other embodiments, the oligosaccharide compositions may be subjected to a spray drying step to produce an oligosaccharide powder. In certain embodiments, the oligosaccharide compositions may be subjected to both an evaporation step and a spray drying step. In some embodiments, the oligosaccharide compositions be subjected to a lyophilization (e.g., freeze drying) step to remove water and produce powdered product.

In some embodiments, the methods described herein further include a fractionation step. Oligosaccharide compositions prepared and purified may be subsequently separated by molecular weight using any method known in the art, including, for example, high-performance liquid chromatography, adsorption/desorption (e.g. low-pressure activated carbon chromatography), or filtration (for example, ultrafiltration or diafiltration). In certain embodiments, oligosaccharide compositions are separated into pools representing 60%, 65%, 70%, 75%, 80%, 85%, 90%, 95%, 97%, 98%, or greater than 98% short (about DP1-2), medium (about DP3-10), long (about DPI 1-18), or very long (about DP>18) species.

In certain embodiments, prepared oligosaccharide compositions are fractionated by adsorption onto a carbonaceous material and subsequent desorption of fractions by washing the material with mixtures of an organic solvent in water at a concentration of 1%, 5%, 10%, 20%, 50%, or 100%. In one embodiment, the adsorption material is activated charcoal. In another embodiment, the adsorption material is a mixture of activated charcoal and a bulking agent such as diatomaceous earth or Celite 545 in 5%, 10%, 20%, 30%, 40%, or 50% portion by volume or weight.

In further embodiments, prepared oligosaccharide compositions are separated by passage through a high-performance liquid chromatography system. In certain variations, prepared oligosaccharide compositions are separated by ion-affinity chromatography, hydrophilic interaction chromatography, or size-exclusion chromatography including gel-permeation and gel-filtration.

In some embodiments, catalyst is removed by filtration. In certain embodiments, a 0.45 μm filter is used to remove catalyst during filtration. In other embodiments, low molecular weight materials are removed by filtration methods. In certain variations, low molecular weight materials may be removed by dialysis, ultrafiltration, diafiltration, or tangential flow filtration. In certain embodiments, the filtration is performed in static dialysis tub apparatus. In other embodiments, the filtration is performed in a dynamic flow filtration system. In other embodiments, the filtration is performed in centrifugal force-driven filtration cartridges. In certain embodiments, the reaction mixture is cooled to below about 85° C. before filtration.

In certain embodiments, the mean degree of polymerization of all oligosaccharides is in a range of 6-16. In certain embodiments, the mean degree of polymerization of all oligosaccharides is in a range of 10-15. In some embodiments, the mean degree of polymerization of all oligosaccharides is in a range of 7-15, 7-12, 7-10, 7-8, 9-10, 10-11, 11-12, 11-15, 12-13, 12-14 13-14, 14-15, 15-16, 17-18, 15-20, 3-8, 4-7, or 5-6.

In certain embodiments, the weight percent of dextrose monomer, galactose monomer, and mannose monomer in the oligosaccharide composition is in a range of 10-18. In certain embodiments, the weight percent of dextrose monomer, galactose monomer, and mannose monomer in the oligosaccharide composition is in a range of 111-17. In certain embodiments, the weight percent of dextrose monomer, galactose monomer, and mannose monomer in the oligosaccharide composition is in a range of 12-16. In certain embodiments, the weight percent of dextrose monomer, galactose monomer, and mannose monomer in the oligosaccharide composition is in a range of 13-15.

In some embodiments, the oligosaccharide composition is a mixture of polymers of dextrose, galactose, and mannose in proportions of approximately 45%, 45%, and 10%, by weight respectively. The formula is $H-[C_6H_{9-11}O_5]_n-OH$, where the total umber of monomer units in a single polymer of the mixture ranges from 2 to approximately 0 (n=2-60), with a mean value for the mixture of approximately 12.6 monomer units. Each monomer unit may be unsubstituted, singly, doubly, or triply substituted with another dextrose, galactose, or mannose unit by any glycosidic isomer.

In some embodiments, the oligosaccharide composition comprises water in a range of 5-75 weight percent. In some embodiments, the oligosaccharide composition comprises water in a range of 25-65 weight percent. In some embodiments, the oligosaccharide composition comprises water in a range of 35-65 weight percent. In some embodiments, the oligosaccharide composition comprises water in a range of 45-55 weight percent.

In some embodiments, the oligosaccharide composition comprises oligosaccharides that have a MWw (g/mol) in a range of 1905-2290. In one embodiments, the oligosaccharide composition comprises oligosaccharides that have a MWw (g/mol) in a range of 1753-2395. In some embodiments, the oligosaccharide composition comprises oligosaccharides that have a MWw (g/mol) in a range of 1750-2400. In some embodiments, the oligosaccharide composition comprises oligosaccharides that have a MWw (g/mol) in a range of 1500-2500. In some embodiments, the oligosaccharide composition comprises oligosaccharides that have a MWw (g/mol) in a range of 1800-2000. In some embodiments, the oligosaccharide composition comprises oligosaccharides that have a MWw (g/mol) in a range of 2000-2300. In some embodiments, the oligosaccharide composition comprises oligosaccharides that have a MWw (g/mol) in a range of 1515-2630. In some embodiments, the oligosaccharide composition comprises oligosaccharides that have a MWw (g/mol) in a range of 1500-2500. In some embodiments, the oligosaccharide composition comprises oligosaccharides that have a MWw (g/mol) in a range of 1740-2400. In some embodiments, the oligosaccharide composition comprises oligosaccharides that have a MWw (g/mol) in a range of 1700-2300. In some embodiments, the oligosaccharide composition comprises oligosaccharides that have a MWw (g/mol) in a range of 1800-1900, 1900-2000, 2000-2100, 2100-2200, 2200-2300, 2300-2400, or 2400-2500.

In some embodiments, the oligosaccharide composition comprises oligosaccharides that have a MWn (g/mol) in a range of 1030-1095. In one embodiments, the oligosaccharide composition comprises oligosaccharides that have a M n (g/mol) in a range of 981-1214. In some embodiments, the oligosaccharide composition comprises oligosaccharides that have a MWn (g/mol) in a range of 980-1220 In some embodiments, the oligosaccharide composition comprises oligosaccharides that have a MWn (g/mol) in a range of 1000-1050. In some embodiments, the oligosaccharide composition comprises oligosaccharides that have a MWn (g/mol) in a range of 1050-1100. In some embodiments, the oligosaccharide composition comprises oligosaccharides that have a MWn (g/mol) in a range of 890-1300. In some embodiments, the oligosaccharide composition comprises oligosaccharides that have a MWn (g/mol) in a range of 975-1155. In some embodiments, the oligosaccharide composition comprises oligosaccharides that have a MWn (g/mol) in a range of 875-1180. In some embodiments, the oligosaccharide composition comprises oligosaccharides that have a MWn (g/mol) in a range of 940-1120. In some embodiments, the oligosaccharide composition comprises oligosaccharides that have a MWn (g/mol) in a range of 900-950, 950-1000, 1000-1050, 1050-1100, 1100-1150, 1150-1200, or 1200-1250.

In some embodiments, a solution comprising the oligosaccharide composition has a pH in a range of 1.50-6.00. In some embodiments, a solution comprising the oligosaccharide composition has a pH in a range of 1.50-5.00. In some embodiments, a solution comprising the oligosaccharide composition has a pH in a range of 2.00-4.00. In some embodiments, a solution comprising the oligosaccharide composition has a pH in a range of 2.50-3.50.

In some embodiments, the oligosaccharide composition comprises oligosaccharides that have a degree of branching in a range of about 8.5% to about 32%. In some embodiments, the oligosaccharide composition comprises oligosaccharides that have a degree of branching in a range of about 10% to about 35%. In some embodiments the oligosaccharide composition comprises oligosaccharides that have a degree of branching in a range of about 13% to about 29%. In some embodiments, the oligosaccharide composition comprises oligosaccharides that have a degree of branching in a range of 5-50%, 5 40%, 5-30%, 5-20%, 5-15%, 10-50%, 10-40%, 10-30%, 10-25%, 15-30%, or 15-20%.

In some embodiments, the oligosaccharide composition comprises oligomers having two or more repeat units (DP2+) in a range of 80-100 weight per ent. In some embodiments, the oligosaccharide composition comprises oligomers having two or more repeat units (DP2+) in a range of 86-96 weight percent. In some embodiments, the oligosaccharide composition comprises oligomers having two or more repeat units (DP2+) in a range of 86-91 weight percent. In some embodiments, the oligosaccharide composition comprises oligomers having two or more repeat units (DP2+) in a range of 91-96 weight percent. In some embodiments, the oligosaccharide composition comprises oligomers having two or more repeat units (DP2+) in a range of 81-100 weight percent. In some embodiment, the oligosaccharide composition comprises oligomers having two or more repeat units (DP2+) in a range of 80-94 weight percent. In some embodiments, the oligosaccharide composition comprises oligomers having two or more repeat units (DP2+) in a range of 91-96 weight percent. In some embodiments, the oligosaccharide composition comprises oligomers having two or more repeat units (DP2+) in a range of 80-85, 85-87, 86-88, 87-90, 88-91, 89-92, 90-93, 91-94, 92-95, 93-96, or 95-98 weight percent.

In some embodiments, the oligosaccharide composition has a polydispersity index (PDI) of 1.8-2.0. In some embodiments, the oligosaccharide composition has a polydispersity index (PDI) of 1.8-2.1. In some embodiments, the oligosaccharide composition has a PDI of 1.0-1.2, 1.2-1.3, 1.3-1.4, 1.4-1.5, 1.5-1.6, 1.7-1.8, 1.8-2.0, 2.0-2.2, 2.2-2.4, or 2.4-2.6. In some embodiments, the oligosaccharide composition has a PDI of about 1.6, a out 1.7, about 1.8, about 1.9, about 2.0, about 2.1, or about 2.2.

In some embodiments, the MWw, MWn, PDI, monomer content (DP1) and/or DP2+ values of oligosaccharides in an oligosaccharide composition are determined using the size exclusion chromatography method described in Example 12.

In some embodiments, the degree of polymerization (DP1-DP7) of oligosaccharides in an oligosaccharide composition are determined using the size exclusion chromatography method described in Example 14.

In some embodiments, the oligosaccharide composition comprises oligomers having at least three linked monomer units (DP3+) in a range of 80-95 weight percent. In some embodiments, the oligosaccharide composition comprises oligomers hating at least three linked monomer units (DP3+) in a range of 85-90 weight percent. In some embodiments, the oligosaccharide composition comprises oligomers having at least three linked monomer units (DP3+) in a range of 80-85, 85-87, 86-88, 87-90, 88-91, 89-92, 90-93, 91-94,or 92-95 weight percent.

In some embodiments, the oligosaccharide composition comprises 4.20% to 6.28% monomer (DP1). In some embodiments, the oligosaccharide co position comprises 4% to 5%, 5% to 6%, or 6% to 7% monomer (DP1). In some embodiments the oligosaccharide composition comprises 6.20% to 8.83% disaccharide (DP2). In some embodiments, the oligosaccharide composition comprises 6% to 6.5%, 6.5% to 7%, 7.5% to 8%, 8% to 8.5%, or 8.5% to 9% disaccharide (DP2). In some embodiments, the oligosaccharide composition comprises 84.91% to 89.58% oligomers having at least three linked monomer units (DP3+). In some embodiments, the oligosaccharide composition comprises 84% to 85%, 85% to 86%, 86% to 87%, 87% to 88%, or 88% to 90% oligomers having at least three linked monomer units (DP3+).

In some embodiments, the oligosaccharide composition comprises less than 0.10% total impurities (excluding monomer). In some embodiments, the oligosaccharide composition comprises less than 0.05% total impurities (excluding monomer). In some embodiments, the oligosaccharide composition comprises less than 0.20%, 0.15%, 0.10%, or 0.05% total impurities (excluding monomer). In some embodiments, the oligosaccharide composition comprises less than 0.10% w/w levoglucosan, less than 0.1% w/w glucuronic acid, less than 0.10% w/w lactic acid, less than 0.10% w/w formic acid, less t an 0.10% w/w acetic acid, and less than 0.10% w/w HMF. In some embodiments, the oligosaccharide composition comprises 0.35% w/w levoglucosan, 0.03% w/w lactic acid, and/or 0.06/w/w formic acid. In some embodiments, the oligosaccharide composition comprises 0.28-0. 3% w/w levoglucosan, 0.00-0.03% w/w lactic acid, and/or 0.05-0.07% w/w formic acid.

In some embodiments, the oligosaccharide composition comprises a MWw of 1753-2395, a MWn of 981-1214, and/or a PDI of 1.8-2.0.

The oligosaccharide compositions described herein, and prepared according to the methods described herein, can be characterized and distinguished from prior art compositions using permethylation analysis. See, e.g., Zhao, Y., et al. 'Rapid, sensitive structure analysis of oligosaccharides,' PNAS Mar. 4, 1997 94 (5) 1629-1633; Kailemia, M.$J_{CH}$., et al. 'Oligosaccharide analysis by mass spectrometry: A review of recent developments,' Anal Chem. 2014 Jan. 7; 86(1): 196-212. Accordingly, in another aspect, oligosaccharide compositions are provided herein that comprise a plurality of oligosaccharides that are minimally digestible in humans, the plurality of oligosaccharides comprising monomer radicals The molar percentages of different types of monomer radicals in the plurality of oligosaccharides can be quantified using a permethylation assay. The permethylation assay is performed on a de-monomerized sample of the composition.

In some embodiments, the plurality of oligosaccharides comprises two or more monomer radicals selected from radicals (1)-(40):

(1) t-manopyranose monoradicals, representing 3.0-4.1 mol % of monomer radicals in the plurality of oligosaccharides;
(2) t-glucopyranose monoradicals, representing 11.4-16.3 mol % of monomer radicals in the plurality of oligosaccharides;
(3) t-galactofuranose monoradicals, representing 1.3-7.8 mol % of monomer radicals in the plurality of oligosaccharides;
(4) t-glucofuranose monoradicals, representing 0-1.4 mol % of monomer radicals in the plurality of oligosaccharides;
(5) t-galactopyranose monoradicals, representing 8.3-12.5 mol % of monomer radicals in the plurality of oligosaccharides;
(6) 3-glucopyranose monoradicals, representing 3.0-4.9 mol % of monomer radicals in the plurality of oligosaccharides;
(7) 2-manopyranose and/or 3-manopyranose monoradicals, representing 1.2-1.9 mol % of monomer radicals in the plurality of oligosaccharides;
(8) 2-glucopyranose monoradicals, representing 2.4-3.2 mol % of monomer radicals in the plurality of oligosaccharides;
(9) 2-galactofuranose and/or 2-glucofuranose monoradicals, representing 0.9-2.3 mol % of monomer radicals in the plurality of oligosaccharides;
(10) 3-galactopyranose monoradicals, representing 2.9-3.9 mol % of ionomer radicals in the plurality of oligosaccharides;
(11) 4-manopyranose and/or 5-manofuranose and/or 3-galactofuranose monoradicals, representing 1.7-2.9 mol % of monomer radicals in the plurality of oligosaccharides;
(12) 6-manopyranose monoradicals, representing 2.0-2.9 mol % of monomer radicals in the plurality of oligosaccharides;
(13) 2-galactopyranose monoradicals, representing 1.8-2.7 mol % of ionomer radicals in the plurality of oligosaccharides;
(14) 6-glucopyranose monoradicals, representing 7.6-10.8 mol % of monomer radicals in the plurality of oligosaccharides;
(15) 4-galactopyranose and/or 5-galactofuranose monoradicals, representing 2.6-3.8 mol % of monomer radicals in the plurality of oligosaccharides;
(16) 4-glucopyranose and/or 5-glucofuranose and/or 6-manofuranose monoradicals, representing 3.0-4.5 mol % of monomer radicals in the plurality of oligosaccharides;
(17) 6-glucofuranose monoradicals, representing 0-1.6 mol % of monomer radicals in the plurality of oligosaccharides;
(18) 6-galactofuranose monoradicals, representing 1.4-5.0 mol % of monomer radicals in the plurality of oligosaccharides;
(19) 6-galactopyranose monoradicals, representing 5.8-9.1 mol % of monomer radicals in the plurality of oligosaccharides;
(20) 3,4-galactopyranose and/or 3,5-galactofuranose and/or/2,3-galactopyranose diradicals, representing 0.9-1.4 mol % of monomer radicals in the plurality of oligosaccharides;
(21) 3,4-glucopyranose and/or 3,5-glucofuranose diradicals, representing 0-1.1 mol % of monomer radicals in the plurality of oligosaccharides;
(22) 2,4-glucopyranose and/or 2,5-glucofuranose and/or 2,4-galactopyranose and/or 2,5-galactofuranose diradicals, representing 0.9-1.4 mol % of monomer radicals in the plurality of oligosaccharides;
(23) 4,6-manopyranose and/or 5,6-manofuranose diradicals, representing 0.5-0.7 mol % of monomer radicals in the plurality of oligosaccharides;
(24) 3,6-manofuranose diradicals, representing 0-0.1 mol % of monomer radicals in the plurality of oligosaccharides;
(25) 3,6-glucopyranose diradicals, representing 1.4-2.8 mol % of monomer radicals in the plurality of oligosaccharides;
(26) 3,6-manopyranose and/or 2,6-manofuranose diradicals, representing 0.4-0.7 mol % of monomer radicals in the plurality of oligosaccharides;
(27) 2,6-manopyranose diradicals, representing 0.3-0.5 mol % of monomer radicals in the plurality of oligosaccharides;
(28) 3,6-glucofuranose diradicals, representing 0.1-0.4 mol % of monomer radicals in the plurality of oligosaccharides;
(29) 2,6-glucopyranose and/or 4,6-glucopyranose and/or 5,6-glucofuranose diradicals, representing 1.1-3.6 mol % of monomer radicals in the plurality of oligosaccharides;
(30) 3,6-galactofuranose diradicals, representing 0.9-1.4 mol % of monomer radicals in the plurality of oligosaccharides;
(31) 4,6-galactopyranose and/or 5,6-galactofuranose diradicals, representing 2.1-2.9 mol % of monomer radicals in the plurality of oligosaccharides;
(32) 3,6-galactopyranose and/or 2,6-galactofuranose diradicals, representing 1.6-3.0 mol % of monomer radicals in the plurality of oligosaccharides;
(33) 2,6-galactopyranose diradicals, representing 0.7-1.6 mol % of monomer radicals in the plurality of oligosaccharides;
(34) 3,4,6-manopyranose and/or 3,5,6-manofuranose and/or 2,3,6-manofuranose triradicals, representing 0-0.3 mol % of monomer radicals in the plurality of oligosaccharides;

(35) 3,4,6-galactopyranose and/or 3,5,6-galactofuranose and/or 2,3,6-galactofuranose triradicals, representing 0.5-1.1 mol % of monomer radicals in the plurality of oligosaccharides;
(36) 3,4,6-glucopyranose and/or 3,5,6-glucofuranose triradicals, representing 0.2-0.5 mol % of monomer radicals in the plurality of oligosaccharides;
(37) 2,3,6-manopyranose and/or 2,4,6-manopyranose and/or 2,5,6-manofuranose triradicals, representing 0-0.5 mol % of monomer radicals in the plurality of oligosaccharides;
(38) 2,4,6-glucopyranose and/or 2,5,6-glucofuranose triradicals, representing 0-1.4 mol % of monomer radicals in the plurality of oligosaccharides;
(39) 2,3,6-galactopyranose and/or 2,4,6-galactopyranose and/or 2,5,6 galactofuranose triradicals, representing 0.4-0.9 mol % of monomer radicals in the plural ty of oligosaccharides; and
(40) 2,3,6-glucopyranose triradicals, representing 0.1-0.5 mol % of monomer radicals in the plurality of oligosaccharides.

In some embodiments, about 8-30% of the total glycosidic bonds in an oligosaccharide composition are 1,2 glycosidic bonds. In some embodiments, about 10.5-25% of the total glycosidic bonds in an oligosaccharide composition are 1,2 glycosidic bonds. In some embodiments, about 9.5-32% of the total glycosidic bonds in an oligosaccharide composition are 1,2 glycosidic bonds. In some embodiments, about 13-27% of the total glycosidic bonds in an oligosaccharide composition are 1,2 glycosidic bonds. In some embodiments, 5-50%, 5-40%, 5-30%, 5-20%, 5-15%, 10-50%, 10-40%, 10-30%, 10-25%, 15-30%, or 1-20% of the total glycosidic bonds in an oligosaccharide composition are 1,2 glycosidic bonds.

In some embodiments, about 14.5-34% of the total glycosidic bonds in an oligosaccharide composition are 1,3 glycosidic bonds. In some embodiments, about 17-30% of the total glycosidic bonds in an oligosaccharide composition are 1,3 glycosidic bonds. In some embodiments, about 9.5-27% of the total glycosidic bonds in an oligosaccharide composition are 1,3 glycosidic bonds. In some embodiments, about 12.5-23.5% of the total glycosidic bonds in an oligosaccharide composition are 1,3 glycosidic bonds. In some embodiments, 5-50%, 10-40%, 10-30%, 10-20%, 5-15%, 10-50%, 10-40%, 10-30%, 10-25%, 15-30%, or 15-20% of the total glycosidic bonds in an oligosaccharide composition are 1,3 glycosidic bonds.

In some embodiments, about 10-26% of the total glycosidic bonds in an oligosaccharide composition are 1,4 glycosidic bonds. In some embodiments, about 12-22% of the total glycosidic bonds in an oligosaccharide composition are 1,4 glycosidic bonds. In some embodiments, about 10-29.5% of the total glycosidic bonds in an oligosaccharide composition are 1,4 glycosidic bonds. In some embodiments, about 13-25% of the total glycosidic bonds in an oligosaccharide composition are 1,4 glycosidic bonds. In some embodiments, 5-50%, 10-40%, 10-30%, 10-20%, 5-15%, 10-50%, 10-40%, 10-30%, 10-25%, 15-30%, or 15-20% of the total glycosidic bonds in an oligosaccharide composition are 1,4 glycosidic bonds.

In some embodiments, about 32-57% of the total glycosidic bonds in an oligosaccharide composition are 1,6 glycosidic bonds. In some embodiments, about 35-52% of the total glycosidic bonds in an oligosaccharide composition are 1,6 glycosidic bonds. In some embodiments, about 23-65% of the total glycosidic bonds in an oligosaccharide composition are 1,6 glycosidic bonds. In some embodiments, about 30-56% of the total glycosidic bonds in an oligosaccharide composition are 1,6 glycosidic bonds. In some embodiments, 15-70%, 20-60%, 20-40%, 25-50%, 30-50%, 30-40%, or 30-60% of the total glycosidic bonds in an oligosaccharide composition are 1,6 glycosidic bonds.

In some embodiments, an oligosaccharide composition comprises 17.543% total furanose. In some embodiments, an oligosaccharide composition comprises 20.5-37% total furanose. In some embodiments, an oligosaccharide composition comprises 14-60% total furanose. In some embodiments, an oligosaccharide composition comprises 20.5-50% total furanose. In some embodiments, an oligosaccharide composition comprises 10-60%, 10-50%, 15-40%, 20-40%, 20-30%, or 30-50% total furanose.

In some embodiments, the oligosaccharide composition comprises at least one glucofuranose or glucopyranose radical, at least one manofuranose or manopyranose radical, and at least one galactofuranose or galactopyranose radical.

In some embodiments, an oligosaccharide composition is provided, comprising a plurality of oligosaccharides comprising monomer radicals (1)-(40) in the molar percentages shown in Table 2.

TABLE 2

Permethylation Data

| Radicals | Mean mol % + 3 STD | Mean mol % | Mean mol % − 3 STD |
|---|---|---|---|
| t-manopyranose | 4.10% | 3.56% | 3.02% |
| t-glucopyranose | 16.33% | 13.89% | 11.44% |
| t-galactofuranose | 7.78% | 4.52% | 1.26% |
| t-glucofuranose | 1.38% | 0.64% | 0.00% |
| t-galactopyranose | 12.48% | 10.38% | 8.29% |
| 3-glucopyranose | 4.88% | 3.95% | 3.02% |
| 2-manopyranose and/or 3-manopyranose | 1.94% | 1.57% | 1.20% |
| 2-glucopyranose | 3.22% | 2.83% | 2.44% |
| 2-galactofuranose and/or 2-glucofuranose | 2.32% | 1.62% | 0.93% |
| 3-galactopyranose | 3.92% | 3.43% | 2.94% |
| 4-manopyranose and/or 5-manofuranose and/or 3-galactofuranose | 2.93% | 2.34% | 1.75% |
| 6-manopyranose | 2.87% | 2.44% | 2.01% |
| 2-galactopyranose | 2.71% | 2.28% | 1.85% |
| 6-glucopyranose | 10.78% | 9.22% | 7.66% |
| 4-galactopyranose and/or 5-galactofuranose | 3.80% | 3.22% | 2.65% |
| 4-glucopyranose and/or 5-glucofuranose and/or 6-manofuranose | 4.25% | 3.66% | 3.06% |
| 6-glucofuranose | 1.55% | 0.81% | 0.08% |
| 6-galactofuranose | 4.96% | 3.19% | 1.42% |
| 6-galactopyranose | 9.06% | 7.44% | 5.81% |
| 3,4-galactopyranose and/or 3,5-galactofuranose and/or 2,3-galactopyranose | 1.42% | 1.16% | 0.90% |
| 3,4-glucopyranose and/or 3,5-glucofuranose | 1.04% | 0.43% | 0.00% |
| 2,4-glucopyranose and/or 2,5-glucofuranose and/or 2,4-galactopyranose and/or 2,5-galactofuranose | 1.39% | 1.16% | 0.92% |
| 4,6-manopyranose and/or 5,6-manofuranose | 0.69% | 0.59% | 0.49% |
| 3,6-manofuranose | 0.11% | 0.02% | 0.00% |
| 3,6-glucopyranose | 2.80% | 2.10% | 1.40% |
| 3,6-manopyranose and/or 2,6-manofuranose | 0.67% | 0.53% | 0.39% |
| 2,6-manopyranose | 0.54% | 0.41% | 0.28% |
| 3,6-glucofuranose | 0.39% | 0.27% | 0.16% |

TABLE 2-continued

| Permethylation Data | | | |
|---|---|---|---|
| Radicals | Mean mol % + 3 STD | Mean mol % | Mean mol % − 3 STD |
| 2,6-glucopyranose and/or 4,6-glucopyranose and/or 5,6-glucofuranose | 3.58% | 2.33% | 1.08% |
| 3,6-galactofuranose | 1.37% | 1.15% | 0.93% |
| 4,6-galactopyranose and/or 5,6-galactofuranose | 2.86% | 2.48% | 2.11% |
| 3,6-galactopyranose and/or 2,6-galactofuranose | 2.98% | 2.28% | 1.58% |
| 2,6-galactopyranose | 1.62% | 1.15% | 0.68% |
| 3,4,6-manopyranose and/or 3,5,6-manofuranose and/or 2,3,6-manofuranose | 0.30% | 0.07% | 0.00% |
| 3,4,6-galactopyranose and/or 3,5,6-galactofuranose and/or 2,3,6-galactofuranose | 1.11% | 0.82% | 0.53% |
| 3,4,6-glucopyranose and/or 3,5,6-glucofuranose | 0.47% | 0.35% | 0.22% |
| 2,3,6-manopyranose and/or 2,4,6-manopyranose and/or 2,5,6-manofuranose | 0.49% | 0.17% | 0.00% |
| 2,4,6-glucopyranose and/or 2,5,6-glucofuranose | 1.36% | 0.56% | 0.00% |
| 2,3,6-galactopyranose and/or 2,4,6-galactopyranose and/or 2,5,6-galactofuranose | 0.91% | 0.66% | 0.41% |
| 2,3,6-glucopyranose | 0.48% | 0.31% | 0.13% |

In certain embodiments, the oligosaccharide compositions are free from monomer. In other embodiments, the oligosaccharide compositions comprise monomer.

The oligosaccharide compositions described herein, and prepared according to the methods described herein, can be characterized and distinguished from prior art compositions using two-dimensional heteronuclear NMR. Accordingly, in another aspect, oligosaccharide compositions are provided that comprise a plurality of oligosaccharides that are minimally digestible in humans, the compositions being characterized by a heteronuclear single quantum correlation (HSQC) NMR spectrum comprising signals 5, 6, 7, and 15, ach signal having a center position and an area:

| | Center Position (ppm) | | Area under the curve (AUC) (% of total |
|---|---|---|---|
| Signal | $^1H$ | $^{13}C$ | areas of all signals) |
| 5 | 3.96 | 70.62 | 9.28-10.71 |
| 6 | 3.92 | 71.26 | 1.52-2.03 |
| 7 | 3.55 | 71.34 | 3.40-6.13 |
| 15 | 4.44 | 103.86 | 1.84-2.44 |

In some embodiments, the spectrum further comprises 1-2 (e.g., one or two) signals selected from signals 10 and 14, and defined as follows:

| | Center Position (ppm) | | Area under the curve (AUC) (% of total |
|---|---|---|---|
| Signal | $^1H$ | $^{13}C$ | areas of all signals) |
| 10 | 3.33 | 73.74 | 10.21-12.09 |
| 14 | 4.5 | 103.29 | 5.03-6.41 |

In some embodiments, the spectrum further comprises 1-3 (e.g., one, two, or three) signals selected from signals 11, 12, and 13, and defined as follows:

| | Center Position (ppm) | | Area under the curve (AUC) (% of total |
|---|---|---|---|
| Signal | $^1H$ | $^{13}C$ | areas of all signals) |
| 11 | 4.06 | 77.34 | 3.68-4.50 |
| 12 | 4.11 | 81.59 | 3.10-3.82 |
| 13 | 4.96 | 98.7 | 10.65-12.31 |

In some embodiments, the spectrum comprises 1-3 (e.g., one, two, or three) signals selected from signals 11, 12, and 13, and defined as follows:

| | Center Position (ppm) | | Area under the curve (AUC) (% of total |
|---|---|---|---|
| Signal | $^1H$ | $^{13}C$ | areas of all signals) |
| 1 | 3.68 | 63.42 | 20.38-25.74 |
| 2 | 3.75 | 66.06 | 3.69-6.38 |
| 3 | 3.97 | 66.15 | 2.21-3.40 |
| 4 | 3.96 | 69.28 | 1.46-3.71 |
| 5 | 3.96 | 70.62 | 9.28-10.71 |
| 6 | 3.92 | 71.26 | 1.52-2.03 |
| 7 | 3.55 | 71.34 | 3.40-6.13 |
| 8 | 3.97 | 71.56 | 3.40-4.41 |
| 9 | 3.72 | 72.35 | 5.66-10.14 |
| 10 | 3.33 | 73.74 | 10.21-12.09 |
| 11 | 4.06 | 77.34 | 3.68-4.50 |
| 12 | 4.11 | 81.59 | 3.10-3.82 |
| 13 | 4.96 | 98.7 | 10.65-12.31 |
| 14 | 4.5 | 103.29 | 5.03-6.41 |
| 15 | 4.44 | 103.86 | 1.84-2.44 |

In some embodiments, the spectrum comprises 1-15 (e.g., one, two, or three) signals selected from signals 1-15, and defined as follows:

| | Center Position (ppm) | | Area under the curve (AUC) (% of total |
|---|---|---|---|
| Signal | $^1H$ | $^{13}C$ | areas of all signals) |
| 1 | 3.68 | 63.42 | 18.59-27.53 |
| 2 | 3.75 | 66.06 | 2.79-7.27 |
| 3 | 3.97 | 66.15 | 1.82-3.8 |
| 4 | 3.96 | 69.28 | 0.71-4.47 |
| 5 | 3.96 | 70.62 | 8.81-11.19 |
| 6 | 3.92 | 71.26 | 1.35-2.2 |
| 7 | 3.55 | 71.34 | 2.48-7.04 |
| 8 | 3.97 | 71.56 | 3.06-4.74 |
| 9 | 3.72 | 72.35 | 4.16-11.64 |
| 10 | 3.33 | 73.74 | 9.58-12.72 |
| 11 | 4.06 | 77.34 | 3.4-4.78 |
| 12 | 4.11 | 81.59 | 2.86-4.06 |
| 13 | 4.96 | 98.7 | 10.09-12.87 |
| 14 | 4.5 | 103.29 | 4.57-6.87 |
| 15 | 4.44 | 103.86 | 1.64-2.64 |

In some embodiments, the spectrum comprises 1-15 (e.g., one, two, or three) signals selected from signals 1-15, and defined as follows:

| | Center Position (ppm) | | Area under the curve (AUC) signals) |
|---|---|---|---|
| Signal | $^1H$ | $^{13}C$ | (% of total areas of all |
| 1 | 3.68 | 63.42 | 20.18-27.11 |
| 2 | 3.75 | 66.06 | 3.31-6.1 |
| 3 | 3.97 | 66.15 | 2.37-3.69 |
| 4 | 3.96 | 69.28 | 0.42-4.72 |

-continued

| | Center Position (ppm) | | Area under the curve (AUC) signals) |
|---|---|---|---|
| Signal | $^1H$ | $^{13}C$ | (% of total areas of all |
| 5 | 3.96 | 70.62 | 8.43-11.69 |
| 6 | 3.92 | 71.26 | 1.09-3.1 |
| 7 | 3.55 | 71.34 | 4.01-6.37 |
| 8 | 3.97 | 71.56 | 2.77-4.29 |
| 9 | 3.72 | 72.35 | 6.28-9.25 |
| 10 | 3.33 | 73.74 | 10.48-12 |
| 11 | 4.06 | 77.34 | 3.04-4.22 |
| 12 | 4.11 | 81.59 | 2.63-3.57 |
| 13 | 4.96 | 98.7 | 9.9-13.39 |
| 14 | 4.5 | 103.29 | 4.45-6.7 |
| 15 | 4.44 | 103.86 | 1.6-2.63 |

In some embodiments, the spectrum comprises 1-15 (e.g., one, two, or three) signals selected from signals 1-15, and defined as follows:

| | Center Position (ppm) | | Area under the curve (AUC) signals) |
|---|---|---|---|
| Signal | $^1H$ | $^{13}C$ | (% of total areas of all |
| 1 | 3.68 | 63.42 | 21.57-25.73 |
| 2 | 3.75 | 66.06 | 3.87-5.54 |
| 3 | 3.97 | 66.15 | 2.63-3.43 |
| 4 | 3.96 | 69.28 | 1.28-3.86 |
| 5 | 3.96 | 70.62 | 9.08-11.04 |
| 6 | 3.92 | 71.26 | 1.49-2.70 |
| 7 | 3.55 | 71.34 | 4.48-5.90 |
| 8 | 3.97 | 71.56 | 3.07-3.99 |
| 9 | 3.72 | 72.35 | 6.87-8.66 |
| 10 | 3.33 | 73.74 | 10.79-11.70 |
| 11 | 4.06 | 77.34 | 3.28-3.99 |
| 12 | 4.11 | 81.59 | 2.82-3.39 |
| 13 | 4.96 | 98.7 | 10.60-12.69 |
| 14 | 4.5 | 103.29 | 4.90-6.25 |
| 15 | 4.44 | 103.86 | 1.81-2.42 |

In some embodiments, signals 5, 6,7, 15, 10, 14, 11, 12, and 13 are each further characterized by an $^1H$ integral region and a $^{13}C$ integral region, defined as follows:

| | $^1H$ Position (ppm) | | | $^{13}C$ Position (ppm) | | |
|---|---|---|---|---|---|---|
| | Center | $^1H$ Integral Region | | Center | $^{13}C$ Integral Region | |
| Signal | Position | from | to | Position | from | to |
| 5 | 3.96 | 3.9 | 4.03 | 70.62 | 70.20 | 71.05 |
| 6 | 3.92 | 3.9 | 3.94 | 71.26 | 71.02 | 71.50 |
| 7 | 3.55 | 3.51 | 3.59 | 71.34 | 71.06 | 71.62 |
| 15 | 4.44 | 4.41 | 4.46 | 103.86 | 103.56 | 104.15 |
| 10 | 3.33 | 3.27 | 3.4 | 73.74 | 73.26 | 74.22 |
| 14 | 4.5 | 4.47 | 4.54 | 103.29 | 102.87 | 103.70 |
| 11 | 4.06 | 4.04 | 4.09 | 77.34 | 76.89 | 77.78 |
| 12 | 4.11 | 4.08 | 4.14 | 81.59 | 81.16 | 82.01 |
| 13 | 4.96 | 4.92 | 5.01 | 98.7 | 98.02 | 99.39 |

In some embodiments, signals 1-15 are each characterize d by an $^1H$ integral region and a $^{13}C$ integral region, defined as follows:

| | $^1H$ Position (ppm) | | | $^{13}C$ Position (ppm) | | |
|---|---|---|---|---|---|---|
| | Center | $^1H$ Integral Region | | Center | $^{13}C$ Integral Region | |
| Signal | Position | from | to | Position | from | to |
| 1 | 3.68 | 3.61 | 3.75 | 63.42 | 62.64 | 64.20 |
| 2 | 3.75 | 3.72 | 3.78 | 66.06 | 65.50 | 66.62 |
| 3 | 3.97 | 3.94 | 4.00 | 66.15 | 65.81 | 66.49 |
| 4 | 3.96 | 3.94 | 3.98 | 69.28 | 69.04 | 69.52 |
| 5 | 3.96 | 3.9 | 4.03 | 70.62 | 70.20 | 71.05 |
| 6 | 3.92 | 3.9 | 3.94 | 71.26 | 71.02 | 71.50 |
| 7 | 3.55 | 3.51 | 3.59 | 71.34 | 71.06 | 71.62 |
| 8 | 3.97 | 3.94 | 4.00 | 71.56 | 71.29 | 71.84 |
| 9 | 3.72 | 3.67 | 3.77 | 72.35 | 71.95 | 72.74 |
| 15 | 4.44 | 4.41 | 4.46 | 103.86 | 103.56 | 104.15 |
| 10 | 3.33 | 3.27 | 3.4 | 73.74 | 73.26 | 74.22 |
| 14 | 4.5 | 4.47 | 4.54 | 103.29 | 102.87 | 103.70 |
| 11 | 4.06 | 4.04 | 4.09 | 77.34 | 76.89 | 77.78 |
| 12 | 4.11 | 4.08 | 4.14 | 81.59 | 81.16 | 82.01 |
| 13 | 4.96 | 4.92 | 5.01 | 98.7 | 98.02 | 99.39 |

In some embodiments, oligosaccharide compositions are provided that are characterized by a HSQC NMR spectrum comprising signals (peaks) corresponding to the presence of one or more anomeric carbons, wherein each anomeric carbon comprises one or more HSQC NMR detectable signals (peaks). In some embodiments, oligosaccharide compositions are provided that are characterized by a HSQC NMR spec rum comprising a peak corresponding to the presence of one or more anomeric carbons as described in Example 11, e.g., FIG. 26. In some embodiments, oligosaccharide compositions are provided that are characterized by a HSQC NMR spectrum comprising a peak corresponding to a Galp-a-reducing anomeric carbon. In some embodiments, oligosaccharide compositions are provided that are characterized by a HSQC NMR spectrum comprising a peak corresponding to a Glup-a-reducing anomeric carbon. In some embodiments, oligosaccharide compositions are provided that are characterized by a HSQC NMR spectrum comprising a peak corresponding to a Manp-a-reducing anomeric carbon. In some embodiments, oligosaccharide compositions are provided that are characterized by a HSQC NMR spectrum comprising a peak corresponding to a Manp-b-reducing anomeric carbon. In some embodiments, oligosaccharide compositions are provided that are characterized by a HSQC NMR spectrum comprising a peak corresponding to a Glup-a,a(1,1) anomeric carbon. In some embodiments, oligosaccharide compositions are provided that are characterized by a HSQC NMR spectrum comprising a peak corresponding to a Glup-b-reducing anomeric carbon. In some embodiments, oligosaccharide compositions are provided that are characterized by a HSQC NMR spectrum comprising a peak corresponding to a Galp-a(1,3) anomeric carbon. In some embodiments, oligosaccharide compositions are provided that are characterized by a HSQC NMR spectrum comprising a peak corresponding to a Galp-b-reducing anomeric carbon. In some embodiments, oligosaccharide compositions are provided that are characterized by a HSQC NMR spectrum comprising a peak corresponding to a Manp-b-reducing anomeric carbon. In some embodiments, oligosaccharide compositions are provided that are characterized by a HSQC NMR spectrum comprising a peak corresponding to a Glup-a(1,2) anomeric carbon. In some embodiments, oligosaccharide compositions are provided that are characterized by a HSQC NMR spectrum comprising a peak corresponding to a Glup-a(1,6) anomeric carbon. In some embodiments, oligosaccharide compositions are provided that are characterized by a HSQC NMR spectrum comprising a peak corresponding to a Glup-a(1,3) anomeric carbon. In some embodiments, oligosaccharide compositions are provided that are characterized by a HSQC NMR spectrum comprising a peak corresponding to a Glup-a(1,4) anomeric carbon. In some embodiments, oligosaccharide compositions are provided that are characterized by a HSQC NMR spectrum comprising a peak corresponding to a Galp-a(1,6) anomeric carbon. In some embodiments, oligosaccharide compositions are provided that are characterized by a HSQC NMR spectrum comprising a peak corresponding to a Manp-a(1,6) anomeric carbon. In some embodiments, oligosaccharide compositions are provided that are characterized by a HSQC NMR spectrum comprising a peak corresponding to a Glup-b(1,3) anomeric carbon. In some embodiments, oligosaccharide compositions are provided that are characterized by a HSQC NMR spectrum comprising a peak corresponding to Glup-b(1,4)+b(1,6) anomeric carbons. In some embodiments, oligosaccharide compositions are provided that are characterized by a HSQC NMR spectrum comprising a peak corresponding to a Galp-b(1,6) anomeric carbon. In some embodiments, oligosaccharide compositions are provided that are characterized by a HSQC NMR spectrum comprising a peak corresponding to Glup-a,b(1,1) anomeric carbons. In some embodiments, oligosaccharide compositions are provided that are characterized by a HSQC NMR spectrum comprising a peak corresponding to Glup-b(1,2)+Galp-b(1,3)+b(1,4) anomeric carbons. In some embodiments, oligosaccharide compositions are provided that are characterized by a HSQC NMR spectrum comprising a peak corresponding to a Galf-b(1,6) anomeric carbon.

In some embodiments, oligosaccharide compositions are provided that are characterized by a HSQC NMR spectrum comprising a plurality of signals (peaks) corresponding to 1, 2, 3, 4, 5, 6, 7, 8, 9, 10, 11, 12, 13, 14, 15, 16, 17, 18, 19, 20, or all of: a Galp-a-reducing anomeric carbon, a Glup-a-reducing anomeric carbon, a Manp-a-reducing anomeric carbon, a Manp-b-reducing anomeric carbon, a Glup-a,a(1,1) anomeric carbon, a Glup-b-reducing anomeric carbon, a Galp-a(1,3) anomeric carbon, a Galp-b-reducing anomeric carbon, a Manp-b-reducing anomeric carbon, a Glup-a(1,2) anomeric carbon, a Glup-a(1,6) anomeric carbon, a Glup-a(1,3) anomeric carbon, a Glup-a(1,4) anomeric carbon, a Galp-a(1,6) anomeric carbon, a Manp-a(1,6) anomeric carbon, a Glup-b(1,3) anomeric carbon, Glup-b(1,4)+b(1,6) anomeric carbons, a Galp-b(1,6) anomeric carbon, Glup-a,b(1,1) anomeric carbons, Glup-b(1,2)+Galp-b(1,3)+b(1,4) anomeric carbons, or a Galf-b(1,6) anomeric carbon.

In certain embodiments, the NMR spectrum is obtained by subjecting a sample of the composition to HSQC NMR, wherein the sample is a solution in a deuterated solvent. Suitable deuterated solvents in include deuterated acetonitrile, deuterated acetone, deuterated methanol, $D_2O$, and mixtures thereof. In a particular embodiment, the deuterated solvent is $D_2O$. In certain embodiments, the NMR spectrum is obtained using the conditions described in Example 11.

Exemplary oligosaccharide compositions may be prepared according to the procedures described herein.

III. Methods of Use

As described herein, oligosaccharide compositions may be used to treat or prevent viral infections in subjects (e.g., human subjects). In some embodiment, oligosaccharide compositions may be used to treat or prevent respiratory viral infections (e.g., coronavirus infections) in subjects (e.g., human subjects). Further, in some embodiments, oligosaccharide compositions may be used to reduce pathogen (e.g., CRE or VRE) levels and/or pathogen colonization in subjects having or recovering from viral infections (e.g., compositons used to prevent a secondary infection, e.g., of the lungs or the gut). In some embodiments, the oligosaccharide composition is formulated as powder, e.g., for reconstitution (e.g., in water) for oral administration. In some embodiments, the oligosaccharide composition is formulated as a pharmaceutical composition. In some embodiments, the oligosaccharide composition is formulated as a pharmaceutical composition for administration to the gastrointestinal tract (e.g., the intestines, e.g., the large intestine). In some embodiments, the oligosaccharide composition is administered in addition to or in combination with use of a standard of are treatment (e.g., standard of care treatment for viral infections, e.g., bed rest, hydration, OTC medication, anti-viral medication, etc.).

In some embodiments, oligosaccharide compositions provided herein effectively treat a subject having or suspected of having a viral infection (e.g., a respiratory viral infection, a coronavirus infection). In some embodiments, oligosaccharide compositions provided herein effectively treat a subject having or suspected of having a viral infection that is asymptomatic or pre-symptomatic. In some embodiments, oligosaccharide compositions provided herein effectively treat a subject who is from 1-14 days, 3-12 days, or 5-10 da s from the onset of the viral illness (e.g., a respiratory viral infection, a coronavirus infection). In some embodiments, oligosaccharide compositions provided herein effectively treat a subject 1-14 days, 3-12 days, or 5-10 days after exposure to the virus causing the viral respiratory infection (e.g., a respiratory viral infection, a coronavirus infection). In some embodiments, oligosaccharide compositions provided herein effectively treat a subject who has developed dyspnea but not yet acute respiratory distress syndrome (ARDS). In some embodiments, oligosaccharide compositions provided herein effectively treat a subject who has developed acute respiratory distress syndrome (ARDS) but has not yet been admitted to the intensive care unit (ICU). In some embodiments, oligosaccharide compositions provided herein effectively treat a subject who has a mild clinical presentation (e.g., absence of viral pneumonia and hypoxia) and is able to manage their illness at home (e.g., in an outpatient setting, without hospitalization).

In some embodiments, oligosaccharide compositions provided herein reduce the viral load in a subject (e.g., in the lungs of a subject). In some embodiments, the viral load is reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100%, e.g., relative to a reference standard. Viral load or viral titer is a numerical expression of the quantity of virus (e.g., viral genome copies) in a given volume (e.g., mL) of a body fluid. Viral load can be measured by any known method (e.g., using a nucleic acid-based test, such as, e.g., by polymerase chain reaction (PCR) or reverse transcription polymerase chain reaction (RT-PCR)). Samples may be obtained, e.g., from nasal or oral fluids (e.g., swabs), or blood (e.g., plasma) or stool.

In some embodiments, oligosaccharide compositions provided herein effectively prevent the hospitalization of a subject having or suspected of having a coronavirus infection. In some embodiments, oligosaccharide compositions provided herein reduce the likelihood that a subject having or suspected of having a viral infection (e.g., a coronavirus infection) will need to be hospitalized.

In some embodiments, oligosaccharide compositions provided herein effectively prevents the hospitalization of at least 1 out of every 100 subjects, at least 5 out of every 100 subjects, at least 10 out of every 100 subjects, at least 20 out of every 100 subjects, at least 30 out of every 100 subjects, at least 40 out of every 100 subjects, at least 50 out of every 100 subjects, at least 60 out of every 100 subjects, at least 70 out of every 100 subjects, at least 80 out of every 100 subjects, at least 90 out of every 100 subjects, or at least 95 out of every 100 subjects. In some embodiments, oligosaccharide compositions provided herein effectively prevents the hospitalization of 10-100%, 10-20%, 15-25%, 20-50%, 40-60%, 50-75%, 60-80%, 75-90%, 80-100%, or 90-100% of subjects.

In some embodiments, oligosaccharide compositions provided herein effectively reduces the length of hospitalization (e.g., by 1-3, 1-5, 1-10, 3-5, 3-10, or 5-15 days) of at least 1 out of every 100 subjects, at least 5 out of every 100 subjects, at least 10 out of every 100 subjects, at least 20 out of every 100 subjects, at least 30 out of every 100 subjects, at least 40 out of every 100 subjects, at least 50 out of every 100 subjects, at least 60 out of every 100 subjects, at least 70 out of every 100 subjects, at least 80 out of every 100 subjects, at least 90 out of every 100 subjects, or at least 95 out of every 100 subjects, relative to a control subject or population of subjects (e.g., a subject or population of subjects not receiving the oligosaccharide composition). In some embodiments, oligosaccharide compositions provided herein effectively reduces the length of hospitalization (e.g., by 1-3, 1-5, 1-10, 3-5, 3-10, or 5-15 days) of 10-100%, 10-20%, 15-25%, 20-50%, 40-60%, 50-75%, 60-80%, 75-90%, 80-100%, or 90-100% of subjects, relative to a control subject or population of subjects (e.g., a subject or population of subjects not receiving the oligosaccharide composition).

In some embodiments, oligosaccharide compositions provided herein effectively reduce the time (e.g., the average time or the median time, e.g., the Median time to resolution of symptoms in 50% of subjects, e.g., as measured using a Kaplan-Meier plot) to resolution of symptoms in a subject having a viral respiratory illness, e.g., a coronavirus infection, e.g., COVID-19, e.g., by 1-3, 1-5, 1-10, 3-5, 3-10, 3-15, 5-10, or 5-15 days, optionally combined with a standard of care treatment (e.g., standard of care treatment for viral in ections, e.g., bed rest, hydration, OTC medication, anti-viral medication, etc.), compared to a control subject (e.g., a subject not receiving the oligosaccharide compositions provided herein) optionally receiving standard of care. In some embodiments, oligosaccharide compositions provided herein effectively reduce the time (e.g., the average time or median time) to resolution of symptoms of a viral respiratory illness, e.g., a coronavirus infection, e.g., COVID-19, (e.g., by 1-3, 1-5, 1-10, 3-5, 3-10, 3-15, 5-10, or 5-15 days) of 10-100%, 10-20%, 15-25%, 20-50%, 40-60%, 50-75%, 60-80%, 75-90%, 80-100%, or 90-100% of subjects, relative to a control subject or population of subjects (e.g., a subject or population of subjects not receiving the oligosaccharide composition). In some embodiments, the time to resolution of symptoms is reduced at least 1, 2, 3, 4, 5, 6, 7, 8, 9, 10, 11, 12, 13, 14, 15, 16, 17, 18, 19, or 20 days (e.g., at least 1-3 or at least 5-10 days). In some embodiments, the symptoms resolved comprise (e.g., consist) of cough, chills and/or repeated shaking with chills, muscle pain, fever, headache, anosmia/ageusia, shortness of breath, and sore throat. In some embodiments, the symptoms resolved comprise (e.g., consist) of cough, chills and/or repeated shaking with chills, muscle pain, fever, headache, anosmia/ageusia, shortness of breath, sore throat, gastrointestinal disturbance symptoms, diarrhea, fatigue, nasal congestion, and chest tightness. In some embodiments, the subject or subjects have at least one (e.g., at least 1, 2, or 3,) comorbidity condition. In some embodiments, the subject or subjects do not have a comorbidity condition. In some embodiments, comorbidity conditions include, but are not limited to, chronic lung disease (e.g., asthma, emphysema, or chronic obstructive pulmonary disease (COPD)), diabetes mellitus, cardiovascular disease, hypertension, renal disease (e.g., chronic renal disease), liver disease (e.g., chronic liver disease), an immunocompromised condition, cancer, a neurologic disorder, stroke, or other chronic disease. In some embodiments, oligosaccharide compositions provided herein effectively minimizes or prevents progression of the infection (e.g., progression from mild or moderate symptoms to severe symptoms, e.g., such that subject requires further intervention, e.g., a ventilator or respirator). In some embodiments, oligosaccharide compositions provided herein effectively minimizes or prevents progression of the infection in at least 1 out of every 100 subjects, at least 5 out of ever 100 subjects, at least 10 out of every 100 subjects, at least 20 out of every 100 subjects, at least 30 out of every 100 subjects, at least 40 out of every 100 subjects, at least 50 out of every 100 subjects, at least 60 out of every 100 subjects, at least 70 out of every 100 subjects, at least 80 out of every 100 subjects, at least 90 out of every 100 subjects, or at least 95 out of every 100 subjects. In some embodiments, oligosaccharide compositions provided herein effectively minimizes or prevents progression of the infection in 10-100%, 10-20%, 15-25%, 20-50%, 40-60%, 50-75%, 60-80%, 75-90%, 80-100%, or 90-100% of subjects.

In some embodiments, oligosaccharide compositions provided herein effectively prevent a viral infection (e.g., a coronavirus infection) in a subject. In some embodiments, compositions prevent viral infections in otherwise healthy subjects who are at risk for developing a viral infection (e.g., essential workers, hospital employees, immunocompromised patients, persons living with a person or persons having a viral infection). In so e embodiments, oligosaccharide compositions are administered prophylactically to otherwise healthy subjects.

In some embodiments, oligosaccharide compositions provided herein effectively prevents a viral infection in at least 1 out of every 100 subjects, at least out of every 100 subjects, at least 10 out of every 100 subjects, at least 20 out of every 100 subjects, at least 30 out of every 100 subjects, at least 40 out of every 100 subjects, at least 50 out of every 100 subjects, at least 60 out of every 100 subjects, at least 70 out of every 100 subjects, at least 80 out of every 100 subjects, at least 90 out of every 100 subjects, or at lea t 95 out of every 100 subjects. In some embodiments, oligosaccharide compositions provide herein effectively a viral infection in 10-100%, 10-20%, 15-25%, 20-50%, 40-60%, 50-75%, 60-80%, 75-90%, 80-100%, or 90-100% of subjects.

In some embodiments, oligosaccharide compositions provided herein effectively prevent a secondary infection (e.g., secondary infection of the lungs, urinary tract or the gut) in a subject having, suspected of having, or recovering from a viral infection (e.g., a coronavirus infection). In some embodiments, a subject having, suspected of having, or recovering from a viral infection who receives an oligosaccharide composition is about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100% less likely to develop a secondary infection than a control subject (e.g., untreated subject).

In some embodiments, oligosaccharide compositions provided herein effectively prevents a secondary infection in at least 1 out of every 100 subjects, at least 5 out of every 100 subjects, at least 10 out of every 100 subjects, at least 20 out of every 100 subjects, at least 30 out of every 100 subjects, at least 40 out of every 100 subjects, at least 50 out of every 100 subjects, at least 60 out of every 100 subjects, at least 70 out of every 100 subjects, at least 80 out of every 100 subjects, at least 90 out of every 100 subjects, or at least 95 out of every 100 subjects. In some embodiments, oligosaccharide compositions provided herein effectively a secondary infection in 10-100%, 10-20%, 15-25%, 20-50%, 40-60%, 50-75%, 60-80%, 75-90%, 80-100%, or 90-100% of subjects.

A secondary infection (e.g., secondary infection of the lung, urinary tract or gut) may be a fungal infection or a bacterial infection. In some embodiments, a secondary infection is caused by any pathogen (e.g., bacterial pathogen or fungal pathogen) as described herein. In certain embodiments, a bacterial infection is caused by a drug or antibiotic resistant bacteria (e.g., vancomycin resistant *Enterococcus* (VRE) or carbapenem resistant Enterobacteriaceae (CRE)). In certain embodiments, a secondary infection is caused by *Mycobacterium tuberculosis*, mycobacteria, *Streptococcus pneumoniae, Haemophilus influenzae, Moraxella catarrhalis, mycoplasma, Staphylococcus aureus*, or *Pseudomonas*. In some embodiments, a secondary infection is caused by *Clostridium difficile*. In some embodiments, a secondary infection is caused by vancomycin resistant *Enterococcus* (VRE). In some embodiments, a secondary infection is caused by carbapenem resistant Enterobacteriaceae (CRE). In some embodiments, a secondary infection is caused by a fungal pathogen. In some embodiments, a secondary infection is caused by *Candida albicans*. In some embodiments, a secondary infection is caused by *Candida glabrata*. In some embodiments, a secondary infection is ca sed by *Candida krusei*. In some embodiments, a secondary infection is caused by *Candida tropicalis*.

In some embodiments, pathogens that may cause a secondary infection includes bacterial pathogens (e.g., *Abiotrophia* spp., (e.g., *A. defective*), *Achromobacter* spp., *Acinetobacter* spp., (e.g., *A. baumanii*), *Actinobaculum* spp., (e.g., *A. schallii*), *Actinomyces* spp., (e.g., *A. israelii*), *Aerococcus* spp., (e.g., *A. urinae*), *Aeromonas* spp., (e.g., *A. hydrophila*), *Aggregatibacter* spp., e.g. *A. aphrophilus, Bacillus anthracis, Bacillus cereus* group, *Bordetella* spp., *Brucella* spp., e.g. *B. henselae, Burkholderia* spp., e.g., *B. cepaciae, Campylobacter* spp., e.g., *C. jejuni, Chlamydia* spp., *Chlamydophila* spp., *Citrobacter* spp., e.g., *C. freundii, Clostridium botulinum, Clostridium difficile, Clostridium perfringens, Corynebacterium* spp., e.g., *C. amycolatum, Cronobacter*, e.g., *C. sakazakii*, Enterobacteriaceae, including many of the genera below, *Ehrlichia* spp., *Enterobacter* spp., e.g., *E. cloacae, Enterococcus* spp., e.g. *E. faecium, Escherichia* spp., including enteropathogenic, uropathogenic, and enterohemorrhagic strains of *E. coli, Francisella* spp., e.g. *F. tularensis, Fusobacterium* spp., e.g. *F. necrophorum, Gemella* spp., e.g. *G. mobillorum, Granulicatella* spp., e.g. *G. adiaciens, Haemophilus* spp., e.g. *H. influenza, Helicobacter* spp., e.g. *H. pylori, Kingella* spp., e.g. *K. kingae, Klebsiella* spp., e.g. *K. pneumoniae, Legionella* spp., e.g. *L. pneumophila, Leptospira* spp., *Listeria* spp., e.g. *L. monocytogenes, Morganella* spp., e.g. *M. morganii, Mycobacterium* spp., e.g. *M. abcessus, Neisseria* spp., e.g. *N. gonorrheae, Nocardia* spp., e.g. *N. asteroids, Ochrobactrum* spp., e.g. *O. anthropic, Pantoea* spp., e.g. *P. agglomerans, Pasteurella* spp., e.g. *P. multocida, Pediococcus* spp., *Plesiomonas* spp., e.g. *P. shigelloides, Proteus* spp., e.g. *P. vulgaris, Providencia* spp., e.g. *P. stuartii, Pseudomonas* spp., e.g. *P. aeruginosa, Raoultella* spp., e.g. *R. ornithinolytica, Rothia* spp., e.g. *R. mucilaginosa, Salmonella* spp., e.g. *S. enterica, Serratia* spp., e.g. *S. marcesens, Shigella* spp., e.g. *S. flexneri, Staphylococcus aureus, Staphylococcus lugdunensis, Staphylococcus pseudintermedius, Staphylococcus saprophyticus, Stenotrophomonas* spp., e.g. *S. maltophilia, Streptococcus agalactiae, Streptococcus anginosus, Streptococcus constellatus, Streptococcus dysgalactiae, Streptococcus intermedius, Streptococcus milleri, Streptococcus pseudopneumoniae, Streptococcus pyogenes, Streptoоccus pneumoniae, Treponema* spp., *Ureaplasma ureolyticum, Vibrio* spp., e.g. *V. cholerae*, and *Yersinia* spp., (e.g., *Y. enterocolitica*)); viral pathogens (e.g., Adenovirus, Astrovirus, Cytomegalovirus, Enterovirus, Norovirus, Rotavirus, and Sapovirus); and gastrointestinal protozoan pathogens (e.g., *Cyclospora* spp., *Cryptosporidium* spp., *Entamoeba histolytica, Giardia lamblia*, an Microsporidia, (e.g., *Encephalitozoon canaliculi*)).

In some embodiments, administration of an oligosaccharide composition reduces the severity of a viral infection (e.g., a coronavirus infection). In some embodiments, the severity of a viral infection is reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100% relative to a control subject (e.g., untreated subject).

In some embodiments, administration of an oligosaccharide composition reduces the severity of the symptoms of a viral infection (e.g., a coronavirus infection). In some embodiments, the severity of the symptoms of a viral infection are reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100% relative to a control subject (e.g., untreated subject).

In some embodiments, a subject who has been administered an oligosaccharide composition experiences fewer treatment emergent adverse events (TEAEs) following administration of the oligosaccharide composition relative to a control subject. In some embodiments, the subject experiences 1-5, 2-10, 3-5, 5-15, or 5-25 fewer TEAEs. In some embodiments, a control subject is a subject treated with a standard of care therapy (e.g., bed rest, hydration, OTC medication, or anti-viral medication) and not the oligosaccharide composition. In some embodiments, a control subject is a subject treated with one or more monoclonal antibodies against an antigen of the viral respiratory illness, e.g., an antibody cocktail, and not the oligosaccharide composition. In some embodiments, a control subject is a subject treated with an anti-inflammatory drug, e.g., a steroid, and not the oligosaccharide composition In some embodiments, a subject who has been administered an oligosaccharide composition experiences a reduction of the severity of any one individual symptom relative to a control subject (e.g., untreated subject, a subject treated with a standard of care therapy, or a subject treated with one or more monoclonal antibodies against an antigen of the viral respiratory illness, or treated with another drug or agent, such as, e.g., an anti-inflammatory agent, e.g., a steroid) or a baseline measurement. In some embodiments, the subject has a reduction in the severity of a cough (e.g., dry cough), fever, shivering, chills, nasal congestion, runny nose, gastrointestinal symptoms (e.g., diarrhea), malaise, fatigue, anosmia, ageusia, nausea, shortness of breath, chest tightness or chest congestion, loss of appetite, body aches, and/or headache. In some embodiments, the severity of a symptom may be rated (i.e., scored) on a scale of 0-3, where 0 means that the symptom is absent, 1 means that the symptom is mild (present but easily tolerated), 2 means that the symptom is moderately severe (bothersome but tolerable), and 3 means that the symptom is very severe (hard to tolerate; interferes considerably with daily activity). In some embodiments, a subject who has been administered an oligosaccharide composition rates the severity of at least one symptom to be lowered following the administration of the oligosaccharide composition. In some embodiments, the subject experiences a reduction of the severity of 2, 3, 4, 5, 6, 7, 8, 9, 10, 11, or ore symptom scores. In some embodiments, the subject who has been administered an oligosaccharide composition experiences a reduction of the severity of a plurality (e.g., a majority, nearly all, or all) of symptoms associated with a viral respiratory illness. In some embodiments, the reduction of the severity in a plurality (e.g., a majority, nearly all, or all) of symptoms is modest, e.g., a reduction of about 1 or about 2 on a 0-3 scale, wherein the plurality of symptoms nay persist after treatment in a milder manner. Without wishing to be bound by theory, by acting to modulate the immune response of a subject having a viral respiratory illness, the oligosaccharide compositions provided herein may act in a generalized manner to reduce the symptoms of the viral respiratory illness, providing relief across symptoms (e.g., rather than targeted relief of a single specific symptom).

In some embodiments, a subject who has been administered an oligosaccharide composition experiences a reduction in bed rest time measured as a patient-assessed daily cumulative total resting in a supine position (measured in hours). In some embodiments, a subject spends at least 1, 2, 3, 4, 5, 6, 7, 8, 9, 10, 11, 12, 13, 14, or 15 fewer hours per day in bed rest (e.g., in a supine position) after administration of an oligosaccharide composition (e.g., relative to a control subject or a baseline measurement).

The oligosaccharide composition may be administered to the subject on a daily, weekly, biweekly, or monthly basis. In some embodiments, the composition is administered to the subject more than once per day (e.g., 2, 3, or 4 times per day). In so ne embodiments, the composition is administered to the subject once or twice per day for one two, three, or four weeks in a row.

In some embodiments, the composition is administered to the subject according to the following schedule: 18 grams on days 1 and 2 of a treatment protocol; 36 grains on days 3 and 4 of a treatment protocol; and 72 grams on days 5-14 of a treatment protocol.

In some embodiments, an effective amount of selected oligosaccharides (e.g., comprised in a formulation) is a total of 5-200 grams, 5-150 grams, 5-1 0 grams, 5-75 grams, 5-50 grams, 5-25 grams, 10-50 grams, 25-50 grams, 30-60 grams, 50-75 grams, 50-100 grams, 18-72 grams, or 36-72 grams administered daily. In some embodiments, an effective amount of oligosaccharides is a total of 15-25 grams administered daily. In some embodiments, an effective amount of oligosaccharides is a total of 30-40 grams administered daily. In some embodiments, an effective amount of oligosaccharides is a total of 70-80 grams administered daily. In some embodiments, an effective amount of oligosaccharides is a total of about 18 grams administered daily. In some embodiments, an effective amount of oligosaccharides is a total of about 36 grams administered daily. In some embodiments, an effective amount of oligosaccharides is a total of about 72 grams administered daily.

The oligosaccharide composition of the disclosure is well tolerated by a subject (e.g., oligosaccharide compositions do not cause or cause minimal discomfort, e.g., production of gas or gastrointestinal discomfort, in subjects). In some embodiments, 5-200 grams, 5-150 grams, 5-100 grams, 5-75 grams, 5-50 grams, 5-25 grams, 10-50 grams 25-50 grams, 30-60 grams, 50-75 grams, 50-100 grams, 18-72 grams, or 36-72 grams of total daily dose are well tolerated by a subject. The amount of an oligosaccharide composition that is administered to the subject at a single time or in a single dose is well tolerated by the subject.

In some embodiments, the amount of the oligosaccharide composition that is administered to the subject at a single time or in a single dose is more tolerated by the subject than a similar amount of commercial low-digestible sugars such as fructooligosaccharides (FOS). Commercial low-digestible sugars are known in the art to be poorly tolerated in subjects (See, e.g., Grabitske, H. A., Critical Reviews in Food Science and Nutrition, 49:327-360 (2009)), e.g., at high doses. For example, tolerability studies of FOS indicate that 20 grams FOS per day causes mild gastrointestinal symptoms and that 30 grams FOS per day causes major discomfort and gastrointestinal symptoms.

A viral infection may be caused by an RNA virus or a DNA virus. In some embodiments, a viral infection is a viral infection of the respiratory and/or pulmonary system (e.g., a respiratory viral infection). In some embodiments, a viral infection is caused by a coronavirus, enterovirus, adenovirus, parainfluenza virus, respiratory syncytial virus, influenza virus, metapneumovirus, rhinovirus, measles virus or bocavirus.

In some embodiments, a coronavirus is an alphacoronavirus, a betacoronavirus, a gammacoronavirus, or a deltacoronavirus. In some embodiments, a coronavirus is selected from the group consisting of: severe acute respiratory syndrome-related coronavirus (SARS-CoV, SARS-CoV-2), human coronavirus 229E, human coronavirus NL63, miniopterus bat coronavirus 1, miniopterus bat coronavirus HKU8, porcine epidemic diarrhea virus, rhinolophus bat coronavirus HKU2, scotophilus bat coronavirus 512, tacoronavirus 1, human coronavirus HKU1, murine coronavirus, *pipistrellus* bat coronavirus HKU5, rousettus bat coronavirus HKU9, *tylonycteris* bat coronavirus HKU4, Middle East respiratory syndrome-related coronavirus, and hedgehog coronavirus 1 (EriCoV). In some embodiments, a coronavirus is a severe acute respiratory syndrome-related coronavirus. In some embodiments, a severe acute respiratory syndrome-related coronavirus is a SARS-CoV-2 strain. In some embodiments, a coronavirus infection is COVID-19.

In some embodiments, the symptoms of a COVID-19 infection comprise 8 so-called ‘cardinal’ symptoms. In some embodiments, the cardinal symptoms are cough, chills and/or repeated shaking with chills, muscle pain, fever, headache, anosmia/ageusia, shortness of breath, and sore throat. In some embodiments, the symptoms of a COVID-19 infection comprise 13 ‘overall’ symptoms. In some embodiments, the overall symptoms are cough, chills and/or repeated shaking with chills, muscle pain, fever, headache, anosmia/ageusia, shortness of breath, sore throat, gastrointestinal disturbance symptoms, diarrhea, fatigue, nasal congestion, and chest tightness. A person of skill in the art will understand that a subject having a COVID-19 infection may have one or a plurality of the cardinal symptoms or overall symptoms, e.g., all or fewer than all of the cardinal symptoms or overall symptoms. A person of skill in t e art will further understand that one or more of the symptoms (e.g., 'cardinal' and 'overall' symptoms) listed here for COVID-19 are substantially similar to symptoms caused by other coronaviruses and more generally respiratory viruses, such as RNA viruses as provided herein. Embodiments and Examples that specially apply to the SARS-CoV-2 strain and/or COVID-19, e.g., with respect to viral treatment, e.g., with the selected oligosaccharide provided herein, thus also apply to other coronaviruses and more generally respiratory viruses, such as, for example, coronavirus, enterovirus, adenovirus, parainfluenza virus, respiratory syncytial virus, influenza virus, metapneumovirus, rhinovirus, measles virus and bocavirus as provided herein.

In some embodiments, oligosaccharide compositions provided herein effectively reduce one or more symptoms of a viral respiratory illness, wherein the ne or more symptoms are early prognosticators of potential disease worsening. In some embodiments, a symptom that is an early prognosticator of potential disease worsening refers to a symptom that a subject having a mild or moderate viral respiratory illness (e.g., COVID-19) may exhibit, the persistence of which correlates with and/or prognoses a worsening of the disease. Without wishing to be bound by theory, the disclosure is directed, in part, to the discovery that treatment with an oligosaccharide composition described herein may attenuate the immune response of a patient having a viral respiratory illness, thereby reducing one or more symptoms of the viral respiratory illness, reducing the time to resolution of said one or more symptoms, and/or preventing worsening of symptoms of the viral respiratory illness (e.g., on average decreasing the likelihood of worsening of symptoms). In some embodiments, early prognosticators of potential disease worsening include one or more respiratory, thoracic and mediastinal disorders, e.g., dyspnoea, oropharyngeal pain, cough, dyspnoea exertional, nasal congestion, hypoxia, pleurisy, acute respiratory failure, or lower respiratory tract congestion.

In some embodiments, oligosaccharide compositions provided herein effectively promotes an increased amount of short-chain fatty acids (SCFAs) in the gut microbiome of the subject. In some embodiments, the amount of short-chain fatty acids in t e gut microbiome of the subject are increased by at least 2-fold (e.g., at least 3-fold, at least 4-fold, at least 5-fold) following the administration of the oligosaccharide composition. Short chain fatty acids include acetate, propionate, and butyrate. In some embodiments, oligosaccharide compositions provided herein cause bacterial organisms in the gut microbiome to produce an increased amount of short-chain fatty acids. In some embodiments, oligosaccharide compositions provided herein cause bacterial organisms in the gut microbiome to produce an increase in SCFAs of at least 1%, at least 2%, at least 3%, at least 4%, at least 5%, at least 10%, at least 15%, at least 20%, at least 30%, at least 35%, at least 40%, at least 45%, at least 50%, at least 55%, at least 60%, at least 65%, at least 70%, at least 75%, at least 80%, at least 85%, at least 90% at least 95%, at least 99%, at least 100%, at least 150%, at least 200%, at least 250%, at least 300%, at least 350%, at least 400%, at least 500%, or at least 1000% relative to control (e.g., treatment of bacteria with water). In some embodiments, oligosaccharide compositions provided herein cause bacterial organisms in the gut microbiome to produce an increase in SCFAs of at least 1.5-fold, 2-fold, 3-fold, 4-fold, 5-fold, 6-fold, 7-fold, 8-fold, 9-fold, or 10-fold relative to control (e.g., treatment of bacteria with water). In some embodiments, oligosaccharide compositions provided herein cause bacterial organisms in the gut microbiome to produce at least 15 mM, 1 mM, 17 mM, 18 mM, 19 mM, 20 mM, 21 mM, 22 mM, 23 mM, 24 mM, 25 mM, 30 mM, 35 mM, 40 mM, 45 mM, or 50 mM of total SCFA (e.g., as measured in a fecal sample). In some embodiments, oligosaccharide compositions provided herein cause bacterial organisms in the gut microbiome to produce at least 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, or 30 mM of total acetate (e.g., as measured in a fecal sample). In some embodiments, oligosaccharide compositions provided herein cause bacterial organisms in the gut microbiome to produce at least 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, or 30 mM of total propionate (e.g., as measured in a fecal sample). In some embodiments, oligosaccharide compositions provided herein cause bacterial organisms in the gut microbiome to produce at least 0.3 mM, 0.4 mM, 0.5 mM, 0.6 mM, 0.7 mM, 0.8 mM, 0.9 mM, 1 mM, 1.25 mM, 1.5 mM, 1.75 mM, 2 mM, 2.25 mM, 2.5 mM, 2.75 mM, or 3 mM of total butyrate (e.g., as measured in a fecal sample).

In some embodiments, oligosaccharide compositions provided herein promote an increased amount of short-chain fatty acids (SCFAs) in the gut microbiome across a plurality of different subjects. Without wishing to be bound by theory, the disclosure is directed in part to the discovery that oligosaccharide compositions provided herein are capable of promoting an increased amount of SCFAs in the gut microbiome in a subject non-specific manner, meaning, e.g., that the oligosaccharide compositions may be useful to a wide segment of potential patients rather than a single individual (or small set of individuals) having a specific microbiome composition. See, e.g., Example 6 and FIGS. 1A-1B. In some embodiments, an oligosaccharide composition provided herein is capable of promoting an increased amount of SCFAs in the gut microbiome of at least 2, 3, 4, 5, 6, 7, 8, 9, 10, 15, 20, 50, or 100 different subjects (e.g., as demonstrated by an increased amount of SCFAs after ex vivo fermentation of selected oligosaccharide composition by fecal communities from at least 2, 3, 4, 5, 6, or 7 different subjects). In some embodiments, an oligosaccharide composition provided herein is capable of promoting an increased amount of SCFAs in the gut microbiome of at least 2, 3, 4, 5, 6, or 7 different subjects (or fecal samples obtained from subjects), e.g., at least 2 or 7 different subjects (or fecal samples obtained from subjects).

In some embodiments, oligosaccharide compositions provided herein promote production of a consistent ratio of different SCFAs in the gut microbiome (e.g., across a plurality of different subjects and/or across administrations to an individual subject). Without wishing to be bound by theory, the disclosure is directed in part to the discovery that oligosaccharide compositions provided herein are capable of promoting production of a ratio of SCFAs (e.g., of butyrate, propionate, and acetate) that is distinct and/or improved relative to the ratio promoted by either a baseline (e.g., water) or a control treatment (e.g., treatment with a commercially available oligosaccharide composition (e.g., fructo-oligosaccharide (FOS), galacto-oligosaccharides (GOS), xylo-oligosaccharides (XOS), or polydextrose (PDX)). Levels of particular SCFAs can be measured by ex vivo methods, e.g., as describe in Example 6. In some embodiments, the oligosaccharide compositions provided herein are capable of promoting production of propionate (e.g., on average, e.g., across a plurality of fecal communities) at a level at least 1.2, 1.3, 1.4, 1.5, 1.75, 2, 2.25, 2.5, 2.75, 3, 3.25, 3.5, 3.75, 4, 4.25, 4.5, 4.75, or 5 fold higher than either negative control treatment (e.g., water) or treatment with a commercially available oligosaccharide composition (e.g., FOS, GOS, XOS, or PDX). In some embodiments, the oligosaccharide compositions provided herein are capable of promoting production of exemplary SCFAs acetate, propionate, and butyrate (e.g., on average, e.g., across a plurality of fecal communities) at a levels (acetate: propionate:butyrate) of about about 40-70% acetate, about 30-50% propionate, and about 5-20% butyrate; or about 45-65% acetate, about 30-45% propionate, and about 5-10% butyrate; or about 50-60% acetate, about 30-40% propionate, and about 5-10% butyrate; or about 54-60% acetate, about 34-40% propionate, and about 6-10% butyrate. In some embodiments, the oligosaccharide compositions provided herein are capable of promoting production of propionate (e.g., on average, e.g., across a plurality of fecal communities), e.g., at the expense of butyrate and/or acetate, to a higher degree compared with a commercially available oligosaccharide composition (e.g., FOS, GOS, XOS, or PDX).

In some embodiments, oligosaccharide compositions provided herein effectively decreases a host immune response of a subject to a viral respiratory illness. Without wishing to be bound by theory, altering the microbiota with a method or oligosaccharide composition described herein may increase or decrease the level of one or more taxa of the gastrointestinal microbiota, altering the microbiota's capacity to process host metabolites and secreted metabolites of its own, thereby influencing features of a host immune response. In some embodiments, a method or oligosaccharide composition described herein decreases a host immune response of a subject to a viral respiratory illness by at least 2-fold (e.g., at least 3-fold, at least 4-fold, at least 5-fold) following the administration of the oligosaccharide composition (e.g., assessed by measuring a suitable immune/inflammatory biomarker panel (e.g., determining the levels of pro-inflammatory cytokines such as, e.g., IL-1 beta, IL-6, and TNF-alpha and anti-inflammatory cytokines, which include, e.g., IL-4, IL-10, and IL-13, and others, such as, e.g., cytokines, such as, e.g., GM-CSF, IFN alpha, IFN gamma, IL-1 alpha, IL-1 beta, IL-4, IL-6, IL-8, IL-10, IL-12p70, IL-13, IL-17A (CTLA-8), TNF alpha, chemokines, such as, e.g., IP-10 (CXCL10), MCP-1 (CCL2), MIP-1 alpha (CCL3), MIP-1 beta (CCL4), and cell adhesion and inflammatory response markers, such as, e.g., ICAM-1, CD62E (E-selectin), CD62P (P-Selectin)). In some embodiments, the host immune response comprises inflammation or a symptom (e.g., one of the 8 cardinal or 13 overall symptoms) described herein.

In some embodiments, oligosaccharide compositions provided herein effectively promote a decreased amount of a biomarker of inflammation, e.g., in the bloodstream of the subject. In some embodiments, the amount of the biomarker of inflammation in the bloodstream of the subject is decreased by at least 2-fold (e.g., at least 3-fold, at least 4-fold, at least 5-fold) following the administration of the oligosaccharide composition. In some embodiments, the amount of the biomarker of inflammation in the bloodstream of the subject is decreased by at least 10, 25, 50, 75, or 90% following the administration of the oligosaccharide composition. Without wishing to be bound by theory, changes in the abundance of different bacterial populations in the microbiome of a subject can decrease the level of inflammatory cytokines and other inflammatory markers in a subject, which may be especially advantageous in a subject exhibiting a viral respiratory illness and a heightened immune response associated with increased inflammation. In some embodiments, the biomarker of inflammation comprises C Reactive Protein (CRP). In some embodiments, a subject with a viral respiratory illness has one or more comorbidities (e.g., associated with chronic inflammation) and the oligosaccharide compositions provided herein effectively promotes a decreased amount of a biomarker of inflammation (e.g., CRP).

In some embodiments, oligosaccharide compositions provided herein effectively boost the innate immune response of a subject having a viral respiratory illness. In some embodiments, oligosaccharide compositions provided herein effectively decrease viral load in the subject, e.g., systemically or locally, e.g., in an organ or tissue of the subject (e.g., the pulmonary system, the respiratory system, etc.).

Without wishing to be bound by theory, by targeting one or more aspects of a subject's immune response to a viral respiratory illness, oligosaccharide compositions provided herein may represent a treatment approach that is independent of specific viral strains (e.g., in contrast to viral antigen dependent treatments, such as antibody-based treatments). In some embodiments, oligosaccharide compositions provided herein are effective at modulating one or more aspects of a subject's immune response to a coronavirus, enterovirus, adenovirus, parainfluenza virus, respiratory syncytial virus, influenza virus, metapneumovirus, rhinovirus, measles virus, bocavirus or other respiratory viruses. In some embodiments, oligosaccharide compositions provided herein are effective at modulating one or more aspects of a subject's innate immune response to a respiratory virus.

In some embodiments, oligosaccharide compositions provided herein effectively reduce colonization with, prevent colonization with, or reduce the risk of an adverse effect of a pathogen to a subject having or recovering from a viral infection. In some embodiments, oligosaccharide compositions prevent a secondary pathogenic bacterial infection. In some embodiments, provided is a method of decolonizing the gastrointestinal tract (e.g., all of the GI tract or part of the GI tract, e.g. the small intestine or the large intestine) from a pathogen or an antibiotic resistance gene carrier. In some embodiments, the method comprises shifting the microbial community in the gastrointestinal tract toward a commensal population, e.g., thereby replacing (e.g. outcompeting) a pathogen or an antibiotic resistance gene carrier.

In some embodiments, provided is a method of reducing pathogen reservoir in a subject having or recovering from a viral infection by administering an oligosaccharide composition to the subject, e.g., in an effective amount and/or to a sufficient number of subjects that the pathogen reservoir is reduced. In some embodiments, the pathogen reservoir is reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100%, e.g., relative to a reference standard. In some embodiments, a pathogen reservoir may represent about 5%, about 10%, about 15%, about 20%, about 30%, about 35%, about 40%, about 45%, about 50%, about 55%, about 60%, about 65%, about 70%, about 75%, about 80%, or about 85% of the total bacterial reservoir of a subject (e.g., about 5%, about 10%, about 15%, about 20%, about 30%, about 35%, about 40%, about 45%, about 50%, about 55%, about 60%, about 65%, about 70%, about 75%, about 80%, or about 85% of the total bacterial population in the gut or intestines of a subject). In some embodiments, the pathogen reservoir comprises the pathogen biomass. In some embodiments, the bacterial reservoir comprises the total bacterial biomass.

Exemplary pathogens include Enterobacteriaciae (e.g., a family comprising *Plesiomonas, Shigella*, or *Salmonella*), *Clostridium* (e.g., a genus comprising *Clostridium difficile*), *Enterococcus, Staphylococcus* (e.g., a genus comprising *Staphylococcus aureus*), *Campylobacter, Vibrio, Aeromonas*, Norovirus, Astrovirus, Adenovirus Sapovirus, or Rotavirus.

In some embodiments, the pathogen is a carbapenem-resistant Enterobacteriaceae (CRE). In some embodiments, the pathogen is a vancomycin-resistant *Enterococcus* (VRE). In some embodiments, the pathogen is an extended-spectrum beta-lactamase (ESBL) producing organism.

In some embodiments, the pathogen includes Enterobacteriaciae (e.g., a genus comprising *Plesiomonas, Shigella*, or *Salmonella*). In some embodiments, the pathogen includes *Clostridium* (e.g., a genus comprising *Clostridium difficile*). In some embodiments, the pathogen includes *Enterococcus*. In some embodiments, the pathogen includes *Staphylococcus*.

In some embodiments, provided is a method of reducing the rate at which a pathogen causes infection or colonization in a subject having or recovering from a viral infection by administering a oligosaccharide composition to the subject, e.g., in a effective amount and/or to a sufficient number of subjects that the rate of infection is reduced. some embodiments, the oligosaccharide composition is administered in an effective amount and/or to a sufficient number of subject (s), that the rate at which a pathogen causes infection, or the severity of pathogen infection, as indicated by assessment of symptoms associated with infection, is reduced. In some embodiments, the rate of infection is reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100%, e.g., relative to a reference standard.

Reduction in the rate of infection or colonization using a method described herein may be prospective or retrospective, e.g., relative to an infection. In sore embodiments, the method described herein comprises monitoring a subject or a population of subjects for a similar infection, e.g., through observation of similar symptoms or similar features to those known to be caused by or identified with a pathogen of interest. Rather than, or in addition to using clinical characteristics, any of the methods described herein might be used to more specifically determine the type of the pathogen involved, and its relationship—if any—to spread or a reservoir.

In some embodiments, provided is a method of modulating the gastrointestinal tract (e.g., all of the GI tract or a part thereof, e.g., the small intestine, the large intestine, the colon, and the like) of a subject. In some embodiments, the method comprises modulating the environment (e.g., chemical or physical environment) of the gastrointestinal tract of a subject to make the gastrointestinal tract (and the microbial community therein) less selective or less receptive for a pathogen or an antibiotic resistance gene carrier. In some embodiments, the method further comprises administering a second agent in combination with a oligosaccharide composition, e.g., charcoal or an antibiotic-degrading enzyme (e.g., beta-lactamase), or a synbiotic (e.g., an engineered beta-lactamase (e.g., a non-infectious beta-lactamase).

In some embodiments, provided is a method of managing a secondary pathogenic bacterial infection in a subject having or recovering from a viral infection. In some embodiments, managing a secondary infection by a pathogen comprises treating, preventing, and/or reducing the risk of developing an infection by a pathogen. In some embodiments, treating a secondary infection by a pathogen comprises administering a oligosaccharide composition to a subject or population having or recovering from a viral infection.

In some embodiments, the method reduces the abundance of pathogens and increases the relative of abundance of commensal bacteria (e.g., *Parabacteroides* and *Bacteroides*), e.g., in a subject, e.g., in the gastrointestinal tract of the subject (e.g, the colon). In some embodiments, the method increases the alpha-diversity (e.g., a high degree of diversity) of a microbial community (e.g., a community of commensal bacteria), e.g., of the gut of a subject.

In some embodiments, oligosaccharide compositions are substantially fermented or consumed by commensal bacteria and are not fermented or consumed by pathogens. In some embodiments, oligosaccharide compositions are substantially fermented or consumed by commensal bacteria and are fermented or consumed by pathogens at low levels. In some embodiments, a oligosaccharide composition that is substantially consumed by commensal bacteria may increase the diversity and biomass of the commensal microbiota and lead to a reduction in the relative abundance of a pathogen(s), such as a bacterial pathogen (e.g., a pathogenic taxa). In some embodiments, a oligosaccharide composition is substantially non-fermented or not consumed by VRE or CRE species. In some embodiments, a oligosaccharide composition is substantially non-fermented or not consumed by *C. difficile*.

In some embodiments, an oligosaccharide composition supports the growth of commensal or probiotic bacteria, e.g., in a gut microbiome. In some embodiments, a oligosaccharide composition does not support the growth of at least one pathogen, e.g., does not support the growth of a CRE, VRE, and/or *C. dificile* species.

In some embodiments, administration of an oligosaccharide composition may increase the concentration, amount or relative abundance of commensal bacteria relative to pathogenic bacteria in the microbiome of a subject (e.g., a human patient). In some embodiments, administration of a oligosaccharide composition and a population of viable commensal or probiotic bacteria may increase the concentration, amount, or relative abundance of commensal bacteria relative to pathogenic bacteria in the microbiome of a subject (e.g., a human patient). In some embodiments, administration of a oligosaccharide composition that supports the growth of commensal or probiotic bacteria, e.g., in a gut microbiome, may increase the concentration, amount or relative abundance of commensal bacteria relative to pathogenic bacteria in the microbiome of a subject (e.g., a human patient). In some embodiments, administration of a oligosaccharide composition that does not support the growth of at least one pathogen, e.g., does not support the growth of a CRE, VRE, and/or *C. dificile* species, e.g., in a gut microbiome, may increase the concentration, amount or relative abundance of commensal bacteria relative to pathogenic bacteria in the microbiome of a subject (e.g., a human patient). In some embodiments, administration of a oligosaccharide composition that supports the growth of commensal or probiotic bacteria and does not support the growth of at least one pathogen, e.g., does not support the growth of a CRE, VRE, and/or *C. difficile* species, e.g., in a gut microbiome, may increase the concentration, amount or relative abundance of commensal bacteria relative to pathogenic bacteria in the microbiome of a subject (e.g., a human patient).

In some embodiments, administration of an oligosaccharide composition may increase the concentration, amount or relative abundance of *Bacteroidetes* (e.g., *Bacteroidales*) relative to pathogenic bacteria in the microbiome of a subject (e.g., a human patient).

In some embodiments, administration of an oligosaccharide composition may increase the concentration, amount or relative abundance of *Parabacteroides* (e.g., *Parabacteroides distasonis* and *Parabacteroides merdae*) and *Bacteroides* (e.g., *Bacteroides thetaiotaomicron, Bacteroides uniformis, Bacteroides caccae*) relative to pathogenic bacteria in the microbiome of a subject (e.g., a human patient).

In embodiments, an oligosaccharide composition described herein is co-administered with commensal or probiotic bacterial taxa and bacteria that are generally recognized as safe (GRAS) or known commensal or probiotic microbes In some embodiments, probiotic or commensal bacterial taxa (or preparations thereof) may be administered to a subject before or after administration of an oligosaccharide composition to the Subject. In some embodiments, probiotic or commensal bacterial taxa (or preparations thereof) may be administered to a subject simultaneously with administration of an oligosaccharide composition to the subject.

In embodiments, an oligosaccharide composition described herein is administered with a population of *Bacteroidetes*. In embodiments, an oligosaccharide composition described herein is administered with a population of *Bacteroidales*.

A commensal or probiotic bacteria is also referred to a probiotic. Probiotics can include the metabolites generated by the probiotic bacteria during fermentation. These metabolites may be released to the medium of fermentation, e.g., into a host organism (e.g., subject), or they may be stored within the bacteria. Probiotic bacteria includes bacteria, bacterial homogenates, bacterial proteins, bacterial extracts, bacterial ferment supernatants and combinations thereof, which perform beneficial functions to the host animal, e.g., when given at a therapeutic dose.

Useful probiotics include at least one lactic acid and/or acetic acid and/or propionic acid producing bacteria, e.g., microbes that produce lactic acid and/or acetic acid and/or propionic acid by decomposing carbohydrates such as glucose and lactose. Preferably, the probiotic bacteria is a lactic acid bacterium. In embodiments, lactic acid bacteria include *Lactobacillus, Leuconostoc, Pediococcus, Streptococcus*, and *Bifidobacterium*. Suitable probiotic bacteria can also include other bacterias which beneficially affect a host by improving the hosts intestinal microbial balance, such as, but not limited to yeasts such as *Saccharomyces, Debaromyces, Candida, Pichia* and *Torulopsis*, molds such as *Aspergillus, Rhizopus, Mucor*, and *Penicillium* and *Torulopsis*, and other bacteria such as but not limited to the genera *Bacteroides, Clostridium, Fusobacterium, Melissococcus, Propionibacterium, Enterococcus, Lactococcus, Staphylococcus, Peptostreptococcus, Bacillus, Pediococcus, Micrococcvs, Leuconostoc, Weissella, Aerococcus*, and *Oenococcus*, and combinations thereof. In some embodiments, probiotic organisms include *Parabacteroides* and *Bacteroides*.

The commensal or probiotic bacteria can be used as a single strain or a combination of multiple strains, wherein the total number of bacteria in a dose of probiotic bacteria is from about $1\times10^3$ to about $1\times10^{14}$, or from about 1×10 to about $1\times10^{12}$, or from about $1\times10^7$ to about $1\times10^{11}$ CFU per dose.

The probiotic bacterias can be used in a powdered, dry form. The probiotic bacterias can also be administered in the oligosaccharide composition or in a separate oligosaccharide composition, administered at the same time or different time as the oligosaccharide compositions.

In some embodiments, a subject having a viral respiratory illness treated by a method described herein further has at least one comorbidity condition. As used herein, a comorbidity condition refers to a medical or health condition (e.g., a disease, disorder, syndrome, or previously resolved version of any of the preceding; or a medical operation (e.g., surgery)), past or present, that may detrimentally affect a subject's prognosis regarding a present or future illness (e.g., a viral respiratory infection, e.g., a coronavirus infection (e.g., COVID-19)). Without wishing to be bound by theory, a subject having at least one comorbidity condition is thought to be at greater risk of more severe and/or more prolonged symptoms of infection, as well as greater risk of adverse effects after recovery from infection. In s me embodiments, the presence of one or more comorbidity conditions in a subject lengthens the time to resolution of symptoms of a viral respiratory illness (e.g., the median time to resolution of symptoms in a population of subjects). In some embodiments, comorbidity conditions include chronic lung disease (e.g., asthma, emphysema, or chronic obstructive pulmonary disease (COPD)), diabetes mellitus, cardiovascular disease, hypertension, renal disease (e.g., chronic renal disease), liver disease (e.g., chronic liver disease), an immunocompromised condition, cancer, a neurologic disorder, stroke, being overweight, obesity, or other chronic disease. In some embodiments, a subject has at least one, two, or at least three comorbidity conditions. In some embodiments, a subset of the comorbidity conditions described herein are considered high-risk comorbidities, which carry a higher risk of more severe and/or more prolonged symptoms of infection relative to other comorbidities, as well as greater risk of adverse effects after recovery from infection relative to other comorbidities. In some embodiments, high-risk comorbidities include chronic lung disease (e.g., asthma, emphysema, or COPD), diabetes mellitus, cardiovascular disease, hypertension, chronic renal disease, or cancer. In other embodiments, subject having a viral respiratory illness treated by a method described herein does not have a comorbidity condition (e.g., and still benefits from treatment with a method or oligosaccharide composition described herein).

In some embodiments, being overweight or obese is expressed by body mass index (BMI). In some embodiments, an overweight subject has a BMI of at least 25, 26, 27, 28, or 29, and optionally less than 30, e.g., 25-29.9. In some embodiments, an obese subject has a BMI of at least 30, 31, 32, 33, 34, 35, 36, 37, 38, 39, or 40, e.g., at least 30 or at least 35.

In some embodiments, a subject having a viral respiratory illness treated by a method described herein is middle-aged, senior, or elderly. Such subjects are referred to herein as having an age-related risk factor. Without wishing to be bound by theory, subjects having an age-related risk factor are thought to be at greater risk of more severe and/or more prolonged symptoms of viral respiratory illness, as well as greater risk of adverse effects after recovery from illness. In some embodiments, a subject having an age-related risk factor is at least 40, 45, 50, 55, 60, 65, 70, 75, or 80 years old, e.g., at least 45, 55, or 65 years old. In some embodiments, oligosaccharide compositions provided herein effectively reduce one or more symptoms of a viral respiratory illness or reduce the time to resolution of one or more symptoms (e.g., the average time) in a subject having an age-related risk factor (e.g., a subject who is at least 45 years old). In some embodiments, a subject having an age-related risk factor is at a greater risk of more severe and/or more prolonged symptoms of viral respiratory illness, as well as greater risk of adverse effects after recovery from illness, where the viral respiratory illness is a rhinovirus, influenza, or coronavirus (e.g., COVID19) infection.

In some embodiments, a subject having a viral respiratory illness treated by a method described herein is a young child or an infant (e.g., less than 48, 36, 24, 12, 11, 10, 9, 8, 7, 6, 5, 4, 3, 2, or 1 month(s) in age). In some embodiments, a young child or an infant is at a greater risk of more severe and/or more prolonged symptoms of viral respiratory illness, as well as greater risk of adverse effects after recovery from illness. In some embodiments, the viral respiratory illness is an respiratory syncytial virus (RSV) infection. This disclosure is directed, in part, to a method of treating a young child or infant prophylactically against a viral respiratory illness (e.g., an RSV infection), comprising administering to the gastrointestinal tract of the young child or infant an effective amount of an oligosaccharide composition provided herein (e.g., in addition to or in combination with a standard of care treatment or prevention measure).

In some embodiments, a subject having a viral respiratory illness treated by a method described herein is immunocompromised. An immunocompromised subject refers to any subject whose immune system is less able or unable to combat infection relative to a non-immunocompromised subject. In some embodiments, an immunocompromised subject is a cancer patient, a transplant recipient (e.g., a previous or future transplant recipient), and/or undergoing chemotherapy, radiation therapy or other therapy associated with immune suppression. In some embodiments, an immunocompromised subject is unable to receive a vaccine against a viral respiratory illness (e.g., a COVID19 vaccine or f u vaccine). Without wishing to be bound by theory, the immune system modulating properties of the oligosaccharide compositions provided herein, their antigen non-specific mode of action, and some immunocompromised subjects' decreased ability to fight viral infections or receive vaccines against viral infections may increase the benefit immunocompromised subjects receive from treatment with the oligosaccharide compositions provided herein.

In some embodiments, oligosaccharide compositions provided herein effectively reduce one or more symptoms of a viral respiratory illness or reduce the time to resolution of one or more symptoms (e.g., the average time) in a high risk subject. As used herein, a high risk subject has one, two, or all of: i) an age-related risk factor, ii) at least one comorbidity, or iii) is overweight or obese. In some embodiments, the at least one comorbidity is a high-risk comorbidity. In some embodiments, the age-related risk factor comprises being at least 45 years old. In some embodiments, being overweight or obese comprises having a BMI of at least 25 (overweight) or at least 30 (obese), e.g., a BMI of at least 35. In some embodiments, a high risk subject has two or three of i) an age-related risk factor (e.g., is at least 4 years old), ii) at least one comorbidity (e.g., a high-risk comorbidity), and/or iii) is overweigh or obese (e.g., has a BMI of at least 35). In a high risk subject having at least two of (i)-(iii), here one of the two factors is (iii) and the other is (ii), (ii) is not being overweight or obese. In some embodiments, a method or oligosaccharide composition described herein reduces the severity of a symptom of a viral respiratory illness or reduces the time to resolution of symptoms of a viral respiratory illness, e.g., when compared to no treatment or when compared to treatment with other drugs or therapies directed at viral illnesses, e.g., a antiviral drug or therapy alone, e.g., without combining these treatments with the method or oligosaccharide composition described herein. In some embodiments, administering an oligosaccharide composition described herein has a lower risk of adverse side effects in a subject than a drug or therapy directed at viral illnesses, e.g., an antiviral drug or therapy. For example, remdesivir is a broad-spectrum antiviral drug which has been used in the treatment of COVID-19. However, remdesivir can cause side effects, including acute kidney injury. In some embodiments, a method or oligosaccharide composition described herein is at least as effective as remdesivir at reducing the severity of a symptom of a viral respiratory illness or reducing the time to resolution of symptoms of a viral respiratory illness.

In some embodiments, a method of treating a viral respiratory illness described herein comprises administering an oligosaccharide composition provided herein to the gastrointestinal tract of a subject, and in addition or in combination administering an additional anti-viral therapy or drug. In some embodiments, the additional anti-viral therapy or drug comprises one or more antibodies (e.g., monoclonal antibodies (mAbs), e.g., an antibody cocktail, e.g., neutralizing antibodies) against an antigen(s), e.g., of the virus associated with the viral respiratory illness. For example, REGN-COV2 is an antibody cocktail drug for treating COVID19 infection. Palivizumab is a monoclonal antibody for preventing RSV infections in children. mAbs have been developed against the hemagglutinin (HA) glycoprotein of influenza virus. In some embodiments, the additional anti-viral therapy or drug is interfering with the viral life cycle, such as, e.g., nucleoside analogs/antimetabolites, with activity against RNA or DNA viruses. For example, ribavirin is used in RSV infections. In some embodiments, the additional anti-viral therapy or drug is administered intravenously. In some embodiments, the additional anti-viral therapy or drug is administered by subcutaneous injection. Without wishing to be bound by theory, administering an oligosaccharide composition provided herein that modulates one or more aspects of a subject's immune response to a viral respiratory illness in addition to or in combination with an additional anti-viral therapy or drug may more effectively treat a viral respiratory illness than either oligosaccharide composition or anti-viral therapy or drug administered individually. In some embodiments, treatment with an oligosaccharide composition provided herein in addition to or in combination with an additional anti- viral therapy or drug may reduce the severity of a symptom of a viral respiratory illness or reduces the time to resolution of symptoms of a viral respiratory illness, e.g., when compared to treatment with oligosaccharide composition or drug/therapy individually. The treatment regimen may comprise administering the oligosaccharide composition provided herein and the additional anti-viral therapy or drug in any suitable order including concurrently or sequentially.

In some embodiments, a method of treating a viral respiratory illness described herein comprises administering an oligosaccharide composition provided herein to the gastrointestinal tract of a subject, and in addition or in combination administering an additional immunomodulating drug. In some embodiments, the additional immunomodulating drug is an anti-inflammatory agent. In some embodiments, the additional immunomodulating drug is a corticosteroid, e.g., budesonide, hydrocortisone, cortisone, bethamethasone, prednisone, or triamcinolone. In some embodiments, the additional immunomodulating drug is self-administered, e.g., at home. In some embodiments, the additional immunomodulating drug is administered as an inhalant. Without wishing to be bound by theory, administering an oligosaccharide composition provided herein that modulates one or more aspects of a subject's immune response to a viral respiratory illness in addition to or in combination with an additional immunomodulating drug may more effectively treat a viral respiratory illness than either oligosaccharide composition or immunomodulating drug administered individually. In some embodiments, treatment with an oligosaccharide composition provided herein in addition to or in combination with an additional immunomodulating drug may reduce the severity of a symptom of a viral respiratory illness or reduces the time to resolution of symptoms of a viral respiratory illness, e.g., when compared to treatment with oligosaccharide composition or drug/therapy individually. In some embodiments, both the oligosaccharide composition and the additional immunomodulating drug can be self-administered, e.g., at home or at a point of care site. The treatment regimen may comprise administering the oligosaccharide composition provided herein and the additional immunomodulating drug or therapy in any suitable order including concurrently or sequentially.

IV. Kits

Kits also are contemplated. For example, a kit can comprise unit dosage forms of the oligosaccharide composition, and a package insert containing instructions for use of the composition in treatment. In some embodiments, the composition is provided in a dry powder format. In some embodiments, the composition is provided in solution. The kits include an oligosaccharide composition in suitable packaging for use by a subject in need thereof. Any of the compositions described herein can be packaged in the form of a kit. A kit can contain an amount of an oligosaccharide composition sufficient for an entire course of treatment, or for a portion of a course of treatment. Doses of an oligosaccharide composition can be individually packaged, or the oligosaccharide composition can be provided in bulk, or combinations thereof. Thus, in one embodiment, a kit provides, in suitable packaging, individual doses of an oligosaccharide composition that correspond to dosing points in a treatment regimen, wherein the doses are packaged in one or more packets.

Kits can further include written materials, such as instructions, expected results, testimonials, explanations, warnings, clinical data, information for health professionals, and the like. In one embodiment, the kits contain a label or other information indicating that the kit is only for use under the direction of a health professional. The container can further include scoops, syringes, bottles, cups, applicators or other measuring or serving devices.

EXAMPLES

Example 1. Production of the Selected Oligosaccharide Composition at 10 kg Scale from Dextrose Monohydrate, Galactose and Mannose Using a Solid Polymeric Catalyst A "selected oligosaccharide composition" was identified in a screen of hundreds of different oligosaccharide compositions for its ability to effectively and consistently stimulate the production of short-chain fatty acids, namely butyrate, propionate, a d acetate, in the microbiome residing in fecal communities of multiple healthy subjects.

A procedure was developed for the synthesis of the selected oligosaccharide composition at a 10 kilogram scale. 4.46 kg of dextrose monohydrate, 4.05 kg of galactose, 0.90 kg of mannose, and 0.90 kg (0.450 kg on a dry solid basis) of pre-conditioned solid polymeric acid catalyst (Dowex® Marathon® C resin) were added to a reaction vessel (22 L Littleford-Day horizontal plow mixer) with an attached distillation condenser unit.

The temperature controller was set to 140° C., and stirring (agitation) of the contents of the vessel at 30 RPM was initiated to promote uniform heat transfer and melting of the sugar solids, as the temperature of the syrup was brought to approximately 140° C., under ambient (atmospheric) pressure gradually over a 2.5 hour period.

The reaction mixture was maintained at temperature of approximately 140° C. for 1.5 hours (90 min), after which the heating was stopped and pre-heated water was gradually added to the reaction mixture at a rate of 60 mL/min until the temperature of the reactor contents decreased to 120° C., then at a rate of 150 mL/min until the temperature of the reactor contents decreased to 110° C., and then at a rate of 480 mL/min until the temperature of the reactor contents decreased below 100° C. and a total of 6 kg of water was added. An additional 1.75 kg of water was added to the reactor for further dilution.

The reaction mixture was drained from the vessel and the solids were removed by filtration, resulting in 15 kg of crude oligosaccharide composition product material as an aqueous solution (approximately 45 wt %).

The oligosaccharide composition composition was purified by flowing it through a cationic exchange resin (Dowex® Monosphere® 8811) column, two columns of decolorizing polymer resin (Dowex® OptiPore® SD-2), and an anionic exchange resin (Dowex® Monosphere®77WBA) column. The resulting purified oligosaccharide composition had a concentration of about 35 wt % and was then concentrated to a final concentration of about 75 wt % solids by vacuum rotary evaporation.

Example 2. Production of the Selected Oligosaccharide Composition at 10 kg Scale from Dextrose Monohydrate, Galactose and Mannose Using a Citric Acid Catalyst A procedure was developed for the synthesis of the selected oligosaccharide composition at a 10 kilogram scale. 4.46 kg of dextrose monohydrate, 4.05 kg of galactose, 0.90 kg of mannose, 0.29 kg citric acid monohydrate acid catalyst (or 0.27 k citric acid anhydrous) and 0.48 kg water were added to a reaction vessel (22L Littleford-Day horizontal plow mixer). A distillation condenser unit was attached to the reactor.

The contents were agitated at approximately 30 RPM and the vessel temperature was gradually increased over a 2.5 hour period to about 139° C. at atmospheric pressure. The mixture was maintained at temperature for one and half hours. The heating was subsequently stopped and pre-heated water was gradually added to the reaction mixture at a rate of 60 mL/min until the temperature of the reactor contents decreased to 120° C., then al 150 mL/min until the temperature of the reactor contents decreased to 110° C., then at 480 mL/min until a total of 6 kg of water was added, and the temperature of the reactor contents decreased below 100° C. An additional 1.75 kg water was added to the reactor for further dilution. The reaction mixture was drained from the vessel, resulting in 15 kg of crude oligosaccharide composition product as an aqueous solution (approximately 53 wt %).

Example 3. Production of Oligosaccharide Composition at 100 g Scale from Dextrose Monohydrate, Galactose and Mannose Using a Solid Polymeric Catalyst A procedure was developed for the synthesis of the selected oligosaccharide composition at a 100 gram scale. 45 g of dextrose monohydrate, 45 g of galactose, 10 g of mannose were added to a reaction vessel (1 L three-neck round-bottom flask). The reaction vessel was equipped with a heating mantle configured with an overhead stirrer. A probe thermocouple was disposed in the vessel through a septum, such that the probe tip sat above the stir blade and not in contact with the walls of the reaction vessel.

The procedure also used an oligomerization catalyst (Dowex Marathon C) (3-5% w/w) and de-ionized water for quenching. In some cases, the catalyst was handled in wet form, e.g., at a nominal moisture content of 45-50 wt % $H_2O$. The exact catalyst moisture content was generally determined on a per-experiment basis using, for example, using a moisture analyzing balance (e.g., Mettler-Toledo MJ-33).

The temperature controller was set to a target temperature (100 to 160° C.), and stirring of the contents of the vessel was initiated to promote uniform heat transfer and melting of the sugar solids, as the temperature of the syrup was brought to the target temperature, under ambient (atmospheric) pressure.

Upon addition of the catalyst, the reaction was maintained at the target temperature under continuous mixing for about 4 hours, determined by following the reaction by HPLC. Next, the heat was turned off while maintaining constant stirring.

The reaction was then quenched by slowly adding approximately 60 mL of hot (~80° C.) deionized (DI) water to dilute and cool the product mixture, to target a final concentration of 70 wt % dissolved solids. Generally, the water addition rate was performed to control the mixture viscosity as the oligosaccharide composition was cooled and diluted.

Following dilution, the oligosaccharide composition was cooled to approximately 60° C. The catalyst was then removed by vacuum filtration through a 100 micron mesh screen or fritted-glass filter, to obtain the final oligosaccharide composition at aro and 40° Bx.

Example 4. De-Monomerization Procedure

Individual batches of oligosaccharide composition, as produced in Examples 1-3 were concentrated on a rotatory evaporator to approximately 50 Brix as measured by a Brix refractometer. The resulting syrup (200 mg) was loaded onto a Teledyne ISCO RediSep Rf Gold Amine column (11 grams stationary phase) using a luer-tip syringe. Other similar columns such as the Biotage SNAP KP-NH Catridges may also be used. The sample was purified on a Biotage Isolera equipped with an ELSD detector using a 20/80 to 50/50 (v/v) deionized water/ACN mobile phase gradient over 55 column volumes. Other flash chromatography systems such as the Teledyne ISCO Rf may also be used. The flow rate was set in accordance with the manufacturer's specifications for the column and system. After the monomer fraction completely eluted at ~20 column volumes, the mobile phase was set to 100% water until the remainder of the oligosaccharide composition eluted and was collected. The non-monomer containing fractions were concentrated by rotary evaporation to afford the de-monomerized product.

Example 5. Collection of Fecal Samples

Fecal samples were collected by providing subjects with the Fisherbrand Commode Specimen Collection System (Fisher Scientific) and associated instructions for use. Collected samples were stored with ice packs or at −80° C. until processing (McInnes & Cutting, Manual of Procedures for Human Microbiome Project: Core Microbiome Sampling Protocol A, 2010, hmpdacc.org/doc/HMP_Clinical_Protocol.pdf). Alternative collection devices may also be used. For example, samples may be collected into the Faeces Tube 54×28 mm (Sarstedt A G, 25 ml SC Feces Container w/Scoop), Globe Scientific Screw Cap Container with Spoon (Fisher Scientific) or the OMNIgene-GUT collection system (DNA Genotek, Inc.), which stabilizes microbial DNA for downstream nucleic acid extraction and analysis. Aliquots of fecal samples were stored at −20° C. and −80° C. following standard protocols known to one skilled in the art.

Example 6. The Selected Oligosaccharide Composition Increases SCFA Production in Fecal Suspensions from Healthy Subjects The ability of the selected oligosaccharide composition comprised of a plurality of oligosaccharides selected from Formula (I), Formula (II), and Formula (III) as produced by a similar process as described in Examples 1-3 to increase the production of short-chain fatty acids (SCFAs) in fecal suspensions of healthy subjects was assessed.

Fecal samples were collected from healthy subjects and stored at −80° C. All fecal sample preparation was performed in a Coy anaerobic chamber. Fecal samples were thawed, 20% (w/v) fecal suspensions were prepared in phosphate-buffered saline (PBS) supplemented with 15% glycerol, dispensed into 1 ml aliquots, and stored at −80° C. 1 ml aliquots of 20% (w/v) fecal suspensions were thawed and sedimented at sedimented by centrifugation 2,000×g for 5 minutes. The supernatants were aspirated and discarded. The fecal pellets were resuspended in 1 ml of PBS. 1% (w/v) fecal suspensions were prepared by adding 12.5 ml of 20% fecal suspension to 237.5 ml of *Clostridium* minimal medium supplemented with 0.1% (w/v) trypticase peptone and 0.75 mM urea. 315 μl of the 1% fecal suspensions were dispensed into the wells of 96-well deep well plates containing 35 μl of water (negative control) or 5% (w/v) oligosaccharide solutions (final oligosaccharide concentration of 0.5%). Three replicates of each sample were prepared. Fecal microbial cultures were incubated anaerobically at 37° C. for 45 hours.

After the 45-hour incubation period, the 96-well deep well plates containing the fecal microbial cultures were removed from the Coy anaerobic chamber and kept on ice. The plates were sedimented by centrifugation (3,000×g) for 10 minutes at 4° C. Fecal microbiota culture supernatants were collected and stored at −80° C. Supernatant samples were thawed and analyzed by gas chromatography with a flame ionization detector (GC-FID) to quantify the short-chain fatty acids (acetate, propionate, and butyrate). Normalized CFA concentrations were calculated by subtracting the value with the negative control (wat r without oligosaccharide) from oligosaccharide composition treatment. This normalized value represents the concentration of SCFA derived from fermentation of the selected oligosaccharide composition. The median normalized SCFA concentrations were determined for each set of three sample replicates.

Figure 2:
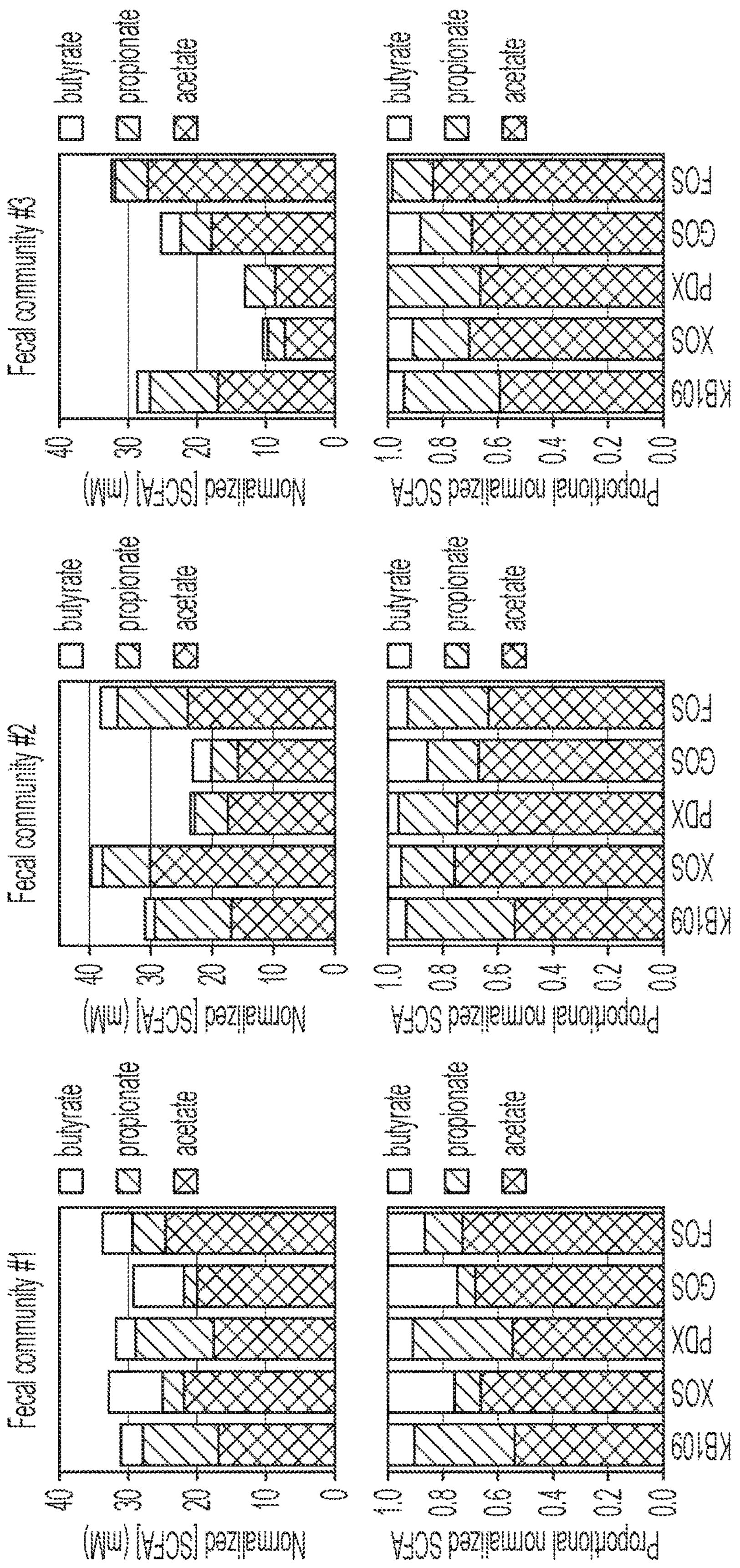
FIG. 2 provides graphs showing the amounts (in mM) of acetate, propionate, and butyrate produced in fecal samples incubated with either the selected oligosaccharide composition or a commercial oligosaccharide selected from xylooligosaccharides (XOS), polydextrose (PDX), galactooligosaccharides (GOS), and fructooligosaccharides (FOS). The selected oligosaccharide provides highly consistent and robust results across the three tested fecal communities, particularly in comparison to the commercial oligosaccharides.
Figure 3:
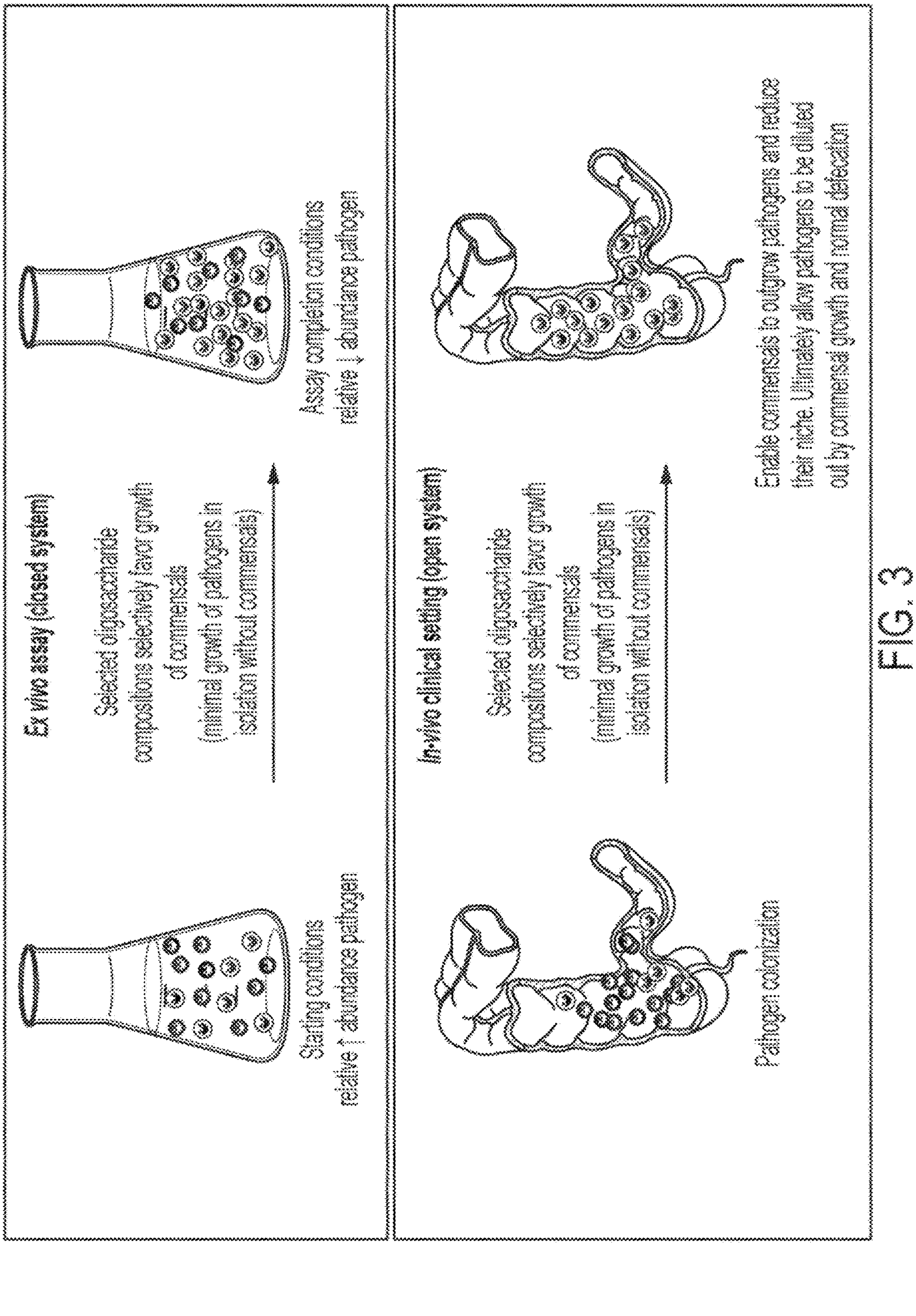
FIG. 3 depicts exemplary uses of oligosaccharide compositions to reduce the colonization of pathogens in an ex vivo assay (closed system) and an in vivo clinical setting (open system).

Three different fecal microbiota from healthy subjects were incubated with 0.5% (w/v) of the selected oligosaccharide composition or one of four different commercial oligosaccharides. Following the incubation, the concentration of three different SCFAs (acetate, propionate, and butyrate) were measured in the fecal microbiota culture supernatants by gas chromatography-flame ionization detection (GC-FID). Incubation with the selected oligosaccharide composition resulted in the production of between 28 and 32 mM total SCFA across the three fecal communities (FIG. 2). In addition to consistent total SCFA production across the fecal communities, the selected oligosaccharide composition also produced consistent proportions of acetate, propionate, and butyrate, with 54-60% acetate, 34-40% propionate, and 6-10% butyrate. Conversely, the commercial oligosaccharides (xylo-oligosaccharide (XOS), polydextrose (PDX), and galacto-oligosaccharide (GOS)) produced less consistent total SCFA concentrations than the selected oligosaccharide composition. Although total SCFA production with fructo-oligosaccharide (FOS) was consistent, the relative proportions of individual SCFAs (acetate, propionate, butyrate) were less consistent. This inconsistency i most apparent with the butyrate proportions. FOS produced 13% butyrate in first fecal community, 7% in the second, and only 2% in the third. These data collectively demonstrate that the selected oligosaccharide composition robustly and consistently increases total SCFA while maintaining a consistent ratio of acetate:propionate:butyrate.

Figure 1B:
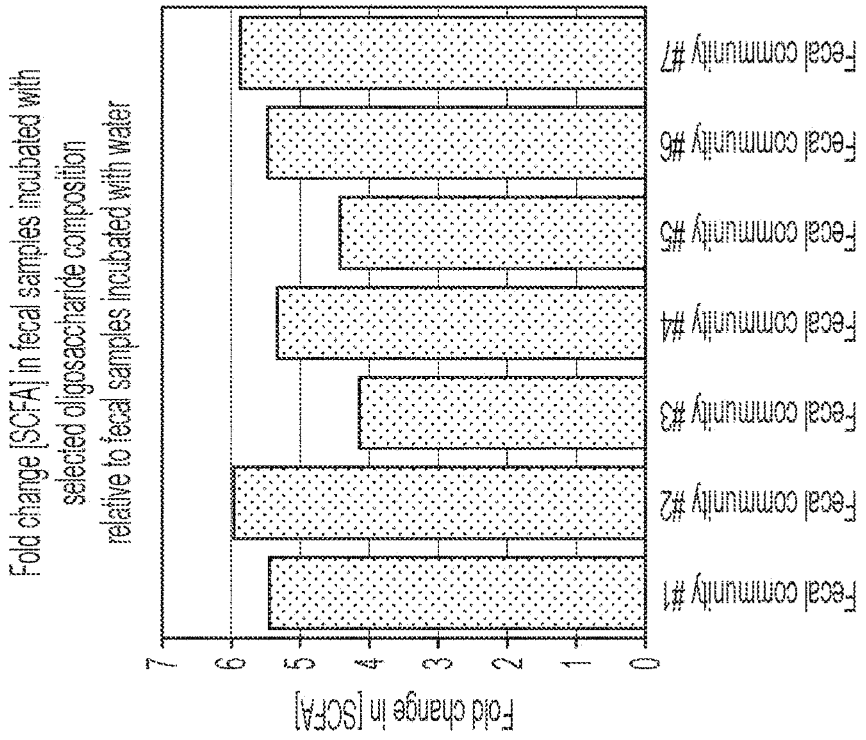

Additionally, seven different fecal microbiota from health y subjects were incubated with the selected oligosaccharide composition. The selected oligosaccharide composition increased the production of SCFA between 4-fold and 6-fold compared to the negative control across the seven fecal communities (FIGS. 1A-1B). These data further demonstrate that the selected oligosaccharide composition robustly and consistently increases total SCFA while maintaining a consistent ratio of acetate:propionate:butyrate across seven different fecal communities.

Example 7. Reduction of Pathogen Growth and Abundance in the Presence of the Selected Oligosaccharide Composition in Cultures of Single Pathogen Strains The selected oligosaccharide composition comprised of a plurality of oligosaccharides selected from Formula (I), Formula (II), and Formula (III) and produced by a similar process as described in Examples 1-3 was further tested for its ability to reduce growth and abundance of single strains of pathogens that frequently encountered in critically ill and immunocompromised patients.

Three Nap1 strains of *C. difficile* and one *C. difficile* strain from ribotype 012 were obtained from the ATCC® (ATCC® BAA-1870™, ATCC® BAA-1803™, ATCC® BAA-1805™, and ATCC® BAA-1382™). Each strain was grown anaerobically in CM media at 37° C. for 24 hours until each strain achieved an optical density ($OD_{600}$) of about 1. Each culture was adjusted to an $OD_{600}$ of 0.01 and then incubated with glucose or a sample of the selected oligosaccharide composition. Water was added to media without any added carbon source as a negative control. The final concentration of glucose or the selected oligosaccharide composition in each assay was 0.5% w/v and each assay was replicated 3 times within each growth plate. Plates were incubated at 37° C. in an anaerobic chamber for a total of 48 hours. Optical density was determined for each strain every 15 minutes for 48 hours.

Figure 8:
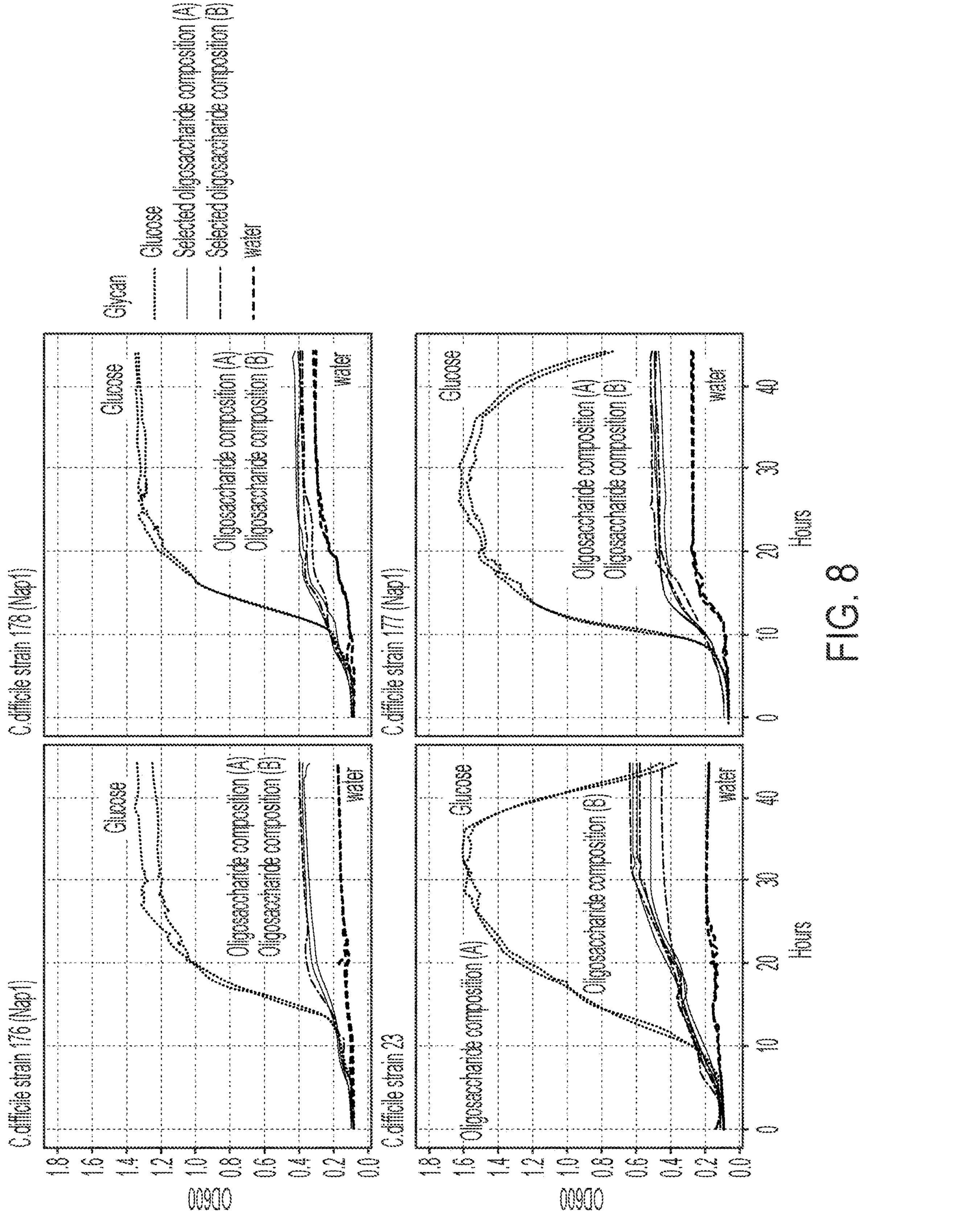
FIG. 8 provides graphs showing reduction in pathogen growth in cultures of single pathogen strains (*Clostridium difficile* strains) incubated in the presence of samples of the selected oligosaccharide composition.

The *C. difficile* strains tested grew minimally on the oligosaccharide compositions, as did the strains grown in the presence of water (FIG. 8). Meanwhile, each of the *C. difficile* strains grew to high $OD_{600}$ in the presence of glucose.

The selected oligosaccharide composition was further tested for its ability to reduce the growth and abundance of individual strains of CRE *Escherichia coli*, CRE *Klebsiella pneumoniae*, and VRE *E. faecium*. Single strains of *E. coli* (one strain obtained from the CDC's Enterobacteriaceae-carbapenem-breakpoint panel, the other isolated from a patient) and *K. pneumoniae* (one strain from CDC panel, the other isolated from a patient) were grown in isolation overnight in CM media with 0.5% D-glucose in a COY anaerobic chamber. Single strains of *E. faecium* (ATCC 700221 and 2 strains isolated from patients were grown in isolation overnight in MM media with 0.5% D-glucose in a COY anaerobic chamber. The media was filter sterilized using a 0.2 μm filter and stored in an anaerobic chamber prior to use to allow any dissolved oxygen to dissipate. 1 mL of each overnight culture was washed with PBS and the $OD_{600}$ of each culture was measured. Each culture was adjusted to an $OD_{600}$ of 0.01 and then incubated with glucose, fructooligosaccharide (FOS), or a sample of the selected oligosaccharide composition. Water was added to media without any added carbon source as a negative control. The final concentration of glucose, FOS, or the selected oligosaccharide composition in each assay was 0.5% w/v and each assay was replicated 3 times within each growth plate. Plates were incubated at 37° C. in an anaerobic chamber for a total of 45 hours. Optical density was determined for each strain every 15 minutes for 48 hours.

Figure 5:
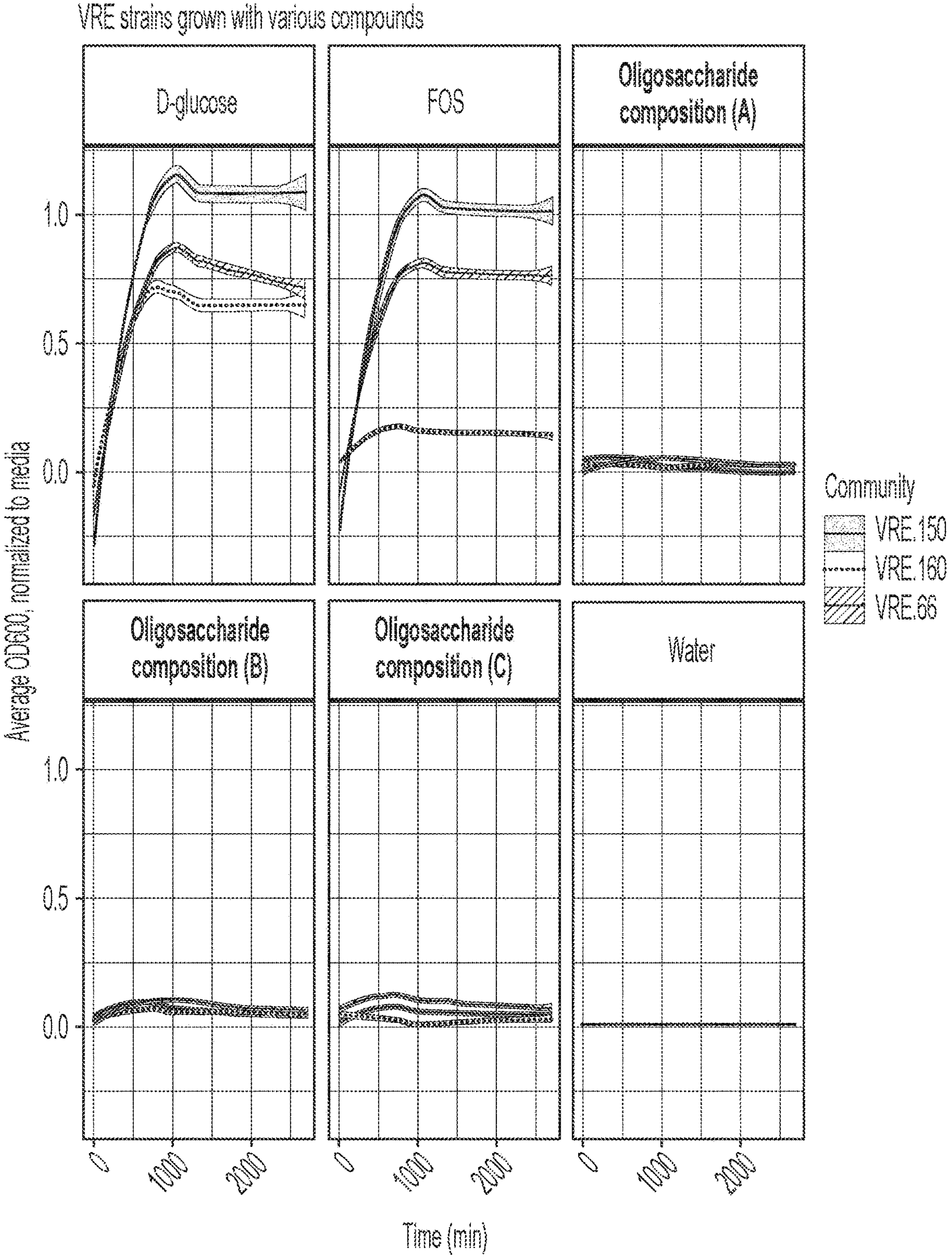
FIG. 5 provides graphs showing reduction in pathogen growth in cultures of single pathogen strains (VRE *Enterococcus faecium*) incubated in the presence of samples of the selected oligosaccharide composition.
Figure 6:
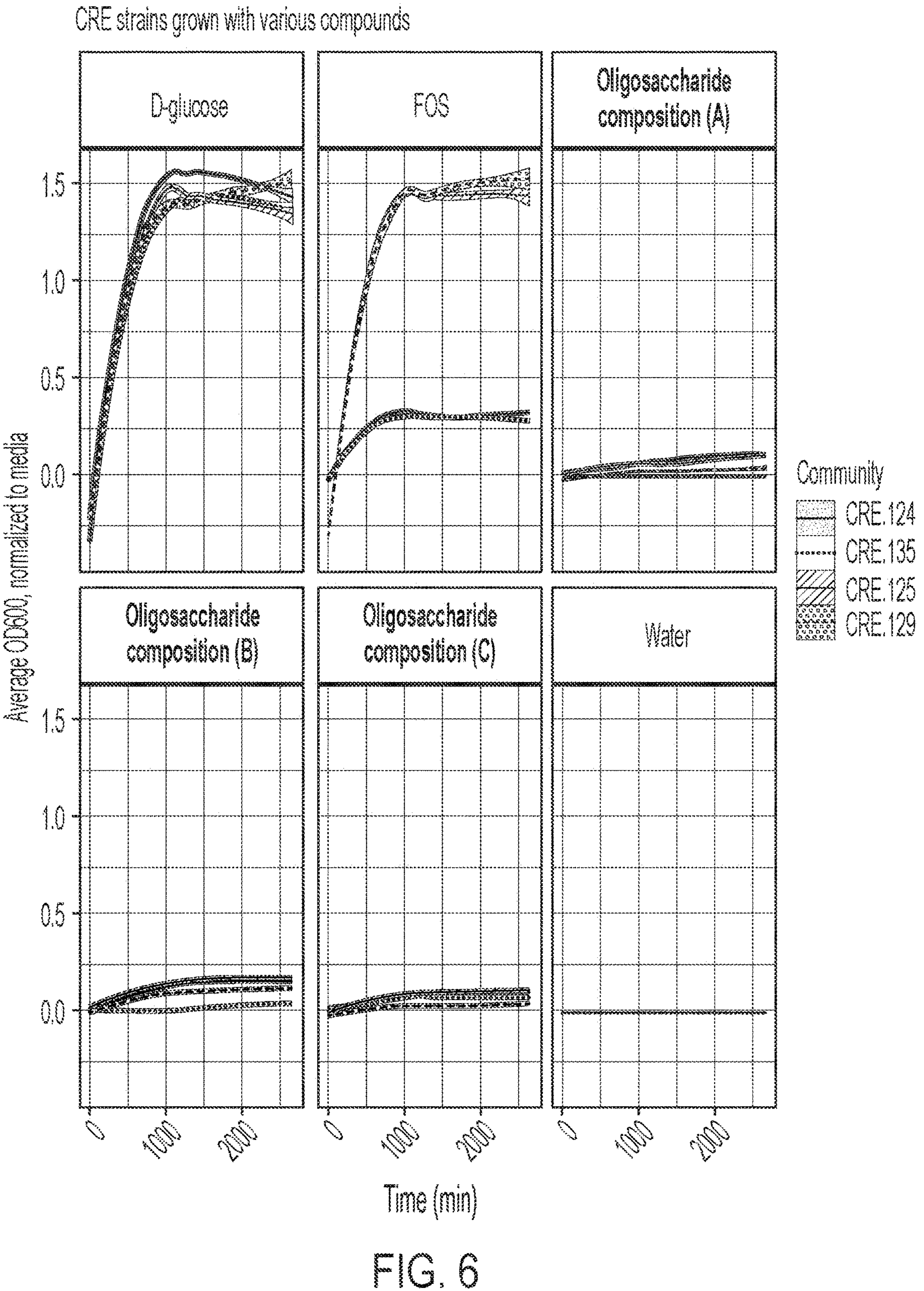
FIG. 6 provides graphs showing reduction in pathogen growth in cultures of single pathogen strains (CRE *Escherichia coli*, CRE *Klebsiella pneumoniae*) incubated in the presence of samples of the selected oligosaccharide composition.

The VRE and CRE pathogens exhibited little-to-no growth in the presence of samples of the selected oligosaccharide composition, similar to the growth of pathogens in the presence of the water control (FIG. 5 and FIG. 6).

The selected oligosaccharide composition was tested for its ability to reduce the growth and abundance of individual strains of fungal pathogens (*Candida albicans, Candida glabrata, Candida krusei*, and *Candida tropicalis*). Each of four strains of *Candida albicans, Candida glabrata, Candida krusei*, and *Candida tropicalis* were obtained from ATCC (ATCC MYA-2950, ATCC 14243, ATCC 201380 and ATCC MYA-2876). Additional strains of *Candida lusitaniae* (ATCC 66035 and ATCC 42720) were also tested. All *Candida* strains were grown aerobically in modified Sabouraud broth (10 g/L peptone solution) with glucose at 2% final concentration at 37° C. for 24 hours until each strain achieved optical density ($OD_{600}$) of about 1. 200 μL of each culture was diluted in 3 mL of modified Sabouraud broth and 120 μL was added to each well of a 96 well plate containing 80 μL of one of the following 5% w/v solutions per well: glucose, FOS, or a sample of the selected oligosaccharide composition. Water was used as a negative control. The final concentration of glucose, FOS, or the selected oligosaccharide composition in each assay to test *Candida albicans, Candida glabrata, Candida krusei*, or *Candida tropicalis* was 2%, each assay was replicated 3 times, and plates were incubated at 37° C. for a total of 65 hours. The final concentration of glucose, FOS, or the selected oligosaccharide composition in each assay to test *Candida lusitaniae* strains was 0.5%, each assay was replicated 3 times, and plates were incubated at 37° C. for a total of 48 hours. Optical density data was collected for each of the *Candida albicans, Candida glabrata, Candida krusei*, or *Candida tropicalis* strains every 15 minutes; optical density data was collected for the *Candida lusitaniae* strains at the end of the experiment.

Figure 9:
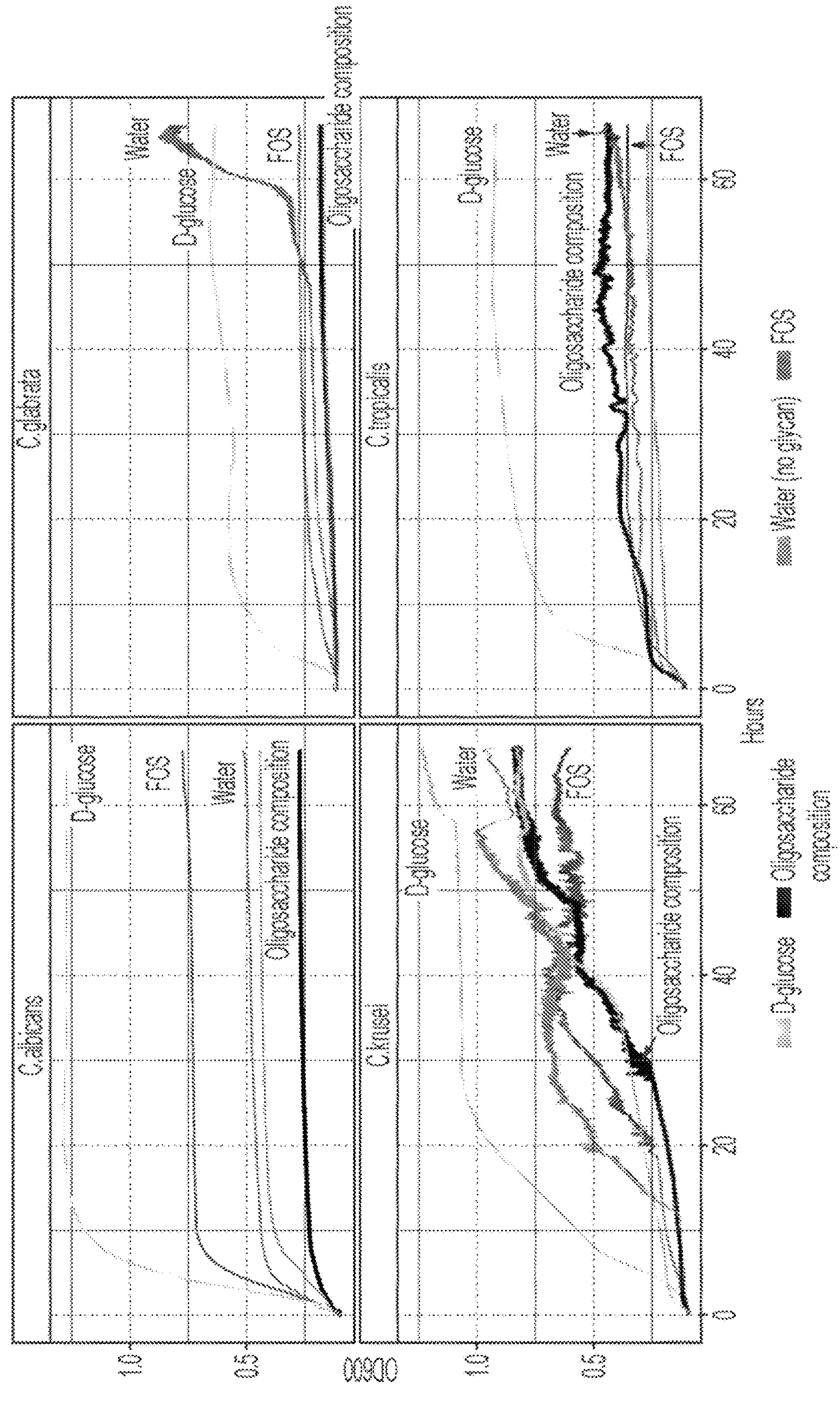
FIG. 9 provides graphs showing reduction in pathogen growth in cultures of single pathogen strains (*Candida albicans, Candida glabrata, Candida krusei, Candida tropicalis*) incubated in the presence of samples of the selected oligosaccharide composition.

Each of the *Candida albicans, Candida glabrata, Candiaa krusei*, or *Candida tropicalis* strains grew minimally in the presence of the samples of selected oligosaccharide composition (FIG. 9). Meanwhile, each of these strains grew to high $OD_{600}$ in the presence of glucose. Further, growth of each *Candida* strain in the presence of the selected oligosaccharide composition was similar to the amount of growth in the presence of water (negative control, no carbon source).

Figure 10A:
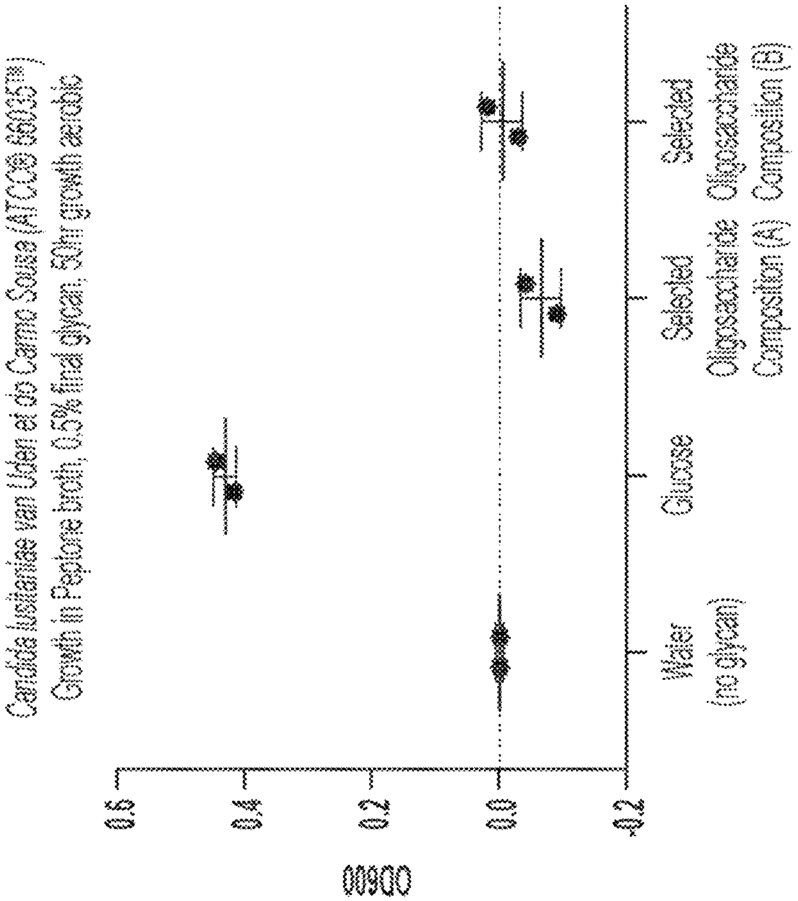
FIGS. 10A-10B provide graphs showing reduction in pathogen growth in cultures of single pathogen strains (*Candida lusitaniae*) incubated in the presence of samples of the selected oligosaccharide composition.
Figure 10B:
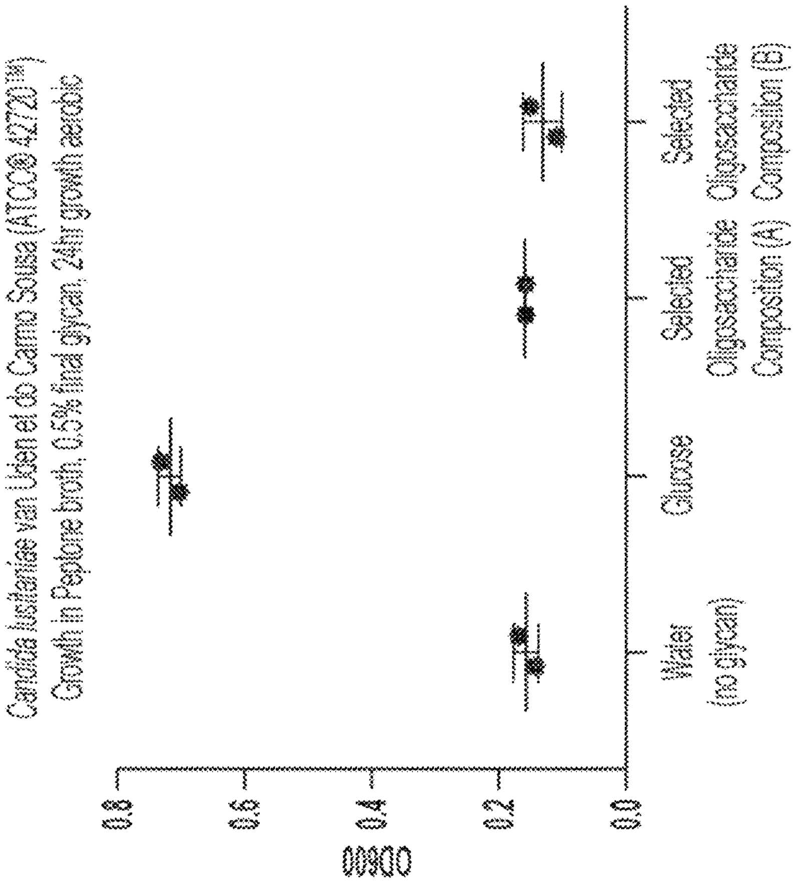

Both of the *Candida lusitaniae* strains grew minimally in the presence of the samples of selected oligosaccharide composition (FIGS. 10A-10B). Meanwhile, each of these strains grew to high $OD_{600}$ in the presence of glucose. Further, growth of both *Candida* strains in the presence of the selected oligosaccharide composition was similar to the amount of growth in the presence of water (negative control, no carbon source).

These data collectively demonstrate that the selected oligosaccharide composition as produced by a similar process as described in Examples 1-3 does not support growth and abundance of pathogenic microbes (bacteria and fungi), as evidenced b the inability of any of the tested *C. difficile*, VRE (*E. faecium*) and CRE (CRE *E. coli*, CRE *K. pneumoniae*), and *Candida* strains. By contrast, all of the tested strains exhibited significant growth in the presence of glucose and/or FOS.

Example 8. Assessment of Selected Oligosaccharide Compositions in Fecal Suspensions from Hospitalized Patients The ability of the selected oligosaccharide composition comprised of a plurality of oligosaccharides selected from Formula (I), Formula (II), and Formula (III) as produced by a similar process as described in Examples 1-3 to reduce pathogen growth in microbiome samples from fecal suspensions of thirteen hospitalized patients receiving antibiotic treatment from an Intensive Care Unit (ICU) facility was assessed.

Fecal samples from ICU patients and healthy subjects were collected and stored at −80° C. To prepare the fecal material for use in the ex vivo assay, aliquots of a 20% w/v suspension in phosphate buffered saline (PBS) and glycerol were thawed in a COY anaerobic chamber. This suspension was then further diluted into a 1% solution of Mega Media (MM). The composition of Mega Media is as described in Romano, K. A. et. al., mBio. 2015 March-April; 6(2): e02481-14. This media was filter sterilized using a 0.2 μm filter and stored in an anaerobic chamber prior to use to allow any dissolved oxygen to dissipate.

A single strain of Carbapenem-resistant Enterobacteriaceae (CRE) and vancomycin-resistant Enterococcaceae (VRE) were grown in isolation overnight in MM with 0.5% D-glucose in a COY chamber. On the day of the experiment, aliquots of the overnight cultures were washed with PBS and the optical density ($OD_{600}$) of the cultures was measured. The culture was adjusted to $OD_{600}$ of 0.1 in MM and added to the 1% fecal suspensions. Fecal suspensions mixed with either Carbapenem-resistant Enterobacteriace (CRE) and vancomycin-resistant Enterococcaceae (VRE) were then subjected to 1 S sequencing to determine the initial relative abundance of pathogen and commensal bacteria. The cultures were then added to 96-well microplates with one of the following carbon sources (final concentration of 0.5% w/v) in each well: maltodextrin, fructooligosaccharide, a sample of the selected oligosaccharide composition, or water (negative control, i.e., no carbon source). These microplates were then incubated at 37° C. in the COY chamber for a total of 45 hours, with each experimental condition being tested in three replicates on each plate.

At the end of the 45-hour incubation, a sample of the culture from each well was subjected to 16S sequencing to determine the final relative abundance of pathogen and commensal bacteria in the community after intervention with oligosaccharide composition.

For the 16S sequencing, genomic DNA was extracted from the fecal suspensions and variable region 4 of the 16S rRNA gene was amplified and sequenced (Earth Microbiome Project protocol www.earthmicrobiome.org/emp-standard-protocols/16s/ and Caporaso J G et al. Ultra-high-throughput microbial community analysis on the Illumina HiSeq and MiSeq platforms. ISME J. (2012) August; 6(8): 1621-4). Raw sequences were demultiplexed, and each sample was processed separately with UNOISE2 (Robert Edgar UNOISE2: improved error-correction for Illumina 16S and ITS amplicon sequencing. bioRxiv (2016) October 15). Reads from 16S rRNA amplicon sequencing data were rarefied to 5000 reads, without replacement, and resulting OTU table used in downstream calculations.

Figure 4:
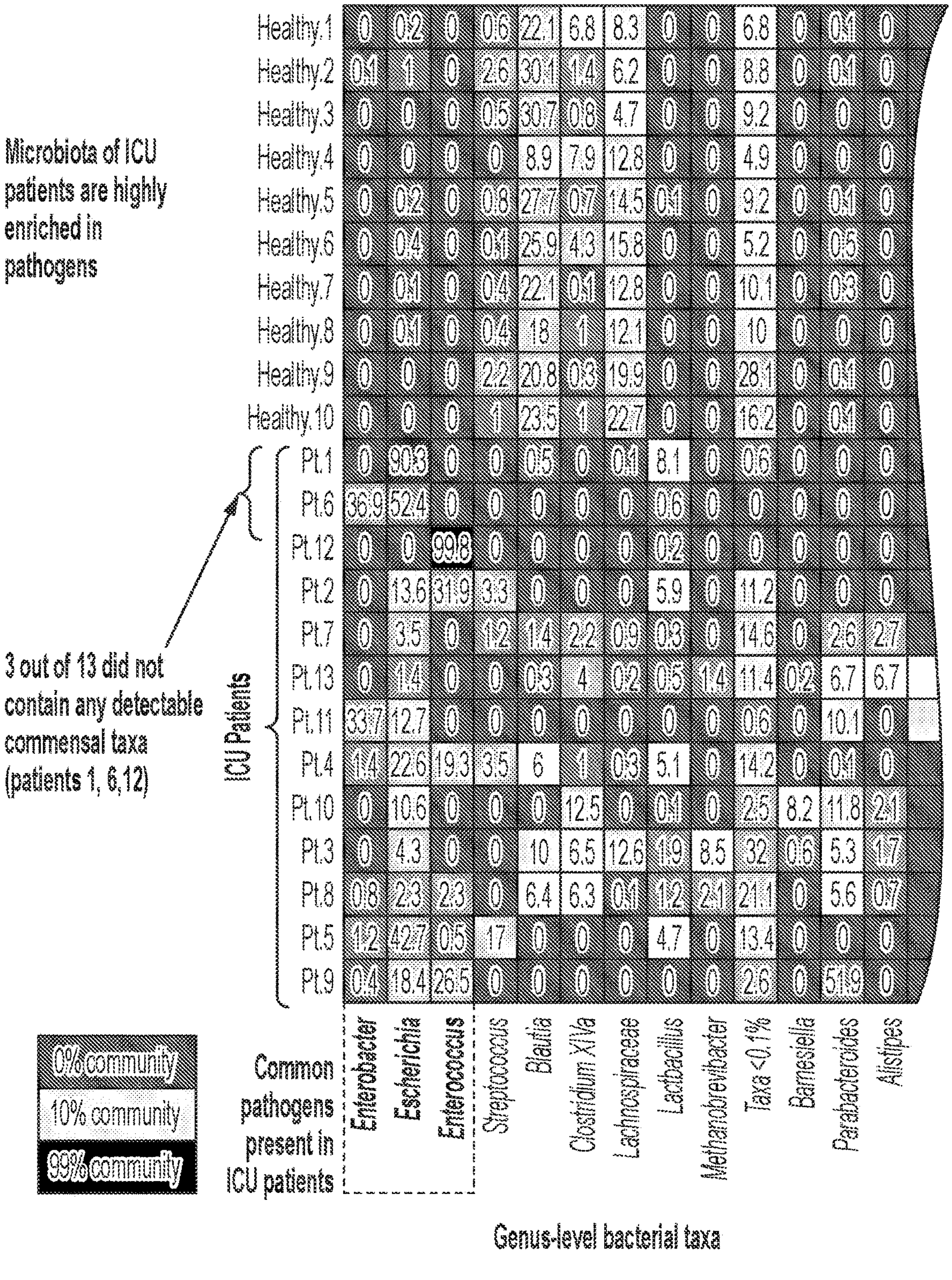
FIG. 4 provides a graph showing the microbial compositions of fecal samples collected from 13 ICU patients and fecal samples collected from healthy subjects. Presented are relative proportions of discrete bacterial taxa (genus-level) in each fecal sample.
Figure 4:
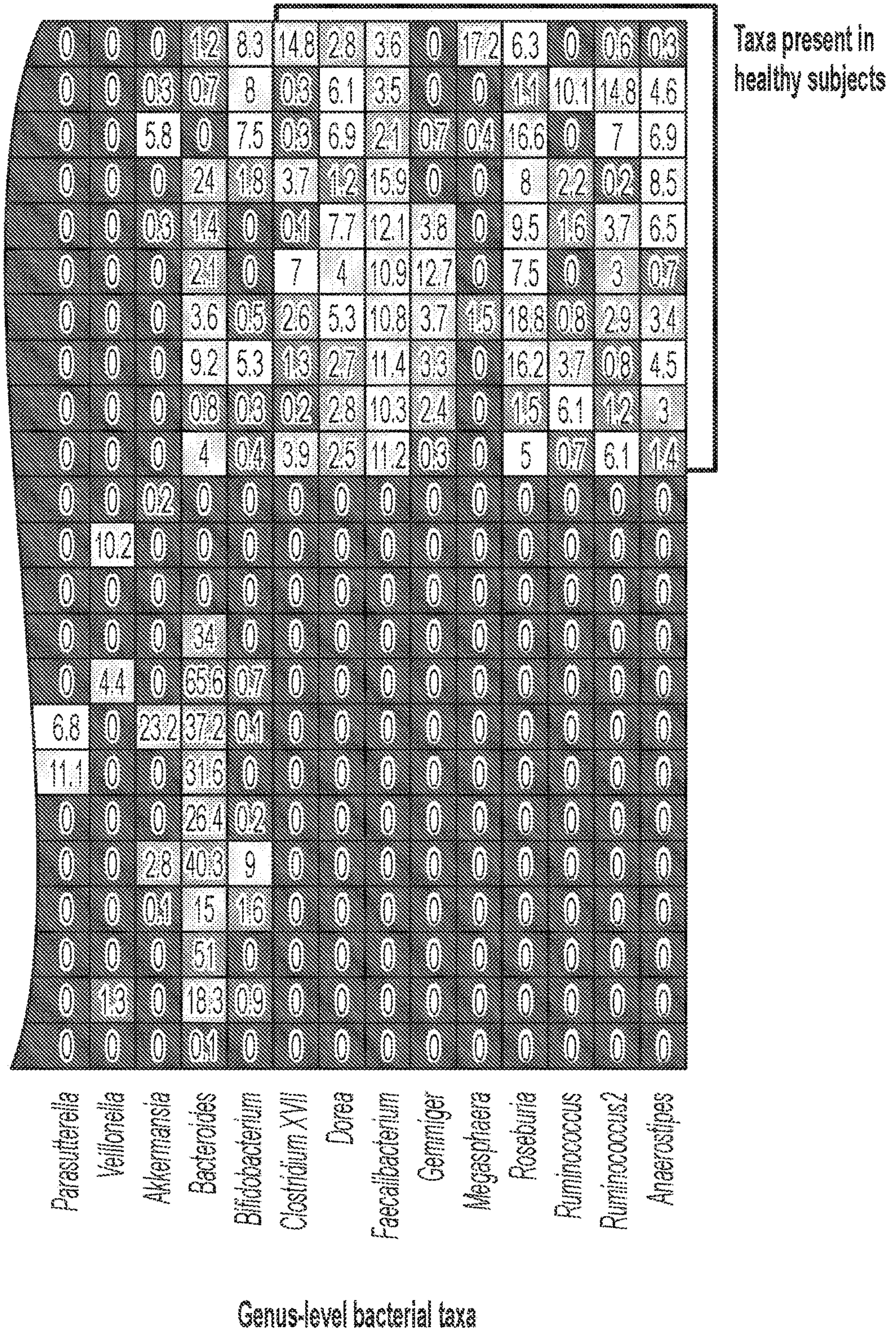

The fecal suspensions from healthy subjects contained a greater diversity in commensal taxa compared to the fecal suspensions from the ICU patients (FIG. 4). For example, the fecal suspensions of three of the thirteen ICU patients contained low levels of commensal bacteria (FIG. 4).

Figure 7A:
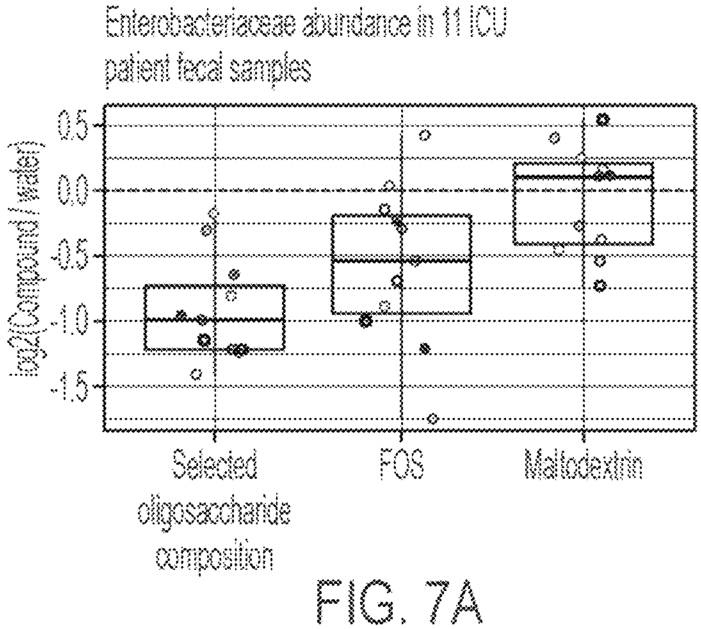
FIGS. 7A-7B provide graphs showing reduction in pathogen growth (normalized to water controls) in an ex vivo pathogen reduction assay where fecal samples from 11 ICU patients were incubated with the selected oligosaccharide composition.
Figure 7B:
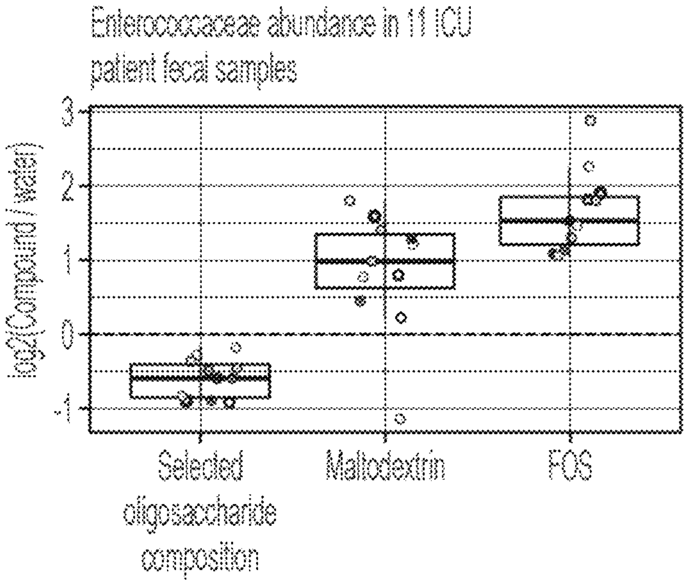

The selected oligosaccharide composition reduced the abundance of Carbapenem-resistant Enterobacteriaceae (FIG. 7A) and vancomycin-resistant Enterococcaceae (FIG. 7B) in spiked fecal suspensions from ICU patients, as assessed by 16S sequencing. A reduction in the relative abundance of Carbapenem-resistant Enterobacteriaceae was observed in the fecal suspensions from ten of the thirteen ICU patients. There was a smaller reduction in the relative abundance of Carbapenem-resistant Enterobacteriaceae in the three ICU patients that had few commensal bacteria, indicating that the relative abundance of commensal bacteria in the gut microbiome can influence the degree of pathogen reduction by the selected oligosaccharide composition. The abundance of each of these pathogens (carbapenem-resistant Enterobacteriaceae and vancomycin-resistant Enterococcaceae) was greater in those spiked fecal suspensions that were incubated in the presence of FOS (a commercial fiber) or maltodextrin. This demonstrates that the selected oligosaccharide composition comprised of a plurality of oligosaccharides selected from Formula (I), Formula (II), and Formula (III) as produced by a similar process as described in Examples 1-3 is capable f reducing or preventing the growth of pathogens such as Carbapenem-resistant Enterobacteriaceae (CRE) and vancomycin-resistant Enterococcaceae (VRE) in a medically relevant model.

Example 9. Clinical Trial to Assess Ability of the Selected Oligosaccharide Composition to Treat Coronavirus (COVID-19) Infection The ability of the selected oligosaccharide composition comprised of a plurality of oligosaccharides selected from Formula (I), Formula (II), and Formula (III) as produced by a similar process as described in Examples 1-3 was assessed for its ability to treat and prevent coronavirus infections.

The study (a non-IND clinical study conducted under regulations supporting research with food, evaluating safety, tolerability and potential markers of human effect) was a randomized, controlled, multi-site, open label clinical study to assess the selected oligosaccharide composition on safety as well as measures of signs, symptoms, healthcare utilization (including hospitalizations), laboratory/biochemical indices a d quality-of-life measures in outpatients who have tested positive with COVID-19 who have mild-to-moderate disease, and have been advised to manage their disease at home with supportive self-care (SSC) under quarantine protocols set forth by the United States Center for Disease Control in 2020.

350 patients enrolled with mild to moderate COVID-19 symptoms were randomized (1:1) to receive either (A) SSC and the selected oligosaccharide composition or (B) remain on SSC alone. The randomization was stratified by site/center, age subgroup (≥18 to <45, ≥45 to <65, ≥65), and comorbidity status (e.g., concurrent medical conditions). The study consisted of a Screening/Randomization Visit, Intake Period (14 Days) followed by a Follow-up Period (21 Days), as detailed in FIG. 14.

Patients were at least 18 years of age, tested positive for OVID-19, and are medically stable at study entry. Patients were also advised by a healthcare provider that self-management of COVID-19 (i.e., SSC) is indicated and recommended.

Patients were recruited via outpatient clinics performing ARS-CoV-2 testing and voluntarily consent into the study either at the time they are making their outpatient clinic appointment, at the outpatient testing center/clinic itself, or following discharge from the outpatient clinic. For eligible patients that were pre-symptomatic at time of COVID-19 testing, new cardinal symptoms must be reported within 7 days of a positive test, and the patient must be screened and randomized within 5 days of them developing symptoms. 11 patients were provided the same level of care and same procedures conducted (e.g., physician examination, COVID-19 testing, etc.).

This study comprised two parts. In Part 1, patients who consented to the study underwent a full assessment of inclusion and exclusion criteria and had one or more of nasal and oropharyngeal swabs taken and blood samples collected for Baseline hematology, chemistry, biomarkers and serological markers of immunity, and quantitative vial load assessments.

Patients self-recorded COVID-19-related symptoms (cough, fever, nasal congestion, gastrointestinal symptoms, fatigue, anosmia, ageusia, diarrhea, shortness of breath, chest tightness, and headache) and scored them using a rating of 0-3 where 0 means that the symptom is absent, 1 means that the symptom is mild (present but easily tolerated), 2 means that the symptom is moderately severe (bothersome but tolerable), and 3 means that the symptom is very severe (hard to tolerate; interferes considerably with daily activity).

It is possible that patients only consented to Part 1 of this study. In this case, if a positive test result for COVID-19 was recorded, then the patient was co acted by a centralized telemedicine provider (physician or nurse practitioner) to review study eligibility criteria, obtain electronic informed consent to Part 2, and conduct an abbreviated virtual physical exam.

Only patients having a positive test result for COVID-19 entered Part 2 of this study. Part 2 of the study comprised an Intake Period and a Follow-up Period. In Part 2, the site notified an independent, third party vendor that a patient was eligible for randomization no later than 48 hours after a positive test result for COVID-19. Upon randomization (SSC and the selected oligosaccharide composition; or SSC alone), an at home Study Kit (KaSK) was provided to the patient. The KaSK included study product and dosing instructions (as applicable), a thermometer, a pulse oximeter, telemedicine contact information, and return shipping materials. Patients continued to record COVID-19-related symptoms using the same scoring rubric until the KaSK was delivered.

The Intake Period (Days 1-14) began the morning after receipt of the KaSK. All patients continued to follow the SSC guidance as provided by the treating healthcare provider throughout study participation. In the Intake Period, all patients continued to record their daily COVID-19-related symptoms, selected COVID-19 signs (temperature and oxygen saturation), and responses to questions related to quality of life measures, and healthcare utilization measures, and concomitant medications taken in the previous 24 hours. Patients randomized to SSC and the selected oligosaccharide composition began consuming the selected oligosaccharide composition on Day 1. On each of days 1 and 2, the patients consumed 18 grams of the selected oligosaccharide composition. On each of days 3 and 4, the patients consumed 36 grains of the selected oligosaccharide composition. On each of days 5-14, the patients consumed 72 grams of the selected oligosaccharide composition.

During the Intake Period, for all patients, one or more of blood, nasal and oropharyngeal swabs were collected by home nursing providers or remotely, as feasible, and as close to the beginning (Day 1) and end (Day 14) of the Intake Period for analysis of laboratory, biochemical and serological measures.

On Day 14, all patients underwent another telemedicine visit where an abbreviated physical examination is conducted, an assessment of safety, and an evaluation of whether follow-up treatment was recommended due to a deterioration of COVID-19 symptoms. Patients in the SSC and selected oligosaccharide composition group stopped taking the selected oligosaccharide composition on Day 14.

On Day 15, all patients entered the Follow-up Period (Days 15 to 35) where COVID-19 signs, symptoms, quality of life and Health Care Utilization indices were collected weekly in the secure online Study Portal. Blood, nasal and oropharyngeal swabs were collected by home nursing providers or remotely, as feasible, and as close to the end of the Follow-up Period (Day 35) for analysis of laboratory, biochemical and serological measures.

On Day 35, all patients underwent another telemedicine visit where an abbreviated physical examination was conducted, an assessment of safety, and an evaluation of whether follow-up treatment is recommended.

The primary endpoint of the study was the number of patients experiencing study product-related treatment emergent adverse events (TEAEs).

The secondary endpoints of the study included:

Time to resolution of overall 13 COVID-19 related symptoms which was defined as from Day 1 until the day at which the overall composite score of 13 COVID- 9 related symptoms became 0 or 1 and remained at 0 or 1 for the rest of the Intake Period and for the Follow-up Period. Overall composite score of 13 COVID-19 related symptoms was the sum of 13 COVID-19 related symptom scores (i.e., cough, chills/repeated shaking with chills, muscle pain, fever, headache, anosmia/ ageusia, shortness of breath, sore throat, gastrointestinal disturbance/symptoms, diarrhea, fatigue, nasal congestion, and chest tightness (CDC 2020)). Each COVID-19 symptom was recorded by patients on a scale of 0: Absent, 1: Mild, 2: Moderately severe, 3: Very severe. The overall composite score ranged from 0 (no symptoms) to 39 (very severe)

Time to resolution of overall 8 cardinal COVID-19 related symptoms which was defined as from Day 1 until the day at which the overall composite score of 8 cardinal COVID-19 related symptoms became 0 or 1 and remained at 0 or 1 for the rest of the Intake Period and for the Follow-up Period. Overall composite score of 8 cardinal COVID-19 repeated symptoms was the sum of 8 cardinal COVID-19 related symptom scores (i.e., cough, chills/repeated shaking with chills, muscle pain, fever, headache, anosmia/ageusia, shortness of breath, and sore throat) ranging from 0 (no symptoms) to 24 (very severe)

Proportion of patients with reduction from Baseline (symptom present at Baseline) in each of 13 individual COVID-19 related symptom at End of Intake Period (EOI) and Follow-up Proportion of patients with symptom that became absent (symptom present at Baseline) at EOI and Follow-up for each of 13 individual COVID-19 related symptom Change from baseline to EOI in overall composite score of 13 COVID-19 related symptoms Change from baseline to EOI in overall composite score of 8 cardinal COVID-19 related symptoms Time to resolution of fever (defined as from Day 1 until the day at which a patient's daily maximum temperature achieves and remains below 100.4° F. for the rest of the Intake Period and for the Follow-up Period without an antipyretic medication)

Proportion of patients with oxygen saturation <95% on Day 14 and Day 35

Proportion of patients with oxygen saturation <98% on Day 14 and Day 35

Proportion of patients experiencing hospital admissions during the Intake Period and Follow-up Period (all cause, and COVID-19-related)

Healthcare utilizations during the Intake Period and Follow-up Period

Exploratory Endpoints to evaluate measures of health and biomarkers in outpatients with mild-to-moderate COVID-19 during the Follow-up Period included:

a. Change from baseline to the EOI in individual-COVID-19 related symptom score: cough, chills/repeated shaking with chills, muscle pain, fever headache, anosmia/ageusia, shortness of breath, sore throat, gastrointestinal disturbance/symptoms, diarrhea, fatigue, nasal congestion, a d chest tightness
b. Individual measures of quality of life (QOL)
c. Change from baseline to EOI in bedrest time measured as patient-assessed daily cumulative total rest (measured in hours)
d. Proportion of patients with increases in patient global impression on COVID-19 condition (PGIC)
e. Proportion of patients with temperature below 100.4° F. without an anti-pyretic medication
f. Biomarkers of infection, antibody response, and inflammation (e.g., D-dimer, lipocalin, cytokines, IgM/IgG sero-conversion, C-reactive protein (CRP), and neutralization assays)

An interim analysis of the study was conducted with 87 patients on SSC (n=87, Arm 1) and 89 patients on SSC and selected oligosaccharide composition (n=89, Arm 2) having mild to moderate COVID-19 symptoms. Baseline characteristics were matched between the groups. A higher proportion of patients reporting comorbidities at baseline were identified, 45% for SSC and selected oligosaccharide composition (Arm 2) versus 36% or SSC alone (Arm 1).

The selected oligosaccharide composition was well tolerated with no treatment-related serious adverse effects (SAEs). There were more GI-related AEs reported in Arm 2, 18% versus 3% for Arm 1, though all AEs reported in Arm 2 were mild/moderate (e.g., diarrhea, abdominal distension, nausea, abdominal pain, flatulence) and none led to study discontinuation. There were also more GI symptoms reported at baseline in Arm 2 arm than Arm 1 (47% vs 33%). Two hospitalizations were reported for Arm 2 and three for Arm 1. One death was reported due to COVID-19 after withdrawal from study in the SSC alone arm (Arm 1).

Figure 17A:
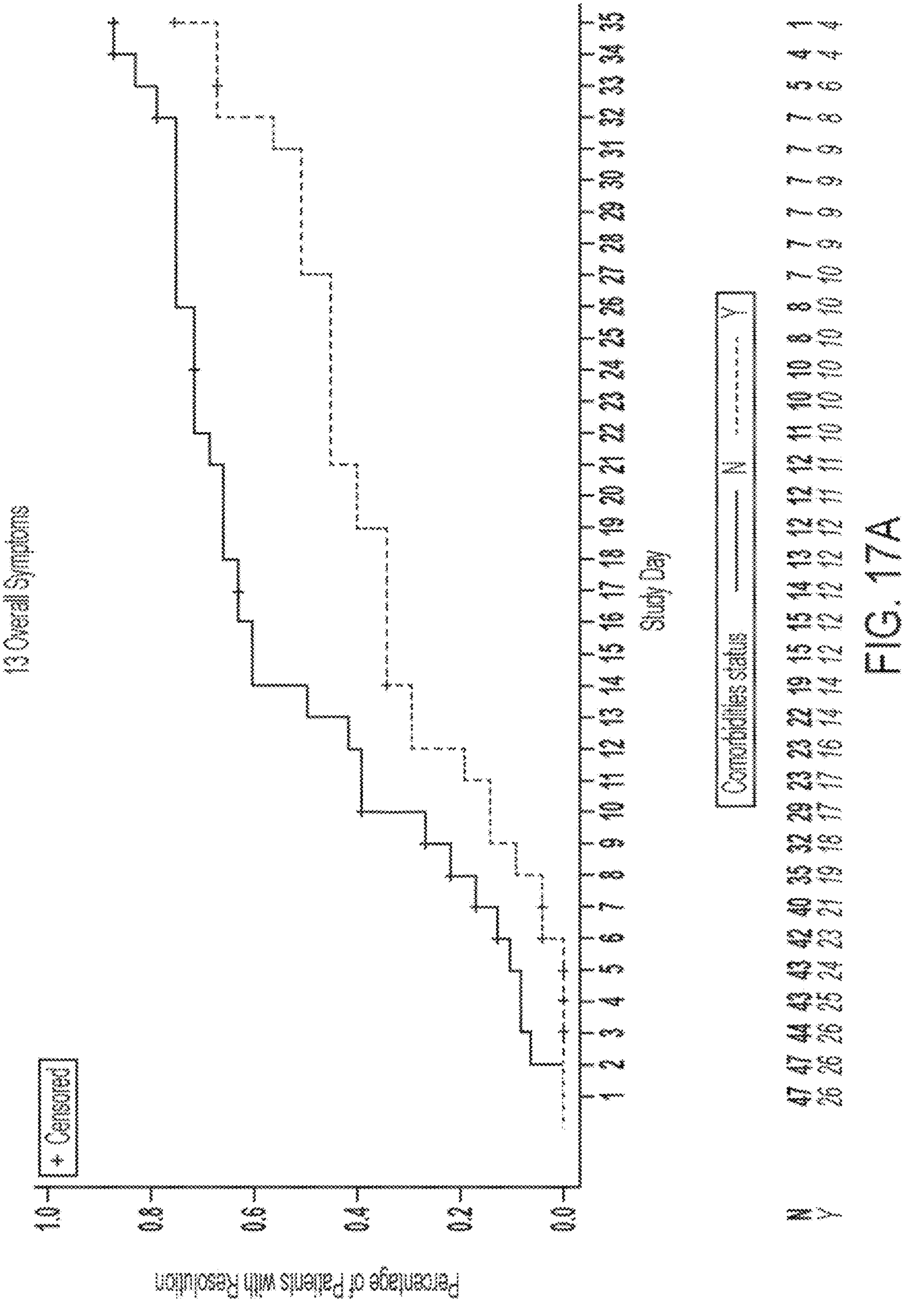
FIGS. 17A-17B provide Kaplan-Meier plots showing a decline in COVID-19 symptoms over time as the infection progresses for patients in Arm 1 (SSC only)
Figure 17B:
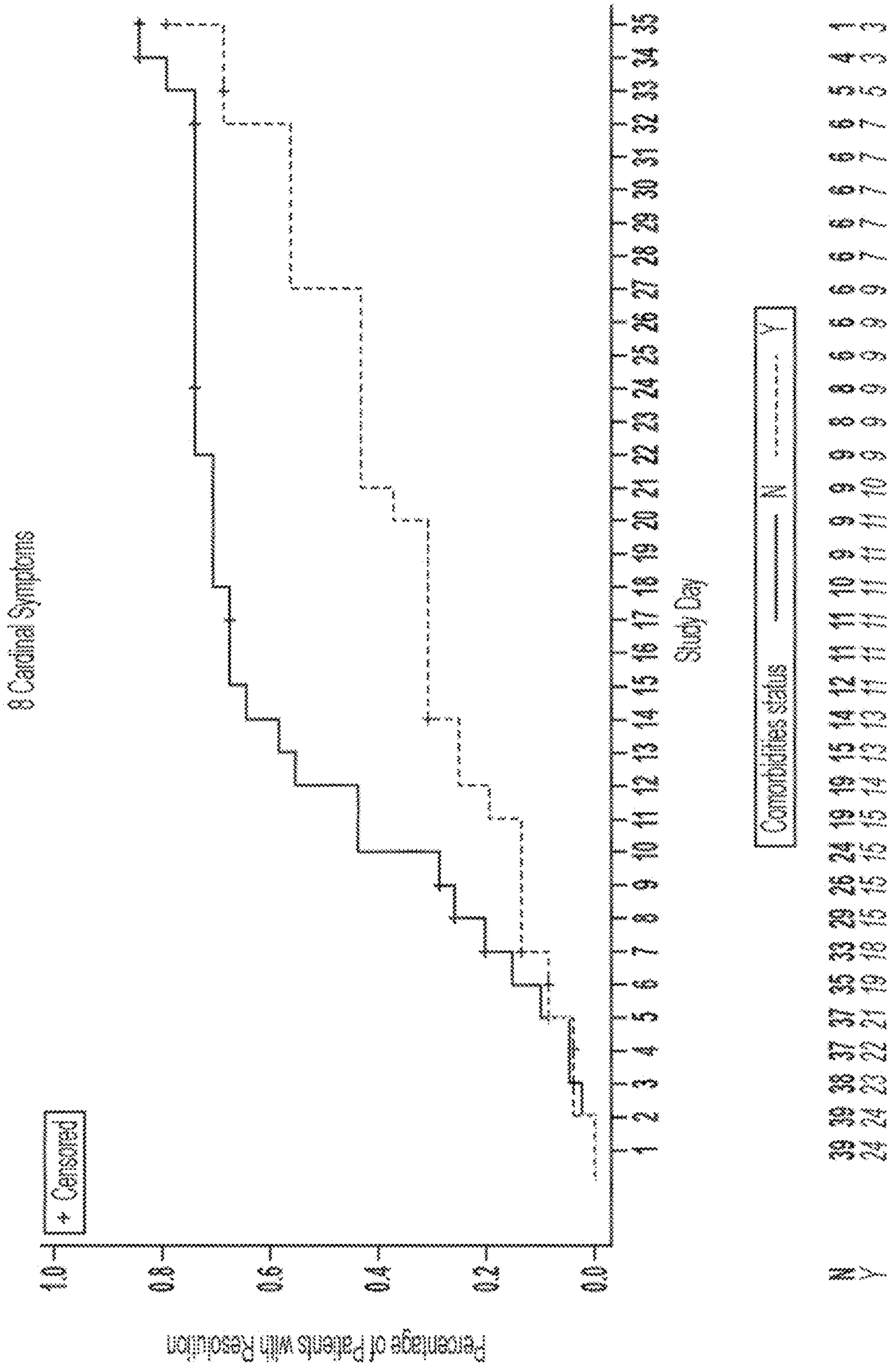

FIGS. 17A and 17B show the decline in COVID-19 symptoms over time as the infection progresses, measured by analysing 13 overall COVID-19 related symptoms (FIG. 17A; 1. Cough, 2. chills/repeated shaking with chills, 3. muscle pain, 4. fever, 5. headache, 6. anosmia/ageusia, 7. shortness of breath, 8. sore throat, 9. gastrointestinal disturbance/symptoms, 10. diarrhea, 11. fatigue, 12. nasal congestion, and 13. chest tightness) and 8 cardinal symptoms (FIG. 17B; 1. cough, 2. chills/repeated shaking with chills, 3. muscle pain, 4. fever, 5. headache, 6. anosmia/ageusia, 7. shortness of breath, and 8. sore throat) as Kaplan Meier curves for patients in Arm 1 (SSC only). A difference for the median time to resolution of symptoms in 50% of patients was measured: 12-14 days for patients without comorbidities versus 27 days for patients with (at least one) comorbidities, suggesting that comorbidities are associated with a delay in COVID-19 symptom resolution, i.e., an extended duration of symptoms exhibited by patients in Arm 1 (SSC only). Comorbidities included patients with one or more of: chronic lung disease (asthma, emphysema, COPD), diabetes mellitus, cardiovascular disease, hypertension, chronic renal disease, chronic liver disease, immunocompromised conditions, cancer, neurologic disorder, prior stroke, and other chronic diseases.

Figure 18A:
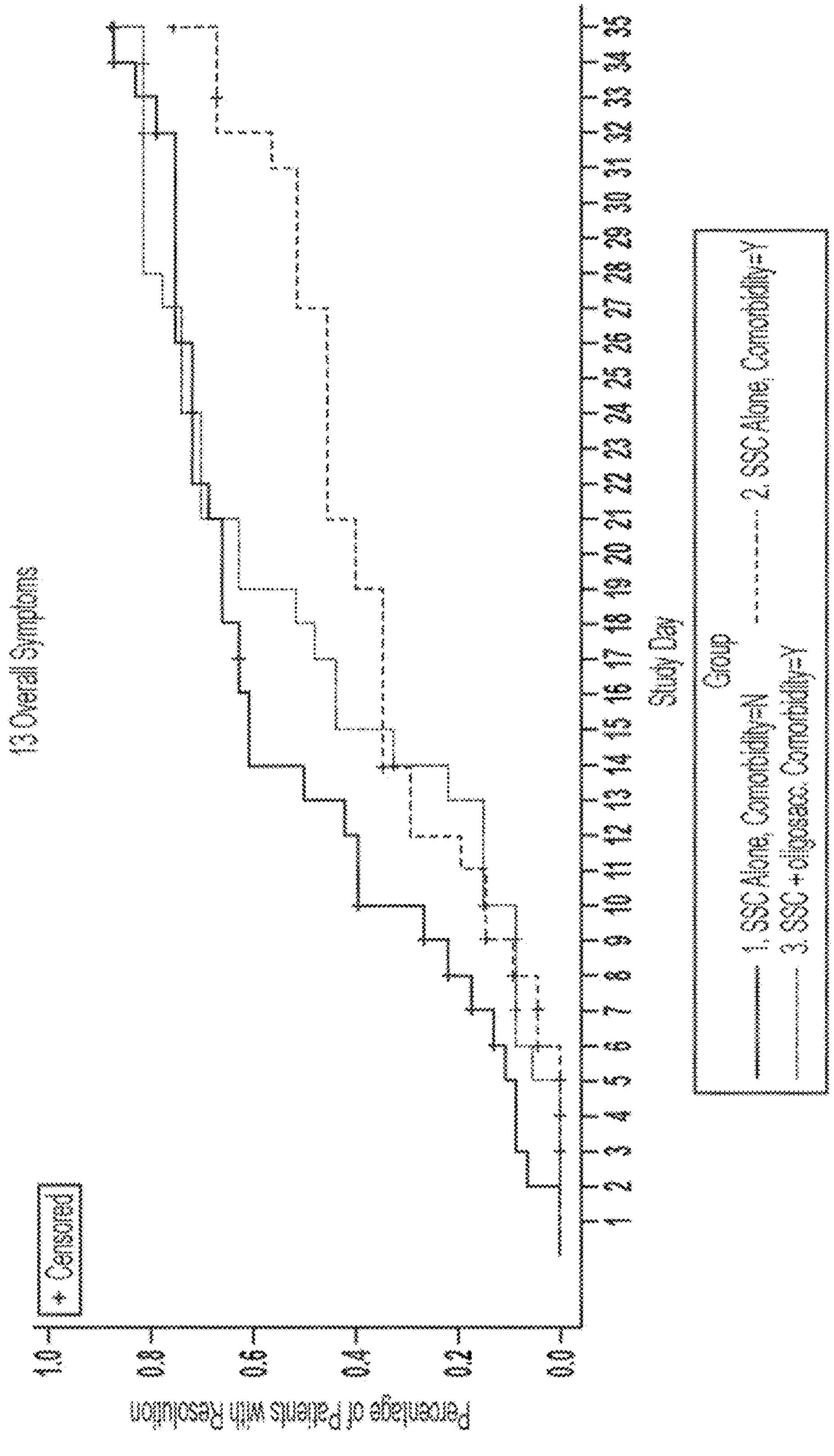
FIGS. 18A-18B provide Kaplan-Meier plots showing a decline in COVID-19 symptoms over time as the infection progresses, measured by analysing 13 overall COVID-19 related symptoms (FIG. 18A) and 8 cardinal symptoms (FIG. 18B) for patients in Arm 1 (SSC only) with no comorbidities (blue line), Arm 1 (SSC only) with comorbidities (red line), and Arm 2 (SSC and selected oligosaccharide) with comorbidities (green line).
Figure 18B:
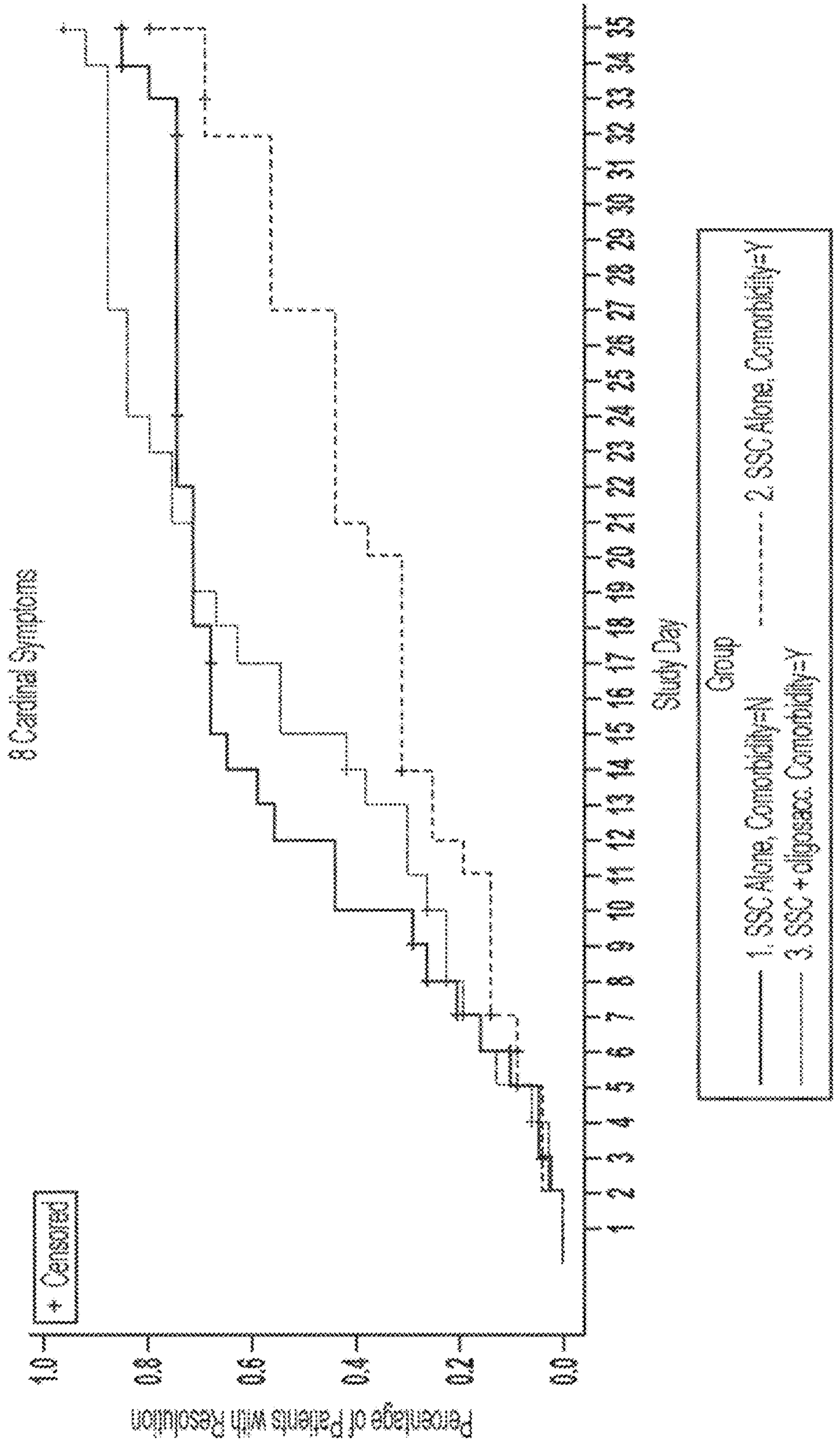
Figure 20:
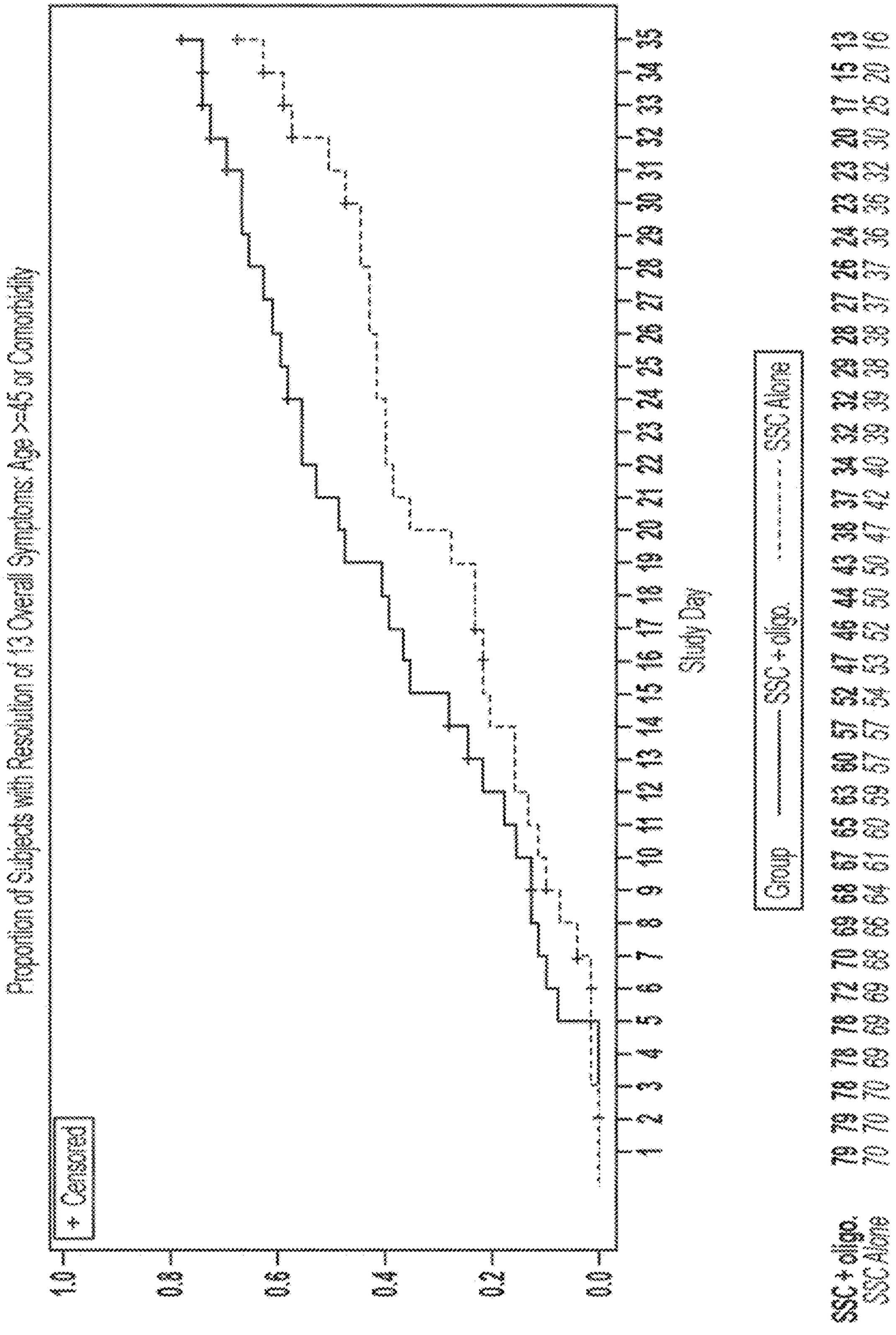
FIG. 20 shows a Kaplan-Meier plot showing proportion of subjects with resolution of COVID-19 symptoms over time measured by analysing 13 overall COVID-19 related symptoms, wherein the subjects were at least 45 years old or having at least one comorbidity, and were treated with either SSC and oligosaccharide composition or SSC alone.
Figure 21:
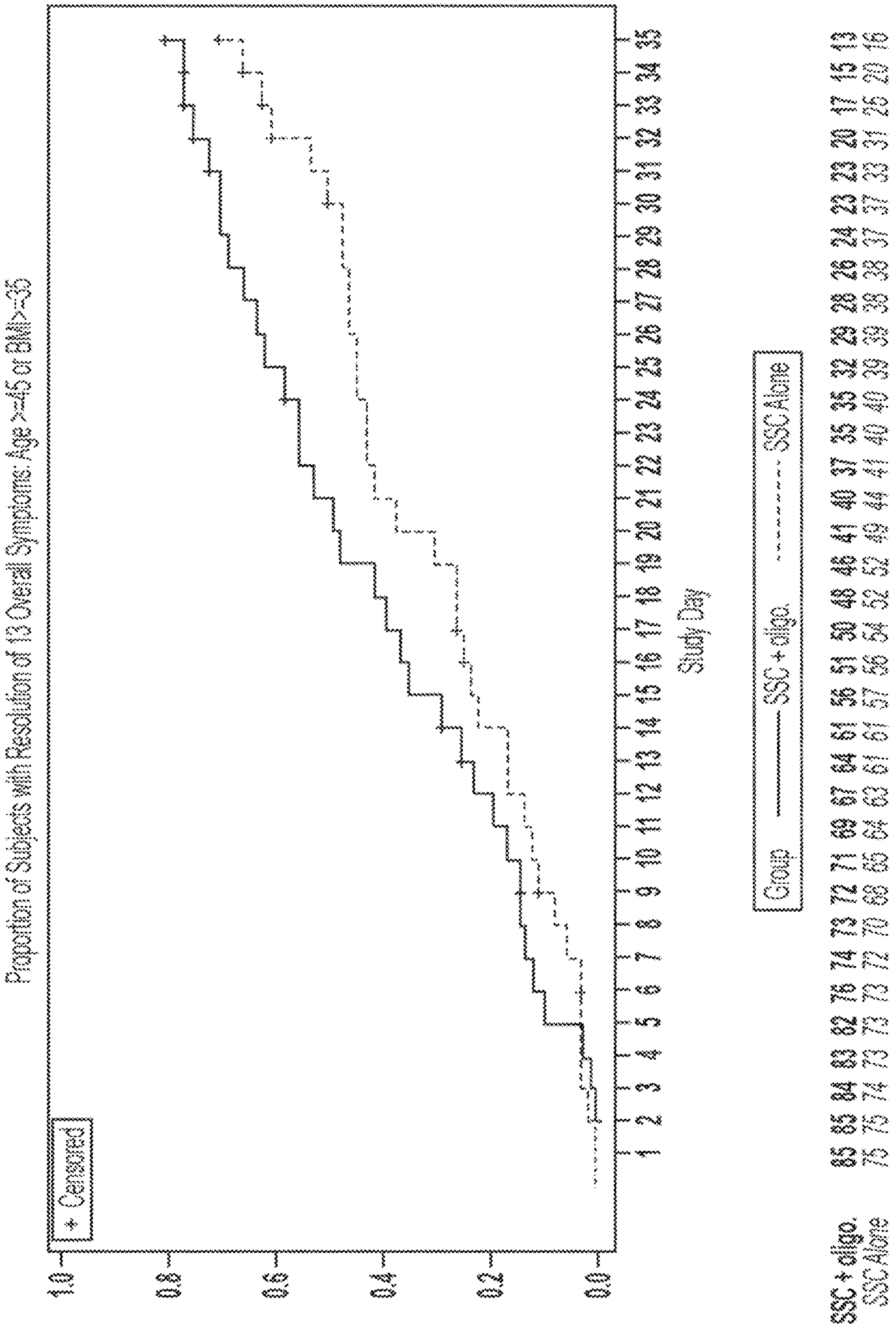
FIG. 21 shows a Kaplan-Meier plot showing proportion of subjects with resolution of COVID-19 symptoms over time measured by analysing 13 overall COVID-19 related symptoms, wherein the subjects were at least 45 years old or having a BMI of at least 35, and were treated with either SSC and oligosaccharide composition or SSC alone.
Figure 22:
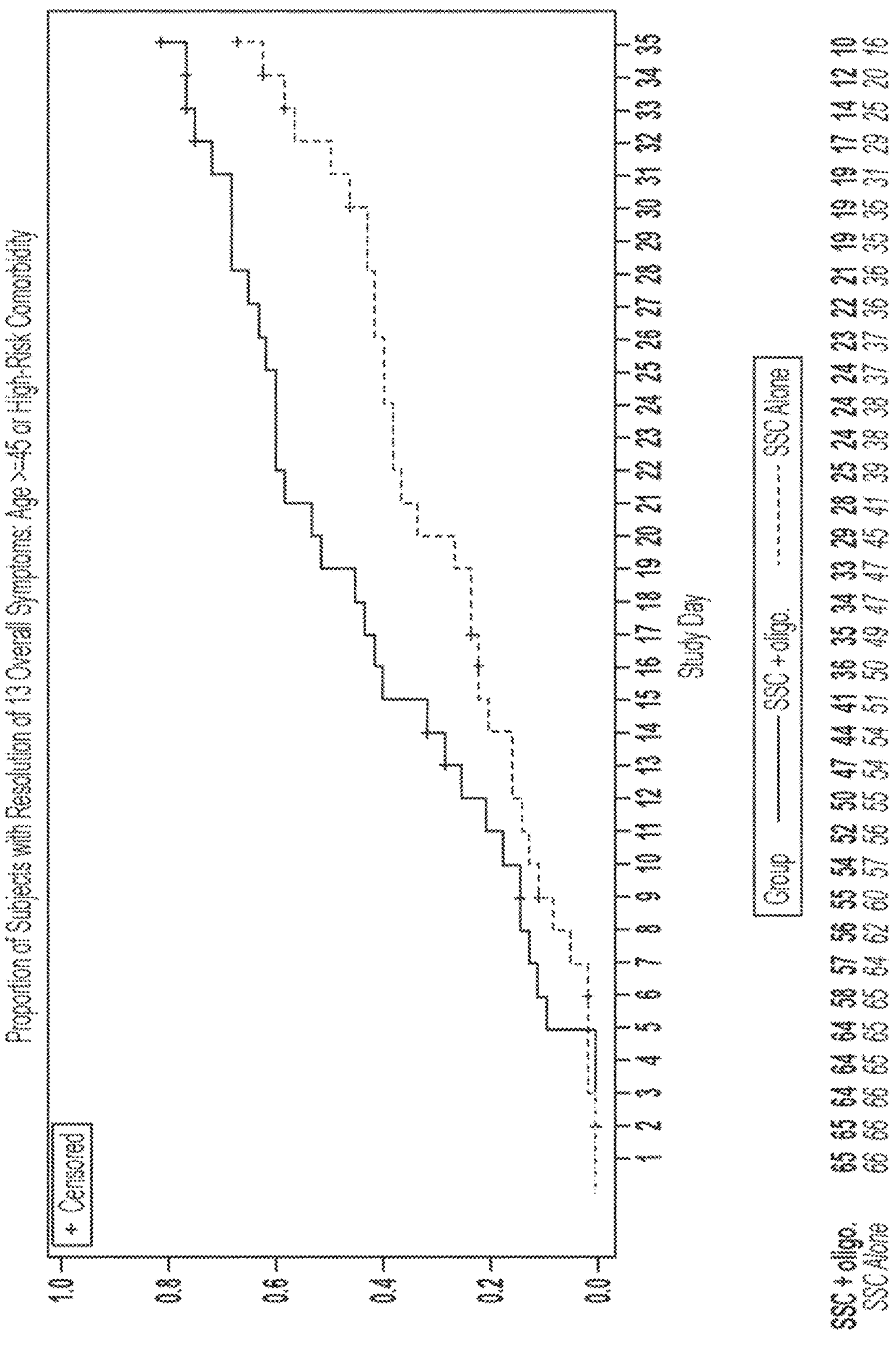
FIG. 22 shows a Kaplan-Meier plot showing proportion of subjects with resolution of COVID-19 symptoms over time measured by analysing 13 overall COVID-19 related symptoms, wherein the subjects were at least 45 years old or having at least one high-risk comorbidity, and were treated with either SSC and oligosaccharide composition or SSC a one.
Figure 23:
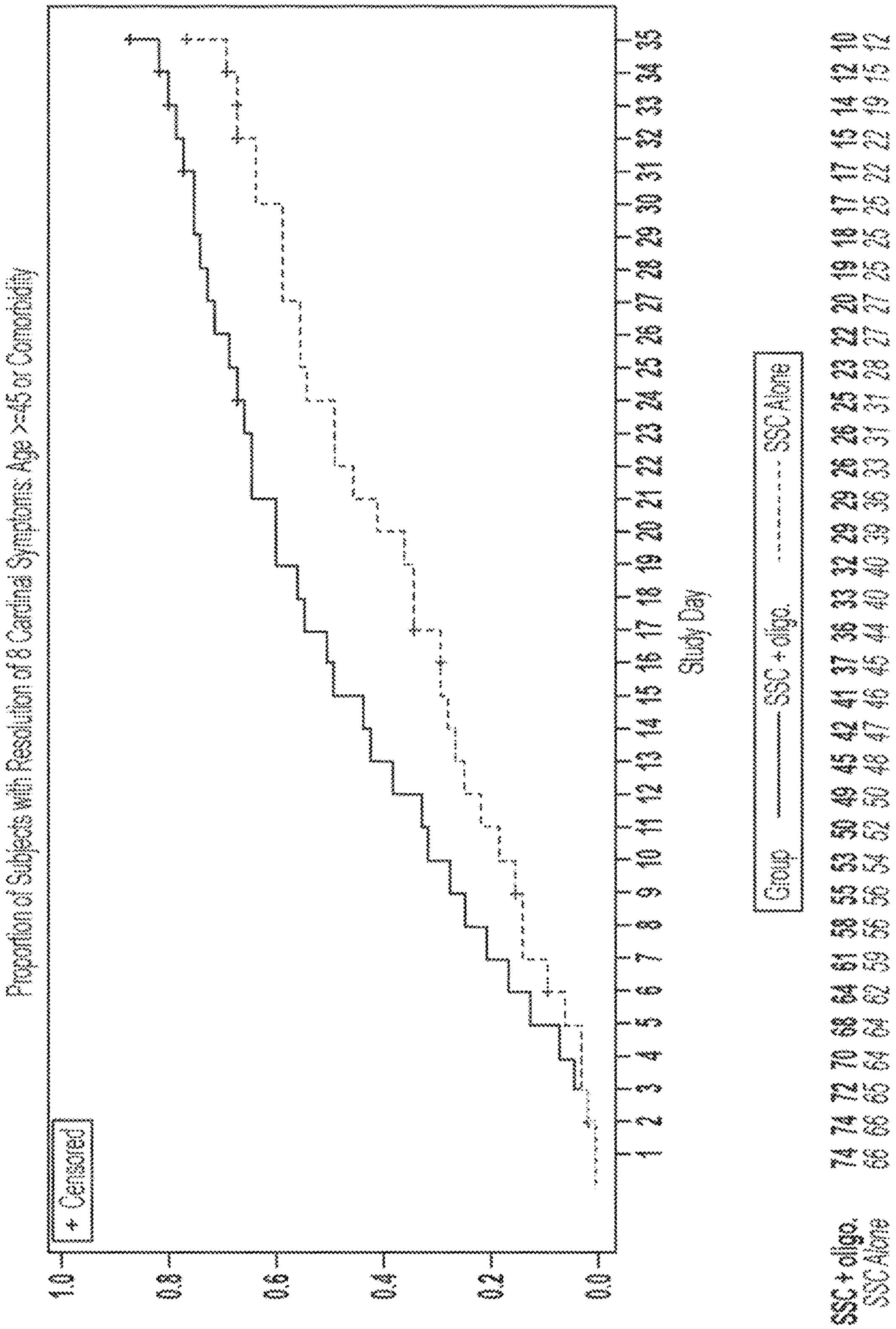
FIG. 23 shows a Kaplan-Meier plot showing proportion of subjects with resolution of COVID-19 symptoms over time measured by analysing 8 cardinal COVID-19 related symptoms, wherein the subjects were at least 45 years old or having at least one comorbidity, and were treated with either SSC and oligosaccharide composition or SSC alone.
Figure 24:
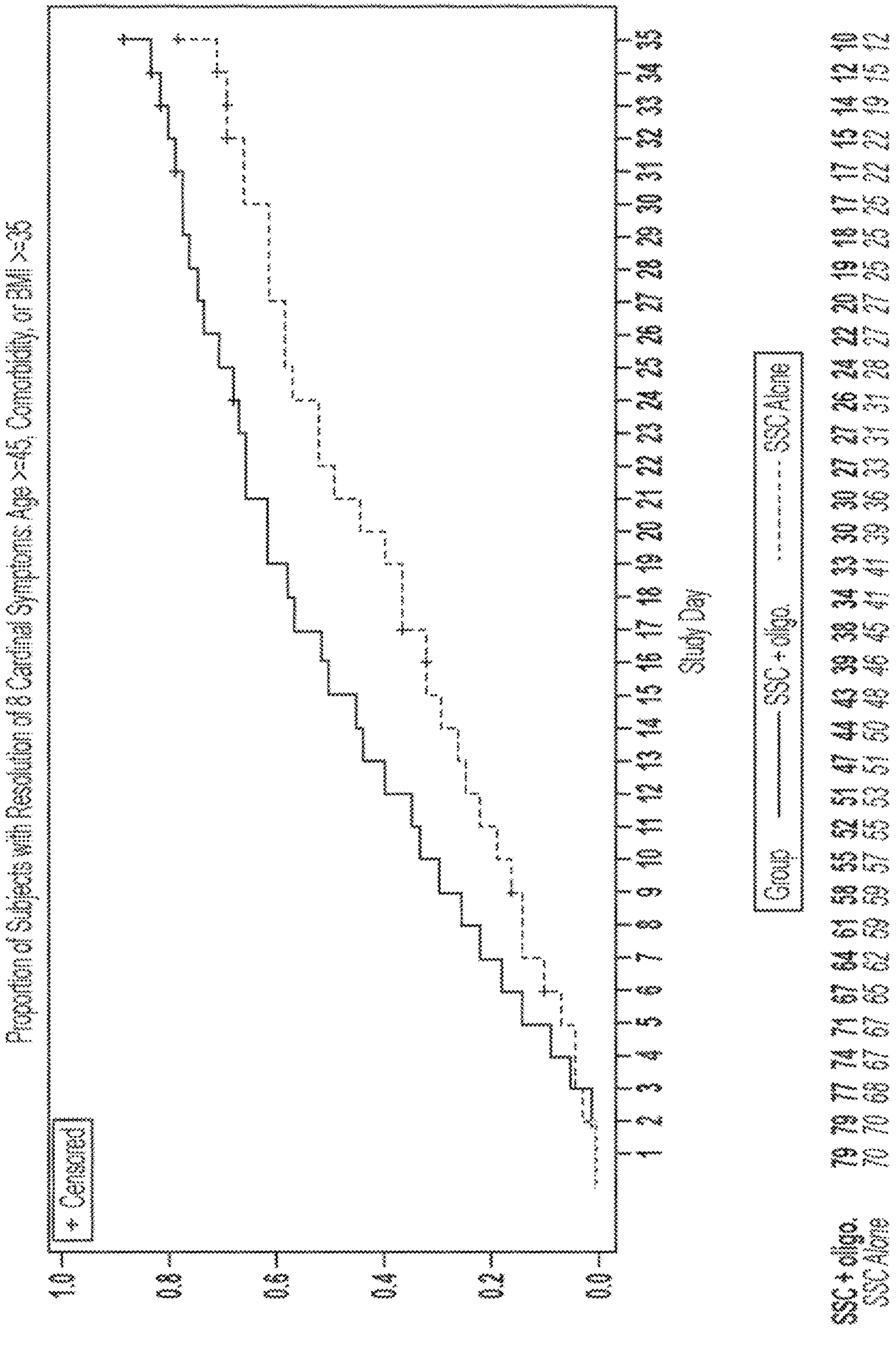
FIG. 24 shows a Kaplan-Meier plot showing proportion of subjects with resolution of COVID-19 symptoms over time measured by analysing 8 cardinal COVID-19 related symptoms, wherein the subjects were at least 45 years old, having at least one comorbidity, or having a BMI of at least 35, and were treated with either SSC and oligosaccharide co position or SSC alone.
Figure 25:
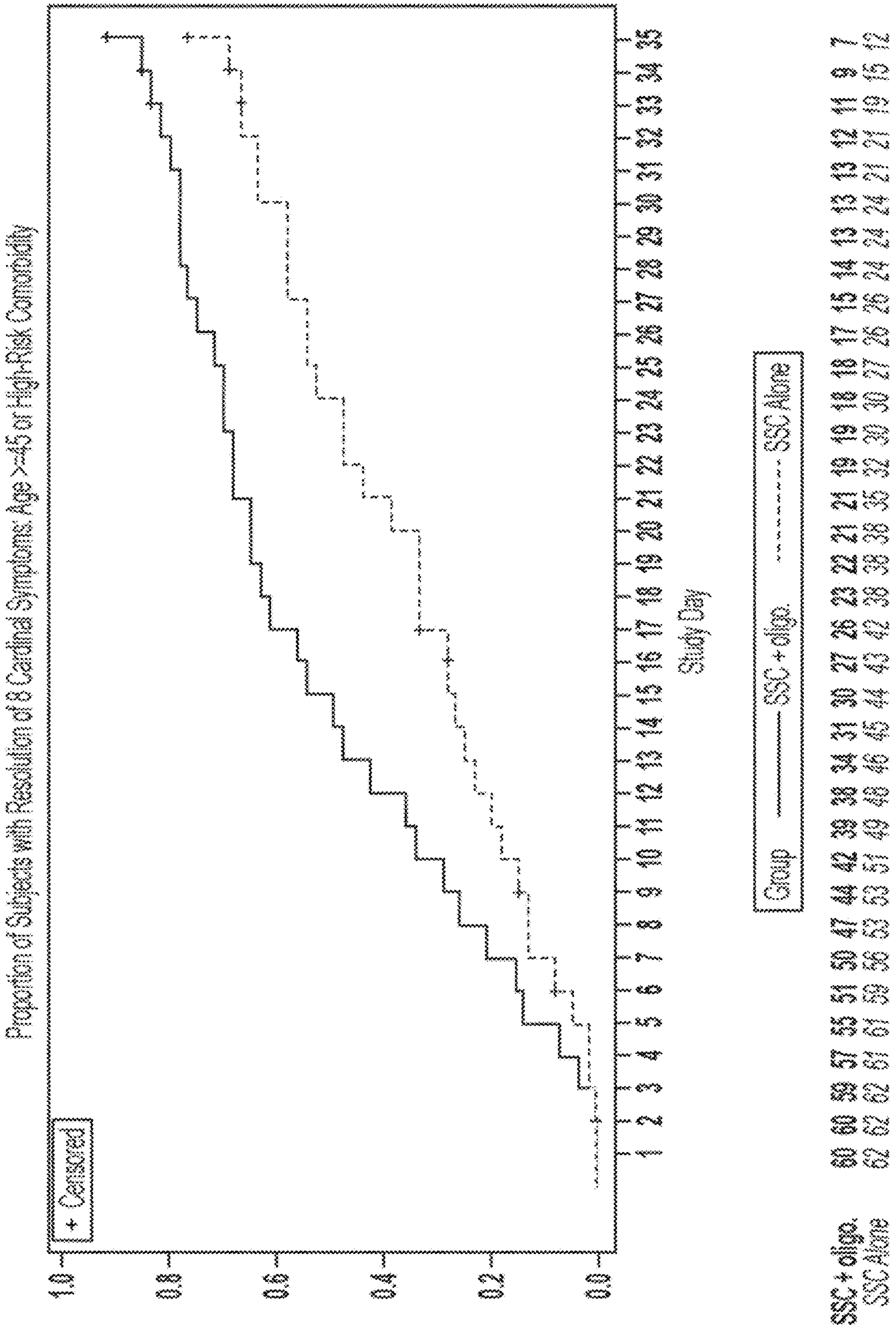
FIG. 25 shows a Kaplan-Meier plot showing proportion of subjects with resolution of COVID-19 symptoms over time measured by analysing 8 cardinal COVID-19 related symptoms, wherein the subjects were at least 45 years old or having at least one hi h-risk comorbidity, and were treated with either SSC and oligosaccharide composition or SSC alone.

FIGS. 18A and 18B show the decline in COVID-19 symptoms over time as the infection progresses, measured by analysing 13 overall COVID-19 related symptoms (FIG. 18A) and 8 cardinal symptoms (FIG. 18B) as Kaplan-Meier curves for patient in Arm 1 (SSC only) with no comorbidities (blue line), Arm 1 (SSC only) with comorbidities (red line), and Arm 2 (SSC and selected oligosaccharide) with comorbidities (green line). A difference for the median time to resolution of symptoms in 50% of patients was measured: 12-14 days for patients without comorbidities versus 27 days for patients with (at least one) comorbidities on SSC alone (Arm 1) versus 15-18 days for patients with comorbidities on SSC and selected oligosaccharide (Arm 2). These data suggest that the selected oligosaccharide may be useful in reducing the time to resolution of symptoms in patients who report at least one comorbidity t baseline compared to SSC alone in this patient group, thereby allowing patients with comorbidities to recover more quickly from COVID-19 infection related symptoms, while being generally safe and tolerable.

Full Analysis

A full analysis was performed on the completed 350 person study data set. There were 176 patients on SSC (n=176, Arm 1) and 174 patients on SSC and selected oligosaccharide composition (n=174, Arm 2) having mild to moderate COVID-19 symptoms. The study was designed to be underpowered statistically, while being optimized to rapidly provide information, in response to the ongoing global pandemic, on a variety of endpoints relating to the safety and tolerability of the selected oligosaccharide composition, and the large and understudied population of patients with mild to moderate COVID-19 symptoms. In general, the full analysis supported the conclusions of the interim analysis.

Demographics 350 subjects were randomized to either SSC alone (181 subjects) or SSC+selected oligosaccharide (169 subjects). The demographics of both arms were generally well balancedThe majority of subjects in the ≥18 to <45 years (234 subjects 66.9%) age group, followed by the ≥45 to <65 years (99 subjects, 28.3%) age group, and a small ≥65 years (17 subjects, 5%) age group. There were more females (207 subjects, 59.1%) than males (143 subjects, 40.9%). The majority of subjects were white (318 subjects, 90.9%): Other races included black/African American (26 subjects, 7.4%), Asian (4 subjects 1.1%) and other (2 subjects, 0.6%).

BMI ranged from 16.4 to 63.9 (with overweight defined as 25-29.9 and obese defined as BMI of 30 or greater) with a mean of 28.74 (+/−6.826) in the SSC+selected oligosaccharide arm and a mean of 28.99 (+/−6.167) in the SSC alone am, and an overall mean of 28.86 (+/−6.49).

In the SSC+selected oligosaccharide arm, 69 subjects (40.8%) had at least one comorbidity, while 66 subjects (36.5%) had at least one comorbidity in the SSC alone arm.

TEAEs

The majority of TEAEs were related to (mostly mild) GI disorders with 35 subjects (20.7%) in the SSC+selected oligosaccharide arm versus 9 subjects (5%) in the SSC alone arm. The overall number of subjects with ant TEAE was 61 subjects (36.1%) in the SSC+selected oligosaccharide arm versus 48 subjects (26.5%) in the SSC alone arm. Two subjects in each group had TEAEs leading to study discontinuation while none lea to death.

Inflammation

The level of C-reactive protein (CRP), a biomarker of systemic inflammation in the bloodstream, was monitored for study participants at days 0, 14, and 35. Participants who had one or more comorbidities might be more likely to suffer from chronic inflammation, independent of their COVID-19 symptoms, and it was hypothesized that they could experience a decrease in inflammation from treatment with an oligosaccharide composition that promotes microbial populations that decrease inflammation in the gastrointestinal tract.

Several biomarkers of inflammation were measured, including C-reactive protein and D-dimer. No significant differences were measured for C-reactive protein for subjects without comorbidity for SSC alone (a) versus SSC+selected oligosaccharide (b): mean values at baseline were 3.128 mg/L for (a) versus 3.018 mg/L for (b), and at 35 days, 2.215 mg/L for (a) versus 2.470 for (b). A trend toward reduction in C-reactive protein was found in subjects with at least one comorbidity in the SSC+selected oligosaccharide arm: at baseline, the mean value was 9.908 mg/L (vs. 5.254 mg/L in the SSC alone arm), and at 35 days, C-reactive protein dropped to 3.876 mg/L in the SSC+selected oligosaccharide arm with subjects with comorbidity (vs. 4.082 mg/L in the SSC alone arm), although there was high variability between subjects. No significant changes were detected for the inflammatory biomarker D-dimer.

While not statistically significant, this is consistent with the idea that the modulation of the microbiome induced by the oligosaccharide composition promotes an attenuation of one or more aspects of a subject's immune response, potentially attenuating undesirable excessive inflammatory responses to viral illness.

The decline in COVID-19 symptoms over time as the infection progresses was assessed as part of the safety assessment in the full subject pool and was measured by analysing 13 overall COVID-19 related symptoms in the overall participant pool, participants having at least one comorbidity, and participants not having a comorbidity. Patients were treated with SSC alone (Arm 1) or SSC and the selected oligosaccharide composition (Arm 2). The data was consistent with the interim analysis described above. The median time t resolution of symptoms in patients was measured:

- 21.0 (95% CI: 16.0, 28.0) days for patients with at least one comorbidity treated with SSC and oligosaccharide versus 30.0 (95% CI: 20.0, 32.0) days for patients with at least one comorbidity on SSC alone;
- 18.0 (95% CI: 14.0, 23.0) days for patients without comorbidities treated with SSC and oligosaccharide versus 21.0 (95% CI: 15.0, 29.0) days for patients without comorbidities on SSC alone;
- 19.0 (95% CI: 16.0, 23.0) days for the overall patient population treated with SSC and oligosaccharide versus 22.0 (95% CI: 19.0, 30.0) days for the overall patient population on SSC alone.

The data confirmed the oligosaccharide composition was generally safe and tolerable. The data further suggest that the selected oligosaccharide may be useful in reducing the time to resolution of the 13 overall COVID-19 symptoms in patients generally, regardless of whether the patient also exhibits a comorbidity. In addition, the data suggests patients displaying one or more comorbidity receive additional benefit, resolving symptoms more than week faster when treated with SSC and oligosaccharide composition compared to SSC alone.

The decline in COVID-19 symptoms over time as the infection progresses was assessed as part of the safety assessment in the full subject pool and was measured by analysing the 8 Cardinal COVID-19 related symptoms in the overall participant pool, participants having at least one co-morbidity, and participants not having a co-morbidity. Patients were treated with SSC alone (Arm 1) or SSC and the selected oligosaccharide composition (Arm 2). The data is consistent with the interim analysis described above. The median time to resolution of symptoms in patients was measured:

- 17.0 (95% CI: 12.0, 21.0) days for patients with at least one comorbidity treated with SSC and oligosaccharide versus 21.0 (95% CI: 17.0, 30.0) days for patients with at least one comorbidity on SSC alone;
- 14.0 (95% CI: 11.0, 21.0) days for patients without comorbidities treated with SSC and oligosaccharide versus 15.0 (95% CI: 12.0, 19.0) days for patients without comorbidities on SSC alone;
- 15.0 (95% CI: 13.0, 19.0) days for the overall patient population treated with SSC and oligosaccharide versus 19.0 (95% CI: 14.0, 21.0) days for the overall patient population on SSC alone.

The data confirm the oligosaccharide composition was generally safe a d tolerable. The data further suggest that the selected oligosaccharide might be effective in reducing the time to resolution of the 8 Cardinal COVID-19 symptoms in patients that exhibits at least one comorbidity. Any apparent difference in effect seen in the 8 Cardinal COVID-19 symptoms data compared to the 13 overall COVID-19 symptoms data may be explained by the lower power of 8 Cardinal COVID-19 symptoms data; by virtue of looking at fewer symptoms, the 8 Cardinal COVID-19 symptoms data captures fewer reportable events, i.e., fewer symptoms may mean fewer opportunities to observe improvement/resolution in patients with mild to moderate COVID-19 who were the primary target of the study. The 8 Cardinal COVID-19 symptoms align with the list of symptoms originally promulgated by the U.S. Centers for Disease Control (CDC) which have been found to correspond to the symptoms of patients with severe COVID-19, rather than those with mild to moderate COVID-19. Including fewer symptoms may also fail to capture the more modest improvements seen in patients without comorbidities.

A challenge of the ongoing COVID-19 pandemic is the overwhelmed and overburdened state of healthcare systems faced with high numbers of COVID-19 patients seeking care. Based upon the improvements observed in time to resolution of symptoms, it was hypothesized that treatment with the selected oligosaccharide composition could effectively decrease the burden on healthcare systems by reducing symptom severity and/or resolving symptoms prior to the need for, e.g., a hospital visit. The number of patients utilizing healthcare via a hospitalization, emergency room visit, or urgent care visit was assessed at the study's completion (FIG. 19). Subjects in the overall population treated with SSC and oligosaccharide composition had a healthcare utilization rate more than 50% lower than subjects treated with SSC alone. Subjects having one or more comorbidity treated with SSC and oligosaccharide composition had a healthcare utilization rate more than 61% lower than similar subjects treated with SSC alone. These data suggest that administration of the oligosaccharide composition may have healthcare system-wide benefits in addition to patient or patient population level benefits, and may be useful for decreasing the burden COVID-19 or other viral respiratory illnesses place on healthcare systems.

Patients having one or more additional risk factor have been shown to be at a higher risk of mild to moderate COVID-19 progressing to severe COVID-19, as well as for experiencing more severe long side effects. A series of subgroups of participants were evaluated—as part of the safety assessment—for their time to resolution of symptoms of COVID-19: patients with an age-related risk factor (e.g., at least 45 years old); patients with one or more comorbidity; patients with one or more high-risk comorbidity (e.g., chronic lung disease (e.g., asthma, emphysema, or COPD), diabetes mellitus, cardiovascular disease, hypertension, chronic renal disease, or cancer); and obese patients (e.g., having a BMI >35). The effect of combinations of these criteria on time to resolution of symptoms was also evaluated. The data can be seen in Tables Y1-Y4 and FIGS. 20-25.

TABLE Y1

Subgroup Analysis of Time to Resolution of Overall 13 Symptoms

| Subgroup | SSC + Oligo. (N = 169) N1 | SSC + Oligo. (N = 169) Patients with Event n (%) | SSC + Oligo. (N = 169) Median Time (95% CI) (day)[1] | SSC Alone (N = 172) N1 | SSC Alone (N = 172) Patients with Event n (%) | SSC Alone (N = 172) Median Time (95% CI) (day)[1] | SSC + Oligo. vs. SSC Alone Hazard Ratio [2] | SSC + Oligo. vs. SSC Alone 95% CI |
|---|---|---|---|---|---|---|---|---|
| Overall | 146 | 113 (66.9) | 19.0 (16.0, 23.0) | 147 | 106 (61.6) | 22.0 (19.0, 30.0) | 1.2539 | (0.9566, 1.6437) |
| Age Group (years) | | | | | | | | |
| >=18 to <45 | 98 | 79 (46.7) | 19.0 (14.0, 23.0) | 98 | 75 (43.6) | 20.0 (17.0, 28.0) | 1.1794 | (0.8539, 1.6290) |
| >=45 to <65 | 41 | 29 (17.2) | 20.0 (15.0, 31.0) | 44 | 26 (15.1) | 32.0 (21.0, NA) | 1.8646 | (1.0674, 3.2570) |
| >=65 | 7 | 5 (3.0) | 28.0 (13.0, NA) | 5 | 5 (2.9) | 19.0 (9.0, NA) | 0.2996 | (0.0104, 8.6610) |
| Comorbidity Status | | | | | | | | |
| Yes | 61 | 45 (26.6) | 21.0 (16.0, 28.0) | 53 | 35 (20.3) | 30.0 (20.0, 32.0) | 1.4217 | (0.8982, 2.2501) |
| No | 85 | 68 (40.2) | 18.0 (14.0, 23.0) | 94 | 71 (41.3) | 21.0 (15.0, 29.0) | 1.1946 | (0.8512, 1.6766) |
| Baseline BMI Subgroup (kg/$m^2$) | | | | | | | | |
| <30 | 96 | 74 (43.8) | 19.0 (15.0, 24.0) | 93 | 67 (39.0) | 22.0 (19.0, 30.0) | 1.2918 | (0.9174, 1.8191) |
| >=30 | 49 | 38 (22.5) | 21.0 (16.0, 27.0) | 53 | 38 (22.1) | 24.0 (18.0, 32.0) | 1.2632 | (0.7911, 2.0171) |
| Ethnicity | | | | | | | | |
| Hispanic or Latino | 89 | 72 (42.6) | 16.0 (14.0, 21.0) | 96 | 70 (40.7) | 20.0 (15.0, 28.0) | 1.4179 | (1.0112, 1.9881) |
| Not Hispanic or Latino | 56 | 40 (23.7) | 23.0 (19.0, 30.0) | 50 | 36 (20.9) | 30.0 (21.0, 32.0) | 1.2161 | (0.7518, 1.9670) |

TABLE Y2

Subgroup Analysis of Time to Resolution of Cardinal 8 Symptoms

| Subgroup | SSC + Oligo. (N = 169) N1 | SSC + Oligo. (N = 169) Patients with Event n (%) | SSC + Oligo. (N = 169) Median Time (95% CI) (day)[1] | SSC Alone (N = 172) N1 | SSC Alone (N = 172) Patients with Event n (%) | SSC Alone (N = 172) Median Time (95% CI) (day)[1] | SSC + Oligo. vs. SSC Alone Hazard Ratio [2] | SSC + Oligo. vs. SSC Alone 95% CI |
|---|---|---|---|---|---|---|---|---|
| Overall | 130 | 107 (63.3) | 15.0 (13.0. 19.0) | 134 | 105 (61.0) | 19.0 (14.0, 21.0) | 1.1262 | (0.8558, 1.4819) |
| Age Group (years) | | | | | | | | |
| >=18 to <45 | 85 | 68 (40.2) | 16.0 (11.0, 21.0) | 89 | 72 (41.9) | 15.0 (13.0, 19.0) | 0.9764 | (0.6978, 1.3662) |
| >=45 to <65 | 38 | 32 (18.9) | 15.0 (12.0, 23.0) | 41 | 29 (16.9) | 24.0 (20.0, 30.0) | 1.9645 | (1.1301, 3.4152) |
| >=65 | 7 | 7 (4.1) | 21.0 (7.0, NA) | 4 | 4 (2.3) | 11.0 (9.0, NA) | 0.0526 | (0.0031, 0.8865) |

TABLE Y2-continued

Subgroup Analysis of Time to Resolution of Cardinal 8 Symptoms

| Subgroup | SSC + Oligo. (N = 169) N1 | SSC + Oligo. (N = 169) Patients with Event n (%) | SSC + Oligo. (N = 169) Median Time (95% CI) (day)[1] | SSC Alone (N = 172) N1 | SSC Alone (N = 172) Patients with Event n (%) | SSC Alone (N = 172) Median Time (95% CI) (day)[1] | SSC + Oligo. vs. SSC Alone Hazard Ratio [2] | SSC + Oligo. vs. SSC Alone 95% CI |
|---|---|---|---|---|---|---|---|---|
| Comorbidity Status | | | | | | | | |
| Yes | 57 | 48 (28.4) | 17.0 (12.0, 21.0) | 49 | 36 (20.9) | 21.0 (17,0, 30.0) | 1.5743 | (0.9974, 2.4848) |
| No | 73 | 59 (34.9) | 14.0 (11.0, 21.0) | 85 | 69 (40.1) | 15.0 (12.0, 19.0) | 0.9623 | (0.6742, 1.3735) |
| Baseline BMI Subgroup (kg/$m^2$) | | | | | | | | |
| <30 | 87 | 72 (42.6) | 15.0 (12.0, 21.0) | 87 | 69 (40.1) | 17.0 (13.0, 21.0) | 1.0754 | (0.7634, 1.5149) |
| >=30 | 42 | 34 (20.1) | 16.5 (11.0, 21.0) | 46 | 35 (20.3) | 20.0 (14.0, 30.0) | 1.5441 | (0.9293, 2.5655) |
| Ethnicity | | | | | | | | |
| Hispanic or Latino | 81 | 69 (40.8) | 15.0 (10.0. 18,0) | 85 | 68 (39.5) | 15.0 (12.0, 20.0) | 1.1566 | (0.8181, 1.6353) |
| Not Hispanic or Latino | 48 | 37 (21.9) | 19.0 (12.0, 25.0) | 48 | 37 (21.5) | 22.0 (17.0, 30.0) | 1.1762 | (0.7325, 1.8888) |

TABLE Y3

Time to Resolution of 13 Overall Symptoms in Subgroups of Interest

| Subgroup | SSC + oligosaccharide composition (N = 169) N1 | SSC + oligosaccharide composition (N = 169) Patients with Event n (%) | SSC + oligosaccharide composition (N = 169) Median Time (95% CI) (day)[1] | SSC Alone (N = 172) N1 | SSC Alone (N = 172) Patients with Event n (%) | SSC Alone (N = 172) Median Time (95% CI) (day)[1] | SSC + Oligo. vs. SSC Alone Hazard Ratio [2] | SSC + Oligo. vs. SSC Alone 95% CI |
|---|---|---|---|---|---|---|---|---|
| Age >=45 or Comorbidity | | | | | | | | |
| Yes | 79 | 57 (71.4) | 21.0 (17.0, 26.0) | 70 | 43 (60.9) | 21.0 (21.0, 34.0) | 1.597 | (1.064, 2.398) |
| No | 67 | 56 (84.0) | 17.0 (13.0, 24.0) | 77 | 63 (81.9) | 18.0 (14.0, 24.0) | 1.068 | (0.741, 1.540) |
| Age >=45 or Comorbidity or BMI >=35 | | | | | | | | |
| Yes | 85 | 63 (73.5) | 21.0 (17.0, 25.0) | 75 | 48 (63.0) | 30.0 (21.0, 33.0) | 1.498 | (1.022, 2.198) |
| No | 61 | 50 (81.9) | 17.0 (13.0, 23.0) | 72 | 58 (79.8) | 18.0 (13.0, 26.0) | 1.048 | (0.712, 1.542) |
| Age >=45 or Comorbidity or BMI >=30 | | | | | | | | |
| Yes | 93 | 70 (75.6) | 19.0 (17.0, 25.0) | 90 | 61 (67.2) | 24.0 (20.0, 32.0) | 1.322 | (0.931, 1.875) |
| No | 53 | 43 (81.9) | 17.0 (12.0, 24.0) | 57 | 45 (79.8) | 22.0 (15.0, 29.0) | 1.154 | (0.754, 1.765) |
| Age >=45 or High-Risk Comorbidity | | | | | | | | |
| Yes | 65 | 49 (75.6) | 19.0 (15.0, 26.0) | 66 | 40 (60.9) | 32.0 (22.0, 34.0) | 1.654 | (1.079, 2.536) |
| No | 81 | 64 (79.8) | 19.0 (15.0, 24.0) | 81 | 66 (81.9) | 19.0 (14.0, 24.0) | 1.039 | (0.728, 1.484) |
| Age >=45 or High-Risk Comorbidity or BMI >=35 | | | | | | | | |
| Yes | 74 | 55 (73.5) | 20.0 (16.0, 26.0) | 71 | 45 (63.0) | 31.0 (21.0, 34.0) | 1.479 | (0.992, 2.205) |
| No | 72 | 58 (79.8) | 18.0 (14.0, 24.0) | 76 | 61 (79.8) | 19.0 (14.0, 24.0) | 1.056 | (0.730, 1.529) |
| Age >=45 or High-Risk Comorbidity or BMI >=30 | | | | | | | | |
| Yes | 84 | 63 (75.6) | 19.0 (16.0, 25.0) | 86 | 58 (67.2) | 26.0 (20.0, 32.0) | 1.306 | (0.908, 1.879) |
| No | 62 | 50 (79.8) | 19.0 (14.0, 24.0) | 61 | 48 (77.7) | 21.0 (17.0, 29.0) | 1.158 | (0.772, 1.736) |
| Comorbidity or BMI >=35 | | | | | | | | |
| Yes | 71 | 55 (77.7) | 21.0 (16.0, 25.0) | 61 | 41 (67.2) | 28.0 (20.0, 32.0) | 1.443 | (0.952, 2.188) |
| No | 75 | 58 (77.7) | 18.0 (14.0, 23.0) | 86 | 65 (75.6) | 22.0 (15.0, 29.0) | 1.130 | (0.785, 1.626) |
| Comorbidity or BMI >=30 | | | | | | | | |
| Yes | 79 | 62 (77.7) | 20.0 (16.0, 25.0) | 78 | 56 (71.4) | 21.0 (19.0, 31.0) | 1.258 | (0.870, 1.821) |
| No | 67 | 51 (75.6) | 19.0 (14.0, 24.0) | 69 | 50 (73.5) | 24.0 (17.0, 31.0) | 1.256 | (0.843, 1.873) |
| High-Risk Comorbidity or BMI >=35 | | | | | | | | |
| Yes | 58 | 46 (79.8) | 21.0 (15.0, 27.0) | 54 | 36 (67.2) | 30.0 (20.0, 32.0) | 1.459 | (0.933, 2.282) |
| No | 88 | 67 (75.6) | 19.0 (15.0, 24.0) | 93 | 70 (75.6) | 21.0 (17.0, 29.0) | 1.134 | (0.802, 1.603) |
| High-Risk Comorbidity or BMI >=30 | | | | | | | | |
| Yes | 68 | 54 (79.8) | 19.0 (15.0, 26.0) | 72 | 52 (71.4) | 22.0 (19.0, 32.0) | 1.276 | (0.863, 1.887) |
| No | 78 | 59 (75.6) | 19.0 (15.0, 24.0) | 75 | 54 (71.4) | 22.0 (18.0, 31.0) | 1.271 | (0.871, 1.856) |

TABLE Y4

Time to Resolution of 8 Cardinal Symptoms in Subgroups of Interest

| | SSC + oligosaccharide composition (N = 169) | | | SSC Alone (N = 172) | | | SSC + Oligo. vs. SSC Alone | |
|---|---|---|---|---|---|---|---|---|
| Subgroup | N1 | Patients with Event n (%) | Median Time (95% CI) (day)[1] | N1 | Patients with Event n (%) | Median Time (95% CI) (day)[1] | Hazard Ratio [2] | 95% CI |
| Age >=45 or Comorbidity | | | | | | | | |
| Yes | 74 | 62 (84.0) | 16.0 (12.0, 21.0) | 66 | 46 (69.3) | 24.0 (20.0, 30.0) | 1.584 | (1.069, 2.347) |
| No | 56 | 45 (79.8) | 14.0 (11.0, 21.0) | 68 | 59 (86.1) | 13.5 (12.0, 17.0) | 0.846 | (0.570, 1.255) |
| Age >=45 or Comorbidity or BMI >=35 | | | | | | | | |
| Yes | 79 | 67 (84.0) | 16.0 (12.0, 19.0) | 70 | 50 (71.4) | 22.0 (19.0, 30.0) | 1.542 | (1.059, 2.246) |
| No | 51 | 40 (77.7) | 14.0 (11.0, 24.0) | 64 | 55 (86.1) | 13.0 (12.0, 17.0) | 0.812 | (0.536, 1.231) |
| Age >=45 or Comorbidity or BMI >=30 | | | | | | | | |
| Yes | 84 | 71 (84.0) | 16.0 (12.0, 19.0) | 82 | 60 (73.5) | 21.0 (17.0, 25.0) | 1.401 | (0.985, 1.992) |
| No | 46 | 36 (77.7) | 14.0 (11.0, 26.0) | 52 | 45 (86.1) | 14.0 (12.0, 19.0) | 0.826 | (0.528, 1.293) |
| Age >=45 or High-Risk Comorbidity | | | | | | | | |
| Yes | 60 | 53 (88.2) | 15.0 (12.0, 18.0) | 62 | 43 (69.3) | 24.0 (20.0, 30.0) | 1.678 | (1.111, 2.534) |
| No | 70 | 54 (77.7) | 18.0 (11.0, 23.0) | 72 | 62 (86.1) | 13.5 (12.0, 17.0) | 0.824 | (0.563, 1.205) |
| Age >=45 or High-Risk Comorbidity or BMI >=35 | | | | | | | | |
| Yes | 68 | 58 (86.1) | 15.0 (12.0, 19.0) | 66 | 47 (71.4) | 22.0 (19.0, 30.0) | 1.519 | (1.026, 2.248) |
| No | 62 | 49 (79.8) | 18.0 (11.0, 23.0) | 68 | 58 (86.1) | 13.0 (12.0, 17.0) | 0.829 | (0.560, 1.228) |
| Age >=45 or High-Risk Comorbidity or BMI >=30 | | | | | | | | |
| Yes | 75 | 63 (84.0) | 15.0 (12.0, 18.0) | 78 | 57 (73.5) | 21.0 (17.0, 27.0) | 1.393 | (0.966, 2.007) |
| No | 55 | 44 (79.8) | 19.0 (11.0, 24.0) | 56 | 48 (86.1) | 14.0 (12.0, 19.0) | 0.842 | (0.553, 1.282) |
| Comorbidity or BMI >=35 | | | | | | | | |
| Yes | 66 | 57 (86.1) | 15.0 (12.0, 21.0) | 56 | 42 (75.6) | 21.0 (17.0, 27.0) | 1.582 | (1.042, 2.400) |
| No | 64 | 50 (77.7) | 16.0 (11.0, 23.0) | 78 | 63 (79.8) | 14.5 (12.0, 19.0) | 0.890 | (0.607, 1.306) |
| Comorbidity or BMI >=30 | | | | | | | | |
| Yes | 71 | 61 (86.1) | 16.0 (12.0, 19.0) | 70 | 54 (77.7) | 20.0 (14.0, 24.0) | 1.397 | (0.957, 2.039) |
| No | 59 | 46 (77.7) | 15.0 (11.0, 24.0) | 64 | 51 (79.8) | 16.0 (13.0, 22.0) | 0.931 | (0.617, 1.405) |
| High-Risk Comorbidity or BMI >=35 | | | | | | | | |
| Yes | 53 | 47 (88.2) | 15.0 (10.0, 21.0) | 49 | 37 (75.6) | 21.0 (17.0, 27.0) | 1.587 | (1.014, 2.483) |
| No | 77 | 60 (77.7) | 17.0 (12.0, 21.0) | 85 | 68 (79.8) | 15.0 (12.0, 19.0) | 0.922 | (0.644, 1.322) |
| High-Risk Comorbidity or BMI >=30 | | | | | | | | |
| Yes | 60 | 52 (86.1) | 15.0 (10.0, 18.0) | 64 | 50 (77.7) | 20.0 (14.0, 25.0) | 1.422 | (0.952, 2.125) |
| No | 70 | 55 (77.7) | 17.0 (12.0, 23.0) | 70 | 55 (77.7) | 17.0 (13.0, 21.0) | 0.971 | (0.660, 1.428) |

The data show that the selected oligosaccharide composition reduces the time to resolution of symptoms, either the 8 Cardinal COVID-19 symptoms or 3 overall COVID-19 symptoms, in patients at least 45 years old; in patients with at least one comorbidity; or being overweight or obese (e.g., a BMI of at least 30 or at least 35). The selected oligosaccharide composition reduces the time to resolution of symptoms, either the 8 Cardinal COVID-19 symptoms or 13 overall COVID-19 symptoms, in patients having at least two of the following criteria: at least 45 years old; in at least one comorbidity; being overweight or obese (e.g., a BMI of at least 30 or at least 35); or at least one high risk comorbidity.

Overall, the study suggests that the selected oligosaccharide composition reduced the time to resolution of symptoms of an exemplary viral respiratory ill ess, COVID-19, in the overall study patient population, irrespective of other health conditions. The study suggests that changes in a subject's microbiome promoted by the selected oligosaccharide composition can reduce systemic inflammation, e.g., a biomarker of systemic inflammation (CRP). The study shows that the selected oligosaccharide composition reduced the time to resolution of symptoms of COVID-19 in patients with at least one comorbidity, an age-related risk factor, who are overweight or obese, or who have two or more of these criteria. The time to resolution of symptoms was further reduced in these high-risk subjects relative to the overall study patient population. The study shows that, in addition to hastening the recovery f patients, patients treated with the selected oligosaccharide composition showed a decrease in healthcare utilization, showing the potential of treatment with the selected oligosaccharide composition to ease the burdens not just on patients themselves, but the overburdened healthcare systems serving them.

Figure 14:
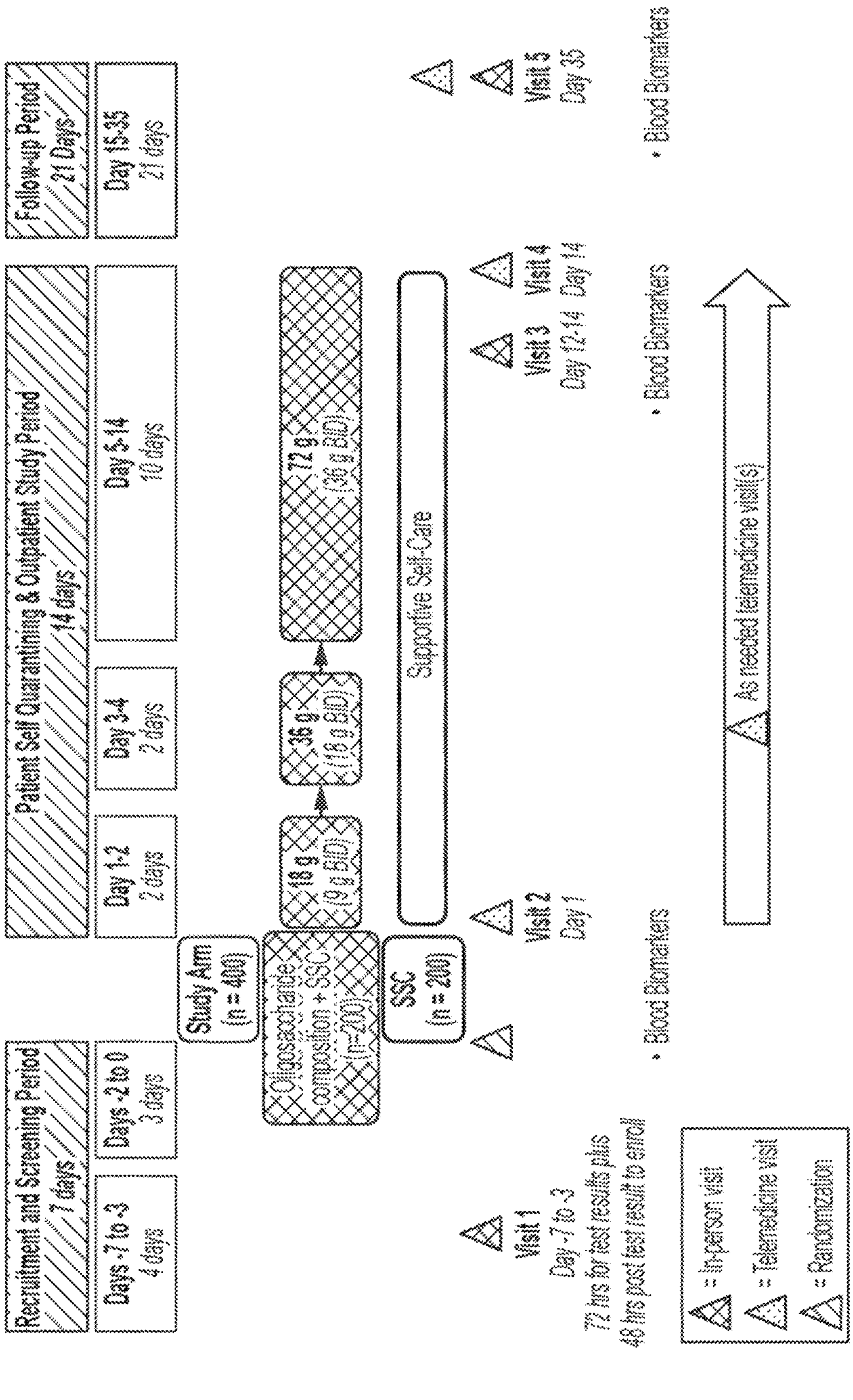
FIG. 14 provides a schematic design for a clinical food study trial.

In a separate study, approximately 50 patients with mild to moderate COVID-19 symptoms are randomized (1:1) to receive either (A) SSC and the selected oligosaccharide composition or (B) remain on SSC alone under the same parameters described above, briefly, the study consists of a Screening/Randomization Visit, Intake Period (14 Days) followed by a Follow-up Period (21 Days), as detailed in FIG. 14. The major endpoint of the study is the assessment of changes in relative abundance of microbial taxa in these patients.

Example 10. Determination of Glycosidic Bond Distribution Using Permethylation Analysis A determination of glycosidic bond distribution of samples of the selected oligosaccharide composition, as produced by a process as described in Example 1 (Marathon C catalyst), was performed using permethylation analysis, according to the protocol described below. Samples were demonomerized prior to permethylation analysis.

Reagents used were methanol, acetic acid, sodium borodeuteride, sodium carbonate, dichioromethane, isopropanol, trifluoroacetic acid (TFA), an acetic anhydride. Equipment included a heating block, drying apparatus, gas chromatograph equipped for capillary columns and with a RID/MSD detector, and a 30 meter RTX®-2330 (RESTEK). All derivation procedures were done in a hood.

Preparation of Alditol Acetates

A. Standard Preparation 1 mg/mL solutions of the following standard analytes we e prepared: arabinose, rhamnose, fucose, xylose, mannose, galactose, glucose, and inositol. The standard was prepared by mixing 50 μL of each of arabinose, xylose, fucose, glucose, mannose, and galactose with 20 L of inositol in a vial. The standard was subsequently lyophilized.

B. Sample Preparation

Each sample was prepared by mixing 100-500 μg of the selected oligosaccharide composition (as weighed on an analytical balance) with 20 μg (20 L) of inositol in a vial.

C. Hydrolysis

200 μL of 2 M tifluoroacetic acid (TFA) was added to the sample(s). The vial containing the sample was capped tightly and incubated on a heating block for 2 hours at 121° C. After 2 hours, the sample was removed from the heating block and allowed to cool to room temperature. The sample was then dried down with $N_2$/air. 200 μL of IPA (isopropanol) was added and dried down again with $N_2$/air. This hydrolysis step (addition f TFA for two hours at 121° C.; washing with isopropanol) was repeated twice.

The standard was similarly subjected to hydrolysis using TFA, as described for the sample.

D. Reduction and Acetylation 10 mg/mL solution of sodium borodeuteride was prepare in 1 M ammonium hydroxide. 200 μL of this solution was added to the sample. The sample was then incubated at room temperature for at least one hour or overnight. After incubation with sodium borodeuteride solution, 5 drops of glacial acetic acid were added to the sample, followed by 5 drops of methanol. The sample was then dried down. 500 μL of 9:1 MeOH:HOAc was added to the sample and subsequently dried down (twice repeated). 500 μL MeOH as then added to the sample and subsequently dried down (once repeated). This produced a rusty white residue on the side of the sample vial.

250 μL acetic anhydride was then added to the sample vial and the sample was vortexed to dissolve. 230 μL concentrated TFA was added to the sample and the sample was incubated at 50° C. for 20 minutes. The sample was removed from the heat and allowed to cool to room temperature. Approximately 1 mL isopropanol was added and the sample was dried down. Then, approximately 200 μL isopropanol was added and the sample was dried down again. Approximately 1 mL of 0.2M sodium carbonate was then added to the sample and it was mixed gently. Approximately 2 mL dichloromethane was finally added to the sample, after which it was vortexed and centrifuged briefly. The aqueous top layer was discarded. mL water was added and the sample was vortexed and centrifuged briefly. This step was repeated before the organic layer (bottom) was removed and transferred to another vial. The sample was concentrated using $N_2$/air to a final volume of about 100 μL. 1 μL of final sample was the injected on GC-MS.

The GC temperature program SP2330 was utilized for GC-MS analysis. The initial temperature was 80° C. and the initial time was 2.0 minutes. The first ramp was at a rate of 30° C./min with a final temperature of 170° C. and a final time of 0.0 minutes. The second ramp was at a rate of 4° C./min with a final temperature of 240° C. and a final time of 20.0 minutes.

Glycosyl-Linkage Analysis of Poly- and Oligosaccharides by Hakomori Methylation

A. Preparation of NaOH Base

In a glass screw top tube, 100 μL of a 50/50 NaOH solution and 200 μL of dry MeOH were combined. Plastic pipets were used for the NaOH and glass pipets were used for the MeOH. The solution was vortexed briefly, approximately 4 mL dry DMSO was added, and the solution was vortexed again. The tube was centrifuged to concentrate the solution and the DMSO and salts were pipetted off from the pellet. The previous two steps were repeated about four times in order to remove all the water from the pellet. All white reside was removed from the sides of the tube. Once all the residue was removed and the pellet was clear, about 1 mL dry DMSO was added and the solution was vortexed. The base was then ready to use. The base was prepared fresh each time it was needed.

B. Permethylation

Each sample was prepared by mixing 600-1000 μg of the selected oligosaccharide composition (as weighed on an analytical balance) with 200 μL DMSO. The sample was stirred overnight until the oligosaccharide composition dissolved.

An equal amount of NaOH base (400 μL) was added to t e sample, after which the sample was placed back on the stirrer and mixed well for 10 minute. 100 μL of iodomethane ($CH_3I$) was added to the sample. The sample was mixed on the stirrer for 20 minutes, and then the previous steps (addition of NaOH base and iodomethane) were repeated.

Approximately 2 mL ultrapure water was added to the sample and the sample was mixed well, such that it turned cloudy. The tip of a pipette was placed into the sample solution at the bottom of the tube and $CH_3I$ was bubbled off with a very low flow of air. The sample became clear as the $CH_3I$ was bubbled off. The pipette was moved around the solution to make certain that all the $CH_3I$ was gone. Approximately 2 mL methylene chloride was then added and the solution was mixed well by vortex for 30 seconds. The sample was then centrifuged and the top aqueous layer was removed. Approximately 2 mL of water were added md the sample was mixed, then briefly centrifuged, then the top aqueous layer was removed. The additions of methylene chloride and water were repeated. The organic bottom layer was removed and transferred into another tube and dried down using $N_2$. The analysis was continued with Alditol Acetates.

C. Hydrolysis

200 μL of 2 M tifluoroacetic acid (TFA) was added to the sample(s). The vial containing the sample was capped tightly and incubated on a heating block for 2 hours at 121° C. After 2 hours, the sample was removed from the heating block and allowed to cool to room temperature. The sample was then dried down with $N_2$/air. 200 μL of IP (isopropanol) was added and dried down again with $N_2$/air. This hydrolysis step (addition of TFA for two hours at 121° C.; washing with isopropanol) was repeated twice.

D. Reduction and Acetylation 10 mg/mL solution of sodium borodeuteride was prepare in 1 M ammonium hydroxide. 200 μL of this solution was added to the sample. The sample was then incubated at room temperature for at least one hour or overnight. After incubation with sodium borodeuteride solution, 5 drops of glacial acetic acid were added to the sample, followed by 5 drops of methanol. The sample was then dried down. 500 μL of 9:1 MeOH:HO c was added to the sample and subsequently dried down (twice repeated). 500 μL MeOH as then added to the sample and subsequently dried down (once repeated). This produced a crusty white residue on the side of the sample vial.

250 μL acetic anhydride was then added to the sample vial and the sample was vortexed to dissolve. 230 μL concentrated TFA was added to the sample and the sample was incubated at 50° C. for 20 minutes. The sample was removed from the heat and allowed to cool to room temperature. Approximately 1 mL isopropanol was added and the sample was dried down. Then, approximately 200 μL isopropanol was added and the sample was dried down again. Approximately 1 mL of 0.2M sodium carbonate was then added to the sample and it was mixed gently. Approximately 2 mL dichloromethane was finally added to the sample, after which it was vortexed and centrifuged briefly. The aqueous top layer was discarded. mL water was added and the sample was vortexed and centrifuged briefly. This step was repeated before the organic layer (bottom) was removed and transferred to another vial. The sample was concentrated using $N_2$/air to a final volume of about 100 μL. 1 μL of final sample was then injected on GC-MS.

The GC temperature program SP2330 was utilized for GC-MS analysis. The initial temperature was 80° C. and the initial time was 2.0 minutes. The first ramp was at a rate of 30° C./min with a final temperature of 170° C. and a final time of 20.0 minutes. The second ramp was at a rate of 4° C./min with a final temperature of 240° C. and a final time of 20.0 minutes.

Results

Permethylation data was collected using the methods described above for four batches of de-monomerized oligosaccharide composition produced by a process as described in Example 1 (Marathon C catalyst). Each batch was analyzed in duplicate. Averaged data relating to the radicals present in these ten batches of de-monomerized oligosaccharide composition are provided below:

| Radicals | Mean mol % + 3 STD | Mean mol % | Mean mol % − 3 STD |
|---|---|---|---|
| t-manopyranose | 4.10% | 3.56% | 3.02% |
| t-glucopyranose | 16.33% | 13.89% | 11.44% |
| t-galactofuranose | 7.78% | 4.52% | 1.26% |
| t-glucofuranose | 1.38% | 0.64% | 0.00% |
| t-galactopyranose | 12.48% | 10.38% | 8.29% |
| 3-glucopyranose | 4.88% | 3.95% | 3.02% |
| 2-manopyranose and/or 3-manopyranose | 1.94% | 1.57% | 1.20% |
| 2-glucopyranose | 3.22% | 2.83% | 2.44% |
| 2-galactofuranose and/or 2-glucofuranose | 2.32% | 1.62% | 0.93% |
| 3-galactopyranose | 3.92% | 3.43% | 2.94% |
| 4-manopyranose and/or 5-manofuranose and/or 3-galactofuranose | 2.93% | 2.34% | 1.75% |
| 6-manopyranose | 2.87% | 2.44% | 2.01% |
| 2-galactopyranose | 2.71% | 2.28% | 1.85% |
| 6-glucopyranose | 10.78% | 9.22% | 7.66% |

-continued

| Radicals | Mean mol % + 3 STD | Mean mol % | Mean mol % − 3 STD |
|---|---|---|---|
| 4-galactopyranose and/or 5-galactofuranose | 3.80% | 3.22% | 2.65% |
| 4-glucopyranose and/or 5-glucofuranose and/or 6-manofuranose | 4.25% | 3.66% | 3.06% |
| 6-glucofuranose | 1.55% | 0.81% | 0.08% |
| 6-galactofuranose | 4.96% | 3.19% | 1.42% |
| 6-galactopyranose | 9.06% | 7.44% | 5.81% |
| 3,4-galactopyranose and/or 3,5-galactofuranose and/or 2,3-galactopyranose | 1.42% | 1.16% | 0.90% |
| 3,4-glucopyranose and/or 3,5-glucofuranose | 1.04% | 0.43% | 0.00% |
| 2,4-glucopyranose and/or 2,5-glucofuranose and/or 2,4-galactopyranose and/or 2,5-galactofuranose | 1.39% | 1.16% | 0.92% |
| 4,6-manopyranose and/or 5,6-manofuranose | 0.69% | 0.59% | 0.49% |
| 3,6-manofuranose | 0.11% | 0.02% | 0.00% |
| 3,6-glucopyranose | 2.80% | 2.10% | 1.40% |
| 3,6-manopyranose and/or 2,6-manofuranose | 0.67% | 0.53% | 0.39% |
| 2,6-manopyranose | 0.54% | 0.41% | 0.28% |
| 3,6-glucofuranose | 0.39% | 0.27% | 0.16% |
| 2,6-glucopyranose and/or 4,6-glucopyranose and/or 5,6-glucofuranose | 3.58% | 2.33% | 1.08% |
| 3,6-galactofuranose | 1.37% | 1.15% | 0.93% |
| 4,6-galactopyranose and/or 5,6-galactofuranose | 2.86% | 2.48% | 2.11% |
| 3,6-galactopyranose and/or 2,6-galactofuranose | 2.98% | 2.28% | 1.58% |
| 2,6-galactopyranose | 1.62% | 1.15% | 0.68% |
| 3,4,6-manopyranose and/or 3,5,6-manofuranose and/or 2,3,6-manofuranose | 0.30% | 0.07% | 0.00% |
| 3,4,6-galactopyranose and/or 3,5,6-galactofuranose and/or 2,3,6-galactofuranose | 1.11% | 0.82% | 0.53% |
| 3,4,6-glucopyranose and/or 3,5,6-glucofuranose | 0.47% | 0.35% | 0.22% |
| 2,3,6-manopyranose and/or 2,4,6-manopyranose and/or 2,5,6-manofuranose | 0.49% | 0.17% | 0.00% |
| 2,4,6-glucopyranose and/or 2,5,6-glucofuranose | 1.36% | 0.56% | 0.00% |
| 2,3,6-galactopyranose and/or 2,4,6-galactopyranose and/or 2,5,6-galactofuranose | 0.91% | 0.66% | 0.41% |
| 2,3,6-glucopyranose | 0.48% | 0.31% | 0.13% |

Permethylation data was collected using the methods described above for five batches of de-monomerized oligosaccharide composition produced by the process described in Example 2 (citric acid catalyst). Each batch was analyzed in duplicate. Averaged data relating to the radicals present in these ten batches of de-monomerized oligosaccharide composition are provided below:

| Radicals | Mean mol % + 3 STD | Mean mol % | Mean mol % − 3 STD |
|---|---|---|---|
| t-mannopyranose | 4.14% | 3.57% | 3.00% |
| t-glucopyranose | 17.59% | 15.58% | 13.58% |
| t-galactofuranose | 4.20% | 3.59% | 2.98% |
| t-glucofuranose | 0.73% | 0.15% | 0.00% |
| t-galactopyranose | 11.69% | 10.67% | 9.65% |
| 3-glucopyranose | 4.61% | 4.22% | 3.84% |
| 2-mannopyranose and/or 3-mannopyranose | 1.99% | 1.41% | 0.83% |

-continued

| Radicals | Mean mol % + 3 STD | Mean mol % | Mean mol % − 3 STD |
|---|---|---|---|
| 2-glucopyranose | 3.03% | 2.88% | 2.72% |
| 2-galactofuranose and/or 2-glucofuranose and/or 3-glucofuranose | 1.78% | 1.30% | 0.83% |
| 3-galactopyranose | 3.77% | 3.28% | 2.79% |
| 3-galactofuranose | 2.24% | 1.92% | 1.60% |
| 6-mannopyranose | 2.47% | 2.28% | 2.08% |
| 2-galactopyranose | 2.42% | 2.03% | 1.65% |
| 6-glucopyranose | 11.06% | 10.29% | 9.53% |
| 4-galactopyranose and/or 5-galactofuranose | 3.06% | 2.75% | 2.45% |
| 4-glucopyranose and/or 5-glucofuranose and/or 6-mannofuranose | 3.89% | 3.45% | 3.00% |
| 2,3-galactofuranose | 0.42% | 0.05% | 0.00% |
| 6-glucofuranose | 0.77% | 0.31% | 0.00% |
| 6-galactofuranose | 2.68% | 2.50% | 2.31% |
| 6-galactopyranose | 8.75% | 7.90% | 7.06% |
| 3,4-galactopyranose and/or 3,5-galactofuranose and/or 2,3-galactopyranose | 1.08% | 0.97% | 0.86% |
| 3,4-glucopyranose and/or 3,5-glucofuranose | 0.75% | 0.61% | 0.47% |
| 2,3-glucopyranose | 2.11% | 0.89% | 0.00% |
| 2,4-mannopyranose and/or 2,5-mannofuranose | 0.85% | 0.21% | 0.00% |
| 2,4-glucopyranose and/or 2,5-glucofuranose and/or 2,4-galactopyranose and/or 2,5-galactofuranose | 1.88% | 1.17% | 0.45% |
| 4,6-mannopyranose and/or 5,6-mannofuranose | 0.70% | 0.53% | 0.35% |
| 3,6-glucopyranose | 2.93% | 2.47% | 2.02% |
| 3,6-mannopyranose | 0.66% | 0.54% | 0.43% |
| 2,6-mannopyranose | 0.51% | 0.45% | 0.39% |
| 3,6-glucofuranose | 0.33% | 0.12% | 0.00% |
| 2,6-glucopyranose and/or 4,6-glucopyranose and/or 5,6-glucofuranose | 2.55% | 2.15% | 1.74% |
| 3,6-galactofuranose | 1.16% | 1.01% | 0.86% |
| 4,6-galactopyranose and/or 5,6-galactofuranose | 2.86% | 2.47% | 2.09% |
| 3,6-galactopyranose | 2.73% | 2.36% | 1.99% |
| 2,6-galactopyranose | 1.49% | 1.24% | 0.99% |
| 3,4,6-mannopyranose and/or 3,5,6-mannofuranose and/or 2,3,6-mannofuranose | 0.12% | 0.01% | 0.00% |
| 3,4,6-galactopyranose and/or 3,5,6-galactofuranose and/or 2,3,6-galactofuranose | 0.96% | 0.75% | 0.54% |
| 3,4,6-glucopyranose and/or 3,5,6-glucofuranose | 0.63% | 0.28% | 0.00% |
| 2,3,6-mannopyranose | 0.34% | 0.12% | 0.00% |
| 2,4,6-glucopyranose and/or 2,5,6-glucofuranose | 0.80% | 0.40% | 0.00% |
| 2,3,6-galactopyranose and/or 2,4,6-galactopyranose and/or 2,5,6-galactofuranose | 1.31% | 0.59% | 0.00% |
| 2,4,6-galactopyranose and/or 2,5,6-galactofuranose | 0.92% | 0.15% | 0.00% |
| 2,3,6-glucopyranose | 0.74% | 0.37% | 0.00% |

Example 11. HSQC NMR Analysis Procedure Using a Varian Unity Inova NMR Machine A determination of HSQC NMR spectra of samples of the selected oligosaccharide composition, as produced by a process as described in Example 1 (Marathon C catalyst), was performed using a Varian Unity Inova NMR, according to the protocol described below.

Method

Sample Preparation:

25 mg of a previously lyophilized solid sample was dissolved in 300 μL of D2O with 0.1% acetone as internal standard. The solution was then placed into a 3 mm NMR tube.

NMR Experiment:

The sample was analyzed in a Varian Unity Inova operating at 499.83 MHz (125.69 MHz 13C) equipped with a XDB broadband probe with Z-axis gradient, tuned to 13C, and operating at 25° C. The sample was subjected to a heteroatomic single quantum coherence (HSQC), echo-antiecho, with gradient selection HSQCETGP pulse sequence experiment using the following acquisition and processing parameters in Table 3:

TABLE 3

| Acquisition Parameter | |
|---|---|
| Number of Scans | 8 |
| Recycle Delay | 1 second |
| Number of data points | 596 × 600 |
| Sweep Width (ppm) | 4 ppm × 110 ppm |
| Carrier Frequency | 4.0 ppm-65 ppm |
| CH Coupling Constant | 146 Hz |
| **Processing Parameter** | |
| Size of Matrix | 1024 × 2048 |
| Window Function | Gaussian (7.66, 26.48 Hz) |
| Baseline correction | No correction |

Spectral Analysis:

The resulting spectrum was analyzed using the MNova software package from Mestrelab Research (Santiago de Compostela, Spain). The spectrum was referenced to the internal acetone signal (1H-2.22 ppm; 13C-30.8 ppm) and phased using the Regions2D method in both the F2 and F1 dimension. Apodization using 90 degree Shifted sine was applied in both the F2 and F1 dimension. Individual signals (C—H correlations) were quantified by integration of their respective peaks using "predefined integral regions" with elliptical integration shapes. The resulting table of integral regions and values were normalized to a sum of 100 in order for the value to represent a percentage of the total. Peak integral regions were selected to avoid peaks associated with monomers.

Results

Ten batches of the selected oligosaccharide composition analyzed by SEC as described in Example 12, and produced according to the process of Example 1 (Marathon C catalyst), were analyzed using the above NMR methods. Collectively, these batches comprised the following NMR peak signals (Table 4)

TABLE 4

HSQC NMR peaks of the selected oligosaccharide composition

| | $^{1}H$ Position (ppm) | | | $^{13}C$ Position (ppm) | | |
|---|---|---|---|---|---|---|
| | Center | $^{1}H$ Integral Region | | Center | $^{13}C$ Integral Region | |
| Signal | Position | from | to | Position | from | to |
| 1 | 3.68 | 3.61 | 3.75 | 63.42 | 62.64 | 64.20 |
| 2 | 3.75 | 3.72 | 3.78 | 66.06 | 65.50 | 66.62 |
| 3 | 3.97 | 3.94 | 4.00 | 66.15 | 65.81 | 66.49 |
| 4 | 3.96 | 3.94 | 3.98 | 69.28 | 69.04 | 69.52 |

TABLE 4-continued

HSQC NMR peaks of the selected oligosaccharide composition

| | $^1$H Position (ppm) | | | $^{13}$C Position (ppm) | | |
|---|---|---|---|---|---|---|
| | Center | $^1$H Integral Region | | Center | $^{13}$C Integral Region | |
| Signal | Position | from | to | Position | from | to |
| 5 | 3.96 | 3.9 | 4.03 | 70.62 | 70.20 | 71.05 |
| 6 | 3.92 | 3.9 | 3.94 | 71.26 | 71.02 | 71.50 |
| 7 | 3.55 | 3.51 | 3.59 | 71.34 | 71.06 | 71.62 |
| 8 | 3.97 | 3.94 | 4.00 | 71.56 | 71.29 | 71.84 |
| 9 | 3.72 | 3.67 | 3.77 | 72.35 | 71.95 | 72.74 |
| 15 | 4.44 | 4.41 | 4.46 | 103.86 | 103.56 | 104.15 |
| 10 | 3.33 | 3.27 | 3.4 | 73.74 | 73.26 | 74.22 |
| 14 | 4.5 | 4.47 | 4.54 | 103.29 | 102.87 | 103.70 |
| 11 | 4.06 | 4.04 | 4.09 | 77.34 | 76.89 | 77.78 |
| 12 | 4.11 | 4.08 | 4.14 | 81.59 | 81.16 | 82.01 |
| 13 | 4.96 | 4.92 | 5.01 | 98.7 | 98.02 | 99.39 |

The relative size of each of the peaks (AUC) collected for the NMR spectra of the selected oligosaccharide composition was further determined, as shown below:

| | Center Position (ppm) | | Area under the curve (AUC) (% of total |
|---|---|---|---|
| Signal | $^1$H | $^{13}$C | areas of all signals) |
| 1 | 3.68 | 63.42 | 20.38-25.74 |
| 2 | 3.75 | 66.06 | 3.69-6.38 |
| 3 | 3.97 | 66.15 | 2.21-3.40 |
| 4 | 3.96 | 69.28 | 1.46-3.71 |
| 5 | 3.96 | 70.62 | 9.28-10.71 |
| 6 | 3.92 | 71.26 | 1.52-2.03 |
| 7 | 3.55 | 71.34 | 3.40-6.13 |
| 8 | 3.97 | 71.56 | 3.40-4.41 |
| 9 | 3.72 | 72.35 | 5.66-10.14 |
| 10 | 3.33 | 73.74 | 10.21-12.09 |
| 11 | 4.06 | 77.34 | 3.68-4.50 |
| 12 | 4.11 | 81.59 | 3.10-3.82 |
| 13 | 4.96 | 98.7 | 10.65-12.31 |
| 14 | 4.5 | 103.29 | 5.03-6.41 |
| 15 | 4.44 | 103.86 | 1.84-2.44 |

Figure 13:
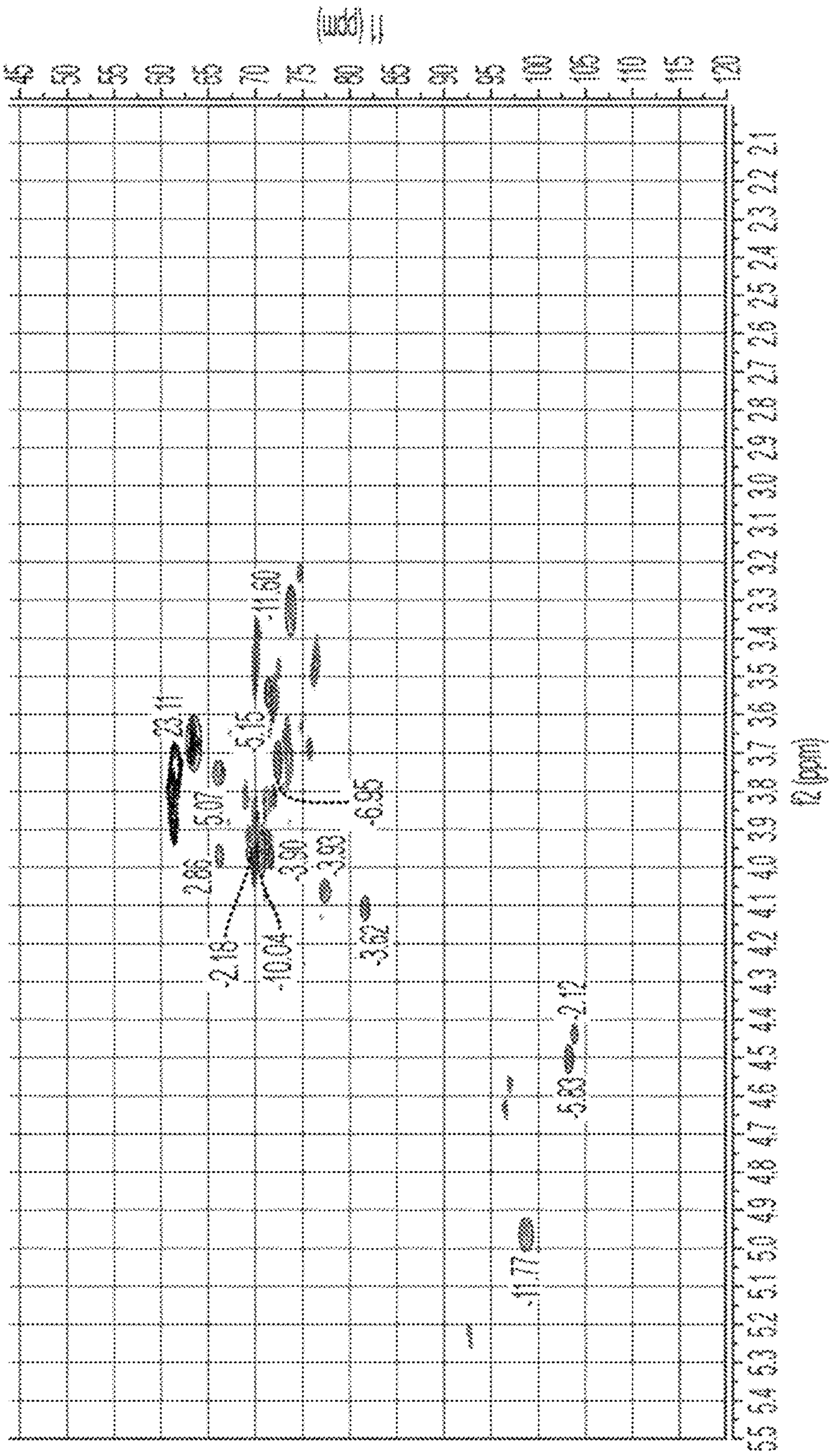
FIG. 13 provides a HSQC NMR spectra of the selected oligosaccharide composition (showing only the most prominent peaks).

A representative HSQC NMR spectra of the selected oligosaccharide composition is provided in FIG. 13.

Twenty-three batches of the selected oligosaccharide composition produced according to the process of Example 2 (citric acid catalyst) and analyzed by SEC s described in Example 12, were analyzed using the above NMR methods. Collectively, these batches comprised the NMR peak signals as shown in Table 4. The relative size of each of the peaks (AUC) collected for the NMR spectra of the selected oligosaccharide composition produced according to the process as described in Example 2 was further determined, as shown below:

-continued

| | Center Position (ppm) | | Area under the curve (AUC) (% of total |
|---|---|---|---|
| Signal | $^1$H | $^{13}$C | areas of all signals) |
| 1 | 3.68 | 63.42 | 21.57-25.73 |
| 2 | 3.75 | 66.06 | 3.87-5.54 |
| 3 | 3.97 | 66.15 | 2.63-3.43 |
| 4 | 3.96 | 69.28 | 1.28-3.86 |
| 5 | 3.96 | 70.62 | 9.08-11.04 |
| 6 | 3.92 | 71.26 | 1.49-2.70 |
| 7 | 3.55 | 71.34 | 4.48-5.90 |
| 8 | 3.97 | 71.56 | 3.07-3.99 |
| 9 | 3.72 | 72.35 | 6.87-8.66 |
| 10 | 3.33 | 73.74 | 10.79-11.70 |
| 11 | 4.06 | 77.34 | 3.28-3.99 |
| 12 | 4.11 | 81.59 | 2.82-3.39 |
| 13 | 4.96 | 98.7 | 10.60-12.69 |
| 14 | 4.5 | 103.29 | 4.90-6.25 |
| 15 | 4.44 | 103.86 | 1.81-2.42 |

Figure 26:
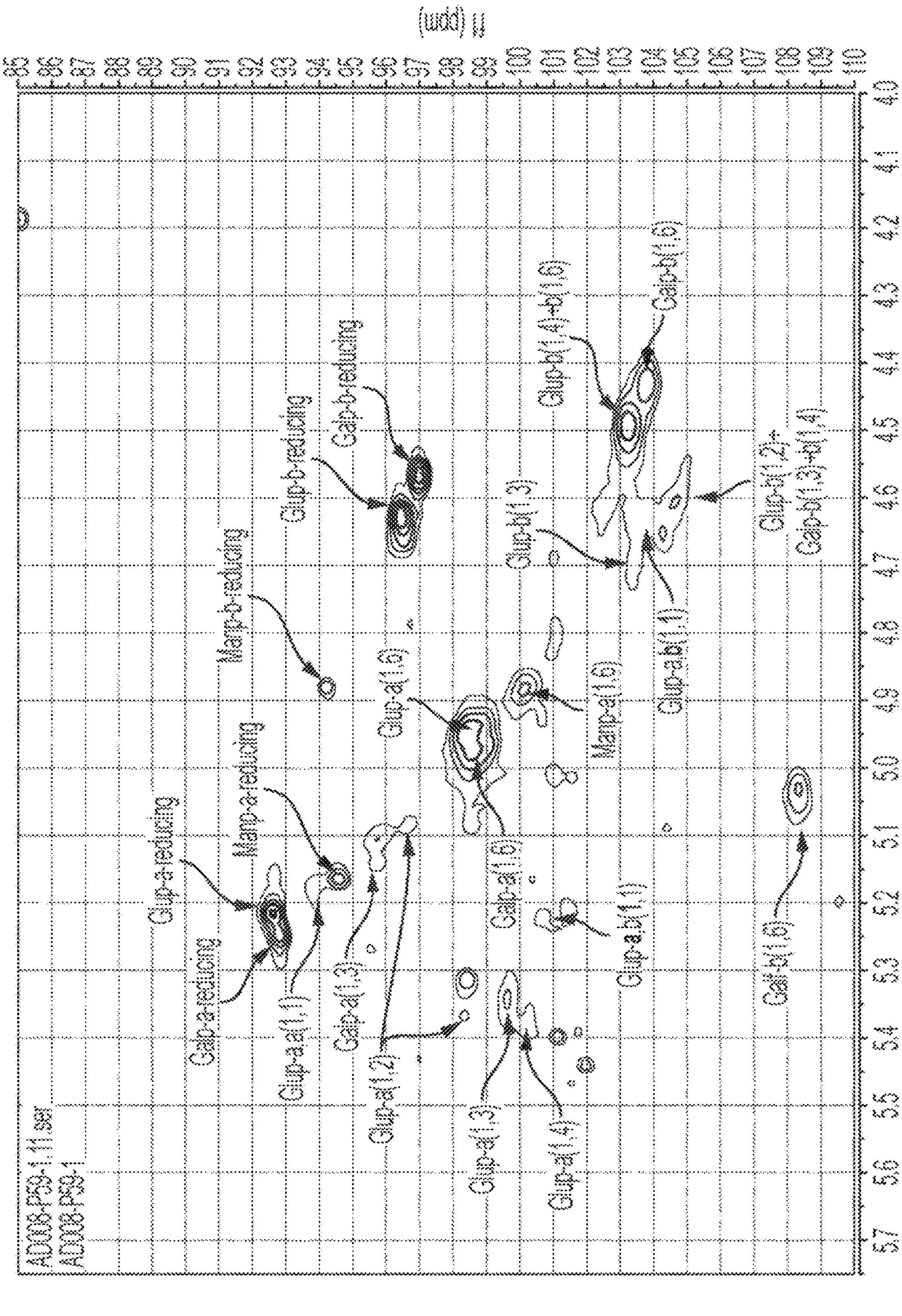
FIG. 26 shows annotation of a $^{1}H$—$^{13}C$ gHSQC NMR spectra of the selected oligosaccharide composition, assigning glycosidic bonds of the oligosaccharide composition to each peak. Annotations indicate glycan locations, not total peak volumes. The exemplary selected oligosaccharide composition examined included approximately 13% monomer content. With reference to FIG. 13.
Figure 27:
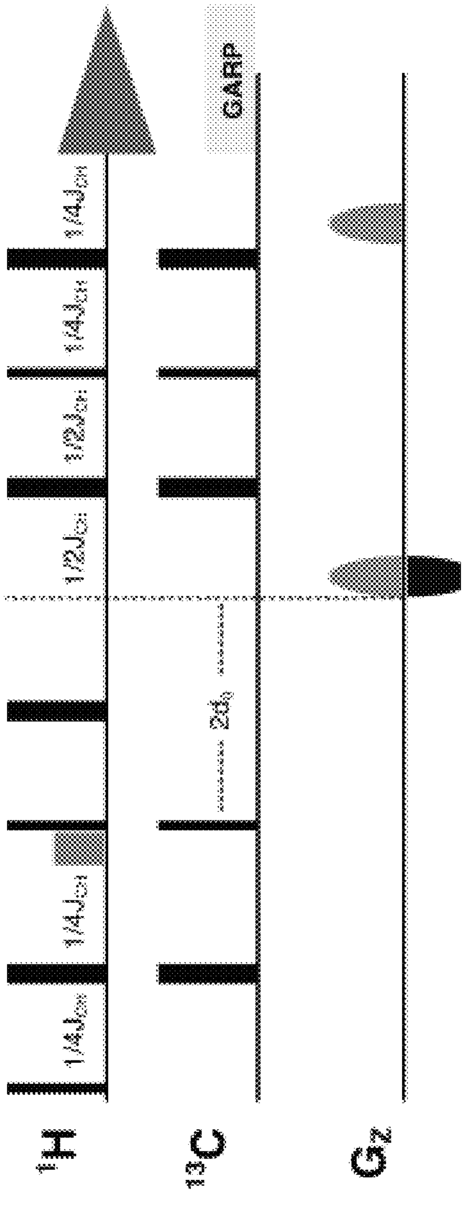
FIG. 27 depicts an NMR pulse sequence diagram.

Peaks of the selected oligosaccharide composition were assigned using commercially sourced dimers from Carbosynth Inc. (FIG. 26). With reference to FIG. 13, FIG. 26 depicts only the anomeric region and was obtained by setting a lower threshold to aid peak annotation of less prominant peaks. Assignments were based on several approaches including those described in, e.g., "1H NMR structural-reporter-group concept" (Leeuwen et al. Carbohydrate Research 343 (2008), 1114-1119). Dimers used in the analysis included: Glup-b(1-2) Glup, Glup-a(1-2)-Glup, Glup-b(1-3)-Glup, Glup-b(1-4)-Glup, Glup-a(1-4)-Glup, Glup-b(1-6)-Glup, Glup-a(1-6)-Glup, Glup-a,b(1-1)-Glup, Glup-a,a(1-1)-Glup, Galp-a(1-6)-Glup, Galp-b(1-4)-Glup, Galp-b(1-6)-Galp, Galp-b(1-4)-Galp, Galp-b(1-3)-Galp, Galp-a(1-3)-Galp, Galp-b(1-2)-Galp, and Galp-a(1-2)-Galp. Linkage abundances were compared with permethylation data and cross referenced with literature values and compositionally pure selected oligosaccharide compositions.

Example 12. Size Exclusion Chromatography Method

The weight-average molecular weight (MWw), number-average molecular weight (MWn), and polydispersity index (PDI) of batches and samples of the selected oligosaccharide composition, as produced by the process in Example 1 (Marathon C catalyst), were determined by SEC HPLC Method These methods involved the use of an Agilent 1100 with refractive index (RI) detector equipped with a guard column (Shodex SUGAR SP-G 6B Guard Column 6×50 mm, m) and two chromatography columns in series: 1) Shodex OHpak SB-802 HQ, 8.0×300 mm, 8 μm, P/N F6429100; 2) Shodex OHpak SB-803 HQ, 8.0×300 mm, 6 μm, P/N F6429102.

The mobile phase (0.1 M $NaNO_3$) was prepared by weighing 17 g of $NaNO_3$ (ACS grade reagent) and dissolving in 2000 mL of deionized (DI) water (from MilliQ water filter). The solution was filtered through a 0.2 μm filter.

Polymer standard solutions (10.0 mg/mL) of each of D-(+) Glucose Mp 180, Carbosynth Ltd Standard, or equivalent (CAS #50-99-7); Maltose Mp 342, Carbosynth Ltd Standard, or equivalent (CAS #69-79-4); Maltotetraose Mp 667, Carbosynth Ltd Standard, or equivalent (CAS #34612-38-9); Maltooctaose Mp 1315, Carbosynth Ltd Standard, or equivalent (CAS #6156-84-9); Nominal Mp 6100 Pullulan Standard, PSS #PPS-p-16k; Nominal Mp 9600 Pullulan Standard, PSS #PPS-pul10k; and Nominal Mp 22000 Pullulan Standard, PSS #PPS-pul22k were prepared by weighing 20 mg of a standard into a separate 20 mL scintillation vial and adding 2.0 mL of DI water to each vial. A polymer solution mixture #1 was prepared by weighing 10 mg of each standard of glucose, maltose, maltooctaose and Mp 9600 into an HPLC vial, adding 1.0 mL of diluent and mixing well. A polymer solution mixture #1 was prepared by weighing 10 mg of each standard of maltotetraose, Mp 6100 and Mp 21100 into an HPLC vial, adding 1.0 mL of diluent and mixing well.

Sample A was prepared in duplicate. Approximately 300 mg of oligosaccharide sample was weighed into a 20 mL scintillation vial and 10 mL of DI water was added. The solution was mixed and filtered through a PES syringe filter with a 0.2 μm polyethersulfone membrane.

Sample B was prepared in duplicate. Approximately 220 mg of oligosaccharide sample was weighed into a 20 mL scintillation vial and 10 mL of DI-water was added. The solution was mixed and filtered a PES syringe filter with a 0.2 μm polyethersulfone membrane.

The flow rate was set to 0.7 mL/min at least 2 hours before running samples with the column temperature set to 65° C. and the RI detector temperature set to 50° C. with the RI detector purge turned on.

Before running samples wherein the injection volume for all samples was 10 μL and run time was 40 minutes, the detector purge was turned off and the pump was run at 0.7 mL/min until an acceptable baseline was obtained.

A blank sample consisting of DI water was run. Samples of standard mixtures #1 and #2 were run. Sample A was run. Sample B was run.

Figure 11:
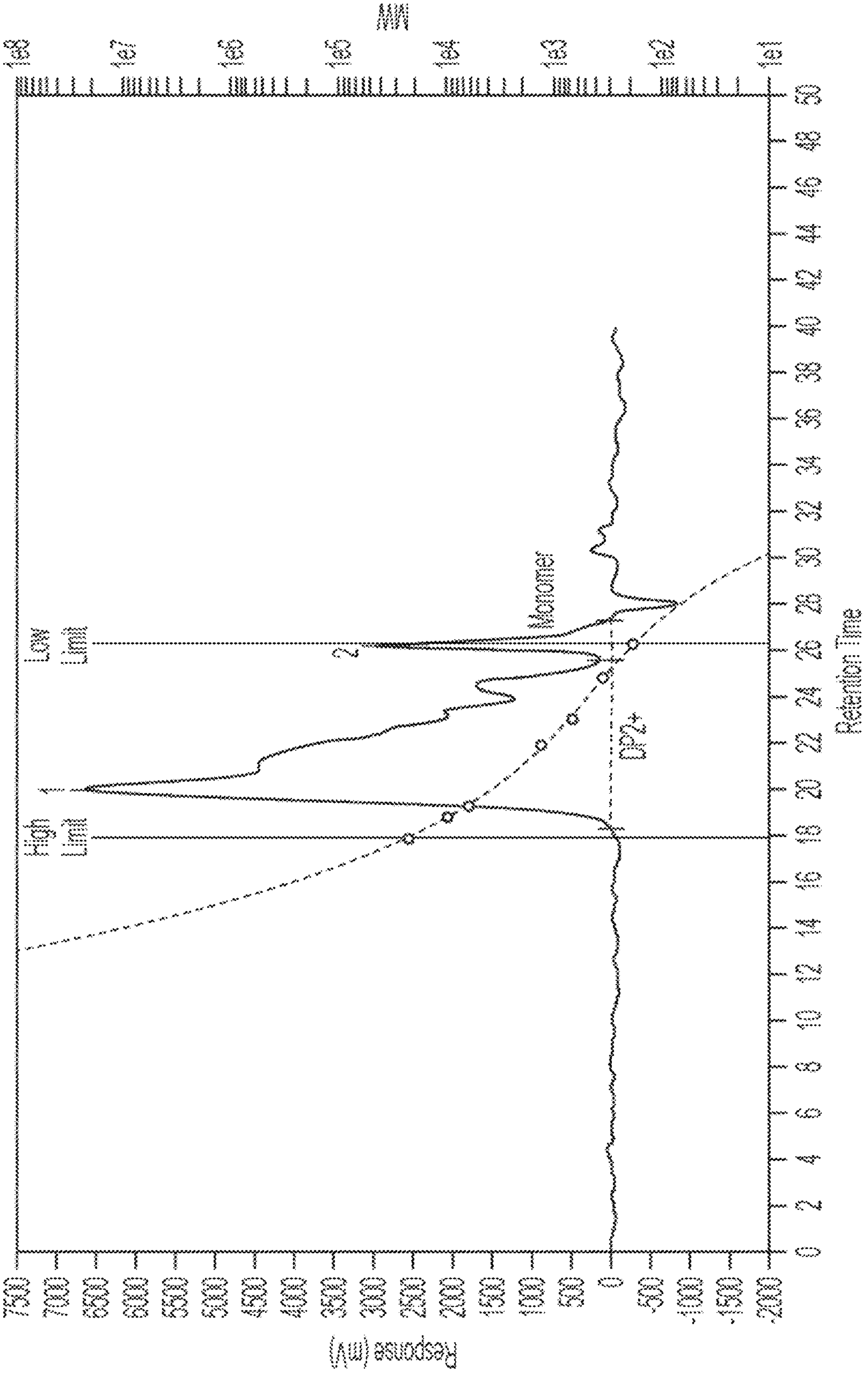
FIG. 11 provides a SEC-HPLC chromatogram of the selected oligosaccharide composition using the method provided in Example 12.

The peaks between 18 and 25.5 minutes were integrated. The monomer and the broad peak (the product) were integrated as shown in the sample chromatogram (FIG. 11). The calibration curve fit type in Empower 3 software was set to $3^{rd}$ order. The molecular weight distributions and polydispersity were calculated using Empower 3 software for the broad peak. The Mw, Mn and polydispersity of the product peak (DP2+) were determined using these methods.

Results

Fourteen batches of the selected oligosaccharide composition produced using the process in Example 1 (Marathon C catalyst) were analyzed using the above SEC methods. The batches of oligosaccharide composition comprised oligosaccharides with an average MWw of 2074 g/mol (ranging from 1905-2286 g/mol), an average MWn of 1097 g/mol (ranging from 1033-1184 g/mol), and an average PDI of 1.9 (ranging from 1.84-1.97). Assayed batches comprised a DP2+ of 91.1% (DP2+ ranging from 86.3-95.9%) and about 8.9% monomer on average (ranging from 4.1-13.8% monomer). Assayed batches had an average degree of polymerization (DP) of 12.7 (ranging from 11.6-14.0).

Twenty-three batches of the selected oligosaccharide co position produced using the process in Example 2 (citric acid catalyst) were analyzed using the above SEC methods. The batches of oligosaccharide composition comprised oligosaccharides with an average MWw of 1998 g/mol (ranging from 1863-2268 g/mol), an average MWn of 1030 g/mol (ranging from 984-1106.00 g/mol), and an average PDI of 1.94 (ranging from 1.88-2.05). Assayed batches comprised a DP2+ of 87.3% (DP2+ ranging from 83.6-91.0%) and about 12.7% monomer on average (ranging from 9.0-16.4% monomer). Assayed batches had an average degree of polymerization (DP) of 12.2 (ranging from 11.4-13.9).

Example 13. SEC HPLC Methodology for Determination of Impurities

The presence of residual organic acid impurities and related substances of batches and samples of the selected oligosaccharide composition, as produced by the processes in Example 1 (Marathon C catalyst), were determined by SEC HPLC.

Methods

These methods involved the use of an Agilent 1100 with refractive index (RI) detector equipped with a guard column (Bio-Rad MicroGuard Cation H Cartridge, PIN 125-0129, or equivalent) and a Bio-Rad Aminex HPX-87H, 300×7.8 mm, 9 μm, PIN 125-0140 column, or equivalent.

The mobile phase (25 mM $H_2SO_4$in water) was prepared by filling a bottle with 2000 mL DI-water and slowly adding 2.7 mL of $H_2SO_4$. The solution was filtered through a 0.2 μm filter.

A standard solution was prepared by measuring 50 f 2 mg of reference standard into a 100-mL volumetric flask, adding mobile phase to 100-mL mark and mixing well.

A sample of the selected oligosaccharide composition (Sample A) was prepared in duplicate. Approximately 1000 mg of oligosaccharide sample was weighed into a 10 mL volumetric flask and mobile phase was added up to the mark. The solution was mixed and filtered through a PES syringe filter with a 0.2 μm polyethersulfone membrane.

A sample of the selected oligosaccharide composition (Sample-B) was prepared in duplicate. Approximately 700 mg of oligosaccharide sample was weighed into a 10 mL volumetric flask and mobile phase was added up to the mark. The solution was mixed and filtered through a PES syringe filter with a 0.2 μm polyethersulfone membrane.

The flow rate was set to 0.65 mL/min at least 2 hours before running samples with the column temperature set to 50° C. and the RI detector temperature set to 50° C. with the RI detector purge turned on.

Before running samples wherein the injection volume for all samples was 50 μL and run time was 40 minutes, the detector purge was turned off and the pump was run at 0.65 mL/min until an acceptable baseline was obtained.

A blank sample consisting of DI water was run. The standard, sample A, and sample B were each independently run.

The peaks at 7.5 min (Glucuronic acid), 9.4 min (Maleic Acid), 11.3 min (Levoglucosan), 11.9 min (Lactic Acid), 13.1 min (Formic Acid), 14.2 min (Acetic Acid), 15.5 min (Levulinic Acid), 31.8 min (HMF), and 8.3 min (Glucose) were integrated. The calibration curve fit type in Empower 3 software was set to $3^{rd}$ order.

Results

Ten batches of the selected oligosaccharide, as produced by the process in Example 1 (Marathon C catalyst), were tested using the method above. The selected oligosaccharide composition comprised 0.35% w/w (±0.05%) levoglucosan, 0.03% w/w (±0.01%) lactic acid, and 0.06% w/w (±0.01%) formic acid. Samples of the selected oligosaccharide composition comprised 0.28-0.43% w/w levoglucosan, 0.00-0.03% w/w lactic acid, and 0.05-0.07% w/w formic acid.

Batches of the selected oligosaccharide, as produced by t e process in Example 2 (citric acid catalyst), were tested using the method above. The selected oligosaccharide composition comprised 0.47% w/w (±0.02%) levoglucosan (23 batches of the selected oligosaccharide), 0.01% w/w lactic acid (11 batches of the selected oligosaccharide), 0.02% w/w formic acid (12 batches of the selected oligosaccharide), and 0.02% w/w citric acid (23 batches of the selected oligosaccharide). Samples of the selected oligosaccharide composition comprised 0.43-0.51% w/w levoglucosan, 0.01-0.02% w/w lactic acid, 0.00-0.03% w/w formic acid, and 0.00-0.03% w/w citric acid.

Example 14. SEC HPLC Methodology for Determination of DP1-DP7

The relative amounts of oligosaccharides with a degree of polymerization (DP) of 1, 2, and 3+ in batches and samples of the selected oligosaccharide composition, as produced by the processes in Example 1 were determined by SEC HPLC.

Methods

These methods involved the use of an Agilent 1100 with refractive index (RI) detector equipped with a guard column (Shodex SUGAR SP-G 6B Guard Column 6×50 mm, 10 μm, P/N F6700081, or equivalent) and a chromatography column (Shodex Sugar SP0810, 8.0 ×300 mm, 8 μm, P/N F6378105, or equivalent).

The mobile phase (0.1 M $NaNO_3$) was prepared by weighing 42.5 g of $NaNO_3$ (ACS grade reagent) and dissolving in 5000 mL of deionized (DI) water (from MiliQ water filter). The solution was filtered through a 0.2 μm filter.

Polymer standard solutions (10.0 mg/mL) of each of D-(+) Glucose Mp 180, Carbosynth Ltd Standard, or equivalent (CAS #50-99-7) (DP1); Maltose Mp 342, Carbosynth Ltd Standard, or equivalent (CAS #69-79-4) (DP2); Maltotriose Mp 504, Carbosynth Ltd Standard, or equivalent (CAS #1109-28-0) (DP3); Maltotetraose Mp 667, Carbosynth Ltd Standard, or equivalent (CAS #34612-38-9) (DP4); Maltopentaose Mp 828, Carbosynth Ltd Standard, or equivalent (CAS #34620-76-3) (DP5); Maltohexaose Mp 90, Carbosynth Ltd Standard, or equivalent (CAS #34620-77-4) (DP6); Maltoheptaose Mp 1153, Carbosynth Ltd Standard, or equivalent (CAS #34620-78-5) (DP7); and Maltooctaose Mp 1315, Carbosynth Ltd Standard, or equivalent (CAS #6156-84-9) (DP8), were prepared by weighing 10 mg of a standard into an individual 1.5 mL centrifuge tube and adding DI water to make 10 mg/mL solution.

Samples of the selected oligosaccharide composition were prepared as 10 mg/mL concentrated samples or dilute aqueous samples to 2.5-3.5 Brix.

The flow rate was set to 1.0 mL/min at least 2 hours before running samples with the column temperature set to 70° C. and the RI detector temperature set to 40° C. with the RI detector purge turned on.

Before running samples wherein the injection volume for all samples was 5 μL and run time was 15 minutes, the detector purge was turned off and the ump was run at 1.0 mL/min until an acceptable baseline was obtained.

A blank sample consisting of DI water, individual standards, and sample were independently run.

Figure 12:
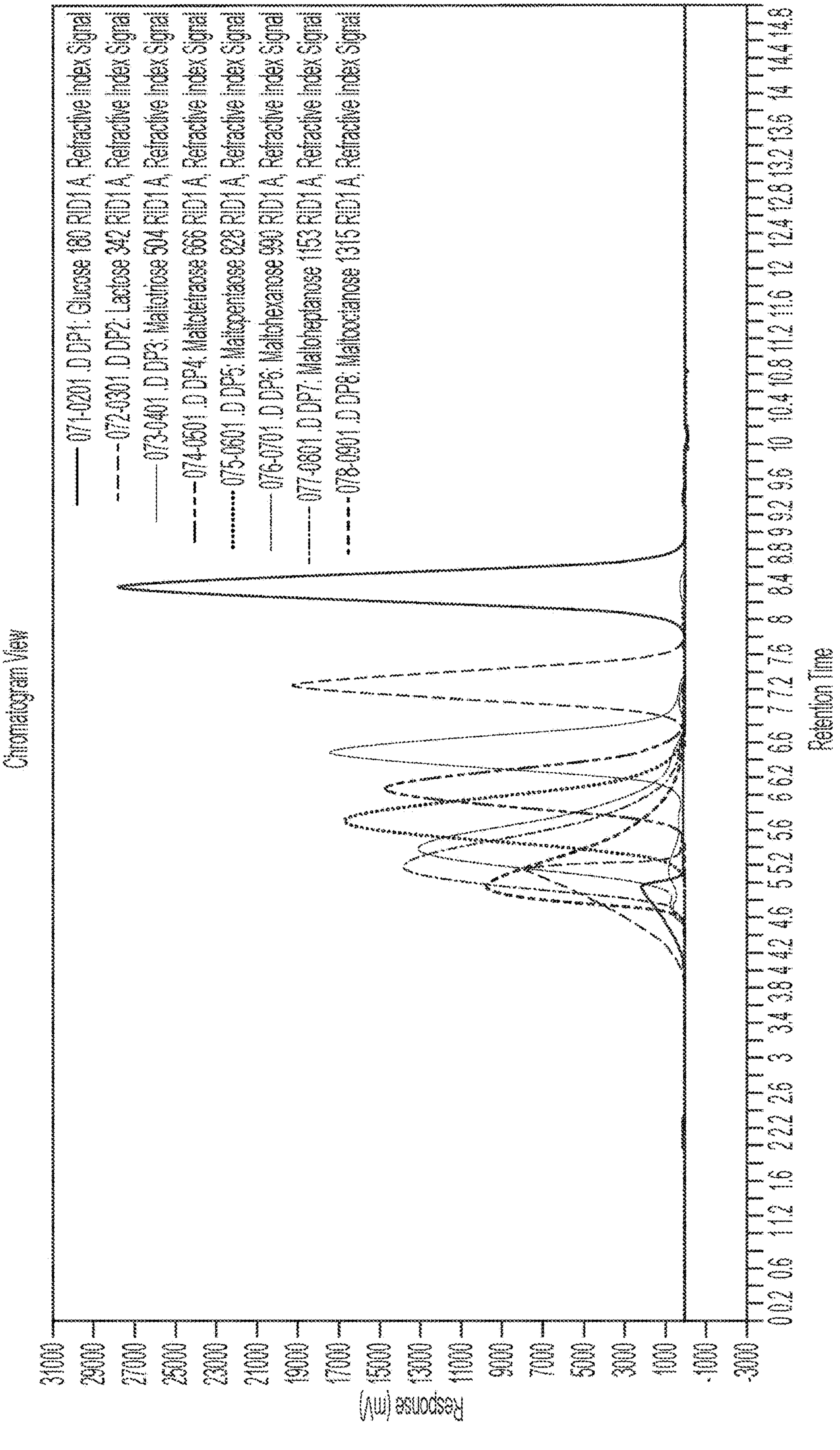
FIG. 12 provides an overlay of SEC-HPLC chromatograms of standard saccharides for use in Example 14.

Each peak between 4 and 9.2 minutes in the sample run, corresponding to individual standards, was integrated. An overlay of the standards in shown in FIG. 12. The calibration curve fit type in Empower 3 software was set to $3^{rd}$ order. The DP1, DP2, and DP3+ values of the samples (samples of selected oligosaccharide composition) were determined using these methods.

Results

Ten samples of selected oligosaccharide composition produced using the process in Example 1 were assayed using this method. The selected oligosaccharide composition comprised 5.24% (±0.35%) monomer (DP1), 7.52% (±0.44%) disaccharide (DP2), and 87.25% (±0.78%) oligomers having at least three linked monomer units (DP3+).

Example 15. Determination of Total Dietary Fiber

The amount of dietary fiber in batches of the selected oligosaccharide composition, as produced by the process in Example 7 (Marathon C catalyst) were measured according to the methods of AOAC 2011.25 (AOAC International, AOAC Official Method 2011.25). The average amount of total dietary fiber was 87.44% (on d basis) across 10 batches (ranging from 84.9-90.5%). The percent Dextrose Equivalent (DE) (dry basis) of these oligosaccharide batches was also measured according to the Food Chemicals Codex (FCC). The average amount of dextrose equivalent (on dry basis) was 16.60% across two batches (one at 15.10% DE and the other at 18.10% DE).

The amount of dietary fiber and dextrose equivalents (DE) in batches of the selected oligosaccharide composition, as produced by the process in Example 9 (citric acid catalyst) were measured according to the methods of AOAC 2011.25 (AOAC International, AOAC Official Method 2011.25). The percent Dextrose Equivalent (DE) (dry basis) of these oligosaccharide batches was also measured according to the Food Chemicals Codex (FCC). The average amount of total dietary fiber was 64.14% (on dry basis) across fourteen batches (ranging from 47.10-73.10%). The average amount of dextrose equivalent (on dry basis) was 20.60% across two batches (one at 18.60% DE and the other at 22.60% DE).

Example 16. Assessment of Selected Oligosaccharide Compositions in Fecal Suspensions from Healthy Subjects The ability of the selected oligosaccharide composition comprised of a plurality of oligosaccharides selected from Formula (I), Formula (II), and Formula (III) as produced by a similar process as described in Examples 1-3 to reduce pathogen growth and promote commensal growth in microbiome samples from fecal suspensions of healthy subjects was assessed.

Fecal samples from healthy subjects were prepared as described in Example 8.

A single strain of vancomycin-resistant Enterococcaceae (VRE) was grown in isolation overnight in MM with 0.5% D-glucose in a COY chamber. On the day of the experiment, aliquots of the overnight cultures were washed with PBS a d the optical density ($OD_{600}$) of the cultures was measured. The culture was adjusted to $OD_{600}$ of 0.1 in MM and added to the 1% fecal suspensions. Fecal suspensions mixed with vancomycin-resistant Enterococcaceae (VRE) were then subjected to 16S sequencing to determine the initial relative abundance of pathogen and commensal bacteria. The cultures were the added to 96-well microplates with one of the following carbon sources (final concentration of 0.5% w/v) in each well: maltodextrin, fructooligosaccharide, a sample of the selected oligosaccharide composition, or water (negative control, i.e., no carbon source). These microplates were then incubated at 37° C. in the COY chamber for a total of 45 hours, with each experimental condition being tested in three replicates on each plate.

At the end of the 45-hour incubation, a sample of the culture from each well was subjected to 16S sequencing to determine the final relative abundance of pathogen and commensal bacteria in the community after intervention with oligosaccharide composition, as described in Example 8.

For the 16S sequencing, genomic DNA was extracted from the fecal suspensions and variable region 4 of the 16S rRNA gene was amplified and sequenced (Earth Microbiome Project protocol www.earthmicrobiome.org/emp-standard-protocols/16s/ and Caporaso J G et al. Ultra-high-throughput microbial community analysis on the Illumina HiSeq and MiSeq platforms. ISME J. (2012) August; 6(8): 1621-4). Raw sequences were de multiplexed, and each sample was processed separately with UNOISE2 (Robert Edgar UNOISE2: improved error-correction for Illumina 16S and ITS amplicon sequencing. bioRxiv (2016) Oct. 15). Reads from 16S rRNA amplicon sequencing data were rarefied to 5000 reads, without replacement, and resulting OTU table used in downstream calculations.

Figure 15:
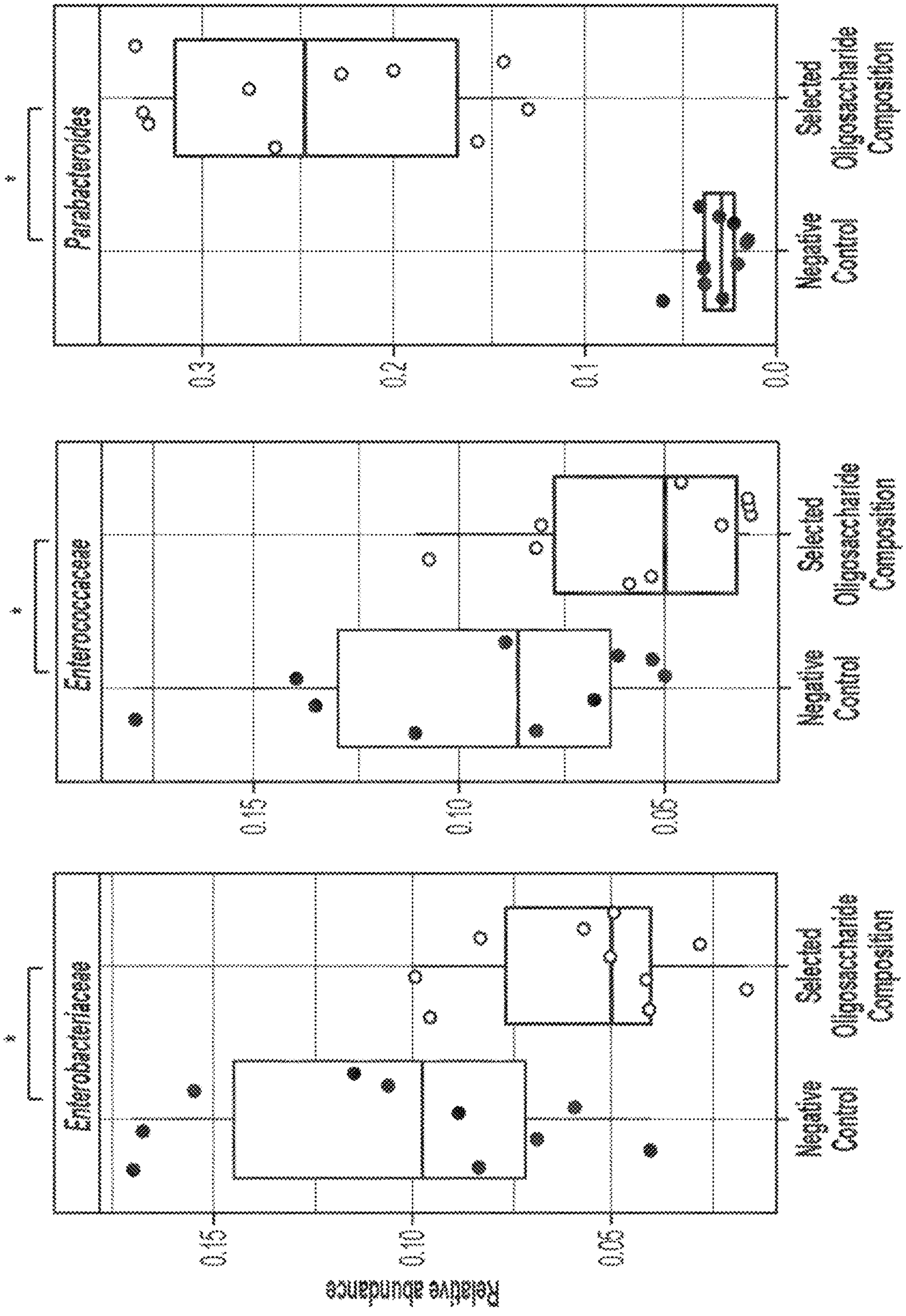
FIG. 15 provides graphs showing reductions in pathogen growth (Enterobacteriaceae and Enterococcaceae) and an increase in commensal growth (*Parabacteroides*) in fecal samples spiked with vancomycin-resistant Enterococcaceae.

The selected oligosaccharide composition significantly reduced the abundance of pathogens (Enterobacteriaceae and Enterococcaceae) (FIG. 15) in spik d fecal suspensions from healthy subjects, as assessed by 16S sequencing and relative to negative control (fecal suspensions spiked with water).

The selected oligosaccharide composition significantly increased the abundance of commensal bacteria (*Parabacteroides*) (FIG. 15) in spiked fecal suspensions from healthy subjects, as assessed by 16S sequencing and relative to negative control (fecal suspensions spiked with water).

This demonstrates that the selected oligosaccharide composition comprised of a plurality of oligosaccharides selected from Formula (I), Formula (II), and Formula (III) as produced by a similar process as described in Examples 1-3 is capable of reducing or preventing the growth of pathogens and promoting or increasing the growth of commensal bacteria in a medically relevant model.

Example 17. Assessment of Selected Oligosaccharide Compositions in Commensal Strains The ability of the selected oligosaccharide composition comprised of a plurality of oligosaccharides selected from Formula (I), Formula (II), and Formula (III) as produced by a similar process as described in Examples 1-3 to promote growth of sing e commensal strains was assessed.

Single strains of *Parabacteroides* species (2 total) and *Bacteroides* species (7 total) were cultured for 16 hours at 37° C. in a COY anaerobic chamber. 1 mL of each culture was washed with phosphate buffered saline and the optical density ($OD_{600}$) of each culture was measured. Each culture was adjusted to $OD_{600}$ of 0.02 in filter-sterilized medium containing 10 g/L tryptone peptone, 5 g/L yeast extract, 4.1 mM L-cysteine, 100 mM potassium phosphate buffer (pH 7.2), 0.008 mM magnesium sulfate, 4.8 mM sodium bicarbonate, 1.37 mM sodium chloride, 5.8 mM vitamin K, 0.8% calcium chloride, 1.44 mM iron (II) sulfate heptahydrate, 4 mM resazurin, 0.1% histidine-hematin, 1% ATCC trace mineral supplement, 1% ATCC vitamin supplement, 29.7 mM acetic acid, 0.9 mM isovaleric acid, 8.1 M propionic acid, and 4.4 mM N-butyric acid, pH 7.0.

Inside of the COY anaerobic chamber, the normalized single strain cultures were added to 96 well flat bottom microplates with either D-glucose (positive control) or the selected oligosaccharide composition as an added carbon source to each well. A negative control in which water was added to the single strain cultures without an added carbon source was also performed. The final concentration of the carbon source (glucose or the selected oligosaccharide composition) in the assay was 0.5%. Each carbon source (glucose or the selected oligosaccharide composition) was represented 3 times within each assay plate (i.e., with each single strain). Plates are covered with a breathable membrane and were incubated at 37° C. in the COY anaerobic chamber for a total of 45 hours. $OD_{600}$ was measured every 15 minutes. These $OD_{600}$ reads generated growth curves for each assay plate using the Biotek BioStack microplate stacker and Bioteck Powerwave HT microplate spectrophotometer. The median $OD_{600}$ normalized to the negative control was determined for the growth curves generated for each strain and compound combination using the growthcurver library in Rstudio.

Figure 16:
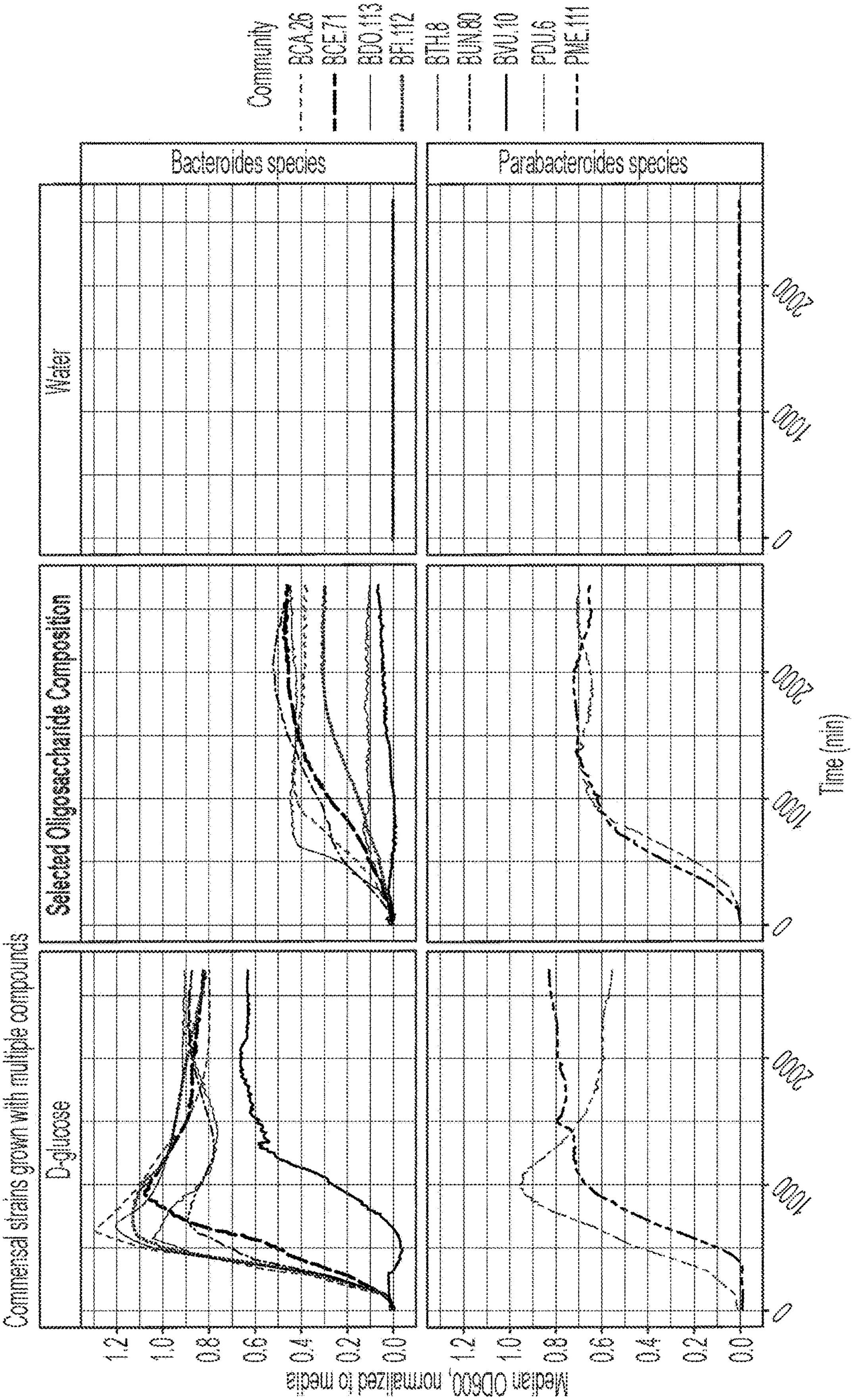
FIG. 16 provides graphs showing the ability of the selected oligosaccharide composition to support the growth of single strains of commensal bacteria (*Parabacteroides* and *Bacteroides*).

The selected oligosaccharide composition supported the growth of *Parabacteroides* species and *Bacteroides* species (FIG. 16). For all species tested, the maximum ability to grow under our conditions was defined by the positive control (D-glucose) and the minimum ability of a strain to grow on the background media was defined by the negative control (water). The growth of *Parabacteroides distasonis* (PDI.6) and *Parabacteroides merdae* (PME.111) were supported by the selected oligosaccharide composition at similar levels of growth compared to D-glucose, indicating almost full utilization of the elected oligosaccharide composition as a carbon source. The growth of *Bacteroides thetaiotaomicron* (BTH.8), *Bacteroides uniformis* (BUN.80), *Bacteroides caccae* (BCA.26), *Bacteroides cellulosilyticus* (BCE.71) were supported by the selected oligosaccharide composition at high levels. The growth of *Bacteroides finegoldii* (BFI.112) and *Bacteroides dorea* (BDO.113) were also supported by the selected oligosaccharide composition relative to negative controls. *Bacteroides vulgatus* (BVU.10) was at least minimally supported by the selected oligosaccharide composition in this experiment.

Example 18. Assessment of the Ability of the Selected Oligosaccharide Composition to Reduce Lung Disease-Associated Symptoms in Mice Infected with SARS-CoV-2

The ability of the selected oligosaccharide composition comprised of a plurality of oligosaccharides selected from Formula (I), Formula (II), and Formula (III) as produced by a similar process as described in Examples 1-3 is assessed for its ability to treat and prevent coronavirus infections in a mouse model.

K18-hACE2 transgenic mice (tgACE2 (034860) mice, as described in Winkler, E. S. et. al, Nat Immunol. 2020 November; 21(11):1327-1335) are treated as described in Table 5.

TABLE 5

| Treatment groups | | | |
|---|---|---|---|
| | Compound | Concentration Dose | Number of mice |
| Group 1 | Selected oligosaccharide composition | 3000 milligrams per kilogram | 12 |
| Group 2 | Selected oligosaccharide composition | 1000 milligrams per kilogram | 12 |
| Group 3 | xylose-based oligosaccharide composition (negative control) | 3000 milligrams per kilogram | 12 |
| Group 4 | Saline | — | 12 |
| Group 5 | MOCK treatment (no compound added) | — | 12 |

Mice are prophylactically dosed once per day for five da s by oral gavage before being subjected to a SARS-CoV-2 viral challenge (e.g., $2.5\times10^4$ p.f.u. SARS-CoV-2 via intranasal administration). Following the viral challenge, mice are dosed once per day by oral gavage for an additional seven days.

Samples of fresh feces (1 pellet per animal) are collected on Day −5 (prior to the first prophylactic dosing), Day 0 (prior to the viral challenge), and Day 7 (following the final dosing). The fecal samples are snap frozen and stored at −80° C. On Day 7, the mice are sacrificed.

The sacrificed mice and associated fecal samples are analyzed for total virus preparation, weight, viral load analysis, viral RNA analysis, lung pathology, cytokines, and microbiome analysis. Protocols for completion of the Example and analyses of sacrificed mice and associated fecal samples are as described in Winkler, E. S. et. al, Nat Immunol. 2020 November; 21(11):1327-1335.

It is expected that administration of the selected oligosaccharide composition provides benefits to the health of the test animals relative to the test animals dosed with xylose-based oligosaccharide composition (negative control), saline, and mock-treatment (e.g., effects on one or more of the following biomarkers and other relevant biomarkers are observed: lowered viral replication in the lung, lowered viral loads, lessened immune cell infiltration, lower levels of inflammation and cytokines, etc.). The outcome of the animal experiments may be affected by the ability of the selected oligosaccharide to modulate the composition of the microbiome in the animals, as it is known that differences between the gastrointestinal microbiota of humans and mice pose experimental challenges (e.g., described in Example 19).

Example 19: Effects of Selected Oligosaccharide in RSV and Influenza Animal Models To assess if the selected oligosaccharide composition comprised of a plurality of oligosaccharides selected from Formula (I), Formula (II), and Formula (III) as produced by a similar process as described in Examples 1-3 is beneficial in respiratory virus infections other than SARS-CoV-2, pilot studies in mouse models of influenza and RSV (respiratory syncytial virus) infection were performed. The microbiome has previously been implicated in protective immune responses to influenza and RSV infection in mice (Antunes, et al. Microbiota-derived acetate protects against respiratory syncytial virus infection through a GPR43-type 1 interferon response. *Nat Commun.* 2019; 10(1):3273; Trompette A, et al Dietary Fiber Confers Protection against Flu by Shaping Ly6c—Patrolling Monocyte Hematopoiesis and CD8+ T Cell Metabolism. *Immunity.* 2018; 48(5):992-1005.e8; Bradley K C, et al. Microbiota-Driven Tonic Interferon Signals in Lung Stromal Cells Protect from Influenza Virus Infection. *Cell Rep.* 2019; 28(1):245-256.e4), suggesting that effects of microbiome modulation by the selected oligosaccharide can be evaluated in these models. The pilot studies were primarily performed to test experimental parameters such as dosing, length of treatment and route of administration and thus data suggesting efficacy and treatment of the selected oligosaccharide are preliminary and limited as they were obtained under conditions that were not optimized or gathering such data. Additionally, differences between the gastrointestinal microbiota of humans and mice pose experimental challenges (Nagpal R, et al. Comparative Microbiome Signatures and Short-Chain Fatty Acids in Mouse, Rat, Non-human Primate, and Human Feces. Front Microbiol. 2018; 9:2897; Hugenholtz F, de Vos W M. Mouse models for human intestinal microbiota research: a critical evaluation. Cell Mol Life Sci. 2018; 75(1):149-160). For example, species of bacteria in the *Parabacteroides* genus that are believed to utilize the selected oligosaccharide as a carbon source in humans (FIG. 16) are usually present only in low abundance in the mouse microbiome (Nagpal R, et al. Front Microbiol. 2018; 9:2897; Xiao L, et al. A catalog of the mouse gut metagenome. Nat Biotechnol. 2015; 33(10): 1103-1108). Despite these challenges and lack of optimization of experimental parameters, preliminary, limited data obtained in mice suggest beneficial effects of the selected oligosaccharide on infections caused by respiratory viruses such as, e.g., influenza and RSV infection.

Mouse models were adapted from existing publications (Antunes K H, et al. Nat Commun. 2019; 10(1):3273; Trompette A, et al. Immunity. 2018; 48(5):992-1005.e8). To better control dosing, the selected oligosaccharide was administered by oral gavage instead of in animal chow.

The design for the RSV pilot study is summarized in Table 6. Briefly, female BALB/c mice between 6-8 weeks of age were weighed one day prior to study start and randomized into 3 groups of n=10, such that each group had approximately the same average weight. Mouse body weight was recorded every 2-3 days before viral challenge and every day after. Clinical symptoms were monitored daily. Fecal pellets were collected on days −8, 0, 2 and 5. Groups 1 and 2 received 200 μL of vehicle (water) once a day (QD) from D-7 to D4 via oral gavage (PO). Group 3 received the selected oligosaccharide at 3000 mg/kg/day QD from D-7 to D4 PO, administered as the appropriate volume of a 0.3 g/mL solution. On Day 0, RSV-A2 was administered to Groups 2 and 3 by intranasal inoculation with 50 μL of a viral stock solution at $8.5\times10^5$ PFU/mL. Group 1 was not infected. The study was terminated at D5. All animals were euthanized, and lungs were harvested for viral plaque assay, histology, and cytokine profiling.

TABLE 6

Summary of the RSV pilot study

| Group | Group size | Group Description | Challenge virus (Intranasal) | Treatment | Dosing Route and Frequency | Endpoints and Analyses |
|---|---|---|---|---|---|---|
| 1 | 10 | Mock | — | Vehicle (water) | PO, QD | Body weight |
| 2 | 10 | RSV negative control | RSV-A2 | Vehicle (water) | PO, QD | Viral titers in the lung |
| 3 | 10 | RSV + selected oligosaccharide (3000 mpk/day) | RSV-A2 | selected oligosaccharide | PO, QD | Lung histopathology Cytokine profiling in lung homogenates |

The design for the influenza pilot study is summarized in Table 7. Briefly, female BALB/c mice between 6-8 weeks of age were weighed one day prior to study start and randomized into 3 groups of n=16, such that each group had approximately the same average weight. All mice were treated with saline or the selected oligosaccharide twice daily (BID) starting 7 days prior to virus inoculation and continuing through end of study. The experimental animals were inoculated intranasally on day 0 with 300 PFU/mouse in a volume of 50 μL. Fecal pellets were collected on days −7, 0, 6, 14 for the health monitoring cohorts and days −7, 0, 6 for the sample collection cohorts. On day 6, animals from the sample collection cohorts were euthanized, and blood, bronchoalveolar (BAL) fluid, and lung samples were collected. On day 14, all the surviving mice from the health monitoring cohorts were euthanized.

TABLE 7

Summary of the influenza pilot study

| Animal | Group | Group size | Challenge virus | Treatment | Dosing Route and Frequency | Endpoints and Analyses |
|---|---|---|---|---|---|---|
| Mock | Health monitoring | 10 | Mock (50 μL PBS/mouse) | Saline (0.9% NaCl) | PO, BID, day −7 to day 14 | Body weight Mortality |
| | Sample collection | 6 | | | PO, BID, day −7 to day 6 | General health Clinical |
| Negative Control | Health monitoring | 10 | Influenza virus A/PR/8/34 | Saline (0.9% NaCl) | PO, BID, day −7 to day 14 | score Lung viral titer |
| | Sample collection | 6 | (H1N1), 300 PFU/mouse | | PO, BID, day −7 to day 6 | BAL fluid cytometry |
| selected oligosaccharide | Health monitoring | 10 | Influenza virus A/PR/8/34 (H1N1), 300 | selected oligosaccharide | PO, 3000 mg/kg/dose, BID, day −7 to day 14 | Lung pathology Cytokines in BAL fluid and |
| | Sample collection | 6 | PFU/mouse | | PO, 3000 mg/kg/dose, BID, day −7 to day 6 | serum |

In the RSV model, the selected oligosaccharide significantly decreased weight loss after RSV infection (p-value <0.05, linear mixed effect model) in comparison to the negative control group. The selected oligosaccharide also reduced lung viral load by approximately 0.16 log 10 PFU/g on average at day 5 (D5), though not statistically significant (p-value=0.076, student t test).

In the influenza model, the selected oligosaccharide did not show effects on body weight, clinical score, and survival compared to the negative control group, but in a flow cytometry analysis of bronchoalveolar (BAL) fluid, the selected oligosaccharide significantly reduced the percentage of infiltrating neutrophils, by about 37% (p-value: 0.035, student t test). Excessive neutrophil influx has been associated with dysregulated and damaging inflammation during lung infection (Antunes K H, et al. Nat Commun. 2019; 10(1):3273; Perrone L A, et al. H5N1 and 1918 Pandemic Influenza Virus Infection Results in Early and Excessive Infiltration of Macrophages and Neutrophils in the Lungs of Mice. Baric R S, ed. PLoS Pathog. 2008; 4(8): e 1000115).

Lung histopathology, cytokine analysis, and fecal microbiome analysis (to explore shifts in the mouse microbiome community) from both studies re analyzed. It is expected that administration of the selected oligosaccharide composition beneficially affects these parameters in these studies relative to mock treated animals and negative control animals; e.g., the selected oligosaccharide may affect on one or more of the following: lowered viral replication in the lung, lowered viral loads, lessened immune cell infiltration, lower levels of inflammation and cytokines, etc.).

The preliminary, limited data obtained thus far for influenza and RSV together with the in-human data obtained for SARS-CoV-2 suggest that the selected oligosaccharide may be able to improve clinical symptoms of, and reduce viral loads in respiratory viral infections in general, independent of the identity of the underlying respiratory virus. Thus, these findings suggest the selected oligosaccharide may be useful in the treatment of a range of respiratory viral infections including those associated with coronavirus, enterovirus, adenovirus, parainfluenza virus, respiratory syncytial virus, influenza virus, metapneumovirus, rhinovirus, measles virus and bocavirus.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms “comprising”, “consisting essentially of”, and “consisting of” may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications an variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms “a” and “an” and “the” and similar referents in the context of describing the invention (especially in the context of the following clai s) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as f it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of t e invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable jaw. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject having one or more symptoms of a viral respiratory illness, wherein treating is facilitating improvement or remediation of damage caused by the viral respiratory illness or reduction in severity and/or frequency of the viral respiratory illness, or a symptom thereof, the method comprising administering to the gastrointestinal tract of the subject an effective amount of an oligosaccharide composition, wherein the oligosaccharide composition comprises a plurality of oligosaccharides, with an average degree of polymerization of 5-20, selected from Formula (I), Formula (II), and Formula (III):

(I)

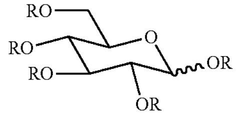

(II)

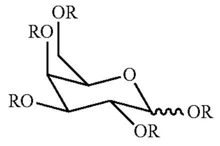

-continued (III)

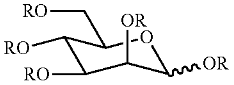

wherein each R independently is selected from hydrogen, and Formulae (Ia), (Ib), (Ic), (Id), (IIa), (IIb), (IIc), (IIId), (IIIa), (IIIb), (IIIc), (IIId):

(Ia)

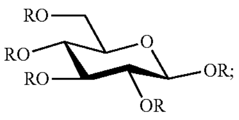

(IIa)

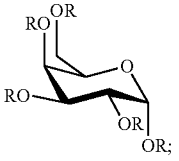

(IIIa)

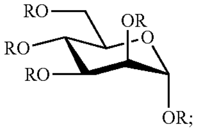

(Ib)

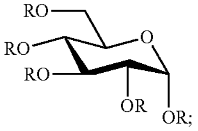

(IIb)

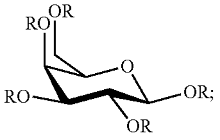

(IIIb)

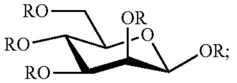

(Ic)

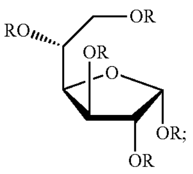

(IIc)

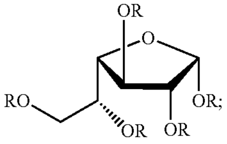

(IIIc)

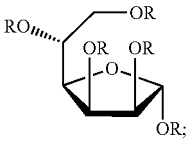

-continued (Id)

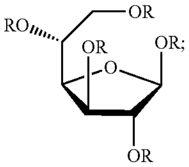

and (IId)

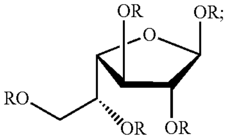

(IIId)

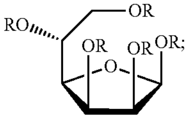

wherein each R independently is selected from hydrogen, and Formulae (Ia), (Ib), (Ic), (Id), (IIa), (IIb), (IIc), (IId), (IIIa), (IIIb), (IIIc), (IIId); wherein the oligosaccharide composition is produced by a process comprising:

(a) forming a reaction mixture comprising about 30-60% dextrose monomer, about 30-60% galactose monomer, and about 5-15% mannose monomer with an acid catalyst comprising positively charged hydrogen ions; and (b) promoting acid catalyzed oligosaccharide formation in the reaction mixture by transferring sufficient heat to the reaction mixture to maintain the reaction mixture at its boiling point, thereby treating the subject.

2. A method comprising:

(A) identifying a human subject having one or more symptoms associated with a viral respiratory infection; and (B) treating the subject with an oligosaccharide composition comprising a plurality of oligosaccharides, having an average degree of polymerization of 5-20, selected from Formula (I), Formula (II), and Formula (III):

(I)

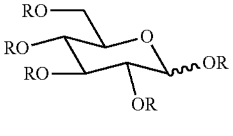

(II)

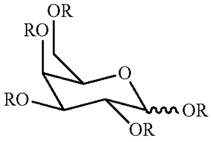

(III)

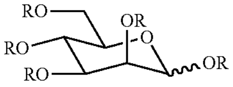

wherein each R independently is selected from hydrogen, and Formulae (Ia), (Ib), (Ic), (Id), (IIa), (IIb), (IIc), (IIId), (IIIa), (IIIb), (IIIc), (IIId):

(Ia)

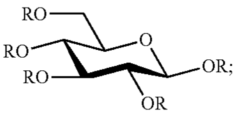

(IIa)

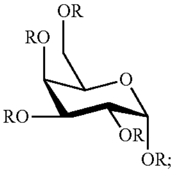

(IIIa)

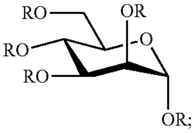

(Ib)

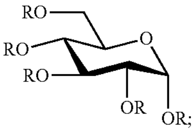

(IIb)

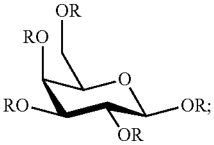

(IIIb)

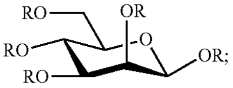

(Ic)

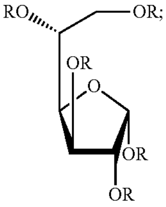

(IIc)

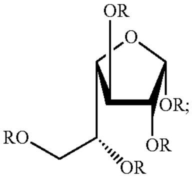

(IIIc)

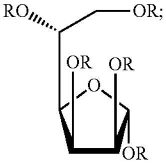

-continued (Id)

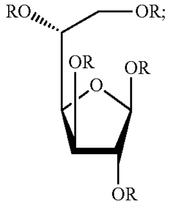

and (IId)

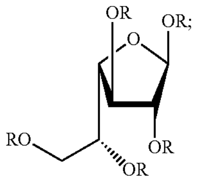

(IIId)

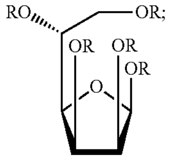

wherein each R independently is selected from hydrogen, and Formulae (Ia), (Ib), (Ic), (Id), (IIa), (IIb), (IIc), (IId), (IIIa), (IIIb), (IIIc), (IIId), wherein treating is facilitating improvement or remediation of damage caused by the viral respiratory infection or reduction in severity and/or frequency of the viral respiratory infection, or a symptom thereof and the oligosaccharide composition is produced by a process comprising:

(a) forming a reaction mixture comprising about 30-60% dextrose monomer, about 30-60% galactose monomer, and about 5-15% mannose monomer with an acid catalyst comprising positively charged hydrogen ions; and (b) promoting acid catalyzed oligosaccharide formation in the reaction mixture by transferring sufficient heat to the reaction mixture to maintain the reaction mixture at its boiling point.

3. A method of attenuating an immune response in a subject having one or more symptoms of a viral respiratory illness, the method comprising administering to the gastrointestinal tract of the subject an effective amount of an oligosaccharide composition, wherein the oligosaccharide composition comprises a plurality of oligosaccharides, with an average degree of polymerization of 5-20, selected from Formula (I), Formula (II), and Formula (III):

(I)

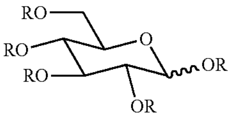

(II)

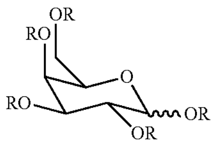

-continued (III)

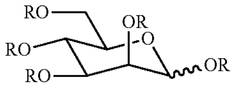

wherein each R independently is selected from hydrogen, and Formulae (Ia), (Ib), (Ic), (Id), (IIa), (IIb), (IIc), (IId), (IIIa), (IIb), (IIIc), (IIId):

(Ia)

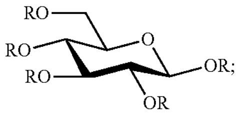

(IIa)

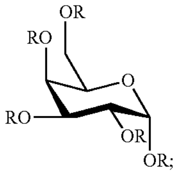

(IIIa)

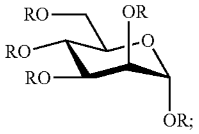

(Ib)

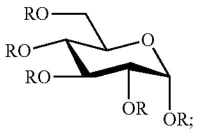

(IIb)

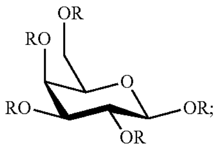

(IIIb)

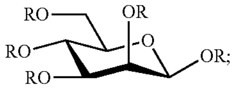

(Ic)

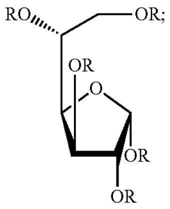

(IIc)

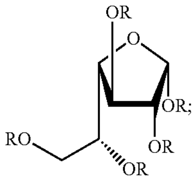

-continued (IIIc)

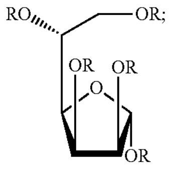

(Id)

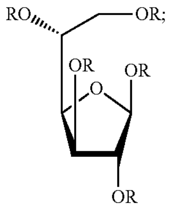

and (IId)

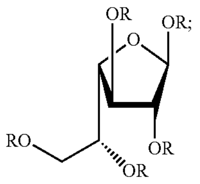

(IIId)

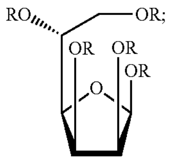

wherein each R independently is selected from hydrogen, and Formulae (Ia), (Ib), (Ic), (Id), (IIa), (IIb), (IIc), (IId), (IIIa), (IIIb), (IIIc), (IIId), wherein the oligosaccharide composition is produced by a process comprising:

(a) forming a reaction mixture comprising about 30-60% dextrose monomer, about 30-60% galactose monomer, and about 5-15% mannose monomer with an acid catalyst comprising positively charged hydrogen ions; and (b) promoting acid catalyzed oligosaccharide formation in the reaction mixture by transferring sufficient heat to the reaction mixture to maintain the reaction mixture at its boiling point; thereby attenuating an immune response in the subject.

4. The method of any one of claims 1-3, wherein the subject has one or more symptoms selected from the group consisting of: fever, shivering, chills, malaise, fatigue, cough, shortness of breath, sore throat, loss of appetite, loss of taste, loss of smell, body aches, muscle pain, headache, diarrhea and nausea.

5. The method of any one of claims 1-3, wherein the viral respiratory illness or infection is caused by an RNA virus.

6. A method of increasing the amount of short-chain fatty acids in the gastrointestinal tract of a subject, the method comprising administering to the gastrointestinal tract an effective amount of an oligosaccharide composition, wherein the oligosaccharide composition comprises a plurality of oligosaccharides, with an average degree of polymerization of 5-20, selected from Formula (I), Formula (II), and Formula (III):

(I)

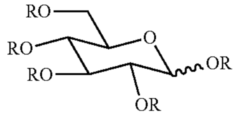

(II)

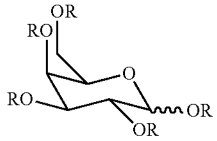

(III)

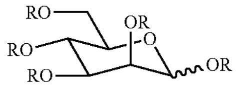

wherein each R independently is selected from hydrogen, and Formulae (Ia), (Ib), (Ic), (Id), (IIa), (IIb), (IIc), (IIId), (IIIa), (IIIb), (IIIc), (IIId):

(Ia)

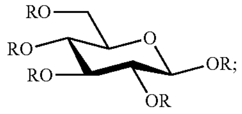

(IIa)

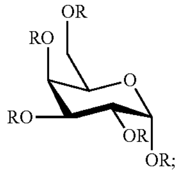

(IIIa)

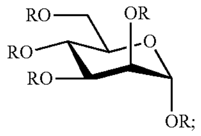

(Ib)

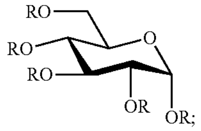

(IIb)

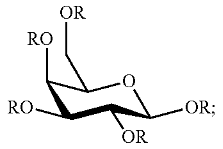

(IIIb)

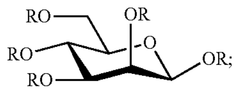

(Ic)

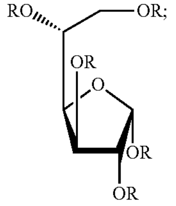

-continued (IIc)

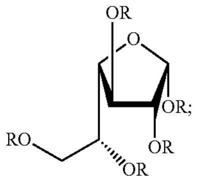

(IIIc)

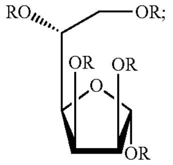

(Id)

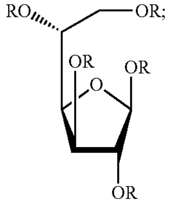

and (IId)

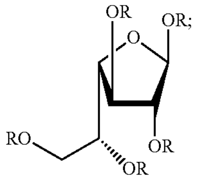

(IIId)

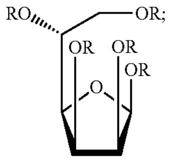

wherein each R independently is selected from hydrogen, and Formulae (Ia), (Ib), (Ic), (Id), (IIa), (IIb), (IIc), (IIId), (IIIa), (IIIb), (IIIc), (IIId), wherein the oligosaccharide composition is produced by a process comprising:

(a) forming a reaction mixture comprising about 30-60% dextrose monomer, about 30-60% galactose monomer, and about 5-15% mannose monomer with an acid catalyst comprising positively charged hydrogen ions; and (b) promoting acid catalyzed oligosaccharide formation in the reaction mixture by transferring sufficient heat to the reaction mixture to maintain the reaction mixture at its boiling point.

7. The method of claim 6, wherein the short-chain fatty acids comprise propionate, butyrate and/or acetate.

8. The method of claim 6, wherein the amounts of short-chain fatty acids are increased by at least 2-fold in an ex vivo fecal sample collected from the subject relative to a baseline measurement or control.

9. The method of claim 7, wherein the amount of propionate is increased by at least 1.2 fold in an ex vivo fecal sample collected from the subject relative to a baseline measurement or control.

10. The method of claim 7, wherein the relative amounts of acetate, propionate, and butyrate produced are about 40-70% acetate, about 30-50% propionate, and about 5-20% butyrate.

11. The method of any one of claims 1 or 3, further comprising identifying a human subject having one or more symptoms associated with a viral respiratory illness.

12. The method of claim 6, further comprising identifying a human subject having one or more symptoms associated with a deficiency in short-chain fatty acids in the gastrointestinal tract.

* * * * *